(12) United States Patent
Barsanti et al.

(10) Patent No.: US 8,415,381 B2
(45) Date of Patent: Apr. 9, 2013

(54) HETEROARYL COMPOUNDS AND THEIR USES

(75) Inventors: Paul A. Barsanti, Pleasant Hill, CA (US); Cheng Hu, Menlo Park, CA (US); Jeff Jin, San Ramon, CA (US); Robert Keyes, Pleasant Prairie, WI (US); Robert Kucejko, Sacramento, CA (US); Xiaodong Lin, Walnut Creek, CA (US); Yue Pan, Albany, CA (US); Keith B. Pfister, San Ramon, CA (US); Martin Sendzik, San Mateo, CA (US); James Sutton, Pleasanton, CA (US); Lifeng Wan, Richmond, CA (US)

(73) Assignee: Novartis AG, Basel (CH)

( * ) Notice: Subject to any disclaimer, the term of this patent is extended or adjusted under 35 U.S.C. 154(b) by 102 days.

(21) Appl. No.: 12/843,494

(22) Filed: Jul. 26, 2010

(65) Prior Publication Data

US 2011/0028492 A1    Feb. 3, 2011

Related U.S. Application Data

(60) Provisional application No. 61/273,154, filed on Jul. 30, 2009, provisional application No. 61/357,720, filed on Jun. 23, 2010.

(51) Int. Cl.
*A01N 43/40* (2006.01)
*A61K 31/44* (2006.01)

(52) U.S. Cl.
USPC .................................... 514/334; 546/264

(58) Field of Classification Search .................. 546/258
See application file for complete search history.

(56) References Cited

U.S. PATENT DOCUMENTS

| 2011/0092505 A1* | 4/2011 | Burgis et al. ............ 514/235.5 |
| 2011/0130380 A1* | 6/2011 | Barsanti et al. ......... 514/210.18 |

FOREIGN PATENT DOCUMENTS

| DE | 40 31 798 A1 | 4/1992 |
| WO | WO 02/24681 A2 | 3/2002 |
| WO | WO 2004/009562 A1 | 1/2004 |
| WO | WO 2008/079933 A2 | 7/2008 |
| WO | WO 2009/150230 A1 | 12/2009 |
| WO | WO 2009150230 A1 * | 12/2009 |

OTHER PUBLICATIONS

Gee-Hong Kuo, "Synthesis and Discovery of Pyrazine-Pyridine Biheteroaryl as a Novel Series of Potent Vascular Endothelial Growth Factor Receptor-2 Inhibitors" *J. Med. Chem. 48*:1886-1900, 2005.
Gee-Hong Kuo, "Synthesis and Identification of [1,3,5]Triazine-pyridine Biheteroaryl as a Novel Series of Potent Cyclin-Dependent Kinase Inhibitors" *J. Med. Chem. 48*:4535-4546, 2005.

\* cited by examiner

*Primary Examiner* — James O Wilson
*Assistant Examiner* — Alexander R Pagano
(74) *Attorney, Agent, or Firm* — Michael G. Smith

(57) ABSTRACT

The present invention provides a compound of formula (I):

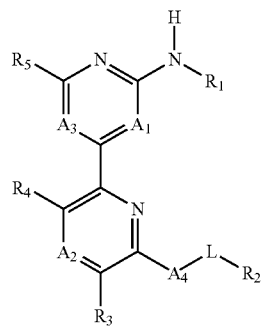

and pharmaceutically acceptable salts, enantiomers, stereoisomers, rotamers, tautomers, diastereomers, or racemates thereof. Also provided is a method of treating a disease or condition mediated by CDK9.

12 Claims, No Drawings

HETEROARYL COMPOUNDS AND THEIR USES

This application claims priority to U.S. provisional application Ser. No. 61/273,154, filed Jul. 30, 2009, and U.S. provisional application Ser. No. 61/357,720, filed Jun. 23, 2010, the contents of which are incorporated herein by reference in their entirety.

BACKGROUND

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (Hardie, G. and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J. 1995, 9, 576-596; Knighton et al, Science 1991, 253, 407-414; Hiles et al, Cell 1992, 70, 419-429; Kunz et al, Cell 1993, 73, 585-596; Garcia-Bustos et al, EMBO J. 1994, 13, 2352-2361).

Many diseases are associated with abnormal cellular responses triggered by the protein kinase-mediated events described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, viral diseases, and hormone-related diseases. Accordingly, there has been a substantial effort in medicinal chemistry to find protein kinase inhibitors that are effective as therapeutic agents.

The cyclin-dependent kinase (CDK) complexes are a class of kinases that are targets of interest. These complexes comprise at least a catalytic (the CDK itself) and a regulatory (cyclin) subunit. Some of the more important complexes for cell cycle regulation include cyclin A (CDK1-also known as cdc2, and CDK2), cyclin B1-B3 (CDK1) and cyclin D1-D3 (CDK2, CDK4, CDK5, CDK6), cyclin E (CDK2). Each of these complexes is involved in a particular phase of the cell cycle. Additionally, CDKs 7, 8, and 9 are implicated in the regulation of transcription.

The activity of CDKs is regulated post-translationally, by transitory associations with other proteins, and by alterations of their intracellular localization. Tumor development is closely associated with genetic alteration and deregulation of CDKs and their regulators, suggesting that inhibitors of CDKs may be useful anti-cancer therapeutics. Indeed, early results suggest that transformed and normal cells differ in their requirement for, e.g., cyclin A/CDK2 and that it may be possible to develop novel antineoplastic agents devoid of the general host toxicity observed with conventional cytotoxic and cytostatic drugs. While inhibition of cell cycle-related CDKs is clearly relevant in, e.g., oncology applications, inhibition of RNA polymerase-regulating CDKs may also be highly relevant in cancer indications.

The CDKs have been shown to participate in cell cycle progression and cellular transcription, and loss of growth control is linked to abnormal cell proliferation in disease (see e.g., Malumbres and Barbacid, Nat. Rev. Cancer 2001, 1:222). Increased activity or temporally abnormal activation of cyclin-dependent kinases has been shown to result in the development of human tumors (Sherr C. J., Science 1996, 274: 1672-1677). Indeed, human tumor development is commonly associated with alterations in either the CDK proteins themselves or their regulators (Cordon-Cardo C, Am. J. Pat1/701. 1995; 147: 545-560; Karp J. E. and Broder S., Nat. Med. 1995; 1: 309-320; Hall M. et al, Adv. Cancer Res. 1996; 68: 67-108).

Naturally occurring protein inhibitors of CDKs such as p16 and p27 cause growth inhibition in vitro in lung cancer cell lines (Kamb A., Curr. Top. Microbiol. Immunol. 1998; 227: 139-148).

CDKs 7 and 9 seem to play key roles in transcription initiation and elongation, respectively (see, e.g., Peterlin and Price. Cell 23: 297-305, 2006, Shapiro. J. Clin. Oncol. 24: 1770-83, 2006;). Inhibition of CDK9 has been linked to direct induction of apoptosis in tumor cells of hematopoetic lineages through down-regulation of transcription of antiapoptotic proteins such as Mcl1 (Chao, S.-H. et al. J. Biol. Chem. 2000; 275: 28345-28348; Chao, S.-H. et al. J. Biol. Chem. 2001; 276: 31793-31799; Lam et. al. Genome Biology 2: 0041.1-11, 2001; Chen et al. Blood 2005; 106: 2513; MacCallum et al. Cancer Res. 2005; 65: 5399; and Alvi et al. Blood 2005; 105: 4484). In solid tumor cells, transcriptional inhibition by downregulation of CDK9 activity synergizes with inhibition of cell cycle CDKs, for example CDK1 and 2, to induce apoptosis (Cai, D.-P., Cancer Res 2006, 66: 9270. Inhibition of transcription through CDK9 or CDK7 may have selective non-proliferative effect on the tumor cell types that are dependent on the transcription of mRNAs with short half lives, for example Cyclin D1 in Mantle Cell Lymphoma. Some transcription factors such as Myc and NF-kB selectively recruit CDK9 to their promoters, and tumors dependent on activation of these signaling pathways may be sensitive to CDK9 inhibition.

Small molecule CDK inhibitors may also be used in the treatment of cardiovascular disorders such as restenosis and atherosclerosis and other vascular disorders that are due to aberrant cell proliferation. Vascular smooth muscle proliferation and intimal hyperplasia following balloon angioplasty are inhibited by over-expression of the cyclin-dependent kinase inhibitor protein. Moreover, the purine CDK2 inhibitor CVT-313 (Ki=95 nM) resulted in greater than 80% inhibition of neointima formation in rats.

CDK inhibitors can be used to treat diseases caused by a variety of infectious agents, including fungi, protozoan parasites such as *Plasmodium falciparum*, and DNA and RNA viruses. For example, cyclin-dependent kinases are required for viral replication following infection by herpes simplex virus (HSV) (Schang L. M. et al, J. Virol. 1998; 72: 5626) and CDK homologs are known to play essential roles in yeast.

Inhibition of CDK9/cyclin T function was recently linked to prevention of HIV replication and the discovery of new CDK biology thus continues to open up new therapeutic indications for CDK inhibitors (Sausville, E. A. Trends Molec. Med. 2002, 8, S32-S37).

CDKs are important in neutrophil-mediated inflammation and CDK inhibitors promote the resolution of inflammation in animal models. (Rossi, A. G. et al, Nature Med. 2006, 12: 1056). Thus CDK inhibitors, including CDK9 inhibitors, may act as anti-inflammatory agents.

Selective CDK inhibitors can be used to ameliorate the effects of various autoimmune disorders. The chronic inflammatory disease rheumatoid arthritis is characterized by synovial tissue hyperplasia; inhibition of synovial tissue proliferation should minimize inflammation and prevent joint destruction. In a rat model of arthritis, joint swelling was substantially inhibited by treatment with an adenovirus expressing a CDK inhibitor protein p 16. CDK inhibitors are effective against other disorders of cell proliferation including psoriasis (characterized by keratinocyte hyperproliferation), glomerulonephritis, chronic inflammation, and lupus.

Certain CDK inhibitors are useful as chemoprotective agents through their ability to inhibit cell cycle progression of normal untransformed cells (Chen, et al. J. Natl. Cancer Institute, 2000; 92: 1999-2008). Pre-treatment of a cancer patient with a CDK inhibitor prior to the use of cytotoxic agents can reduce the side effects commonly associated with chemotherapy. Normal proliferating tissues are protected from the cytotoxic effects by the action of the selective CDK inhibitor.

Accordingly, there is a great need to develop inhibitors of protein kinases, such as CDK1, CDK2, CDK3, CDK4, CDK5, CDK6, CDK7, CDK8 and CDK9, as well as combinations thereof.

SUMMARY OF THE INVENTION

There remains a need for new treatments and therapies for protein kinase-associated disorders. There is also a need for compounds useful in the treatment or prevention or amelioration of one or more symptoms of cancer, inflammation, cardiac hypertrophy, and HIV. Furthermore, there is a need for methods for modulating the activity of protein kinases, such as CDK1, CDK2, CDK3, CDK4, CDK5, CDK6, CDK7, CDK8 and CDK9, and combinations thereof, using the compounds provided herein. In one aspect, the invention provides a compound of Formula I:

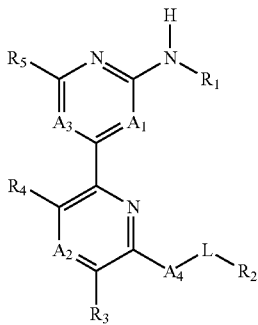

or a pharmaceutically acceptable salt thereof, wherein: $A_1$ is N or $CR_6$;

$A_2$ is N, N(O) or $CR_7$;

$A_3$ is N or $CR_8$;

$A_4$ is selected from a bond, $SO_2$, $NR_9$, or O;

L is selected from a bond, optionally substituted $C_{1-4}$alkyl, $C_{3-6}$ cycloalkyl, $C_{3-6}$heterocycloalkyl, or $C_{2-4}$ alkenyl;

$R_1$ is X—$R_{16}$;

X is a bond, or $C_{1-4}$ alkyl and;

$R_{16}$ is selected from the group consisting of $C_{1-6}$ alkyl, $C_{3-6}$branched alkyl, $C_{3-8}$cycloalkyl, heterocycloalkyl, $C_{3-8}$-partially unsaturated cycloalkyl, aryl, and heteroaryl;

wherein $R_{16}$ is substituted with one to three groups independently selected from halogen, hydrogen, $C_{1-6}$alkyl, $C_{1-6}$haloalkyl, $C_{3-6}$branched alkyl, $C_{3-6}$branched haloalkyl, OH, $C_{1-6}$alkoxy, $R_{22}$—$OR_{12}$, $S(O)_{0-2}R_{12}$, $R_{22}$—$S(O)_{0-2}R_{12}$, $S(O)_2NR_{13}R_{14}$, $R_{22}$—$S(O)_2NR_{13}R_{14}$, $C(O)OR_{12}$, $R_{22}$—C(O)$OR_{12}$, $C(O)R_{19}$, $R_{22}$—$C(O)R_{19}$, O—$C_{1-3}$alkyl, $OC_{1-3}$haloalkyl, $OC(O)R_{19}$, $R_{22}$—$OC(O)R_{19}$, $C(O)NR_{13}R_{14}$, $R_{22}$—$C(O)NR_{13}R_{14}$, $NR_{15}S(O)_2R_{12}$, $R_{22}$—$NR_{15}S(O)_2R_{12}$, $NR_{17}R_{18}$, $R_{22}$—$NR_{17}R_{18}$, $NR_{15}C(O)R_{19}$, $R_{22}$—$NR_{15}C(O)R_{19}$, $NR_{15}C(O)OCH_2Ph$, $R_{22}$—$NR_{15}C(O)OCH_2Ph$, $NR_{15}C(O)OR_{12}$, $R_{22}$—$NR_{15}C(O)OR_{12}$, $NR_{15}C(O)NR_{13}R_{14}$, and $R_{22}$—$NR_{15}C(O)NR_{13}R_{14}$;

$R_{17}$ and $R_{18}$ are each, independently, selected from the group consisting of hydrogen, hydroxyl, $C_{1-6}$alkyl, $C_{1-6}$haloalkyl, $C_{3-6}$branched alkyl, $C_{3-6}$ cycloalkyl, $R_{22}$—$OR_{12}$, $R_{22}$—$S(O)_{0-2}R_{12}$, $R_{22}$—$S(O)_2NR_{13}R_{14}$, $R_{22}$—$C(O)OR_{12}$, $R_{22}$—$C(O)R_{19}$, $R_{22}$—$OC(O)R_{19}$, $R_{22}$—$C(O)NR_{13}R_{14}$, $R_{22}$—$NR_{15}S(O)_2R_{12}$, $R_{22}$—$NR_{23}R_{24}$, $R_{22}$—$NR_{15}C(O)R_{19}$, $R_{22}$—$NR_{15}C(O)OCH_2Ph$, $R_{22}$—$NR_{15}C(O)OR_{12}$, $R_{22}$—$NR_{15}C(O)NR_{13}R_{14}$, cycloalkyl, heterocycloalkyl and heteroaryl; alternatively, $R_{17}$ and $R_{18}$ along with the nitrogen atom to which they are attached to can be taken together to form a four to six membered heterocyclic ring wherein the carbon atoms of said ring are optionally substituted with $R_{20}$, and the nitrogen atoms of said ring are optionally substituted with $R_{21}$;

$R_{19}$ is selected from optionally substituted alkyl, optionally substituted cycloalkyl, optionally substituted heterocycloalkyl, optionally substituted aryl, and optionally substituted heteroaryl;

$R_{20}$ is selected from the group consisting of $C_{1-6}$ alkyl or $C_{1-6}$ haloalkyl;

$R_{21}$ is selected from the group consisting of $C_{1-6}$alkyl, $C_{1-6}$haloalkyl, $C(O)R_{12}$, $C(O)OR_{12}$, $S(O)_2R_{12}$;

$R_{22}$ is selected from the group consisting of $C_{1-6}$ alkyl, $C_{1-6}$haloalkyl, $C_{3-6}$ branched alkyl, $C_{3-6}$branched haloalkyl;

$R_{23}$ and $R_{24}$ are each, independently, selected from the group consisting of hydrogen, $C_{1-6}$ alkyl, $C_{1-6}$haloalkyl, $C_{3-6}$ branched alkyl, $C_{3-6}$ branched haloalkyl;

$R_2$ is selected from the group consisting of optionally substituted $C_{1-6}$ alkyl, optionally substituted $C_{3-6}$ branched alkyl, optionally substituted $C_{3-8}$ cycloalkyl, optionally substituted heterocycloalkyl, optionally substituted aryl, and optionally substituted heteroaryl;

$R_4$, $R_5$, and $R_5$ are each, independently, selected from the group consisting of hydrogen, hydroxyl, cyano, halogen, $C_{1-4}$ alkyl, $C_{1-4}$haloalkyl, $C_{2-4}$ alkenyl, $C_{2-4}$alkynyl, amino, $NR_{10}R_{11}$, and alkoxy;

$R_3$, $R_7$ and $R_8$ are each, independently, selected from the group consisting of hydrogen, hydroxyl, cyano, halogen, alkyl, haloalkyl, alkenyl, alkynyl, alkoxy, $NR_{10}R_{11}$, $C(O)R_{12}$, $C(O)OR_{12}$, $C(O)NR_{13}R_{14}$, $S(O)_{0-2}R_{12}$, $S(O)_{0-2}NR_{13}R_{14}$, and optionally substituted $C_{3-4}$ cycloalkyl;

$R_9$ is selected from the group consisting of hydrogen, $C_{1-4}$ alkyl, alkoxy, $C(O)R_{12}$, $C(O)OR_{15}$, $C(O)NR_{13}R_{14}$, $S(O)_{0-2}R_2$, $S(O)O$—$_{0-2}NR_{13}R_{14}$, optionally substituted $C_{3-4}$cycloalkyl, and optionally substituted heterocycloalkyl;

$R_{10}$ and $R_{11}$ are each, independently, selected from the group consisting of hydrogen, hydroxyl, alkyl, alkoxy, $C(O)R_{12}$, $C(O)OR_{12}$, $C(O)NR_{13}R_{14}$, $S(O)_{0-2}R_{12}$, and $S(O)O$—$_{0-2}NR_{13}R_{14}$; alternatively, $R_{10}$ and $R_{11}$ along with the nitrogen atom to which they are attached to can be taken together to form an optionally substituted four to six membered heteroaromatic, or a non-aromatic heterocyclic ring;

$R_{12}$ and $R_{15}$ are each, individually, selected from the group consisting of hydrogen, alkyl, branched alkyl, haloalkyl, branched haloalkyl, $(CH_2)_{0-3}$-cycloalkyl, $(CH_2)_{0-3}$-heterocycloalkyl, $(CH_2)_{0-3}$-aryl, and heteroaryl;

$R_{13}$ and $R_{14}$ are each, independently, selected from the group consisting of hydrogen, hydroxyl, alkyl, branched alkyl, haloalkyl, branched haloalkyl, alkoxy, cycloalkyl or heterocycloalkyl; and alternatively, $R_{13}$ and $R_{14}$ along with the nitrogen atom to which they are attached to can be taken together to form an optionally substituted four to six membered heteroaromatic, or non-aromatic heterocyclic ring.

One preferred embodiment of the present invention provides a compound of Formula I wherein, $A_1$ is N; $A_2$ is N; and $A_3$ is $CR_8$. Another aspect of the present invention provides a compound of Formula I wherein $A_1$ is $CR_6$, $A_2$ is $CR_7$, and $A_3$ is $CR_8$. Yet another preferred embodimentt provides a compound of Formula I wherein, $A_1$ is N; $A_2$ is $CR_7$; and $A_3$ is $CR_8$. A further preferred embodiment of the preceding aspects of the present invention provides a compound of Formula I wherein, $R_8$ is selected from halogen, hydrogen, CN, $CF_3$, O—$C_{1-3}$-alkyl, and $C_{1-3}$-alkyl, with Cl, F, and methyl being the preferred $R_8$ substituents, and Cl being the particularly preferred $R_8$ substituent. Other preferred embodiment of the present invention provides a compound of Formula I wherein, $R_1$ is X—$R_{16}$; X is a bond, or $C_{1-2}$ alkyl; $R_{16}$ is selected from the group consisting of $C_{1-2}$-alkyl, $C_{4-6}$cycloalkyl, heterocycloalkyl, phenyl, and heteroaryl; wherein $R_{16}$ is substituted with one to three groups independently selected from halogen, hydrogen, $C_{1-3}$alkyl, $C_{3-6}$branched alkyl, OH, $C_{1-2}$alkoxy, $R_{22}$—$OR_{12}$, $S(O)_{1-2}R_{12}$, $C(O)OR_{12}$, $R_{22}$—$C(O)OR_{12}$, $C(O)R_{19}$, $R_{22}$—$OC(O)R_{19}$, $C(O)NR_{13}R_{14}$, $NR_{15}S(O)_2R_{12}$, $NR_{17}R_{18}$, $R_{22}$—$NR_{17}R_{18}$, $NR_{15}C(O)R_{19}$, $R_{22}$—$NR_{15}C(O)R_{19}$, and $NR_{15}C(O)OCH_2Ph$. Particularly preferred $R_{16}$ substituents are selected from the group consisting of $C_{1-2}$-alkyl, cyclopentyl, cyclohexyl, piperidine, piperazine, morpholine, pyridine, pyrrolidine, cyclohexenyl, and tetrahydro-2H-pyran; wherein $R_{16}$ is substituted with one to three groups selected from amino, hydroxyl, $NHCH_2$-phenyl, $CH_2$-amino, COO-t-butyl, H, methoxy, NH—$SO_2$-ethyl, $CH_2$—$NHSO_2$-ethyl, $SO_2$-ethyl, t-butyl, methyl, $CH_2$—COOH, CO—$NHCH_3$, $CON(CH_3)_2$, $NHC(CH_3)$—$CH_2$—$SO_2$—$CH_3$, NH—COO—$CH_2$-phenyl, hydroxy-methyl, $CH_2$—NH—$CH_3$, $CH_2$—NH-ethyl, NH—$CH_2$—$CH_2$-methoxy, $CH_2$—NH—CO—$CH_3$, NH—$CH_2$—$CH_2$OH, NH—CO—$CH_2$—$N(CH_3)_2$, NH—CO-methylpyrrolidine, NH—$CH_2$—C($CH_3$)-dioxolane, NH—CO-pyridyl, NH-ethyl, pyrrolidine, $CH_2$—NH—CO-pyridyl, NH-tetrahydropyran, $COCH_2$—N($CH_3$)$_2$, NH—$CH_2$—C($CH_3$)-dimethyldioxolane, tetrahydropyran, CO-methylpyrrolidine, $CH_2$-methylpiperidine, NH—CO—$CH_3$, NH—$SO_2$—$CH_3$, NH—$CH(CH_2$—$OCH_3)_2$, NH—$CH_2$-tetrahydrofuran, NH—$CH_2$-oxetane, NH-tetrahydropyran, NH—$CH_2$-dioxane, N($CH_3$)—$CH_2CH_2$—$OCH_3$, CH(OH)—$CH_2$-amino, NH—$CH_2CH_2$—$OCF_3$, $NHCH_2$—$OCH_3$, NH—$CH_2$—$CH(CF_3)$—$OCH_3$, NH—$CH(CH_3)$—$CH_2$—OH, F, NH-oxetane, $CH_2$—$CH_2$—$OCH_3$, $CH_2$—$OCH_3$, $CH_2$-tetrahydropyran, $CH_2$-methylpiperizine, $NH_2$—$CH_2$—CH(OH)—$CF_3$, piperidine, $CH_2$-pyrrolidine, NH—$CH(CH_3)CH_2OCH_3$, NH-tetrahydrofuran, $(CH_2)_3$—$NH_2$, hydroxyethyl, propyl, $CH_2$-pyridyl, $CH_2$-piperidine, morpholine, NH-chloropyrimidine, NH—$CH_2CH_2$—$SO_2$-methyl, $(CH_3)_3$—$N(CH_3)_2$, piperizine,

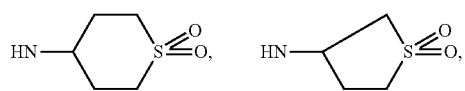

and $CH_2$-morpholine.

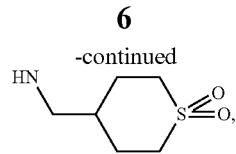

Another preferred embodiment of the present invention provides a compound of Formula I wherein, $R_3$ is selected from H, methyl, cyano, chloro, $CONH_2$, amino, cyclopropyl, ethyl, and fluoro; $R_4$ is selected from halogen, methyl, hydrogen, and halo-methyl; $R_6$ is H; $R_7$ is selected from H, COOH, Cl, F, $CONH_2$, CN, and $CF_3$; $R_8$ is Cl; $R_{17}$ and $R_{18}$ are each, independently, selected from the group consisting of hydrogen, $C_{1-3}$alkyl, $C_{1-4}$haloalkyl, $C_{3-6}$branched alkyl, $R_{22}$—$OR_{12}$, $R_{22}$—$S(O)_2R_{12}$, $R_{22}$—$NR_{15}S(O)_2R_{12}$, heterocycloalkyl or heteroaryl; alternatively, $R_{17}$ and $R_{18}$ along with the nitrogen atom to which they are attached to can be taken together to form a four to six membered heterocyclic ring wherein said ring carbon atoms are optionally substituted with $R_{20}$, and the ring nitrogen atoms are optionally substituted with $R_{21}$;

$R_{19}$ is selected from $C_{1-3}$-alkyl, optionally substituted heterocycloalkyl, optionally substituted aryl or optionally substituted heteroaryl; $R_{20}$ represents the group $C_{1-3}$alkyl; and $R_{22}$ is selection from the group consisting of $C_{1-4}$alkyl, and $C_{3-6}$ branched alkyl. Further preferred are compounds of Formula I wherein, $A_4$ is selected from $NR_9$, O, and a bond; L is selected from a bond, $C_{1-4}$-alkyl, and cyclopropyl; $R_2$ is selected from the group consisting of $C_{3-7}$ cycloalkyl, a five to seven membered heterocycloalkyl, phenyl, and pyridyl, wherein each said $R_2$ group is substituted with one, two, or three substituents independently selected from hydrogen, cyano, CO—$NH_2$, halogen, methoxy, dihalo-methoxy, trihalo-methoxy, trihalo alkyl, $C_{1-3}$-alkyl, and hydroxy; and $R_9$ represents methyl, hydrogen, or ethyl.

Provided in a particularly preferred embodiment are compounds of Formula I, wherein, $A_1$ is $CR_6$; $A_2$ is $CR_7$; $A_3$ is $CR_8$; $A_4$ is selected from $NR_9$, O, and a bond; L is a bond, $C_{1-2}$ alkyl, or $C_{3-4}$-cycloalkyl; $R_1$ is X—$R_{16}$; X is a bond, or $C_{1-2}$ alkyl; $R_{16}$ is selected from the group consisting of $C_{1-2}$-alkyl, cyclopentyl, cyclohexyl, piperidine, piperazine, morpholine, pyridine, pyrrolidine, cyclohexenyl, and tetrahydro-2H-pyran; wherein $R_{16}$ is substituted with one to three groups independently selected from amino, hydroxyl, $NHCH_2$-phenyl, $CH_2$-amino, COO-t-butyl, H, methoxy, NH—$SO_2$-ethyl, $CH_2$—$NHSO_2$-ethyl, $SO_2$-ethyl, t-butyl, methyl, $CH_2$—COOH, CO—$NHCH_3$, $CON(CH_3)_2$, $NHCH_2$—$SO_2$—$CH_3$, NH—COO—$CH_2$-phenyl, hydroxy-methyl, $CH_2$—NH—$CH_3$, $CH_2$—NH-ethyl, NH—$CH_2$—$CH_2$-methoxy, $CH_2$—NH—CO—$CH_3$, NH—$CH_2$—$CH_2$OH, NH—CO—$CH_2$—$N(CH_3)_2$, NH—CO-methylpyrrolidine, NH—CO-pyridyl, NH-ethyl, pyrrolidine, $CH_2$—NH—CO-pyridyl, $COCH_2$—$N(CH_3)_2$, tetrahydropyran, CO-methylpyrrolidine, $CH_2$-methylpiperidine, NH—CO—$CH_3$, NH—$SO_2$—$CH_3$, NH—$CH_2$-tetrahydrofuran, NH—$CH_2$-dioxane, $N(CH_3)$—$CH_2CH_2$—$OCH_3$, CH(OH)—$CH_2$-amino, NH—$CH_2CH_2$—$OCF_3$, $NH(CH_3)$—$CH_2$—$OCH_3$, NH—$CH_2$—$CH(CF_3)$—$OCH_3$, F, NH-oxetane, $CH_2$—$CH_2$—$OCH_3$, $CH_2$—$OCH_3$, $CH_2$-tetrahydropyran, $CH_2$-methylpiperizine, $NH_2$—$CH_2$—CH(OH)—$CF_3$, piperidine, $CH_2$-pyrrolidine, NH—$CH(CH_3)CH_2OCH_3$, NH-tetrahydrofuran, $(CH_2)_3$—$NH_2$, hydroxyethyl, propyl, $CH_2$-pyridyl, $CH_2$-piperidine, morpholine, NH-chloropyrimidine, NH—$CH_2CH_2$—$SO_2$-methyl, $(CH_3)_3$—$N(CH_3)_2$, piperizine, $CH_2$-morpholine, NH—$CH_2$—$C(CH_3)$-dioxolane, NH-tetrahydropyran, NH—$CH_2$—$C(CH_3)$-dimethyldioxolane, NH—CH(CH₂—OCH₃)₂, NH—CH₂-oxetane, NH-tetrahydropyran, N(CH₃)—CH₂CH₂—OCH₃, NH—CH(CH₃)—CH₂—OH,

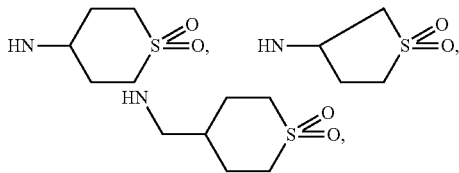

and NH—CH(CH₃)—CH₂—OH;

R₂ is selected from the group consisting of cyclohexyl, 1,3-dioxane, pyridinyl, phenyl, tetrahydropyranyl, cycloheptyl, 1,4-dioxane, morpholinyl, alkyl substituted dioxane, tetrahydrofuranyl, dioxepane, piperidinyl, and

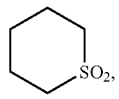

wherein each said R₂ group is substituted with one, two, or three substituents independently selected from Cl, Br, F, methoxy, hydroxy-methyl, hydrogen, carboxamide, cyano, dihalo-methoxy, trihalo-methoxy, trifluoro-methyl, hydroxyl, and methyl; and R₄, is chloro, hydrogen, trifluoro-methyl, fluoro, or bromo;

R₅, and R₆ are each independently hydrogen;

R₃ is selected from hydrogen, fluoro, cyano, CO—NH₂, chloro, amino, methyl, and cyclopropyl;

R₇ is selected from H, trifluoro-methyl, COOH, CO—NH₂, and cyano;

R₈ represents Cl; and

R₉ is selected from the group consisting of H, ethyl, and methyl.

Provided in a specifically preferred embodiment of the present invention is a compound of Formula I selected from:

N2'-(trans-4-aminocyclohexyl)-5'-chloro-3,5-difluoro-N6-((tetrahydro-2H-pyran-4-yl)methyl)-2,4'-bipyridine-2',6-diamine;

N2'-(trans-4-aminocyclohexyl)-5'-fluoro-N6-(3-fluorobenzyl)-2,4'-bipyridine-2',6-diamine;

3,5'-dichloro-N2'-(trans-4-(((R)-2,2-dimethyl-1,3-dioxolan-4-yl)methyl)aminocyclohexyl)-N6-((tetrahydro-2H-pyran-4-yl)methyl)-2,4'-bipyridine-2',6-diamine;

5'-chloro-N6-((tetrahydro-2H-pyran-4-yl)dideuteromethyl)-N2'-(trans-4-(((S)-tetrahydrofuran-2-yl)methyl)aminocyclohexyl)-2,4'-bipyridine-2',6-diamine;

5'-chloro-5-fluoro-N2'-(trans-4-(2-(methylsulfonyl)ethylamino)cyclohexyl)-N6-((tetrahydro-2H-pyran-4-yl)methyl)-2,4'-bipyridine-2',6-diamine;

5'-chloro-5-fluoro-N2'-(trans-4-(oxetan-2-yl-methylamino)cyclohexyl)-N6-((tetrahydro-2H-pyran-4-yl)methyl)-2,4'-bipyridine-2',6-diamine;

3,5'-dichloro-N2'-(trans-4-((R)-1-methoxypropan-2-ylamino)cyclohexyl)-N6-(((S)-tetrahydro-2H-pyran-3-yl)methyl)-2,4'-bipyridine-2',6-diamine;

3,5'-dichloro-N2'-(trans-4-((R)-1-methoxypropan-2-ylamino)cyclohexyl)-N6-(((R)-tetrahydro-2H-pyran-3-yl)methyl)-2,4'-bipyridine-2',6-diamine;

4-((5'-chloro-2'-(trans-4-((R)-1-methoxypropan-2-ylamino)cyclohexylamino)-2,4'-bipyridin-6-yl-amino)methyl)tetrahydro-2H-pyran-4-carbonitrile;

N2'-(trans-4-aminocyclohexyl)-5'-chloro-5-fluoro-N6-(3-fluorobenzyl)-2,4'-bipyridine-2',6-diamine;

2'-(trans-4-aminocyclohexylamino)-5'-chloro-6-(3-fluorobenzylamino)-2,4'-bipyridine-5-carbonitrile;

N2'-(trans-4-aminocyclohexyl)-3-chloro-5'-fluoro-N6-((tetrahydro-2H-pyran-4-yl)methyl)-2,4'-bipyridine-2',6-diamine;

5'-chloro-N6-(3-fluorobenzyl)-N2'-((1R,3S)-3-((methylamino)methyl)cyclopentyl)-2,4'-bipyridine-2',6-diamine;

3,5'-dichloro-N2'-(trans-4-((R)-1-methoxypropan-2-ylamino)cyclohexyl)-N6-((tetrahydro-2H-pyran-4-yl)methyl)-2,4'-bipyridine-2',6-diamine;

5'-chloro-3-fluoro-N2'-(trans-4-((R)-1-methoxypropan-2-yl-amino)cyclohexyl)-N6-((tetrahydro-2H-pyran-4-yl)methyl)-2,4'-bipyridine-2',6-diamine;

5'-chloro-5-fluoro-N2'-(trans-4-((R)-1-methoxypropan-2-yl-amino)cyclohexyl)-N6-((tetrahydro-2H-pyran-4-yl)methyl)-2,4'-bipyridine-2',6-diamine;

5'-chloro-N6-((2,2-dimethyltetrahydro-2H-pyran-4-yl)methyl)-N2'-(trans-4-((R)-1-methoxypropan-2-yl-amino)cyclohexyl)-2,4'-bipyridine-2',6-diamine;

5'-chloro-N6-(((S)-2,2-dimethyltetrahydro-2H-pyran-4-yl)methyl)-N2'-(trans-4-((R)-1-methoxypropan-2-yl-amino)cyclohexyl)-2,4'-bipyridine-2',6-diamine;

5'-chloro-5-fluoro-N6-((tetrahydro-2H-pyran-4-yl)methyl)-N2'-(trans-4-(((1,1-dioxotetrahydro-2H-thiopyran-4-yl)methyl)aminocyclohexyl)-2,4'-bipyridine-2',6-diamine;

5'-chloro-5-fluoro-N2'-(trans-4-(2-methoxyethylamino)cyclohexyl)-N6-((tetrahydro-2H-pyran-4-yl)methyl)-2,4'-bipyridine-2',6-diamine;

N2'-(trans-4-aminocyclohexyl)-5'-chloro-N6-(3-fluorobenzyl)-2,4'-bipyridine-2',6-diamine;

N2'-(trans-4-aminocyclohexyl)-5'-chloro-N6-(3,5-difluorobenzyl)-2,4'-bipyridine-2',6-diamine;

N2'-(trans-4-aminocyclohexyl)-5'-chloro-N6-((5-fluoropyridin-3-yl)methyl)-2,4'-bipyridine-2',6-diamine;

trans-4-(5'-chloro-6-(3,5-difluorobenzylamino)-2,4'-bipyridin-2'-yl-amino)cyclohexanol;

(R)-5'-chloro-N6-(3-fluorobenzyl)-N2'-(2-(piperidin-3-yl)ethyl)-2,4'-bipyridine-2',6-diamine;

N2'-(trans-4-aminocyclohexyl)-3,5'-dichloro-N6-((tetrahydro-2H-pyran-4-yl)methyl)-2,4'-bipyridine-2',6-diamine;

N2'-(trans-4-aminocyclohexyl)-3,5'-dichloro-N6-((tetrahydro-2H-pyran-4-yl)methyl)-2,4'-bipyridine-2',6-diamine;

3,5'-dichloro-N2'-(trans-4-(2-methoxyethylamino)cyclohexyl)-N6-((tetrahydro-2H-pyran-4-yl)methyl)-2,4'-bipyridine-2',6-diamine;

2-(trans-4-(3,5'-dichloro-6-((tetrahydro-2H-pyran-4-yl)methyl)amino-2,4'-bipyridin-2'-yl-amino)cyclohexylamino)ethanol;

trans-N1-(5-chloro-4-(6-(((R)-tetrahydro-2H-pyran-3-yl)methyl)aminopyrazin-2-yl)pyridin-2-yl)cyclohexane-1,4-diamine;

3,5'-dichloro-N6-((tetrahydro-2H-pyran-4-yl)methyl)-N2'-(trans-4-(((R)-tetrahydrofuran-2-yl)methyl)aminocyclohexyl)-2,4'-bipyridine-2',6-diamine;

3,5'-dichloro-N6-((tetrahydro-2H-pyran-4-yl)methyl)-N2'-(trans-4-(((S)-tetrahydrofuran-2-yl)methyl)aminocyclohexyl)-2,4'-bipyridine-2',6-diamine;

3,5'-dichloro-N2'-(trans-4-((2-methoxyethyl)(methyl)amino)cyclohexyl)-N6-((tetrahydro-2H-pyran-4-yl)methyl)-2,4'-bipyridine-2',6-diamine;

5'-chloro-N6-((tetrahydro-2H-pyran-4-yl)methyl)-N2'-(trans-4-(((R)-tetrahydrofuran-2-yl)methyl)aminocyclohexyl)-2,4'-bipyridine-2',6-diamine;

5'-chloro-N6-((tetrahydro-2H-pyran-4-yl)methyl)-N2'-(trans-4-(((S)-tetrahydrofuran-2-yl)methyl)aminocyclohexyl)-2,4'-bipyridine-2',6-diamine;
N2'-(trans-4-aminocyclohexyl)-5'-chloro-3-fluoro-N6-((tetrahydro-2H-pyran-4-yl)methyl)-2,4'-bipyridine-2',6-diamine;
5'-chloro-3-fluoro-N2'-(trans-4-(2-methoxyethylamino)cyclohexyl)-N6-((tetrahydro-2H-pyran-4-yl)methyl)-2,4'-bipyridine-2',6-diamine;
N2'-(trans-4-aminocyclohexyl)-3-bromo-5'-chloro-N6-((tetrahydro-2H-pyran-4-yl)methyl)-2,4'-bipyridine-2',6-diamine;
3-bromo-5'-chloro-N2'-(trans-4-(2-methoxyethylamino)cyclohexyl)-N6-((tetrahydro-2H-pyran-4-yl)methyl)-2,4'-bipyridine-2',6-diamine;
trans-4-(3,5'-dichloro-6-((2,2-dimethyltetrahydro-2H-pyran-4-yl)methyl)amino-2,4'-bipyridin-2'-yl-amino)cyclohexanol;
(2S)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol;
(2R)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol;
3,5'-dichloro-N6-((tetrahydro-2H-pyran-4-yl)methyl)-N2'-(trans-4-(2-(trifluoromethoxy)ethylamino)cyclohexyl)-2,4'-bipyridine-2',6-diamine;
N2'-(trans-4-aminocyclohexyl)-5'-chloro-N6-(((R)-2,2-dimethyltetrahydro-2H-pyran-4-yl)methyl)-2,4'-bipyridine-2',6-diamine;
N2'-(trans-4-aminocyclohexyl)-5'-chloro-N6-(((S)-2,2-dimethyltetrahydro-2H-pyran-4-yl)methyl)-2,4'-bipyridine-2',6-diamine;
N2'-(trans-4-aminocyclohexyl)-3,5,5'-trichloro-N6-((tetrahydro-2H-pyran-4-yl)methyl)-2,4'-bipyridine-2',6-diamine;
N2'-(trans-4-aminocyclohexyl)-5'-chloro-5-fluoro-N6-((tetrahydro-2H-pyran-4-yl)methyl)-2,4'-bipyridine-2',6-diamine;
N2'-(trans-4-aminocyclohexyl)-5'-chloro-N6-((4-methyltetrahydro-2H-pyran-4-yl)methyl)-2,4'-bipyridine-2',6-diamine;
N2'-(trans-4-aminocyclohexyl)-5'-chloro-5-fluoro-N6-((4-methyltetrahydro-2H-pyran-4-yl)methyl)-2,4'-bipyridine-2',6-diamine;
N2'-(trans-4-aminocyclohexyl)-5'-chloro-N6-((4-fluorotetrahydro-2H-pyran-4-yl)methyl)-2,4'-bipyridine-2',6-diamine;
trans-4-(5'-chloro-6-(3-fluorobenzylamino)-2,4'-bipyridin-2'-yl-amino)cyclohexanol;
5'-chloro-N2'-(trans-4-(dimethylamino)cyclohexyl)-N6-(3-fluorobenzyl)-2,4'-bipyridine-2',6-diamine;
5'-chloro-N6-(3-fluorobenzyl)-N2'-(trans-4-(2-methoxyethylamino)cyclohexyl)-2,4'-bipyridine-2',6-diamine;
2-(trans-4-(5'-chloro-6-(3-fluorobenzylamino)-2,4'-bipyridin-2'-yl-amino)cyclohexylamino)ethanol;
5'-chloro-N6-(3,5-difluorobenzyl)-N2'-(trans-4-(2-methoxyethylamino)cyclohexyl)-2,4'-bipyridine-2',6-diamine;
5'-chloro-N6-(3-fluorobenzyl)-N2'-(trans-4-((2-methoxyethyl)(methyl)amino)cyclohexyl)-2,4'-bipyridine-2',6-diamine;
N2'-(trans-4-aminocyclohexyl)-5'-chloro-N6-(((2R,6S)-2,6-dimethyltetrahydro-2H-pyran-4-yl)methyl)-2,4'-bipyridine-2',6-diamine;
4-((5'-chloro-5-fluoro-2'-(trans-4-(2-methoxyethylamino)cyclohexylamino)-2,4'-bipyridin-6-yl-amino)methyl)tetrahydro-2H-pyran-4-carbonitrile;
4-((2'-(trans-4-aminocyclohexylamino)-5'-chloro-5-fluoro-2,4'-bipyridin-6-yl-amino)methyl)tetrahydro-2H-pyran-4-carbonitrile;
4-((5'-chloro-5-fluoro-2'-(trans-4-(propylamino)cyclohexylamino)-2,4'-bipyridin-6-yl-amino)methyl)tetrahydro-2H-pyran-4-carbonitrile;
4-((5'-chloro-2'-(trans-4-(dipropylamino)cyclohexylamino)-5-fluoro-2,4'-bipyridin-6-yl-amino)methyl)tetrahydro-2H-pyran-4-carbonitrile;
4-((5'-chloro-5-fluoro-2'-(trans-4-((R)-1-methoxypropan-2-yl-amino)cyclohexylamino)-2,4'-bipyridin-6-yl-amino)methyl)tetrahydro-2H-pyran-4-carbonitrile;
4-((5'-chloro-2'-(trans-4-((2-methyl-1,3-dioxolan-2-yl)methyl)aminocyclohexylamino)-2,4'-bipyridin-6-yl-amino)methyl)tetrahydro-2H-pyran-4-carbonitrile;
(4-((5'-chloro-2'-(trans-4-((R)-1-methoxypropan-2-yl-amino)cyclohexylamino)-2,4'-bipyridin-6-yl-amino)methyl)tetrahydro-2H-pyran-4-yl)methanol; and
5'-chloro-5-fluoro-N6-((4-methyltetrahydro-2H-pyran-4-yl)methyl)-N2'-(trans-4-(1,1-dioxotetrahydrothiophen-3-yl-amino)cyclohexyl)-2,4'-bipyridine-2',6-diamine.

Yet another preferred embodiment of the present invention provides a compound of Formula I selected from:
trans-N1-(4-(3-chloro-6-((tetrahydro-2H-pyran-4-yl)methyl)aminopyrazin-2-yl)pyridin-2-yl)cyclohexane-1,4-diamine;
trans-N1-(5-chloro-4-(3-chloro-6-((tetrahydro-2H-pyran-4-yl)methyl)aminopyrazin-2-yl)pyridin-2-yl)cyclohexane-1,4-diamine;
trans-4-(5-chloro-4-(5-chloro-6-((tetrahydro-2H-pyran-4-yl)methyl)aminopyrazin-2-yl)pyridin-2-yl-amino)cyclohexanol;
trans-N1-(5-chloro-4-(5-chloro-6-((tetrahydro-2H-pyran-4-yl)methyl)aminopyrazin-2-yl)pyridin-2-yl)cyclohexane-1,4-diamine;
trans-4-(5-chloro-4-(6-(((S)-tetrahydro-2H-pyran-3-yl)methyl)aminopyrazin-2-yl)pyridin-2-yl-amino)cyclohexanol;
trans-4-(5-chloro-4-(6-(((R)-tetrahydro-2H-pyran-3-yl)methyl)aminopyrazin-2-yl)pyridin-2-yl-amino)cyclohexanol;
trans-N1-(5-chloro-4-(6-(((S)-tetrahydro-2H-pyran-3-yl)methyl)aminopyrazin-2-yl)pyridin-2-yl)cyclohexane-1,4-diamine;
trans-N1-(5-chloro-4-(6-(((R)-tetrahydro-2H-pyran-3-yl)methyl)aminopyrazin-2-yl)pyridin-2-yl)cyclohexane-1,4-diamine;
trans-N1-(5-chloro-4-(6-(methyl((tetrahydro-2H-pyran-4-yl)methyl)amino)pyrazin-2-yl)pyridin-2-yl)cyclohexane-1,4-diamine;
trans-N1-(5-chloro-4-(6-((tetrahydro-2H-pyran-4-yl)methyl)aminopyrazin-2-yl)pyridin-2-yl)-N4-(2-methoxyethyl)cyclohexane-1,4-diamine;
trans-4-(5-chloro-4-(6-((tetrahydro-2H-pyran-3-yl)methyl)aminopyrazin-2-yl)pyridin-2-yl-amino)cyclohexanol;
trans-4-(5-chloro-4-(6-((tetrahydro-2H-pyran-4-yl)methyl)aminopyrazin-2-yl)pyridin-2-yl-amino)cyclohexanol; and
trans-N1-(5-chloro-4-(6-(3-fluorobenzylamino)pyrazin-2-yl)pyridin-2-yl)cyclohexane-1,4-diamine.

Another aspect of the present invention provides a compound of Formula I, or pharmaceutically acceptable salt or solvate thereof, for use in therapy. Yet another aspect of the present invention provides a compound of Formula I or a pharmaceutically acceptable salt or solvate thereof for use in a method of treating a disease or condition mediated by CDK9.

Yet another aspect of the present invention provides a method of treating a disease or condition mediated by CDK9 comprising administration to a subject in need thereof a therapeutically effective amount of a compound of Formula I, or a pharmaceutically acceptable salt thereof. Provided in yet another aspect of the present invention is a compound of Formula I for use in a method of treating a disease or condition mediated by CDK9 is selected from cancer, cardiac hypertrophy, HIV and inflammatory diseases.

Another aspect of the present invention provides a method of treating a cancer selected from the group consisting of bladder, head and neck, breast, stomach, ovary, colon, lung, brain, larynx, lymphatic system, hematopoetic system, genitourinary tract, gastrointestinal, ovarian, prostate, gastric, bone, small-cell lung, glioma, colorectal, and pancreatic cancer.

Yet another aspect of the present invention provides a pharmaceutical composition comprising a compound of Formulas I, or a pharmaceutically acceptable salt thereof, and a pharmaceutically acceptable carrier, diluent or excipient.

In another aspect, the invention provides a method of regulating, modulating, or inhibiting protein kinase activity which comprises contacting a protein kinase with a compound of the invention. In one embodiment, the protein kinase is selected from the group consisting of CDK1, CDK2, CDK3, CDK4, CDK5, CDK6, CDK7, CDK8 and CDK9, or any combination thereof. In another embodiment, the protein kinase is selected from the group consisting of CDK1, CDK2 and CDK9, or any combination thereof. In still another embodiment, the protein kinase is in a cell culture. In yet another embodiment, the protein kinase is in a mammal.

In another aspect, the invention provides a method of treating a protein kinase-associated disorder comprising administering to a subject in need thereof a pharmaceutically acceptable amount of a compound of the invention such that the protein kinase-associated disorder is treated. In one embodiment, the protein kinase is selected from the group consisting of CDK1, CDK2, CDK3, CDK4, CDK5, CDK6, CDK7, CDK8 and CDK9.

In one embodiment, the protein kinase-associated disorder is cancer. In still another embodiment, the cancer is selected from the group consisting of bladder, head and neck, breast, stomach, ovary, colon, lung, brain, larynx, lymphatic system, hematopoetic system, genitourinary tract, gastrointestinal, ovarian, prostate, gastric, bone, small-cell lung, glioma, colorectal and pancreatic cancer.

In one embodiment, the protein kinase-associated disorder is inflammation. In another embodiment, the inflammation is related to rheumatoid arthritis, lupus, type 1 diabetes, diabetic nephropathy, multiple sclerosis, glomerulonephritis, chronic inflammation, and organ transplant rejections.

In another embodiment, the protein kinase-associated disorder is a viral infection. In one embodiment, the viral infection is associated with the HIV virus, human papilloma virus, herpes virus, poxvirus virus, Epstein-Barr virus, Sindbis virus, or adenovirus.

In still another embodiment, the protein kinase-associated disorder is cardiac hypertrophy.

In another aspect, the invention provides a method of treating cancer comprising administering to a subject in need thereof a pharmaceutically acceptable amount of a compound of the invention such that the cancer is treated. In one embodiment, the cancer is selected from the group consisting of bladder, head and neck, breast, stomach, ovary, colon, lung, brain, larynx, lymphatic system, hematopoetic system, genitourinary tract, gastrointestinal, ovarian, prostate, gastric, bone, small-cell lung, glioma, colorectal and pancreatic cancer.

In another aspect, the invention provides a method of treating inflammation comprising administering to a subject in need thereof a pharmaceutically acceptable amount of a compound such that the inflammation is treated, wherein the compound is a compound of the invention. In one embodiment, the inflammation is related to rheumatoid arthritis, lupus, type 1 diabetes, diabetic nephropathy, multiple sclerosis, glomerulonephritis, chronic inflammation, and organ transplant rejections.

In another aspect, the invention provides a method of treating cardiac hypertrophy comprising administering to a subject in need thereof a pharmaceutically acceptable amount of a compound such that the cardiac hypertrophy is treated, wherein the compound is a compound of the invention.

In another aspect, the invention provides a method of treating a viral infection comprising administering to a subject in need thereof a pharmaceutically acceptable amount of a compound such that the viral infection is treated, wherein the compound is a compound of the invention. In one embodiment, the viral infection is associated with the HIV virus, human papilloma virus, herpes virus, poxyirus virus, Epstein-Barr virus, Sindbis virus, or adenovirus.

In one embodiment, the subject to be treated by the compounds of the invention is a mammal. In another embodiment, the mammal is a human.

In another aspect, the compounds of the invention is administered, simultaneously or sequentially, with an antiinflammatory, antiproliferative, chemotherapeutic agent, immunosuppressant, anti-cancer, cytotoxic agent or kinase inhibitor or salt thereof. In one embodiment, the compound, or salt thereof, is administered, simultaneously or sequentially, with one or more of a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, CVT-313, agents blocking the interaction between CD40 and gp39, fusion proteins constructed from CD40 and gp39, inhibitors of NF-kappa B function, non-steroidal antiinflammatory drugs, steroids, gold compounds, FK506, mycophenolate mofetil, cytotoxic drugs, TNF-α inhibitors, anti-TNF antibodies or soluble TNF receptor, rapamycin, leflunimide, cyclooxygenase-2 inhibitors, paclitaxel, cisplatin, carboplatin, doxorubicin, caminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

In another aspect, the invention provides a packaged protein kinase-associated disorder treatment, comprising a protein kinase-modulating compound of the Formula I or Formula II, packaged with instructions for using an effective amount of the protein kinase-modulating compound to treat a protein kinase-associated disorder.

In certain embodiments, the compound of the present invention is further characterized as a modulator of a protein kinase, including, but not limited to, protein kinases selected from the group consisting of abl, ATK, Bcr-abl, Blk, Brk, Btk, c-fms, e-kit, c-met, c-src, CDK, cRaf1, CSFIR, CSK, EGFR, ErbB2, ErbB3, ErbB4, ERK, Fak, fes, FGFRI, FGFR2, FGFR3, FGFR4, FGFR5, Fgr, FLK-4, flt-1, Fps, Frk, Fyn, GSK, Gst-Flk1, Hck, Her-2, Her-4, IGF-1R, INS-R, Jak, JNK, KDR, Lck, Lyn, MEK, p38, panHER, PDGFR, PLK, PKC, PYK2, Raf, Rho, ros, SRC, TRK, TYK2, UL97, VEGFR, Yes, Zap70, Aurora-A, GSK3-alpha, HIPK1, HIPK2, HIP3, IRAK1, JNK1, JNK2, JNK3, TRKB, CAMKII, CK1, CK2, RAF, GSK3Beta, MAPK1, MKK4, MKK7, MST2, NEK2, AAK1, PKCalpha, PKD, RIPK2 and ROCK-II. (I think we should consider whether to include such an expansive list. May be restrict to those that are identified in the expanded cell plate assay?)

In a preferred embodiment, the protein kinase is selected from the group consisting of CDK1, CDK2, CDK3, CDK4, CDK5, CDK6, CDK7, CDK8 and CDK9 and any combination thereof, as well as any other CDK, as well as any CDK not yet identified. In a particularly preferred embodiment, the protein kinase is selected from the group consisting of CDK1, CDK2 and CDK9. In a particularly preferred embodiment, the protein kinase is selected from the group consisting of CDK9.

In a particular embodiment, CDK combinations of interest include CDK4 and CDK9; CDK1, CDK2 and CDK9; CDK9 and CDK7; CDK9 and CDK1; CDK9 and CDK2; CDK4, CDK6 and CDK9; CDK1, CDK2, CDK3, CDK4, CDK6 and CDK9.

In other embodiments, the compounds of the present invention are used for the treatment of protein kinase-associated disorders. As used herein, the term "protein kinase-associated disorder" includes disorders and states (e.g., a disease state) that are associated with the activity of a protein kinase, e.g., the CDKs, e.g., CDK1, CDK2 and/or CDK9. Non-limiting examples of protein kinase-associated disorders include abnormal cell proliferation (including protein kinase-associated cancers), viral infections, fungal infections, autoimmune diseases and neurodegenerative disorders.

Non-limiting examples of protein-kinase associated disorders include proliferative diseases, such as viral infections, auto-immune diseases, fungal disease, cancer, psoriasis, vascular smooth cell proliferation associated with atherosclerosis, pulmonary fibrosis, arthritis glomerulonephritis, chronic inflammation, neurodegenerative disorders, such as Alzheimer's disease, and post-surgical stenosis and restenosis. Protein kinase-associated diseases also include diseases related to abnormal cell proliferation, including, but not limited to, cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia.

Additional non-limiting examples of protein kinase-associated cancers include carcinomas, hematopoietic tumors of lymphoid lineage, hematopoietic tumors of myeloid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

Protein kinase-associated disorders include diseases associated with apoptosis, including, but not limited to, cancer, viral infections, autoimmune diseases and neurodegenerative disorders.

Non-limiting examples of protein-kinase associated disorders include viral infections in a patient in need thereof, wherein the viral infections include, but are not limited to, HIV, human papilloma virus, herpes virus, poxvirus, Epstein-Barr virus, Sindbis virus and adenovirus.

Non-limiting examples of protein-kinase associated disorders include tumor angiogenesis and metastasis. Non-limiting examples of protein-kinase associated disorders also include vascular smooth muscle proliferation associated with atherosclerosis, postsurgical vascular stenosis and restenosis, and endometriosis.

Further non-limiting examples of protein-kinase associated disorders include those associated with infectious agents, including yeast, fungi, protozoan parasites such as Plasitiodium falciparum, and DNA and RNA viruses.

In another embodiment, the compound of the present invention is further characterized as a modulator of a combination of protein kinases, e.g., the CDKs, e.g., CDK1, CDK2 and/or CDK9. In certain embodiments, a compound of the present invention is used for protein kinase-associated diseases, and/or as an inhibitor of any one or more protein kinases. It is envisioned that a use can be a treatment of inhibiting one or more isoforms of protein kinases.

The compounds of the invention are inhibitors of cyclin-dependent kinase enzymes. Without being bound by theory, inhibition of the CDK4/cyclin D1 complex blocks phosphorylation of the Rb/inactive E2F complex, thereby preventing release of activated E2F and ultimately blocking E2F-dependent DNA transcription. This has the effect of inducing $G_1$ cell cycle arrest. In particular, the CDK4 pathway has been shown to have tumor-specific deregulation and cytotoxic effects. Accordingly, the ability to inhibit the activity of combinations of CDKs will be of beneficial therapeutic use.

Furthermore, the cell's ability to respond and survive chemotherapeutic assault may depend on rapid changes in transcription or on activation of pathways which are highly sensitive to CDK9/cyclinT1 (PTEF-b) activity. CDK9 inhibition may sensitize cells to TNFalpha or TRAIL stimulation by inhibition of NF-kB, or may block growth of cells by reducing myc-dependent gene expression. CDK9 inhibition may also sensitize cells to genotoxic chemotherapies, HDAC inhibition, or other signal transduction based therapies.

As such, the compounds of the invention can lead to depletion of anti-apoptotic proteins, which can directly induce apoptosis or sensitize to other apoptotic stimuli, such as cell cycle inhibition, DNA or microtubule damage or signal transduction inhibition. Depletion of anti-apoptotic proteins by the compounds of the invention may directly induce apoptosis or sensitize to other apoptotic stimuli, such as cell cycle inhibition, DNA or microtubule damage or signal transduction inhibition.

The compounds of the invention can be effective in combination with chemotherapy, DNA damage arresting agents, or other cell cycle arresting agents. The compounds of the invention can also be effective for use in chemotherapy-resistant cells.

The present invention includes treatment of one or more symptoms of cancer, inflammation, cardiac hypertrophy, and HIV infection, as well as protein kinase-associated disorders as described above, but the invention is not intended to be limited to the manner by which the compound performs its intended function of treatment of a disease. The present invention includes treatment of diseases described herein in any manner that allows treatment to occur, e.g., cancer, inflammation, cardiac hypertrophy, and HIV infection.

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged protein kinase-associated disorder treatment. The packaged treatment includes a compound of the invention packaged with instructions for using an effective amount of the compound of the invention for an intended use.

The compounds of the present invention are suitable as active agents in pharmaceutical compositions that are efficacious particularly for treating protein kinase-associated disorders, e.g., cancer, inflammation, cardiac hypertrophy, and HIV infection. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially the regulating, modulating, or inhibiting protein kinase activity, e.g., inhibition of the activity of a protein kinase, or treatment of cancer, inflammation, cardiac hypertrophy, and HIV infection.

In other embodiments, the present invention provides a method for inhibiting the activity of a protein kinase. The method includes contacting a cell with any of the compounds of the present invention. In a related embodiment, the method further provides that the compound is present in an amount effective to selectively inhibit the activity of a protein kinase.

In other embodiments, the present invention provides a use of any of the compounds of the invention for manufacture of a medicament to treat cancer, inflammation, cardiac hypertrophy, and HIV infection in a subject.

In other embodiments, the invention provides a method of manufacture of a medicament, including formulating any of the compounds of the present invention for treatment of a subject.

DETAILED DESCRIPTION OF CERTAIN EMBODIMENTS

The term "treat," "treated," "treating" or "treatment" includes the diminishment or alleviation of at least one symptom associated or caused by the state, disorder or disease being treated. In certain embodiments, the treatment comprises the induction of a protein kinase-associated disorder, followed by the activation of the compound of the invention, which would in turn diminish or alleviate at least one symptom associated or caused by the protein kinase-associated disorder being treated. For example, treatment can be diminishment of one or several symptoms of a disorder or complete eradication of a disorder.

The term "use" includes any one or more of the following embodiments of the invention, respectively: the use in the treatment of protein kinase-associated disorders; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from cancer, inflammation, cardiac hypertrophy, and HIV infection, as well as those diseases that depend on the activity of protein kinases. The term "use" further includes embodiments of compositions herein which bind to a protein kinase sufficiently to serve as tracers or labels, so that when coupled to a fluor or tag, or made radioactive, can be used as a research reagent or as a diagnostic or an imaging agent.

The term "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, inflammation, cardiac hypertrophy, and HIV infection, and other diseases or conditions described herein (e.g., a protein kinase-associated disorder). In another embodiment, the subject is a cell.

The language "protein kinase-modulating compound," "modulator of protein kinase" or "protein kinase inhibitor" refers to compounds that modulate, e.g., inhibit, or otherwise alter, the activity of a protein kinase. Examples of protein kinase-modulating compounds include compounds of the invention, i.e., Formula I and Formula II, as well as the compounds of Table A, Table B, and Table C (including pharmaceutically acceptable salts thereof, as well as enantiomers, stereoisomers, rotamers, tautomers, diastereomers, atropisomers or racemates thereof).

Additionally, a method of the invention includes administering to a subject an effective amount of a protein kinase-modulating compound of the invention, e.g., protein kinase-modulating compounds of Formula I and Formula II, as well as Table A, Table B, and Table C (including pharmaceutically acceptable salts thereof, as well as enantiomers, stereoisomers, rotamers, tautomers, diastereomers, atropisomers or racemates thereof).

Where linking groups are specified by their conventional chemical formula herein, written from left to right, they equally encompass the chemically identical substituents that would result from writing the structure from right to left, e.g., —CH$_2$O— is intended to include —OCH$_2$— for this purpose only.

The term "alkyl," by itself or as part of another substituent, means, unless otherwise stated, a fully saturated straight-chain (linear; unbranched) or branched chain, or a combination thereof, having the number of carbon atoms specified, if designated (i.e. $C_1$—$C_{10}$ means one to ten carbons). Examples include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. If no size is designated, the alkyl groups mentioned herein contain 1-10 carbon atoms, typically 1-8 carbon atoms, and often 1-6 or 1-4 carbon atoms, and preferably 1-2 carbon atoms. If the alkyl group is a branched alkyl group, and the number of carbon atoms is not mentioned, the branched alkyl group will consist of 3-8 carbon atoms, typically about 3-6 carbon atoms, and particularly 3-4 carbon atoms.

The term "alkenyl" refers to unsaturated aliphatic groups including straight-chain (linear; unbranched), branched-chain groups, and combinations thereof, having the number of carbon atoms specified, if designated, which contain at least one double bond (—C═C—). All double bonds may be independently either (E) or (Z) geometry, as well as mixtures thereof. Examples of alkenyl groups include, but are not limited to, —CH$_2$—CH═CH—CH$_3$; —CH═CH—CH═CH$_2$ and —CH$_2$—CH═CH—CH(CH$_3$)—CH$_2$—

CH₃. If no size is specified, the alkenyl groups discussed herein contain 2-6 carbon atoms.

The term "alkynyl" refers to unsaturated aliphatic groups including straight-chain (linear; unbranched), branched-chain groups, and combinations thereof, having the number of carbon atoms specified, if designated, which contain at least one carbon-carbon triple bond (—C≡C—). Examples of alkynyl groups include, but are not limited to, —CH₂—C≡C—CH₃; —C≡C—C≡CH and —CH₂—C≡C—CH(CH₃)—CH₂—CH₃. If no size is specified, the alkynyl groups discussed herein contain 2-6 carbon atoms.

Alkynyl and alkenyl groups can contain more than one unsaturated bond, or a mixture of double and triple bonds, and can be otherwise substituted as described for alkyl groups.

The terms "alkoxy," "alkenyloxy," and "alkynyloxy" refer to —O-alkyl, —O-alkenyl, and —O-alkynyl, respectively.

The term "cycloalkyl" by itself or in combination with other terms, represents, unless otherwise stated, cyclic versions of alkyl, alkenyl, or alkynyl, or mixtures thereof. Additionally, cycloalkyl may contain fused rings, but excludes fused aryl and heteroaryl groups, and cycloalkyl groups can be substituted unless specifically described as unsubstituted. Examples of cycloalkyl include, but are not limited to, cyclopropyl, cyclobutyl, cyclopentyl, cyclohexyl, 1-cyclohexenyl, 3-cyclohexenyl, cyclohexynyl, cyclohexynyl, cyclohexadienyl, cyclopentadienyl, cyclopentenyl, cycloheptyl, norbornyl, and the like. If no ring size is specified, the cycloalkyl groups described herein contain 3-8 ring members, or 3-6 ring members.

The term "heterocyclic" or "heterocycloaklyl" or "heterocyclyl," by itself or in combination with other terms, represents a cycloalkyl radical containing at least one annular carbon atom and at least one annular heteroatom selected from the group consisting of O, N, P, Si and S, preferably from N, O and S, wherein the ring is not aromatic but can contain unsaturations. The nitrogen and sulfur atoms in a heterocyclic group may optionally be oxidized and the nitrogen heteroatom may optionally be quaternized. In many embodiments, the annular heteroatoms are selected from N, O and S. The heterocyclic groups discussed herein, if not otherwise specified, contain 3-10 ring members, and at least one ring member is a heteroatom selected from N, O and S; commonly not more than three of these heteroatoms are included in a heterocyclic group, and generally not more than two of these heteroatoms are present in a single ring of the heterocyclic group. The heterocyclic group can be fused to an additional carboclic, heterocyclic, or aryl ring. A heterocyclic group can be attached to the remainder of the molecule at an annular carbon or annular heteroatom, and the heterocyclic groups can be substituted as described for alkyl groups. Additionally, heterocyclic may contain fused rings, but excludes fused systems containing a heteroaryl group as part of the fused ring system. Examples of heterocyclic groups include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, 1,2,3,4-tetrahydropyridyl, dihydroindole (indoline), tetrahydrofuran-3-yl, tetrahydrothien-2-yl, tetrahydrothien-3-yl, 1-piperazinyl, 2-piperazinyl, and the like.

As with other moieties described herein, heterocycloalkyl moieties can be unsubstituted, or substituted with various substituents known in the art, e.g., hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, loweralkyl, cycloalkyl or haloalkyl. Non-limiting examples of substituted heterocycloalkyl groups include the following, where each moiety may be attached to the parent molecule at any available valence:

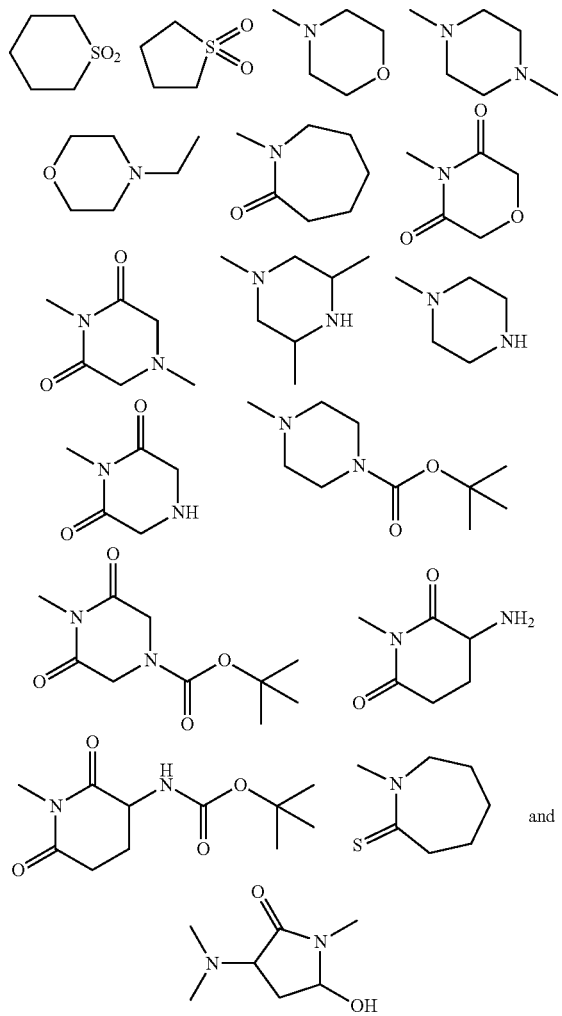

Also included within heterocyclic are piperidine, morpholine, thiomorpholine, piperazine, pyrrolidine, tetrahydrofuran, oxetane, oxepane, oxirane, tetrahydrothiofuran, thiepane, thiirane, and optionally substituted versions of each of these.

The terms "cycloalkyloxy" and "heterocycloalkyloxy" refer to —O-cycloalkyl and —O-heterocycloalkyl groups, respectively (e.g., cyclopropoxy, 2-piperidinyloxy, and the like).

The term "aryl" means, unless otherwise stated, an aromatic hydrocarbon group which can be a single ring or multiple rings (e.g., from 1 to 3 rings) which are fused together. Aryl may contain fused rings, wherein one or more of the rings is optionally cycloalkyl, but not including heterocyclic or heteroaromatic rings; a fused system containing at least one heteroaromatic ring is described as a heteroaryl group, and a phenyl ring fused to a heterocyclic ring is described herein as a heterocyclic group. An aryl group will include a fused ring system wherein a phenyl ring is fused to a cycloalkyl ring. Examples of aryl groups include, but are not limited to, phenyl, 1-naphthyl, tetrahydro-naphthalene, dihydro-1H-indene, 2-naphthyl, tetrahydronaphthyl and the like.

The term "heteroaryl" as used herein refers to groups comprising a single ring or two or three fused rings, where at least one of the rings is an aromatic ring that contain from one to four heteroatoms selected from N, O, and S as ring members (i.e., it contains at least one heteroaromatic ring), wherein the nitrogen and sulfur atoms are optionally oxidized, and the nitrogen atom(s) are optionally quaternized. A heteroaryl group can be attached to the remainder of the molecule through an annular carbon or annular heteroatom, and it can be attached through any ring of the heteroaryl moiety, if that moiety is bicyclic or tricyclic. Heteroaryl may contain fused rings, wherein one or more of the rings is optionally cycloalkyl or heterocycloalkyl or aryl, provided at least one of the rings is a heteroaromatic ring. Non-limiting examples of heteroaryl groups are 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Aryl and/or heteroaryl groups commonly contain up to four substituents per ring (0-4), and sometimes contain 0-3 or 0-2 substituents. The terms "aryloxy" and "heteroaryloxy" refer to aryl and heteroaryl groups, respectively, attached to the remainder of the molecule via an oxygen linker (—O—).

The term "arylalkyl" or "aralkyl" designates an alkyl-linked aryl group, where the alkyl portion is attached to the parent structure and the aryl is attached to the alkyl portion of the arylalkyl moiety. Examples are benzyl, phenethyl, and the like. "Heteroarylalkyl" or "heteroaralkyl" designates a heteroaryl moiety attached to the parent structure via an alkyl residue. Examples include furanylmethyl, pyridinylmethyl, pyrimidinylethyl, and the like. Aralkyl and heteroaralkyl also include substituents in which at least one carbon atom of the alkyl group is present in the alkyl group and wherein another carbon of the alkyl group has been replaced by, for example, an oxygen atom (e.g., phenoxymethyl, 2-pyridylmethoxy, 3-(1-naphthyloxy)propyl, and the like).

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and perhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like. The prefix "perhalo" refers to the respective group wherein all available valences are replaced by halo groups. For example "perhaloalkyl" includes —$CCl_3$, —$CF_3$, —$CCl_2CF_3$, and the like. The terms "perfluoroalkyl" and "perchloroalkyl" are a subsets of perhaloalkyl wherein all available valences are replaced by fluoro and chloro groups, respectively. Non limiting examples of perfluoroalkyl include —$CF_3$ and —$CF_2CF_3$. Non limiting examples of perchloroalkyl include —$CCl_3$ and —$CCl_2CCl_3$.

"Amino" refers herein to the group —$NH_2$ or —NRR', where R and R' are each independently selected from hydrogen or an alkyl (e.g, lower alkyl). The term "arylamino" refers herein to the group —NRR' where R is aryl and R' is hydrogen, alkyl, or an aryl. The term "aralkylamino" refers herein to the group —NRR' where R is an aralkyl and R' is hydrogen, an alkyl, an aryl, or an aralkyl. "Substituted amino" refers to an amino wherein at least one of R and R' is not H, i.e., the amino has at least one substituent group on it. The term alkylamino refers to -alkyl-NRR' where R and R' are each independently selected from hydrogen or an alkyl (e.g, lower alkyl).

The term "aminocarbonyl" refers herein to the group —C(O)—$NH_2$, i.e., it is attached to the base structure through the carbonyl carbon atom. "Substituted aminocarbonyl" refers herein to the group —C(O)—NRR' where R is alkyl and R' is hydrogen or an alkyl. The term "arylaminocarbonyl" refers herein to the group —C(O)—NRR' where R is an aryl and R' is hydrogen, alkyl or aryl. "Aralkylaminocarbonyl" refers herein to the group —C(O)—NRR' where R is aralkyl and R' is hydrogen, alkyl, aryl, or aralkyl.

"Aminosulfonyl" refers herein to the group —$S(O)_2$—$NH_2$. "Substituted aminosulfonyl" refers herein to the group —$S(O)_2$—NRR' where R is alkyl and R' is hydrogen or an alkyl. The term "aralkylaminosulfonlyaryl" refers herein to the group -aryl-$S(O)_2$—NH-aralkyl.

"Carbonyl" refers to the divalent group —C(O)—.

The term "sulfonyl" refers herein to the group —$SO_2$—. "Alkylsulfonyl" refers to a substituted sulfonyl of the structure —$SO_2$R in which R is alkyl. Alkylsulfonyl groups employed in compounds of the present invention are typically loweralkylsulfonyl groups having from 1 to 6 carbon atoms in R. Thus, exemplary alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —$SO_2$-aryl. The term "aralkylsulfonyl" refers herein to the group —$SO_2$-aralkyl. The term "sulfonamido" refers herein to —$SO_2NH_2$, or to —$SO_2NRR'$ if substituted.

Unless otherwise stated, each radical/moiety described herein (e.g., "alkyl," "cycloalkyl," "heterocycloalkyl," "aryl," "heteroaryl," "alkoxy," etc.) is meant to include both substituted and unsubstituted forms.

"Optionally substituted" as used herein indicates that the particular group or groups being described may have no non-hydrogen substituents (i.e., it can be unsubstituted), or the group or groups may have one or more non-hydrogen substituents. If not otherwise specified, the total number of such substituents that may be present is equal to the number of H atoms present on the unsubstituted form of the group being described. Typically, a group will contain up to three (0-3) substituents. Where an optional substituent is attached via a double bond, such as a carbonyl oxygen (=O), the group takes up two available valences on the group being substituted, so the total number of substituents that may be included is reduced according to the number of available valences. Suitable substituent groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, loweralkoxy, loweralkoxy-alkyl, alkylcarbonyl, aminocarbonyl, arylcarbonyl, aralkylcarbonyl, carbonylamino, heteroarylcarbonyl, heteroaralkylcarbonyl, alkylthio, aminoalkyl, cyanoalkyl, aryl, alkylamino, alkylsulfonyl, aralkylamino, alkylcarbonylamino, carbonyl, piperidinyl, morpholinyl, pyrrolidinyl and the like. Deuterium, when introduced into a compound at levels at least 5× above natural abundance, can also be considered a substituent for purposes of describing the compounds herein. Note that because deuterium is an isotope of hydrogen that does not substantially change the shape of the molecule, deuterium is exempt from the typical numerical limitations placed on numbers of substituents: deuterium (D) can be included in place of hydrogen (H) in addition to other substituents and should not be counted in the numerical limitations that apply to other substituents.

A substituent group can itself be substituted by the same groups described herein for the corresponding type of structure. The group substituted onto the substituted group can be carboxyl, halo, nitro, amino, cyano, hydroxyl, loweralkyl, loweralkenyl, loweralkynyl, loweralkoxy, aminocarbonyl, —SR, thioamido, —SO$_3$H, —SO$_2$R, N-methylpyrrolidinyl, piperidinyl, piperazinyl, N-methylpiperazinyl, 4-chloropyrimidinyl, pyrindinyl, tetrahydropyranyl (or heterocycloalkyl, heteroaryl?) or cycloalkyl, where R is typically hydrogen or loweralkyl.

When the substituted substituent includes a straight chain group, the substituent can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms (N, O or S).

The term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "isomer" includes all stereoisomers of the compounds referred to in the formulas herein, including enantiomers, diastereomers, as well as all conformers, rotamers, and tautomers, unless otherwise indicated. The invention includes all enantiomers of any chiral compound disclosed, in either substantially pure levorotatory or dextrorotatory form, or in a racemic mixture, or in any ratio of enantiomers. For compounds disclosed as an (R)-enantiomer, the invention also includes the (S)-enantiomer; for compounds disclosed as the (S)-enantiomer, the invention also includes the (R)-enantiomer. The invention includes any diastereomers of the compounds referred to in the above formulas in diastereomerically pure form and in the form of mixtures in all ratios.

Unless stereochemistry is explicitly indicated in a chemical structure or chemical name, the chemical structure or chemical name is intended to embrace all possible stereoisomers, conformers, rotamers, and tautomers of the compound depicted. For example, a compound containing a chiral carbon atom is intended to embrace both the (R) enantiomer and the (S) enantiomer, as well as mixtures of enantiomers, including racemic mixtures; and a compound containing two chiral carbons is intended to embrace all enantiomers and diastereomers (including (R,R), (S,S), (R,S), and (R,S) isomers).

In all uses of the compounds of the formulas disclosed herein, the invention also includes use of any or all of the stereochemical, enantiomeric, diastereomeric, conformational, rotomeric, tautomeric, solvate, hydrate, polymorphic, crystalline form, non-crystalline form, salt, pharmaceutically acceptable salt, metabolite and prodrug variations of the compounds as described.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —CH$_3$ and —CH$_2$CH$_2$CH$_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

The description of the disclosure herein should be construed in congruity with the laws and principals of chemical bonding. For example, it may be necessary to remove a hydrogen atom in order accommodate a substitutent at any given location. Furthermore, it is to be understood that definitions of the variables (i.e., "R groups"), as well as the bond locations of the generic formulae of the invention (e.g., formulas I or II), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

As used herein, "isomer" includes all stereoisomers of the compounds referred to in the formulas herein, including enantiomers, diastereomers, as well as all conformers, rotamers, and tautomers, unless otherwise indicated. The invention includes all enantiomers of any chiral compound disclosed, in either substantially pure levorotatory or dextrorotatory form, or in a racemic mixture, or in any ratio of enantiomers. For compounds disclosed as an (R)-enantiomer, the invention also includes the (S)-enantiomer; for compounds disclosed as the (S)-enantiomer, the invention also includes the (R)-enantiomer. The invention includes any diastereomers of the compounds referred to in the above formulas in diastereomerically pure form and in the form of mixtures in all ratios.

Unless stereochemistry is explicitly indicated in a chemical structure or chemical name, the chemical structure or chemical name is intended to embrace all possible stereoisomers, conformers, rotamers, and tautomers of the compound depicted. For example, a compound containing a chiral carbon atom is intended to embrace both the (R) enantiomer and the (S) enantiomer, as well as mixtures of enantiomers, including racemic mixtures; and a compound containing two chiral carbons is intended to embrace all enantiomers and diastereomers (including (R,R), (S,S), (R,S), and (R,S) isomers).

In all uses of the compounds of the formulas disclosed herein, the invention also includes use of any or all of the stereochemical, enantiomeric, diastereomeric, conformational, rotomeric, tautomeric, solvate, hydrate, polymorphic, crystalline form, non-crystalline form, salt, pharmaceutically acceptable salt, metabolite and prodrug variations of the compounds as described.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Certain compounds of the present invention can exist in unsolvated forms as well as solvated forms (i.e., solvates). Compounds of the invention may also include hydrated forms (i.e., hydrates). In general, the solvated and hydrated forms are equivalent to unsolvated forms for purposes of biological utility and are encompassed within the scope of the present invention. The invention also includes all polymorphs, including crystalline and non-crystalline forms. In general, all physical forms are equivalent for the uses contemplated by the present invention and are intended to be within the scope of the present invention.

The present invention includes all salt forms of the compounds described herein, as well as methods of using such salts. The invention also includes all non-salt forms of any salt of a compound named herein, as well as other salts of any salt of a compound named herein. In one embodiment, the salts of the compounds comprise pharmaceutically acceptable salts. "Pharmaceutically acceptable salts" are those salts which retain the biological activity of the free compounds and which can be administered as drugs or pharmaceuticals to humans and/or animals. The desired salt of a basic functional group of a compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, hippuric acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts.

Pharmaceutically acceptable metabolites and prodrugs of the compounds referred to in the formulas herein are also embraced by the invention. The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, PRO-DRUGS AS NOVEL DELIVERY SYSTEMS, Vol. 14 of the A.C.S. Symposium Series, and in Edward B. Roche, ed., BIOREVERSIBLE CARRIERS IN DRUG DESIGN, American Pharmaceutical Association and Pergamon Press, 1987.

Pharmaceutically acceptable esters of the compounds referred to in the formulas herein are also embraced by the invention. As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The invention further provides deuterated versions of the above-described compounds. As used herein, "deuterated version" refers to a compound in which at least one hydrogen atom is enriched in the isotope deuterium beyond the natural rate of deuterium occurrence. Typically, the hydrogen atom is enriched to be at least 50% deuterium, frequently at least 75% deuterium, and preferably at least about 90% deuterium. Optionally, more than one hydrogen atom can be replaced by deuterium. For example, a methyl group can be deuterated by replacement of one hydrogen with deuterium (i.e., it can be —$CH_2D$), or it can have all three hydrogen atoms replaced with deuterium (i.e., it can be —$CD_3$). In each case, D signifies that at least 50% of the corresponding H is present as deuterium.

A substantially pure compound means that the compound is present with no more than 15% or no more than 10% or no more than 5% or no more than 3% or no more than 1% of the total amount of compound as impurity and/or in a different form. For instance, substantially pure S,S compound means that no more than 15% or no more than 10% or no more than 5% or no more than 3% or no more than 1% of the total R,R; S,R; and R,S forms are present.

As used herein, "therapeutically effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition. Therapeutically effective amounts of the compounds of the invention generally include any amount sufficient to detectably inhibit Raf activity by any of the assays described herein, by other Raf kinase activity assays known to those having ordinary skill in the art or by detecting an inhibition or alleviation of symptoms of cancer.

As used herein, the term "pharmaceutically acceptable carrier," and cognates thereof, refers to adjuvants, binders, diluents, etc. known to the skilled artisan that are suitable for administration to an individual (e.g., a mammal or non-mammal). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutical compositions described herein include at least one pharmaceutically acceptable carrier or excipient; preferably, such compositions include at least one carrier or excipient other than or in addition to water.

As used herein, the term "pharmaceutical agent" or "additional pharmaceutical agent," and cognates of these terms, are intended to refer to active agents other than the claimed compounds of the invention, for example, drugs, which are administered to elicit a therapeutic effect. The pharmaceutical agent(s) may be directed to a therapeutic effect related to the condition that a claimed compound is intended to treat or prevent (e.g., conditions mediated by Raf kinase, including, but not limited to those conditions described herein (e.g., cancer)) or, the pharmaceutical agent may be intended to treat or prevent a symptom of the underlying condition (e.g., tumor growth, hemorrhage, ulceration, pain, enlarged lymph nodes, cough, jaundice, swelling, weight loss, cachexia, sweating, anemia, paraneoplastic phenomena, thrombosis, etc.) or to further reduce the appearance or severity of side effects of administering a claimed compound.

When used with respect to methods of treatment/prevention and the use of the compounds and formulations thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound of the invention is disclosed herein, the invention further contemplates a step of identifying an individual or subject in need of the particular treatment to be administered or having the particular condition to be treated.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. Examples of non-mammals include, but are not limited to, birds, and the like. The term "individual" does not denote a particular age or sex.

In some variations, the individual has been identified as having one or more of the conditions described herein. Identification of the conditions as described herein by a skilled physician is routine in the art (e.g., via blood tests, X-rays, CT scans, endoscopy, biopsy, etc.) and may also be suspected by the individual or others, for example, due to tumor growth, hemorrhage, ulceration, pain, enlarged lymph nodes, cough, jaundice, swelling, weight loss, cachexia, sweating, anemia, paraneoplastic phenomena, thrombosis, etc. In some embodiments, the individual has further been identified as having a cancer that expresses a mutated Raf, such as a mutated B-Raf.

In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

As used herein and in the appended claims, the singular forms "a", "an" and "the" include plural forms, unless the context clearly dictates otherwise.

Unless defined otherwise or clearly indicated by context, all technical and scientific terms used herein have the same meaning as commonly understood by one of ordinary skill in the art to which this invention belongs.

General Synthetic Methods

The compounds disclosed herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds disclosed herein may contain one or more chiral centers. Accordingly, if desired, such compounds can be prepared or isolated as pure stereoisomers, i.e., as individual enantiomers or diastereomers, or as stereoisomerenriched mixtures. All such stereoisomers (and enriched mixtures) are included within the scope of the embodiments, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley and Sons, 1991), Rodd's *Chemistry of Carbon Compounds*, Volumes 1-5 and Supplemental (Elsevier Science Publishers, 1989), *Organic Reactions*, Volumes 1-40 (John Wiley and Sons, 1991), March's *Advanced Organic Chemistry*, (John Wiley and Sons, 4th Edition), and Larock's *Comprehensive Organic Transformations* (VCH Publishers Inc., 1989).

The various starting materials, intermediates, and compounds of the embodiments may be isolated and purified where appropriate using conventional techniques such as precipitation, filtration, crystallization, evaporation, distillation, and chromatography. Characterization of these compounds may be performed using conventional methods such as by melting point, mass spectrum, nuclear magnetic resonance, and various other spectroscopic analyses.

Compounds of the embodiments may generally be prepared using a number of methods familiar to one of skill in the art, and may generally be made in accordance with the following reaction Schemes 1 and 2, which are described in detail in the Examples below.

EXAMPLES

Referring to the examples that follow, compounds of the embodiments were synthesized using the methods described herein, or other methods known to one skilled in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18 5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on LCMS instruments: Waters System (Acuity HPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; cone Voltage 20 V; column temperature 50° C.). All masses were reported as those of the protonated parent ions.

GCMS analysis is performed on a Hewlett Packard instrument (HP6890Series gas chromatograph with a Mass Selective Detector 5973; injector volume: 1 ⌠L; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.) or Varian 400 MHz MR NMR (Palo Alto, Calif.). The spectral reference was either TMS or the known chemical shift of the solvent. Some compound samples were run at elevated temperatures (e.g., 75° C.) to promote increased sample solubility.

The purity of some of the compounds is assessed by elemental analysis (Desert Analytics, Tucson, Ariz.).

Melting points are determined on a Laboratory Devices MeI-Temp apparatus (Holliston, Mass.).

Preparative separations are carried out using a Combiflash Rf system (Teledyne Isco, Lincoln, Nebr.) with RediSep silica gel cartridges (Teledyne Isco, Lincoln, Nebr.) or SiliaSep silica gel cartridges (Silicycle Inc., Quebec City, Canada) or by flash column chromatography using silica gel (230-400 mesh) packing material, or by HPLC using a Waters 2767 Sample Manager, C-18 reversed phase column, 30×50 mm, flow 75 mL/min. Typical solvents employed for the Combiflash Rf system and flash column chromatography are dichloromethane, methanol, ethyl acetate, hexane, heptane, acetone, aqueous ammonia (or ammonium hydroxide), and triethyl amine. Typical solvents employed for the reverse phase HPLC are varying concentrations of acetonitrile and water with 0.1% trifluoroacetic acid.

The examples below as well as throughout the application, the following abbreviations have the following meanings. If not defined, the terms have their generally accepted meanings.

ABBREVIATIONS

ACN: Acetonitrile
BINAP: 2,2'-bis(diphenylphosphino)-1,1'-binapthyl
DCM: Dichloromethane
DIEA: diisopropylethylamine
DIPEA: N,N-diisopropylethylamine
DME: 1,2-dimethoxy ethane
DMF: N,N-dimethylformamide
DMSO dimethyl sulfoxide
DPPF 1,1'-bis(diphenylphosphino)ferrocene
eq equivalent
EtOAc ethyl acetate
EtOH ethanol
HATU 2-(7-aza-1H-benzotriazole-1-yl)-1,1,3,3-tetramethyluronium hexafluorophosphate
HPLC high performance liquid chromatography
MCPBA meta-chloroperoxybenzoic acid
MeOH methanol
NBS N-bromosuccinimide
NMP N-methyl-2-pyrrolidone
Rt rentention time
THF tetrahydrofuran

SYNTHETIC EXAMPLES

Compounds of the present invention can be synthesized by the schemes outlined b

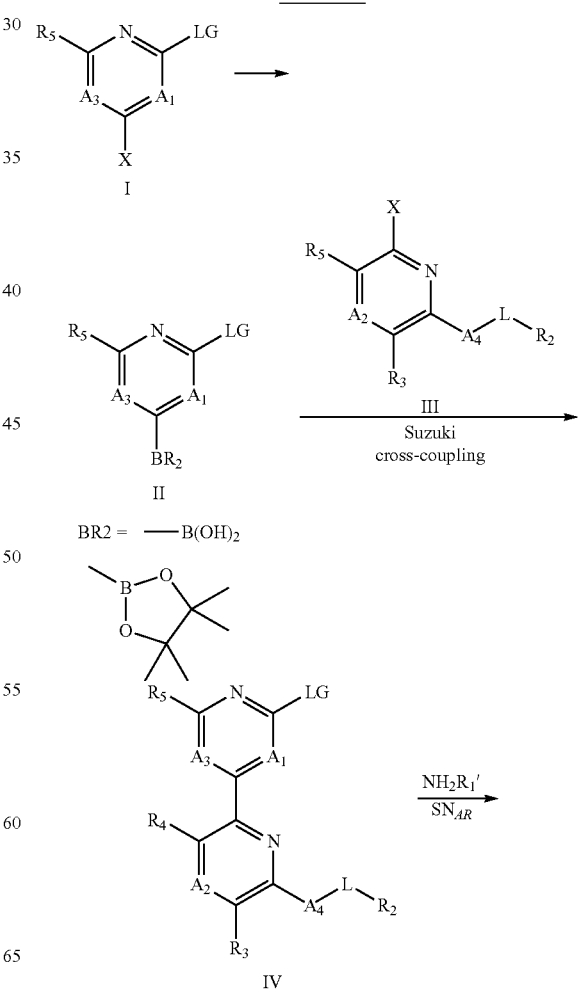

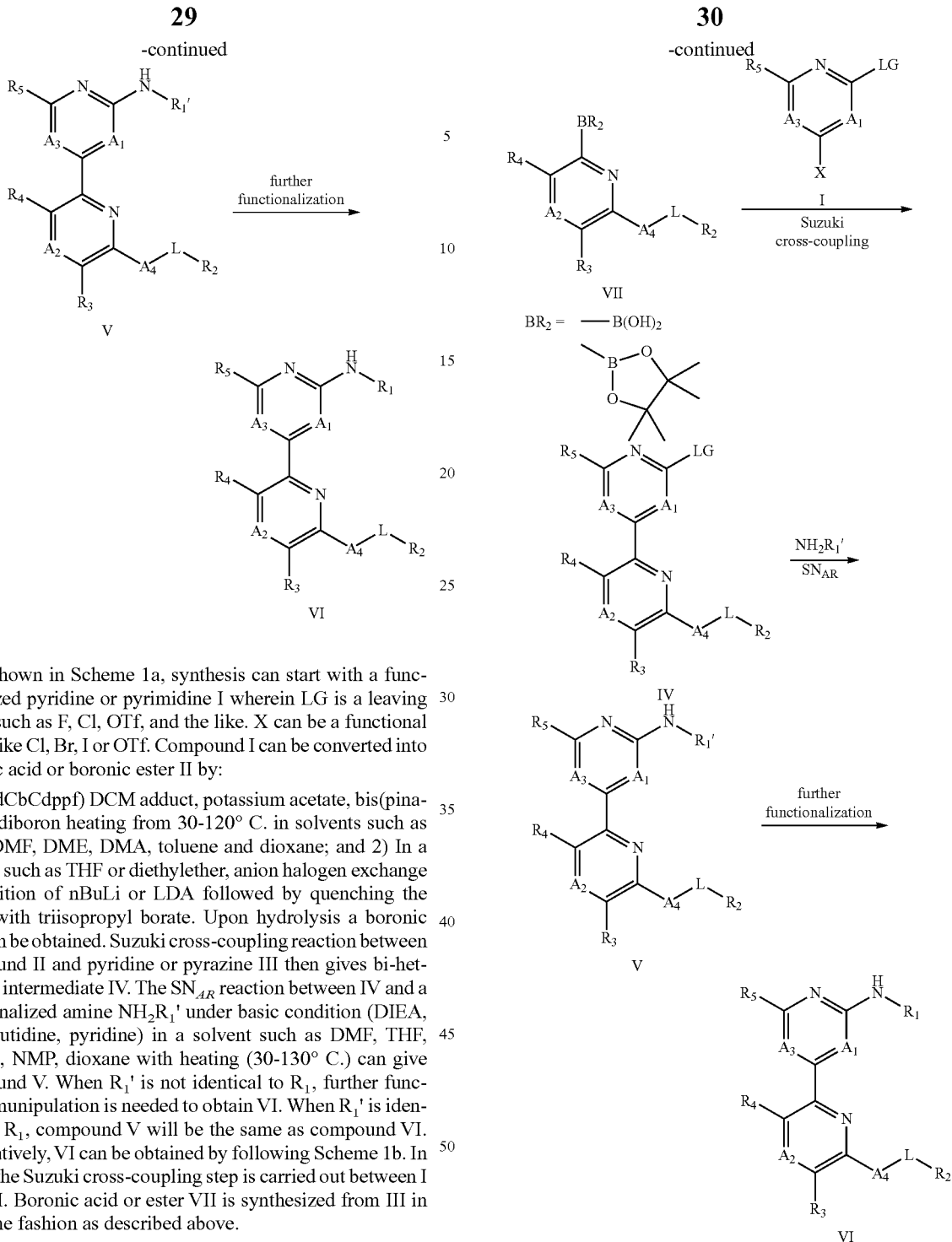

As shown in Scheme 1a, synthesis can start with a functionalized pyridine or pyrimidine I wherein LG is a leaving group such as F, Cl, OTf, and the like. X can be a functional group like Cl, Br, I or OTf. Compound I can be converted into boronic acid or boronic ester II by:

1) PdCbCdppf) DCM adduct, potassium acetate, bis(pinacolato)diboron heating from 30-120° C. in solvents such as THF, DMF, DME, DMA, toluene and dioxane; and 2) In a solvent such as THF or diethylether, anion halogen exchange by addition of nBuLi or LDA followed by quenching the anion with triisopropyl borate. Upon hydrolysis a boronic acid can be obtained. Suzuki cross-coupling reaction between compound II and pyridine or pyrazine III then gives bi-heteroaryl intermediate IV. The $SN_{AR}$ reaction between IV and a functionalized amine $NH_2R_1'$ under basic condition (DIEA, TEA, lutidine, pyridine) in a solvent such as DMF, THF, DMSO, NMP, dioxane with heating (30-130° C.) can give compound V. When $R_1'$ is not identical to $R_1$, further functional munipulation is needed to obtain VI. When $R_1'$ is identical to $R_1$, compound V will be the same as compound VI. Alternatively, VI can be obtained by following Scheme 1b. In which the Suzuki cross-coupling step is carried out between I and VII. Boronic acid or ester VII is synthesized from III in the same fashion as described above.

Scheme 1b.

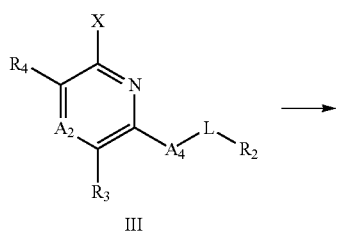

Another alternative route is illustrated in Scheme 2. As described in Scheme 1a, boronic ester or acid, X, can be prepared from aminopyridine or aminopyrimidine IX. Suzuki cross-coupling reaction between compound X and pyridine or pyrazine XI then can give the bi-heteroaryl intermediate XII. The $SN_{AR}$ reaction between XII and functionalized amine $HA_4LR_2$ under basic condition (DIEA, TEA, lutidine, pyridine) in a solvent such as DMF, THF, DMSO, NMP, dioxane with heating (30-130° C.) can give compound V. When $R_1'$ is not identical to $R_1$, further functional manipulation will be needed to obtain VI. When $R_1'$ is identical with $R_1$, compound V will be the same as compound VII.

Scheme 2

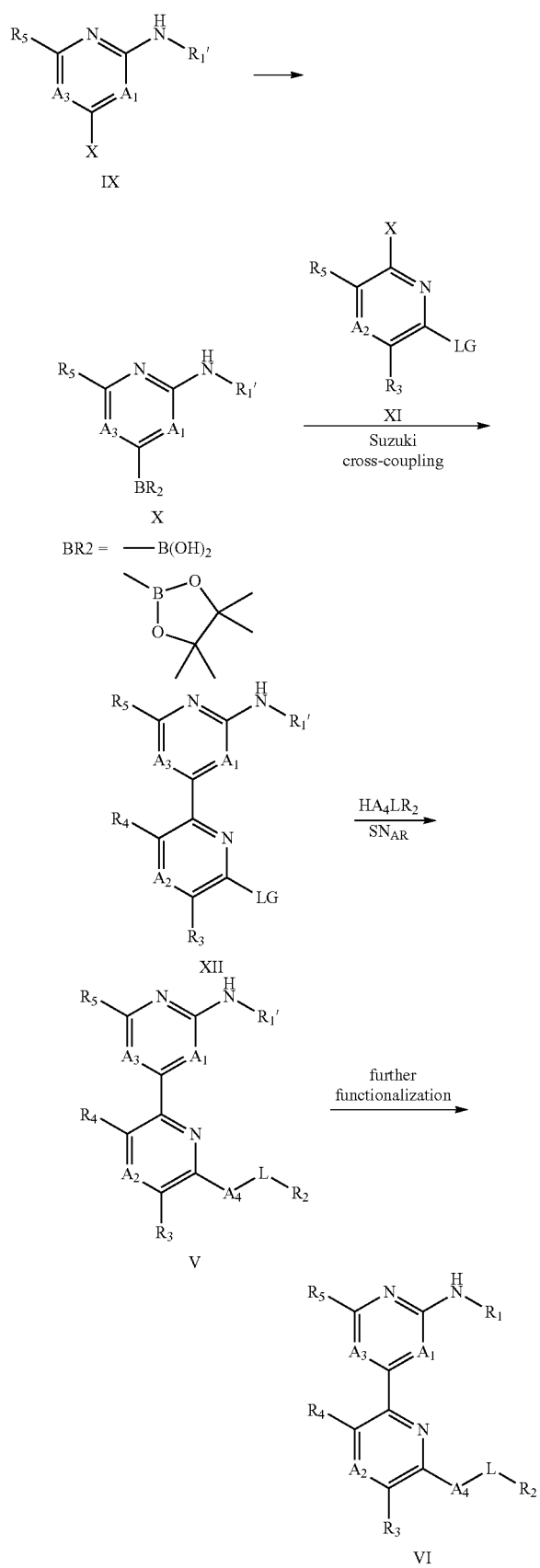

Compounds of the present invention, listed in Table I, were prepared by following the specific procedures outlined below. The procedures include synthesis of intermeidates and using these intermediates to make compounds of Formula I.

Synthesis of Intermediates

Synthesis of 6-bromo-N-(3-fluorobenzyl)pyridin-2-amine (Intermediate A)

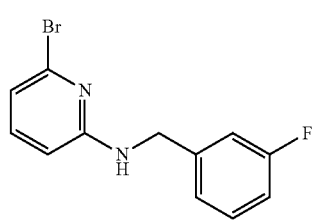

A solution of 2,6-dibromopyridine (7.1 g, 30.0 mmol) in NMP (16 mL) was mixed with a mixture of (3-fluorophenyl)methanamine (4.13 g, 33.0 mmol) and Huenig's Base (5.76 mL, 33.0 mmol). The resulting mixture was stirred under argon at 115-120° C. for about 168 hr. The mixture was then cooled to ambient temperature and diluted with EtOAc (250 mL). The organic layer was separated, washed with saturated aqueous sodium bicarbonate (2×), water (2×), brine (1×), dried over sodium sulfate, filtered, and concentrated in vacuo to yield a crude material. The crude material was purified by column chromatography [SiO$_2$, 120 g, EtOAc/hexane=0/100 to 20/80] providing 6-bromo-N-(3-fluorobenzyl)pyridin-2-amine (7.11 g) as an off-white solid. LCMS (m/z): 281.1/283.1[M+H]+; Retention time=1.03 min.

Synthesis of 5'-chloro-2'-fluoro-N-(3-fluorobenzyl)-2,4'-bipyridin-6-amine (Intermediate B)

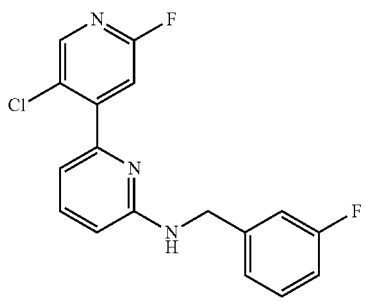

A mixture of 6-bromo-N-(3-fluorobenzyl)pyridin-2-amine (A, 2.0 g, 7.11 mmol), 5-chloro-2-fluoropyridin-4-ylboronic acid (2.0 g, 11.4 mmol), PdCl$_2$(dppf).CH$_2$Cl$_2$ adduct (0.465 g, 0.569 mmol), DME (27 mL) and 2M aqueous Na$_2$CO$_3$ (9.25 mL, 18.50 mmol) was stirred at about 100° C. for 3 hr. After cooling to ambient temperature, the mixture was diluted with EtOAc (25 mL) and MeOH (20 mL), filtered, and concentrated in vacuo to yield a crude material. The crude material was purified by column chromatography [silica gel, 120 g, EtOAc/hexane=0/100 to 20/80] providing 5'-chloro-2'- fluoro-N-(3-fluorobenzyl)-2,4'-bipyridin-6-amine (1.26 g) as an off-white solid. LCMS (m/z): 332.2 [M+H]+; Retention time=0.92 min.

Synthesis of 6-bromo-N-((tetrahydro-2H-pyran-4-yl)methyl)pyridin-2-amine (Intermediate C)

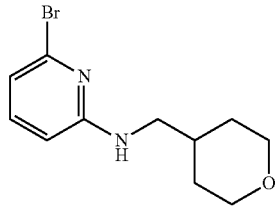

C

A mixture of 2-bromo-6-fluoropyridine (750 mg, 4.26 mmol) in DMSO (3 mL) was mixed with (tetrahydro-2H-pyran-4-yl)methanamine hydrochloride (775 mg, 5.11 mmol) and NEt₃ (1.426 mL, 10.23 mmol). The resulting mixture was heated at about 110° C. for 18 hr. The mixture was cooled to ambient temperature and diluted with EtOAc. The organic layer was separated, washed with saturated aqueous sodium bicarbonate solution, water, and brine, dried over sodium sulfate, filtered and concentrated in vacuo to yield a resulting residue. The resulting residue was purified by column chromatography [SiO₂, 40 g, EtOAc/heptane=0/100 to 30/70]. Pure fractions were combined and concentrated in vacuo providing 6-bromo-N-((tetrahydro-2H-pyran-4-yl)methyl)pyridin-2-amine (B1, 940 mg) as a white solid. LCMS (m/z): 271.0/272.9 [M+H]+; Retention time=0.81 min.

Synthesis of 5'-chloro-2'-fluoro-N-((tetrahydro-2H-pyran-4-yl)methyl)-2,4'-bipyridin-6-amine (Intermediate D)

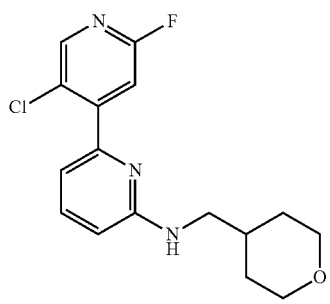

D

A mixture of 6-bromo-N-((tetrahydro-2H-pyran-4-yl)methyl)pyridin-2-amine (C, 271 mg, 1 mmol), 5-chloro-2-fluoropyridin-4-ylboronic acid (351 mg, 2.000 mmol), PdCl₂(dppf).CH₂Cl₂ adduct (82 mg, 0.100 mmol) in DME (4.5 mL) and 2M Na₂CO₃ (318 mg, 3.00 mmol) was heated in a sealed tube at about 103° C. for about 2 hr. The mixture then was cooled to ambient temperature, diluted with EtOAc (~25 mL) and MeOH (~5 mL), filtered, and concentrated in vacuo to yield a resulting residue. The resulting residue was purified by column chromatography [SiO₂, 12 g, EtOAc/heptane=10/90 to 50/50]. Fractions were combined and concentrated in vacuo providing 5'-chloro-2'-fluoro-N-((tetrahydro-2H-pyran-4-yl)methyl)-2,4'-bipyridin-6-amine (260 mg) as a yellow thick oil. LCMS (m/z): 322.1/323.9 [M+H]+; Retention time=0.60 min.

Synthesis of 6-bromo-5-chloro-N-((tetrahydro-2H-pyran-4-yl)methyl)pyridin-2-amine (E) and 6-bromo-3-chloro-N-((tetrahydro-2H-pyran-4-yl)methyl)pyridin-2-amine (Intermediate F)

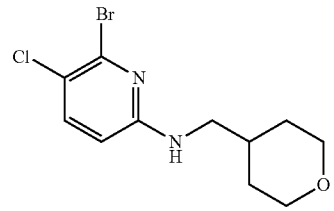

E

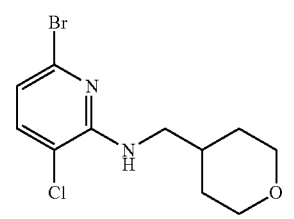

F

A solution of 6-bromo-N-((tetrahydro-2H-pyran-4-yl)methyl)pyridin-2-amine (C, 1000 mg, 3.69 mmol) in chloroform (15 mL) was diluted with 1-chloropyrrolidine-2,5-dione (NCS, 492 mg, 3.69 mmol). The mixture then was heated in a sealed tube at about 33° C. for about 16 hr, followed by heating the reaction mixture for about 24 hr at about 37° C., and then for an additional 5 days at about 43° C. The reaction mixture then was cooled to ambient temperature, diluted with 1N aqueous sodium hydroxide solution and DCM. The organic layer was separated, washed with brine, dried over sodium sulfate, filtered off and concentrated in vacuo. The resulting resulting residue was purified by column chromatography [ISCO, SiO2, 80 g, EtOAc/heptane=5/95 2 min, 5/95 to 30/70 2-15 min, to 35/65 15-18 min, then 35%]. Fractions were combined and concentrated in vacuo yielding 6-bromo-3-chloro-N-((tetrahydro-2H-pyran-4-yl)methyl)pyridin-2-amine (F, 453 mg), and 6-bromo-5-chloro-N-((tetrahydro-2H-pyran-4-yl)methyl)pyridin-2-amine (E, ~500 mg). (F): LCMS (m/z): 305.0[M+H]+; Retention time=1.01 min. (E): LCMS (m/z): 305.0 [M+H]+; Retention time=0.96 min.

Synthesis of 3,5'-dichloro-2'-fluoro-N-((tetrahydro-2H-pyran-4-yl)methyl)-2,4'-bipyridin-6-amine (Intermediate G)

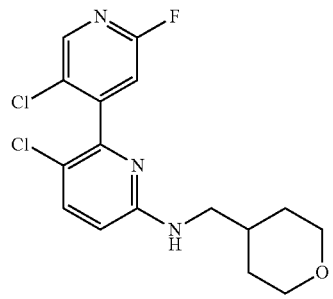

G

A mixture of 6-bromo-5-chloro-N-((tetrahydro-2H-pyran-4-yl)methyl)pyridin-2-amine (E, 300 mg, 0.982 mmol), 5-chloro-2-fluoropyridin-4-ylboronic acid (344 mg, 1.963 mmol), PdCl2(dppf).CH$_2$Cl$_2$ adduct (80 mg, 0.098 mmol) in DME (4.5 mL) and 2M aqueous sodium carbonate (4.5 mL, 4.50 mmol) was heated in a sealed tube at about 103° C. for about 16 hr. The reaction mixture was cooled to ambient temperature, diluted with EtOAc (~100 mL) and saturated aqueous sodium carbonate solution. The organic layer was separated, washed with saturated aqueous sodium carbonate solution (2×), dried over sodium sulfate, filtered off and concentrated in vacuo. The resulting resulting residue was purified by column chromatography [ISCO, SiO2, 25 g, EtOAc/heptane=0/100 to 25/75]. Fractions were combined and concentrated in vacuo providing 3,5'-dichloro-2'-fluoro-N-((tetrahydro-2H-pyran-4-yl)methyl)-2,4'-bipyridin-6-amine (140 mg) as a light brown liquid. LCMS (m/z): 356.1 [M+H]+; Retention time=0.96 min.

Synthesis of 5,5'-dichloro-2'-fluoro-N-((tetrahydro-2H-pyran-4-yl)methyl)-2,4'-bipyridin-6-amine (Intermediate H)

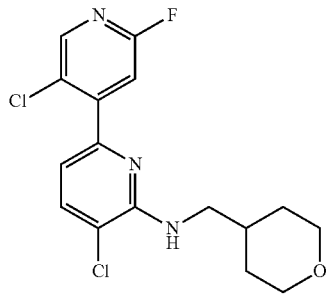

H

A mixture of 6-bromo-3-chloro-N-((tetrahydro-2H-pyran-4-yl)methyl)pyridin-2-amine (F, 200 mg, 0.654 mmol), 5-chloro-2-fluoropyridin-4-ylboronic acid (230 mg, 1.309 mmol), PdCl2 (dppf).CH2Cl2 adduct (53.4 mg, 0.065 mmol) in DME (3 mL) and 2M aqueous sodium carbonate (3 mL, 6.00 mmol) was heated in a sealed tube at about 103° C. for 16 hr. The reaction mixture was cooled to ambient temperature, diluted with EtOAc (~100 mL) and saturated aqueous sodium bicarbonate solution. The organic layer was separated, washed with saturated aqueous sodium bicarbonate solution (2×), dried over sodium sulfate, filtered off and concentrated in vacuo. The resulting residue was purified by column chromatography [ISCO, SiO2, 25 g, EtOAc/heptane=0/100 to 30/70]. Fractions were combined and concentrated in vacuo providing 5,5'-dichloro-2'-fluoro-N-((tetrahydro-2H-pyran-4-yl)methyl)-2,4'-bipyridin-6-amine (130 mg) as a nearly colorless liquid. LCMS (m/z): 356.1 [M+H]+; Retention time=1.10 min.

Synthesis of 5'-chloro-2',5-difluoro-N-((tetrahydro-2H-pyran-4-yl)methyl)-2,4'-bipyridin-6-amine (Intermediate I)

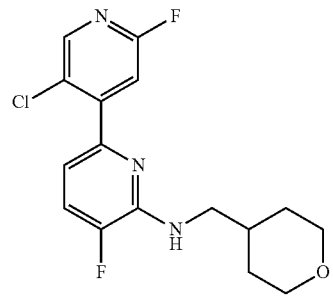

I

Step 1. Preparation of 3,6-difluoro-N-((tetrahydro-2H-pyran-4-yl)methyl)pyridin-2-amine A mixture of 2,3,6-trifluoropyridine (3 g, 22.54 mmol), (tetrahydro-2H-pyran-4-yl)methanamine (3.89 g, 33.8 mmol) and triethylamine (7.86 mL, 56.4 mmol) in NMP (60 mL) was heated at about 70° C. for about 1 hr. The reaction mixture was cooled to ambient temperature, diluted with EtOAc (~100 mL), brine (~50 mL) and water (~50 mL). The separated organic layer was washed with brine (1×), 0.3N aqueous HCl (2×), saturated aqueous NaHCO$_3$ solution (1×), brine (1×), dried over Na$_2$SO$_4$, filtered off and concentrated in vacuo providing crude 3,6-difluoro-N-((tetrahydro-2H-pyran-4-yl)methyl)pyridin-2-amine, which was directly used in the next reaction without further purification. Yield: 3.5 g. LCMS (m/z): 229.1 [M+H]+; Retention time=0.79 min.

Step 2. Preparation of 3-fluoro-6-methoxy-N-((tetrahydro-2H-pyran-4-yl)methyl)pyridin-2-amine To a solution of 3,6-difluoro-N-((tetrahydro-2H-pyran-4-yl)methyl)pyridin-2-amine (5 g, 21.91 mmol) in MeOH (35 mL) was added sodium methoxide (25 wt. % in MeOH, 15.03 mL, 65.7 mmol). The resulting mixture was heated in a steel bomb at about 135° C. for ~18 hr. The mixture then was cooled to ambient temperature and concentrated in vacuo. The resulting residue was taken up in water (~250 mL) yielding a precipitate, which was collected by filteration, and then washed with water. The solid then was dissolved in toluene (10 mL)/DCM (10 mL), decanted from the dark brownish film and concentrated in vacuo. The resulting residue was dried in high vacuo providing crude 3-fluoro-6-methoxy-N-((tetrahydro-2H-pyran-4-yl)methyl)pyridin-2-amine as a nearly colorless oil, which was directly used in the next reaction without further purification. Yield: 4.96 g. LCMS (m/z): 241.1 [M+H]+; Retention time=0.87 min.

Step 3. Preparation of 5-fluoro-6-((tetrahydro-2H-pyran-4-yl)methyl)aminopyridin-2-ol To a solution of 3-fluoro-6-methoxy-N-((tetrahydro-2H-pyran-4-yl)methyl)pyridin-2-amine (4.6 g, 19.14 mmol) in acetonitrile (50 mL) was added sodium iodide (20.09 g, 134 mmol) and TMS-chloride (17.13 mL, 134 mmol). The resulting mixture was stirred at about 95° C. for 20 hr. The reaction mixture was cooled to ambient temperature and then diluted with EtOAc (80 mL) and water (40 mL). The diluted mixture was stirred vigorously for about 30 min. The organic layer was separated and washed with 0.1N aqueous HCl solution. The combined aqueous layers were carefully neutralized (pH ~7) with solid NaHCO$_3$ solution and extracted with EtOAc (1×100 mL) and DCM (2×50 mL). The combined organic layers were washed with saturated aqueous NaHCO$_3$ solution and brine, dried over Na$_2$SO$_4$, filtered off and concentrated in vacuo. The resulting resulting residue was purified by column chromatography [SiO$_2$, 80 g, EtOAc/heptane=10/90 for 2 min, EtOAc/heptane=10/90 to 100/0 over 23 min, then EtOAc/heptane=100/0] providing 5-fluoro-6-((tetrahydro-2H-pyran-4-yl)methyl)aminopyridin-2-ol as a highly viscous oil which turned to purple upon standing at room temperature. Yield: 780 mg. LCMS (m/z): 227.1 [M+H]+; Retention time=0.42 min.

Step 4. Preparation of 5-fluoro-6-((tetrahydro-2H-pyran-4-yl)methyl)aminopyridin-2-yl trifluoromethanesulfonate A solution of 5-fluoro-6-((tetrahydro-2H-pyran-4-yl)methyl)aminopyridin-2-ol (500 mg, 2.210 mmol) and triethylamine (0.462 mL, 3.31 mmol) in DCM (20 mL) was gradually diluted at about 0° C. with trifluoromethanesulfonic anhydride (1.120 mL, 6.63 mmol). The resulting mixture was stirred for about 2 hr at 0° C. and carefully mixed with ice-cooled saturated aqueous NaHCO$_3$ solution. The aqueous layer was separated, and extracted with DCM (2×). The combined organic layers were dried over Na$_2$SO$_4$, filtered off and concentrated in vacuo. The resulting residue was purified by column chromatography [SiO$_2$, 40 g, 30 min, EtOAc/heptane=5/95 to 40/60] providing 5-fluoro-6-((tetrahydro-2H-pyran-4-yl)methyl)aminopyridin-2-yl trifluoromethanesulfonate as a colorless oil. Yield: 743 mg. LCMS (m/z): 359.0 [M+H]+; Retention time=1.02 min.

Step 5. Preparation of 5'-chloro-2',5-difluoro-N-((tetrahydro-2H-pyran-4-yl)methyl)-2,4'-bipyridin-6-amine A mixture of 5-fluoro-6-((tetrahydro-2H-pyran-4-yl)methyl)aminopyridin-2-yl trifluoromethanesulfonate (712 mg, 1.987 mmol), 5-chloro-2-fluoropyridin-4-ylboronic acid (697 mg, 3.97 mmol), PdCl$_2$(dppf).CH$_2$Cl$_2$ adduct (162 mg, 0.199 mmol) in DME (8 mL) and 2 M aqueous Na$_2$CO$_3$ solution (2.6 mL, 1.987 mmol) in a sealed tube was heated at 95° C. for 3 hr. The mixture was allowed to cool to ambient temperature and was diluted with EtOAc (~100 mL) and saturated aqueous NaHCO$_3$ solution. The separated organic layer was washed with saturated aqueous NaHCO$_3$ (2×), dried over Na$_2$SO$_4$, filtered off and concentrated in vacuo. The resulting residue was purified by column chromatography [SiO$_2$, 40 g, EtOAc/heptane=0/100 to 25/75 over 20 min] providing 5'-chloro-2',5-difluoro-N-((tetrahydro-2H-pyran-4-yl)methyl)-2,4'-bipyridin-6-amine as a white solid. Yield: 570 mg. LCMS (m/z): 340.1 [M+H]+; Retention time=0.99 min.

Synthesis of (R/S)-5'-chloro-N-((2,2-dimethyltetrahydro-2H-pyran-4-yl)methyl)-2'-fluoro-2,4'-bipyridin-6-amine (Intermediate J)

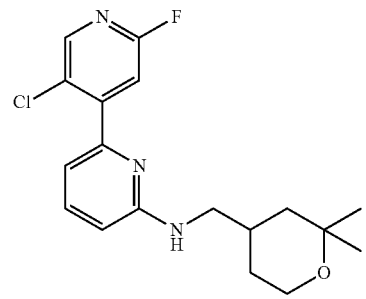

Step 1. Preparation of tert-butyl 6-bromopyridin-2-ylcarbamate

To a solution of 6-bromopyridin-2-amine (3 g, 17.34 mmol), triethylamine (3.14 mL, 22.54 mmol) and DMAP (0.424 g, 3.47 mmol) in DCM (24 mL) was added slowly a solution of BOC-anhydride (4.83 mL, 20.81 mmol) in DCM (6 mL). The reaction mixture was stirred at ambient temperature for 24 hr. The mixture was diluted with water, brine and EtOAc. The separated aqueous layer was extracted with EtOAc. The combined organic layers were dried over sodium sulfate and concentrated in vacuo. The resulting residue was purified by column chromatography providing tert-butyl 6-bromopyridin-2-ylcarbamate as a white solid. Yield: 1.67 g. LCMS (m/z): 274.9 [M+H]+; Retention time=0.95 min.

Step 2: Preparation of (R/S)-(2,2-dimethyltetrahydro-2H-pyran-4-yl)methyl 4-methylbenzenesulfonate To a solution of (2,2-dimethyltetrahydro-2H-pyran-4-yl)methanol (1 g, 6.93 mmol) in DCM (5 mL) and pyridine (5 mL, 61.8 mmol) was added para-toluenesulfonyl chloride (1.586 g, 8.32 mmol) and DMAP (0.042 g, 0.347 mmol). The mixture was stirred for 18 hr at ambient temperature. The reaction mixture was concentrated in vacuo and the resulting residue was diluted with water and DCM. The separated organic layer was washed with 0.2N aqueous HCl (1×), 1N aqueous HCl (2×), brine, dried over sodium sulfate, filtered off and concentrated in vacuo. The resulting residue was purified by column chromatography [SiO$_2$, 40 g, EtOAc/hexane=0/100 to 50/50; 25 min] providing (R/S)-(2,2-dimethyltetrahydro-2H-pyran-4-yl)methyl 4-methylbenzenesulfonate as a colorless oil. Yield: 2.05 g. LCMS (m/z): 299.1 [M+H]+; Retention time=0.96 min.

Step 3: Preparation of (R/S)-tert-butyl 6-bromopyridin-2-yl((2,2-dimethyltetrahydro-2H-pyran-4-yl)methyl)carbamate To a mixture of tert-butyl 6-bromopyridin-2-ylcarbamate (686 mg, 2.51 mmol), K$_2$CO$_3$ (347 mg, 2.51 mmol), (2,2-dimethyltetrahydro-2H-pyran-4-yl)methyl 4-methylbenzenesulfonate (750 mg, 2.51 mmol) in DMF (10 mL) was added carefully NaH (60 wt. %, 141 mg, 3.52 mmol) in portions [Caution: gas development!]. The resulting mixture was stirred at about 45° C. for 4 hr. The mixture was warmed to ambient temperature and was diluted with EtOAc (~50 mL) and saturated aqueous NaHCO$_3$. The organic layer was separated, washed with saturated aqueous NaHCO$_3$ solution (1×), dried over Na$_2$SO$_4$, filtered off and concentrated in vacuo. The resulting residue was purified by column chromatography [SiO₂, 40 g, 25 min, EtOAc/heptane=0/100 to 25/75 over 25 min] providing (R/S)-tert-butyl 6-bromopyridin-2-yl((2,2-dimethyltetrahydro-2H-pyran-4-yl)methyl)carbamate as highly viscous, colorless oil. Yield: 723 mg. LCMS (m/z): 344.9 {loss of tert Bu-group}/(399.0)[M+H]+; Retention time=1.22 min.

Step 4: Preparation of (R/S)-tert-butyl 5'-chloro-2'-fluoro-2,4'-bipyridin-6-yl((2,2-dimethyltetrahydro-2H-pyran-4-yl)methyl)carbamate A mixture of tert-butyl 6-bromopyridin-2-yl((2,2-dimethyltetrahydro-2H-pyran-4-yl)methyl)carbamate (710 mg, 1.778 mmol), 5-chloro-2-fluoropyridin-4-ylboronic acid, PdCl₂(dppf).CH₂Cl₂ adduct (145 mg, 0.178 mmol) in DME (7 mL) and 2M aqueous Na₂CO₃ solution (2.3 mL, 1.778 mmol) was heated in a sealed tube at about 98° C. for 2 hr. The mixture was cooled to ambient temperature and diluted with EtOAc (~100 mL) and saturated aqueous NaHCO₃ solution. The separated organic layer was washed with saturated aqueous NaHCO3 (2×), dried over Na₂SO₄, filtered off and concentrated in vacuo. The resulting residue was purified by column chromatography [SiO₂, 40 g, 25 min, EtOAc/heptane=0/100 to 25/75over 25 min] providing (R/S)-tert-butyl 5'-chloro-2'-fluoro-2,4'-bipyridin-6-yl((2,2-dimethyltetrahydro-2H-pyran-4-yl)methyl)carbamate as a highly viscous, colorless oil. Yield: 605 mg. LCMS (m/z): 394.1 {loss of tert Bu-group}/450.2[M+H]+; Retention time=1.24 min.

Step 5. Preparation of (R/S)-5'-chloro-N-((2,2-dimethyltetrahydro-2H-pyran-4-yl)methyl)-2'-fluoro-2,4'-bipyridin-6-amine To a solution of tert-butyl 5'-chloro-2'-fluoro-2,4'-bipyridin-6-yl((2,2-dimethyltetrahydro-2H-pyran-4-yl)methyl)carbamate (950 mg, 2.111 mmol) in methanol (5 mL) was added 4M HCl/dioxane (15 mL, 494 mmol). The resulting mixture was stirred for ~45 min at ambient temperature. The mixture then was concentrated in vacuo and the resulting residue was dissolved in EtOAc (~50 mL) and saturated aqueous NaHCO₃ solution (~50 mL). The separated organic layer was washed with saturated aqueous NaHCO₃ solution (1×), brine (1×), dried over Na₂SO₄, filtered off and concentrated in vacuo providing crude (R/S)-5'-chloro-N-((2,2-dimethyltetrahydro-2H-pyran-4-yl)methyl)-2'-fluoro-2,4'-bipyridin-6-amine as a colorless oil, which was directly used in the next reaction without further purification. Yield: 740 mg. LCMS (m/z): 350.1 [M+H]+; Retention time=0.69 min.

Synthesis of 5'-chloro-2',3,6-trifluoro-2,4'-bipyridine (Intermediate K)

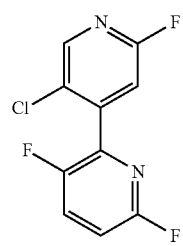

Step 1. Preparation of 3,6-difluoro-2-methoxypyridine 2,3,6-Trifluoropyridine (17.91 ml, 188 mmol) was dissolved in anhydrous MeOH (300 ml) and the resulting mixture was placed under argon. This mixture then was treated with a 25 wt % methanolic solution of sodium methoxide (43.0 ml, 188 mmol). The resulting mixture was then heated at about 65° C. for 2 hr. The reaction mixture was cooled to ambient temperature, and concentrated in vacuo to yield a residue which then was mixed with brine (200 mL), and extracted with Et2O (3×200 ml). The combined extracts were dried (Na2SO₄), filtered, and concentrated in vacuo to give 21.5 g (79% yield) of crude 3,6-difluoro-2-methoxypyridine as a white solid which was carried on to the next step without purification.

Step 2. Preparation of 3,6-difluoro-2-hydroxypyridine

To 3,6-difluoro-2-methoxypyridine (21.5 g, 148 mmol) in acetonitrile (250 ml) was added sodium iodide (66.6 g, 445 mmol) and chlorotrimethylsilane (56.8 ml, 445 mmol). The resulting mixture was heated at 80-85° C. for 2.5 hr. The mixture was cooled to ambient temperature and diluted with EtOAc (300 mL) and water (300 mL) and vigorously stirred for another hr. The layers were separated, and the aqueous phase was extracted with additional ethyl acetate (200 mL). The combined organic layers were washed sequentially with 0.6 N aqueous HCl (250 mL) and brine (250 mL) and concentrated in vacuo to yield a slurry. The slurry was filtered and rinsed three times with cold acetonitrile to yield 10.8 g of desired product as a white solid. The filtrate was concentrated and purified by flash chromatography over silica gel (heptanes:ethyl acetate gradient) to give an additional 4.2 g (77% yield combined) of 3,6-difluoro-2-hydroxypyridine as a white solid. LCMS (m/z): 132.0 [M+H]+; retention time=0.47 min.

Step 3. Preparation of 3,6-difluoropyridin-2-yl trifluoromethanesulfonate

An ice water bath-cooled solution of 3,6-difluoro-2-hydroxypyridine (10.75 g, 82 mmol) and triethylamine (22.86 ml, 164 mmol) in DCM (550 ml) was mixed with a solution of trifluoromethanesulfonic anhydride (16.63 ml, 98 mmol) in DCM (100 ml) over 20 min. The resulting mixture then was stirred for 2 hr at 0° C., with the progress of the reaction followed by TLC (2:1 heptanes:ethyl acetate). The reaction mixture was quenched with saturated aqueous NaHCO3 solution (200 mL). The separated aqueous layer was extracted with DCM (2×). The combined organic layers were dried over sodium sulfate, filtered, and concentrated in vacuo. The resulting residue was purified by column chromatography over silica gel (EtOAc/heptane gradient) to give 16.3 g (76% yield) of 3,6-difluoropyridin-2-yl trifluoromethanesulfonate as a yellow oil.

Step 4. Preparation of 5'-chloro-2',3,6-trifluoro-2,4'-bipyridine

A mixture of 3,6-difluoropyridin-2-yl trifluoromethanesulfonate (3.50 g, 13.30 mmol) and 5-chloro-2-fluoropyridine-4-boronic acid (3.27 g, 18.62 mmol) in THF (27 ml) was degassed by bubbling Argon gas for 10 min. Aqueous sodium carbonate (13.30 ml, 26.6 mmol) and PdCl₂(dppf).CH₂Cl₂ adduct (0.652 g, 0.798 mmol)were added, and the mixture was degassed for an additional 5 min. The resulting reaction mixture was stirred at about 100° C. for 2 hr in a sealed vessel. The reaction mixture was cooled to ambient temperature, diluted with EtOAc and water. The separated organic layer was dried over $Na_2SO_4$, filtered, and concentrated in vacuo. The resulting residue was purified by column chromatography over silica gel (heptanes/ethyl acetate gradient) to yield 2.78 g (85% yield) of 5'-chloro-2',3,6-trifluoro-2,4'-bipyridine as a crystalline solid. LCMS (m/z): 244.9 [M+H]+; retention time=0.86 min.

Synthesis of 5'-chloro-N-(((2R,6S)-2,6-dimethyltetrahydro-2H-pyran-4-yl)methyl)-2'-fluoro-2,4'-bipyridin-6-amine (Intermediate L)

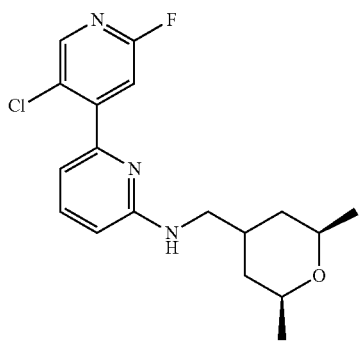

L

Step 1. Preparation of (2R,6S)-2,6-dimethyldihydro-2H-pyran-4(3H)-one

A solution of 2,6-dimethyl-4H-pyran-4-one (2 g, 16.1 mmol) in 20 ml ethanol was stirred over 10% Pd/C (0.2 g) under hydrogen (15 psi) for 16 hours at ambient temperature. TLC showed two spots; one was desired product and second one was side product in a 1:1 ratio. GCMS M+ 128 for product, and M+ 130 for side product.

Suspension was filtered off, and the filtrate was concentrated to remove solvent to give 2.3 g crude product which contained ~30% of the side product. The resulting oily residue was treated with 2.3 g Dess-Martin periodinane in 15 ml DCM at ambient temperature for 16 hours. GCMS showed oxidation was complete, desired product formation was confirmed by GCMS at M+ 128. ~3 ml NaS2CO3 was added to the suspension and the resulting mixture was stirred for 1 hour at ambient temperature, then 20 ml saturated sodium bicarbonate solution was added to, and new mixture was stirred for another hour. The organic phase was separated, washed with water, brine, dried and filtered through celite. The filtrate was concentrated and resulting residue was purified by ISCO eluting with 10% ethyl acetate in heptane to yield 600 mg of the desired product. GCMS: M=128. HNMR: 1.5 ppm (6H), 2.3 ppm (4H), 3.75 ppm (2H).

Step 2. Preparation of (2R,6S,E)-4-(methoxymethylene)-2,6-dimethyltetrahydro-2H-pyran To a suspension of (methoxymethyl)triphenyl phosphine chloride (1.5 g, 4.45 mmol) in 8 ml THF at −10° C., was added dropwise 4.45 ml 1.0M/THF solution of sodium bis(trimethylsilyl)amide. The resulting reaction mixture was stirred for 1 hour, followed by addition of a solution of (2R,6S)-2,6-dimethyldihydro-2H-pyran-4(3H)-one (380 mg, 2.96 mmol) in 2 ml THF. The resulting mixture was warmed to ambient temperature and stirred for an additional 3 hours. GCMS showed formation of desired product at M+156, as major component. The reaction mixture was quenched with 15 ml water, and was extracted with diethyl ether (2×30 ml). The combined organic phase was washed with brine, dried and concentrated. The resulting residue was purified by ISCO eluting with 10% ethyl acetate in heptane to yield 240 mg of the desired product as a colorless oil, GCMS showed M=156. HNMR: 5.9 ppm (1H), 3.45 ppm (3H), 3.25 ppm (2H), 2.45 ppm (1H), 1.85 ppm (1H), 1.6 ppm (1H), 1.38 ppm (1H), 1.1 ppm (6H).

Step 3. Preparation of (2R,6S)-2,6-dimethyltetrahydro-2H-pyran-4-carbaldehyde

A mixture of (2R,6S,E)-4-(methoxymethylene)-2,6-dimethyltetrahydro-2H-pyran (240 mg, 1.53 mmol) and 88% formic acid (1.5 ml, 34.4 mmol) in water was heated in an oil bath under Argon to about 90° C. for 1 hour. GCMS indicated that reaction was complete under the condition. The reaction mixture was cooled in an ice bath, neutralised with 6N NaOH to a pH=6, and extracted with diethyl ether. The organic phase were dried and concentrated to dryness to yield 120 mg of the desired product as yellow colored oil. GCMS M=142. FlNMR showed 9.51 ppm (s, 1H, CHO).

Step 4. Preparation of 6-bromo-N-(((2R,6S)-2,6-dimethyltetrahydro-2H-pyran-4-yl)methyl)pyridin-2-amine The mixture of (2R,6S)-2,6-dimethyltetrahydro-2H-pyran-4-carbaldehyde (120 mg, 0.84 mmol) and 6-bromo-2-aminopyridine (219 mg, 1.26 mmol) in 5 ml DCM was stirred at ambient temperature for about 40 min. To this solution was added sodium triacetoxy borohydride (268 mg, 1.26 mmol), followed by the addition of 0.01 ml acetic acid. The resulting solution was stirred at ambient temperature for about 40 hours. The reaction mixture was concentrated in vacuo to yield a residue was diluted with ethyl acetate, washed with sodium bicarbonate, brine, dried, concentrated. The resulting residue was purified by ISCO eluting with 10% to 20% ethyl acetate in heptane to yield 110 mg of the desired product as colorless oil. LCMS (m/z): 299/301 (MH+), retention time=1.01 min.

Step 5. Preparation of 5'-chloro-N-(((2R,6S)-2,6-dimethyltetrahydro-2H-pyran-4-yl)methyl)-2'-fluoro-2,4'-bipyridin-6-amine A mixture of 6-bromo-N-(((2R,6S)-2,6-dimethyltetrahydro-2H-pyran-4-yl)methyl)pyridin-2-amine (110 mg, 0.36 mmol), 5-chloro-2-fluoro-pyridine-4-boronic acid (193 mg, 1.10 mmol), 0.55 ml 2.0M saturated sodium carbonate aqueous solution in 2 ml DME was purged with Argon for 3 min, $PdCl_2(dppf)CH_2Cl_2$ (30 mg, 0.037 mmol) was added to this purged. The resulting mixture was heated at about 95° C. in an oil bath for 3.5 hours. Formation of the desired product was confirmed by LCMS: MH+ 350, 0.70 min. The preceding reaction mixture was diluted with ethyl acetate, washed with water, brine, dried over sodium sulfate and concentrated. The resulting residue was purified by ISCO eluting with 10% ethyl acetate in heptane to give 90 mg desired product as colorless oil. LCMS (m/z): 350 (MH+), retention time=0.70 min.

Synthesis of 5'-chloro-N6-(((2R,6S)-2,6-dimethyltetrahydro-2H-pyran-4-yl)methyl)-2,4'-bipyridine-2',6-diamine (Intermediate M)

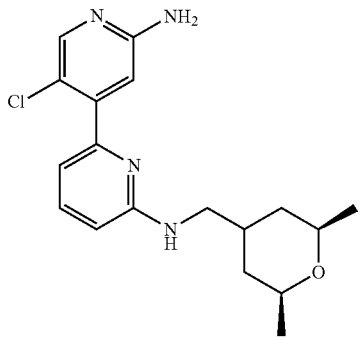

A mixture of 5'-chloro-N-(((2R,6S)-2,6-dimethyltetrahydro-2H-pyran-4-yl)methyl)-2'-fluoro-2,4'-bipyridin-6-amine (60 mg, 0.17 mmol), and 3.0 ml 28% ammonium hydroxide aqueous solution was heated at about 130° C. in an oil bath for 17 hours. Formation of compound M was Reaction confirmed by LCMS/LC data. The reaction mixture was diluted with ethyl acetate, washed with water, saturated sodium bicarbonate, and brine, dried over sodium sulfate and concentrated to yield 50 mg of the desired product. LCMS (m/z): 347 (MH+), retention time=0.53 min.

Synthesis of 3-bromo-5'-chloro-2'-fluoro-N-((tetrahydro-2H-pyran-4-yl)methyl)-2,4'-bipyridin-6-amine (Intermediate N)

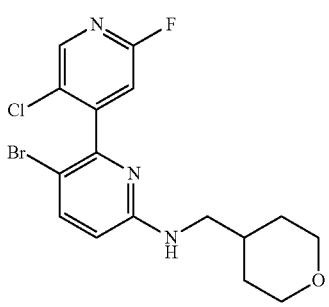

A mixture of 5'-chloro-2'-fluoro-N-((tetrahydro-2H-pyran-4-yl)methyl)-2,4'-bipyridin-6-amine (516 mg, 1.60 mmol) and N-bromosuccinimide (286 mg, 1.60 mmol) in acetonitrile (12 mL) was stirred at 90° C. for 3 hr in a sealed vessel. Volatiles were removed under reduced pressure. The resulting residue was dissolved in ethyl acetate and washed sequentially with saturated aqueous sodium bicarbonate and brine. The organic phase was dried (Na2SO4), filtered, and concentrated. The crude material was purified by column chromatography over silica gel (heptanes/ethyl acetate gradient) to yield 608 mg of the desired product. LCMS (m/z): 402.0 [M+H]+; Retention time=1.03 min.

Synthesis of intermediate (4-methoxytetrahydro-2H-pyran-4-yl)methyl 4-methylbenzenesulfonate (Intermediate O)

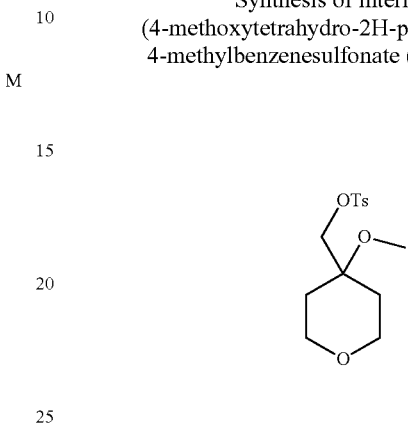

Step 1. Synthesis of 1,6-dioxaspiro[2.5]octane

To a clear solution of trimethylsulfonium iodide (3.27 g, 16 mmol) in 20 ml of DMSO was added dihydro-2H-pyran-4(3H)-one (11.0 g, 10 mmol) with stirring. To this mixture, under nitrogen, was then slowly added KO$^t$Bu (1.68 g, 15 mmol) in 15 ml of DMSO. The resulting solution was then stirred overnight at ambient temperature. Water (50 ml) was slowly added to the mixture, and the resulting mixture was extracted with diethyl ether (3×20 ml). The ether layers were combined, dried and concentrated in vacuo to yield 650 mg of the crude product. 1H NMR (300 MHz, CHLOROFORM-d) δ ppm 1.44-1.62 (m, 2 H) 1.76-1.98 (m, 2 H) 2.70 (s, 2 H) 3.70-3.98 (m, 4 H).

Step 2. Synthesis of (4-methoxytetrahydro-2H-pyran-4-yl)methanol

To a solution of 1,6-dioxaspiro[2.5]octane (600 mg, 5.26 mmol) in methanol (10 ml) at 0° C. (ice-water) under nitrogen was added camphorsulfonic acid (50 mg, 0.21 mmol) and the resulting mixture was stirred at about 0° C. for 2 hours. The mixture was concentrated in vacuo and the crude residue was used in the next step without purification. The desired product was obtained as a light yellow oil (707 mg).

Step 3. To a solution of (4-methoxytetrahydro-2H-pyran-4-yl)methanol (300 mg, 2.05 mmol) in pyridine (4 ml) at ambient temperature was added toluenesulfonic chloride (430 mg, 2.25 mmol) and the resulting mixture was stirred overnight at about 25° C. The stirred mixture was concentrated and the solid residue was dissolved in DCM and purified by silica gel chromatography using a 12 g column, eluting with 0-30% ethyl acetate in heptane to yield the desired compound "O" as a light yellow solid (360 mg). 1H NMR (300 MHz, CHLOROFORM-d) δ ppm 1.45-1.63 (m, 2 H) 1.61-1.79 (m, 2 H) 2.46 (s, 3 H), 3.16 (s, 3 H) 3.53-3.75 (m, 4 H) 3.93 (s, 2 H), 7.36 (d, J=8.20 Hz, 2 H) 7.81 (d, J=8.20 Hz, 2 H).

Synthesis of tert-butyl 6-bromo-5-chloropyridin-2-yl ((4-methoxytetrahydro-2H-pyran-4-yl)methyl)carbamate (Intermediate P)

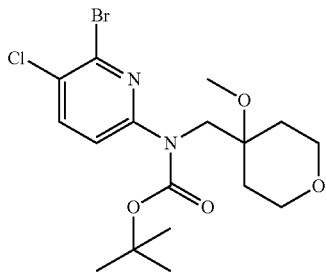 [SMILES: COC1(CN(C(=O)OC(C)(C)C)c2ccc(Cl)c(Br)n2)CCOCC1]

To a stirred solution of tert-butyl 6-bromo-5-chloropyridin-2-ylcarbamate (140 mg, 0.455 mmol) in DMF (2 ml) under nitrogen was added NaH (60%, 30 mg, 0.774 mmol). The resulting mixture was stirred at ambient temperature for one hour. A solution of (4-methoxytetrahydro-2H-pyran-4-yl)methyl 4-methylbenzenesulfonate (intermediate O, 164 mg, 0.546 mmol) in DMF (1.5 ml) was then added to the preceding mixture. The resulting mixture was then stirred overnight at about 85° C. The stirred mixture was diluted with 30 ml of ethyl acetate, washed with water (20 ml×3) and dried. After concentration the resulting residue was purified by silica gel chromatography using a 12 g column, eluting with 5-20% ethyl acetate in hexane to yield the desired compound "P" as a viscous oil (92 mg), which solidified upon standing overnight. LCMS (m/z): 437.0 [M+H]+; Retention time=1.158 min.

Synthesis of (1-methoxycyclohexyl)methyl 4-methylbenzenesulfonate (Intermediate Q)

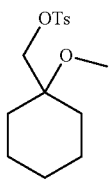

This compound was synthesized from cyclohexanone following the procedure described for (4-methoxytetrahydro-2H-pyran-4-yl)methyl 4-methylbenzenesulfonate (Intermediate O).
LCMS (m/z): 299.2 [M+H]+; Retention time=1.055 min.

Synthesis of 4-(aminomethyl)tetrahydro-2H-pyran-4-carbonitrile (Intermediate R)

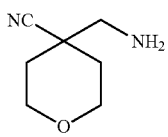

Step 1. Synthesis of dihydro-2H-pyran-4,4(3H)-dicarbonitrile

A mixture of malononitrile (0.991 g, 15 mmol), 1-bromo-2-(2-bromoethoxy)ethane (3.83 g, 16.50 mmol) and DBU (4.97 ml, 33.0 mmol) in DMF (6 ml) was heated at about 85° C. for 3 hours, and then cooled to ambient temperature. The mixture was concentrated in vacuo, the resulting residue was diluted with ethyl acetate, washed three times with water and dried overnight under high vacuum to yield the desired product as a light brown solid (1.65 g). GC-MS: 136 [M]; Retention time=5.76 min. 1H NMR (300 MHz, CHLOROFORM-d) δ ppm 2.14-2.32 (m, 4 H) 3.77-3.96 (m, 4 H).

Step 2. A mixture of dihydro-2H-pyran-4,4(3H)-dicarbonitrile (450 mg, 3.31 mmol) and Sodium borohydride (375 mg, 9.92 mmol) in EtOH (15 ml) was stirred at ambient temperature for about 4 hours. The mixture was concentrated and the resulting residue was diluted with ethyl acetate, washed with water and dried. Concentration in vacuo afforded 388 mg of the crude product which was used directly in the next step. LCMS (m/z): 141.0 [M+H]+; Retention time=0.18 min.

Synthesis of 4-((6-bromopyridin-2-yl-amino)methyl) tetrahydro-2H-pyran-4-carbonitrile (Intermediate S)

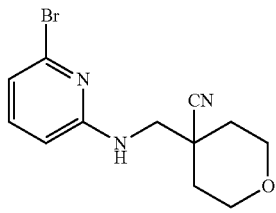 [SMILES: N#CC1(CNc2cccc(Br)n2)CCOCC1]

To 2-bromo-6-fluoropyridine (400 mg, 2.273 mmol) in DMSO (4 ml) at ambient temperature was sequentially added 4-(aminomethyl)tetrahydro-2H-pyran-4-carbonitrile (Intermediate R, 382 mg, 2.73 mmol) and triethylamine (0.792 ml, 5.68 mmol). The resulting light brown mixture was heated at 110° C. in a sealed glass bomb for 18 hours. The reaction mixture then was cooled to ambient temperature, reaction mixture diluted with EtOAc, washed with saturated NaHCO3 solution and brine, dried over sodium sulfate and concentrated in vacuo to yield 890 mg of a light brown liquid. The crude material was purified by silica gel chromatography using a 12 g column, eluting with 5%-20% ethyl acetate in hexane to afford 410 mg (60.9%) of the desired product "S". LCMS (m/z): 297.9 [M+H]+; Retention time=0.823 min. 1H NMR (400 MHz, CHLOROFORM-d) δ ppm: 1.67-1.96 (m, 4H), 3.59-3.78 (m, 4H), 3.98 (m, 2H), 4.82 (t, J=6.65 Hz, 1H), 6.39 (d, J=8.22, 1H), 6.72-6.84 (m, 1H), 7.16-7.33 (m, 1H).

Synthesis of 5'-chloro-2'-fluoro-N-((tetrahydro-2H-pyran-4-yl)methyl)-5-(trifluoromethyl)-2,4'-bipyridin-6-amine (Intermediate T) and 5'-chloro-2'-fluoro-N-((tetrahydro-2H-pyran-4-yl)methyl)-3-(trifluoromethyl)-2,4'-bipyridin-6-amine (Intermediate U)

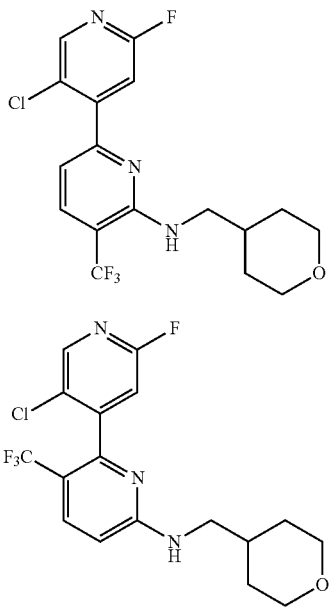

Step 1. Synthesis of 6-chloro-N-((tetrahydro-2H-pyran-4-yl)methyl)-5-(trifluoromethyl)pyridin-2-amine and 6-chloro-N-((tetrahydro-2H-pyran-4-yl)methyl)-3-(trifluoromethyl)pyridin-2-amine

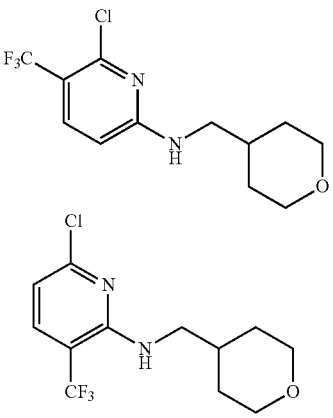

To a solution of 2,6-dichloro-3-(trifluoromethyl)pyridine (320 mg, 1.482 mmol) in DMSO (1.5 ml) at ambient temperature was added (tetrahydro-2H-pyran-4-yl)methanamine (188 mg, 1.630 mmol) and triethylamine (0.207 ml, 1.482 mmol). The resulting light brown mixture was heated at about 120° C. in a sealed glass bomb for about 18 hours. The reaction mixture was cooled to ambient temperature, diluted with EtOAc (20 mL), washed with saturated NaHCO₃ solution and brine, dried over sodium sulfate and concentrated in vacuo to yield 502 mg of a light brown crude liquid, which was purified by column chromatography (5 to 50% ethyl acetate in heptane)to yield the desired products.

6-chloro-N-((tetrahydro-2H-pyran-4-yl)methyl)-5-(trifluoromethyl)pyridin-2-amine: 340 mg, 78%: LCMS (m/z): 295.2 [M+H]+; Retention time=0.971 min; and 6-chloro-N-((tetrahydro-2H-pyran-4-yl)methyl)-3-(trifluoromethyl)pyridin-2-amine: 80 mg, 18%. LCMS (m/z): 295.1 [M+H]+; Retention time=1.033 min.

Step 2a. A mixture of 6-chloro-N-((tetrahydro-2H-pyran-4-yl)methyl)-3-(trifluoromethyl)pyridin-2-amine (100 mg, 0.339 mmol), 5-chloro-2-fluoropyridin-4-ylboronic acid (89 mg, 0.509 mmol), PdCl₂(dppf). CH₂Cl₂ adduct (27.7 mg, 0.034 mmol), DME (1.5 mL) and 2M aqueous Na₂CO₂ (0.5 mL, 1 mmol) was stirred in a sealed glass vessel at about 100° C. for about 3 hours. After cooling to ambient temperature the mixture was diluted with EtOAc (25 mL) and MeOH (20 mL), filtered and concentrated in vacuo. The resulting crude material was purified by column chromatography [silica gel, 12 g, EtOAc/hexane=5/100 to 50/50] to yield 5'-chloro-2'-fluoro-N-((tetrahydro-2H-pyran-4-yl)methyl)-5-(trifluoromethyl)-2,4'-bipyridin-6-amine (Intermediate T, 102 mg, 77%). LCMS (m/z): 390.2 [M+H]+; Retention time=1.12 min.

Step 2b. Intermediate U was synthesized following the procedure described for 5'-chloro-2'-fluoro-N-((tetrahydro-2H-pyran-4-yl)methyl)-5-(trifluoromethyl)-2,4'-bipyridin-6-amine LCMS (m/z): 390.2 [M+H]+; Retention time=1.01 min.

Synthesis of 3,5'-dichloro-N-((2,2-dimethyltetrahydro-2H-pyran-4-yl)methyl)-2'-fluoro-2,4'-bipyridin-6-amine (Intermediate V)

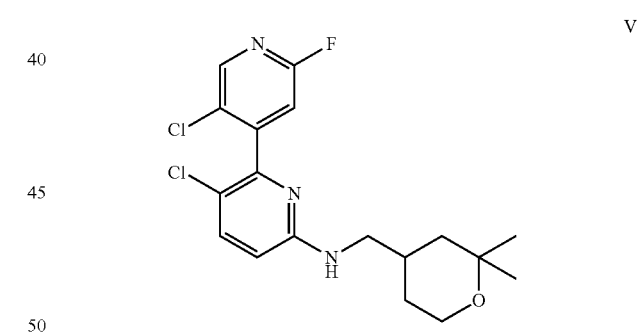

Step 1. 6-Bromo-2-aminopyridine (15 g, 87 mmol) and TEA (13.3 mL, 95 mmol) were dissolved in 173 mL of DCM. BOC-anhydride (20.8 g, 95 mmol) was then dissolved in 100 mL of DCM and added over 10 min using a syringe pump. The reaction mixture was stirred at ambient temperature for 72 hr. The solvents were evaporated and the resulting residue was purified by silica gel chromatography (heptane: EtOAc 1:0 to 7:3) to give the product as a colorless solid (23.0 g, 97%). LCMS (m/z): 272.8/274.8 (M+H), retention time=0.97 min.

Step 2. tert-Butyl 6-bromopyridin-2-ylcarbamate (23.0 g, 84 mmol) was mixed with acetonitrile, (CH₃CN, 281 mL), and NCS (11.24 g, 84 mmol). The reaction mixture was heated at about 85° C. for 3 hours, and an additional 5.5 g of NCS was then added. Heating was continued at about 85° C. for an additional 3 hours, followed by addition of 5.5 g of NCS. All starting materials were consumed after about 1 hour. Brine (50 mL) was added and acetonitrile was evaporated under vacuum. The residual aqueous solution was extracted three times with EtOAc. All EtOAc layers were combined, dried over Na2SO4, filtered through a fritted filter and concentrated under vacuum. The resulting residue was purified on silica gel, eluting with 3% EtOAc in heptane to afford the product as a colorless solid (14.6 g, 56.3%). LCMS (m/z): 306.9/308.9/310.9 (M+H), retention time=1.14 min.

Step 3. A solution of tert-Butyl 6-bromo-5-chloropyridin-2-ylcarbamate (2.32 g, 7.54 mmol) in DMF (25 mL) was mixed with sodium hydride (60% dispersion in mineral oil, 513 mg, 12.8 mmol), and the resulting mixture reaction mixture was stirred for 30 minutes at ambient temperature. (2,2-dimethyltetrahydro-2H-pyran-4-yl)methyl 4-methylbenzenesulfonate (3.15 g, 10.56 mmol), dissolved in 5 mL DMF, was then added and the resulting mixture was stirred at about 25° C. for 3 hours. The reaction mixture was partitioned between water and EtOAc. The layers were separated and the EtOAc layer was washed twice with water. The EtOAc layer was then dried over sodium sulfate, filtered through a fritted filter and concentrated under vacuum. The resulting residue was purified using silica gel chromatography (0 to 30% EtOAc in heptane) to yield the product as a colorless solid (2.16 g, 66%). LCMS (m/z): 432.9/434.9/436.9 (M+H), retention time=1.28 min.

Step 4. A mixture of tert-butyl 6-bromo-5-chloropyridin-2-yl((2,2-dimethyltetrahydro-2H-pyran-4-yl)methyl)carbamate (1.86 g, 4.29 mmol), 5-chloro-2-fluoropyridin-4-ylboronic acid (1.50 g, 8.58 mmol), PdCl2(dppf)*DCM adduct (350 mg, 0.429 mmol), DME (15.6 mL) and 2 M aqueous sodium carbonate solution (5.4 mL) were combined in a glass bomb. The bomb was sealed and heated at about 98° C. for 2 hours. The reaction mixture was cooled to ambient temperature and then diluted with EtOAc. The diluted mixture was washed three times with saturated aqueous NaHCO3 solution, dried over sodium sulfate, filtered through a fritted filter and concentrated under vacuum. Purification was done using silica gel chromatography (15% EtOAc in heptane) to yield the product as a colorless solid (1.5 g, 72%). LCMS (m/z): 484.2/486.1 (M+H), retention time=1.33 min.

Step 5. tert-Butyl 3,5'-dichloro-2'-fluoro-2,4'-bipyridin-6-yl((2,2-dimethyltetrahydro-2H-pyran-4-yl)methyl)carbamate (8 mg, 0.017 mmol), DCM (1 mL) and TFA (0.1 mL, 1.3 mmol) were combined in a 4 mL screw cap vial. The vial was capped and the reaction mixture mixture was stirred at ambient temperature for 1 hour. The solvent was evaporated under vacuum and the residual material was converted to the free base using sodium bicarbonate. (5.8 mg, 91%). LCMS (m/z): 3484.2/386.1/388.2 (M+H), retention time=1.07 min.

Synthesis of 2,3-difluoropyridin-4-ylboronic acid (Intermediate W)

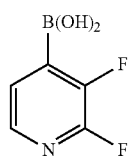

W

A mixture of THF and hexanes (6 mL, 1:1 v:v), and diisopropyl amine (0.681 mL, 4.78 mmol) was cooled to −78° C. BuLi (2.5 M in hexanes, 2.00 mL, 5.00 mmol) was added to the cooled mixture, followed by addition of 2,3-difluoropyridine after about 15 minutes. The mixture was stirred for 1 hour at −78° C. before being transferred to a 3 mL THF solution of triisopropyl borate (1.11 mL, 4.78 mmol) at −78° C. via a cannula. The resulting solution was stirred at −78° C. for 1 hour, slowly warmed up to ambient temperature and then quenched with 2 M NaOH solution (20 mL). The two layers were separated and the aqueous phase was washed once with ether. The aqueous phase was then acidified with HCl to pH 5 and extracted three times with EtOAc. The organic layers were combined, dried over sodium sulfate and concentrated to yield the product as a light yellow solid, which was used in the next step without purification. LCMS (m/z): 159.9 (M+H), retention time=0.35 min.

Synthesis of trans-N1-(1,3-dimethoxypropan-2-yl)cyclohexane-1,4-diamine (Intermediate X)

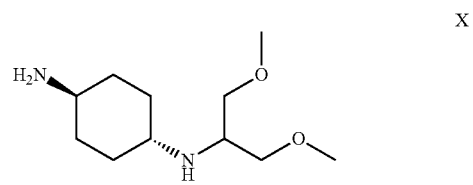

X

Step 1. To NaH (0.366 g, 9.16 mmol) in THF (12 mL) at 0° C. was added 1,3-dimethoxy-2-propanol (1 g, 8.32 mmol) in THF (8 mL) solution. The mixture was warmed to ambient temperature and stirred for 0.5 hour. To this was added tosyl chloride (1.587 g, 8.32 mmol) in one portion. The resulting white cloudy mixture then was stirred at ambient temperature for 16 hours. LC/MS showed complete conversion to 1,3-dimethoxypropan-2-yl 4-methylbenzenesulfonate. The reaction mixture mixture was poured into water and extracted with EtOAc. The organic extracts were combined, washed with brine, dried with sodium sulfate and concentrated in vacuo to yield 2 g of a colorless oil. The crude mixture was purified by Analogix system (silica gel column 80 g, gradient: 0 min, 100% n-heptane; 5-12 min, 20% EtOAc in Heptane; 12-15 min. 30% EtOAc in Heptane and hold until 30 min). The pure fractions were combined and concentrated in vacuo to yield 1.25 g of the tosylate product 1,3-dimethoxypropan-2-yl 4-methylbenzenesulfonate as a colorless oil, which solidified upon standing.

Step 2. To the tosylate obtained in Step 1 (0.8 g, 2.92 mmol) in DMSO (8 ml) was added 1,4-trans-cyclohexane diamine (0.999 g, 8.75 mmol). The resulting brown mixture was heated in a capped vial to about 95° C., with stirring, for 2 hours. The reaction mixture mixture was poured into 10% HCl in water (10 mL) at 0° C. (ice cubes in HCl) and extracted with DCM (1×20 mL). The aqueous (light pink) was basified with 6N NaOH to a pH>12 and extracted with DCM (2×20 mL). The organic extracts were combined, dried with sodium sulfate and concentrated in vacuo to yield compound "X" as a purple liquid. LC/MS showed containing desired product (M+1=217, Rt=0.32 min, no UV absorption at 214 nm wavelength). This was used in the next step without further purification.

Synthesis of 4-((5'-chloro-2',5-difluoro-2,4'-bipyridin-6-yl-amino)methyl)tetrahydro-2H-pyran-4-carbonitrile (Intermediate AA)

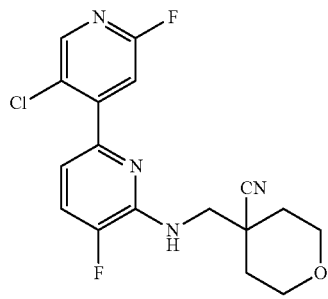 [SMILES: N#CC1(CNc2nc(-c3cc(F)ncc3Cl)ccc2F)CCOCC1]

Step 1: Synthesis of 4-((3,6-difluoropyridin-2-yl-amino)methyl)tetrahydro-2H-pyran-4-carbonitrile

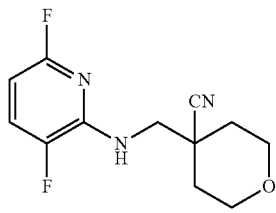 [SMILES: N#CC1(CNc2nc(F)ccc2F)CCOCC1]

To 2,3,6-Trifluoropyridine (0.6 g, 4.5 mmol) in DMSO (5 ml) at room temperature was added 4-(aminomethyl)tetrahydro-2H-pyran-4-carbonitrile (Intermediate R, 1.01 g, 7.23 mmol) and triethylamine (1.57 ml, 11.24 mmol) sequentially. The light brown mixture was heated at 105° C. in a sealed glass bomb for 18 hours. After cooled to room temperature the reaction mixture was extracted with EtOAc (40 ml), washed with saturated NaHCO₃ solution and brine, dried over sodium sulfate and concentrated in vacuo to give a light brown liquid. This crude material was purified by silica gel chromatography using a 12 g column, eluting with 5%-20% ethyl acetate in hexane to afford 550 mg (48.2% yield) of the desired product. LCMS (m/z): 254.1 [M+H]+; retention time=0.743 min. 1H NMR (400 MHz, CHLOROFORM-d) δ ppm 1.69-1.95 (m, 4 H) 3.60-3.82 (m, 4 H) 4.00 (ddd, J=12.13, 4.30, 1.96 Hz, 2 H) 5.02 (br. S., 1 H) 6.12 (td, J=5.58, 2.54 Hz, 1 H) 7.19-7.33 (m, 1 H).

Step 2: Synthesis of 4-((6-(benzyloxy)-3-fluoropyridin-2-yl-amino)methyl)tetrahydro-2H-pyran-4-carbonitrile

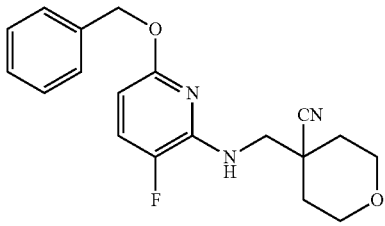 [SMILES: N#CC1(CNc2nc(OCc3ccccc3)ccc2F)CCOCC1]

Benzyl alcohol (352 mg, 3.26 mmol) was dissolved in anhydrous DMF (2 ml) and placed under argon. This was then treated with a 60% dispersion in oil of SODIUM HYDRIDE (78.7 mg, 3.26 mmol). This resultant suspension was then stirred at room temperature for 15 min. At this time it was treated with a solution of 4-((3,6-difluoropyridin-2-ylamino)methyl)tetrahydro-2H-pyran-4-carbonitrile (275 mg, 1.09 mmol) dissolved in anhydrous DMF (2 ml). Once the addition was complete the reaction was stirred at 90° C. for 5 hours. The reaction was allowed to cool to room temperature. It was then poured into brine (20 ml). This was extracted with EtOAc (3×15 ml). The combined extracts were washed with H₂O (3×10 ml) followed by brine (1×10 ml). The organic layer was dried (Na₂SO₄), filtered, and the solvent removed in vacuo to give the crude material which was purified using the ISCO and a 12 g SiO₂ column. Eluted using 100 hexanes to 30 EtOAc/70 hexanes over 20 min. 245 mg (66% yield) of the desired product was obtained as a viscous liquid. LCMS (m/z): 342.1 [M+H]+; retention time=1.017 min.

Step 3: Synthesis of 4-((3-fluoro-6-hydroxypyridin-2-yl-amino)methyl)tetrahydro-2H-pyran-4-carbonitrile

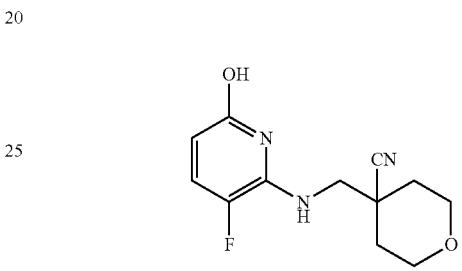

A mixture of 4-((6-(benzyloxy)-3-fluoropyridin-2-ylamino)methyl)tetrahydro-2H-pyran-4-carbonitrile (200 mg, 0.586 mmol), AMMONIUM FORMATE (111.3 mg, 1.758 mmol) and Pd—C (10%, wet, 25 mg) in methanol (4 ml) was stirred at 70° C. for 45 min and cooled. The mixture was then filtered to remove Pd—C and inorganics, the filterate was then concentrated and dried further via high vacuum to afford 141 mg (96% yield) of the crude product as a light pink solid. LCMS (m/z): 252.1 [M+H]+; retention time=0.540 min.

Step 4: Synthesis 6-((4-cyanotetrahydro-2H-pyran-4-yl)methyl)-amino-5-fluoropyridin-2-yl trifluoromethanesulfonate

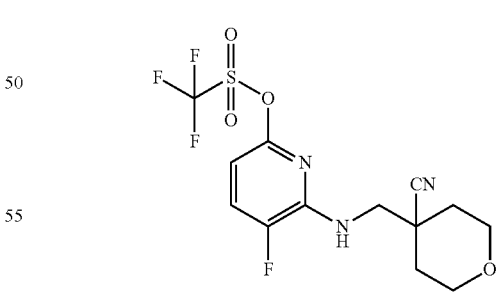

To a solution of 5-fluoro-6-((4-cyano-tetrahydro-2H-pyran-4-yl)methyl)aminopyridin-2-ol (141 mg, 0.562 mmol) and TEA (0.782 ml, 5.60 mmol) in DCM (6 ml) was added trifluoromethanesulfonic anhydride (0.142 ml, 0.842 mmol) slowly at 0° C. The mixture was stirred for 2 hours at 0° C. and one hour at room temperature and poured carefully into ice-cooled saturated aqueous NaHCO₃ solution. The separated aqueous layer was extracted with DCM (2×10 ml). The combined organic layers were dried over Na$_2$SO$_4$, filtered off and concentrated in vacuo. The residue was purified by column chromatography [ISCO, SiO$_2$, 12 g, 15 min, EtOAc/heptane=5/95 for 2 min, then EtOAc/heptane=5/95 to 40/60 for 2 min-17 min]. Pure fractions were combined and concentrated in vacuo to give a colorless oil (200 mg, 0.522 mmol, 93% yield) as the desired product. LCMS (m/z): 384.0 [M+H]+; Rt=0.946 min.

Step 5: Synthesis of 4-((5'-chloro-2',5-difluoro-2,4'-bipyridin-6-yl-amino)methyl)tetrahydro-2H-pyran-4-carbonitrile (Intermediate AA)

A mixture of 5-fluoro-6-((4-cyano-tetrahydro-2H-pyran-4-yl)methylamino)
pyridin-2-yl trifluoromethanesulfonate (200 mg, 0.522 mmol), 5-chloro-2-fluoropyridin-4-ylboronic acid (183.2 mg, 1.044 mmol), PdC$_2$(dppf)-CH$_2$Cl$_2$; adduct (85.1 mg, 0.104 mmol), and SODIUM CARBONATE (221.6 mg, 2.08 mmol, in 1 ml of water) in DME (3 ml) was de-gassed and heated at 110° C. for 20 min in a sealed microwave vial, cooled. The upper layer of mixture was separated, the bottom one was extracted with ethyl acetates, the organic layers were combined and concentrated to afford the crude product, which was purified by ISCO (10 to 50% ethyl acetate in heptane, 20 min) to afford 150 mg (79% yield) of the desired product was an off-white solid. LCMS (m/z): 365.1 [M+H]+; retention time=0.929 min.

Synthesis of 4-((5'-chloro-2'-fluoro-2,4'-bipyridin-6-yl-amino)methyl)tetrahydro-2H-pyran-4-carbonitrile (Intermediate AB)

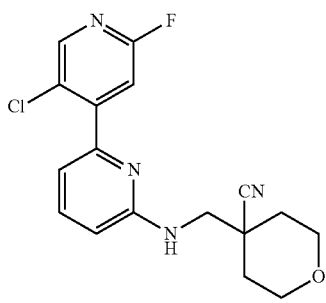 [SMILES: N#CC1(CNc2cccc(-c3cc(F)ncc3Cl)n2)CCOCC1]

A mixture of 4-((6-bromopyridin-2-yl-amino)methyl)tetrahydro-2H-pyran-4-carbonitrile (Intermediate S, 410 mg, 1.384 mmol), 5-chloro-2-fluoropyridin-4-ylboronic acid (362.2 mg, 2.07 mmol), PdCl$_2$(dppf).CH$_2$Cl$_2$ adduct (113 mg, 0.14 mmol), DME (5 Ml) and 2 M aqueous Na$_2$CO$_2$ (1.75 Ml, 3.5 mmol) was sealed and stirred at 110° C. for 20 min using microwave reactor. After cooling to room temperature the mixture was extracted with EtOAc (35 Ml), filtered and concentrated in vacuo. The crude material was purified by column chromatography [silica gel, 24 g, EtOAc/hexane=5/100 to 50/50] to provide 4-((5'-chloro-2'-fluoro-2,4'-bipyridin-6-ylamino)methyl)tetrahydro-2H-pyran-4-carbonitrile (360 mg, 75% yield). LCMS (m/z): 347 [M+H]+; retention time=0.814 min.

Synthesis of 5'-chloro-2'-fluoro-N-((4-methoxytetrahydro-2H-pyran-4-yl)methyl)-2,4'-bipyridin-6-amine (Intermediate AC)

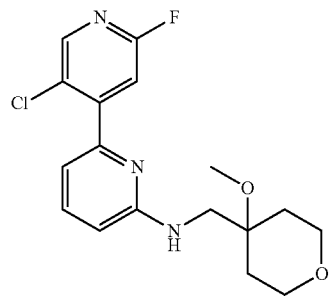 [SMILES: COC1(CNc2cccc(-c3cc(F)ncc3Cl)n2)CCOCC1]

Step 1: Synthesis of tert-butyl 6-bromopyridin-2-yl ((4-methoxytetrahydro-2H-pyran-4-yl)methyl)carbamate

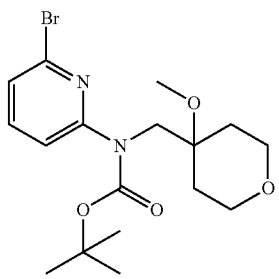 [SMILES: COC1(CN(C(=O)OC(C)(C)C)c2cccc(Br)n2)CCOCC1]

To a solution of tert-butyl 6-bromo-pyridin-2-ylcarbamate (136 mg, 0.50 mmol) in DMF (2 ml) under nitrogen was added NaH (60%, 40 mg, 1.0 mmol) under stirring. The resultant mixture was stirred at room temperature for one hour. A solution of (4-methoxytetrahydro-2H-pyran-4-yl)methyl 4-methylbenzenesulfonate (Intermediate O, 152 mg, 0.506 mmol) in DMF (1.5 ml) was then added. The resulting mixture was then stirred at 85° C. for about 18 hours. The mixture was diluted with 30 ml of ethyl acetate, washed with water (20 ml×3) and dried with sodium sulfate. After concentration the residue was purified by silica gel chromatography using a 12 g column, eluting with 5-20% ethyl acetate in hexane to give the desired title compound as a viscous oil (92 mg, 46% yield), which solidified upon standing overnight. LCMS (m/z): 403.1[M+H]+; Rt=1.026 min.

Step 2: Synthesis of tert-butyl 5'-chloro-2'-fluoro-2,4'-bipyridin-6-yl((4-methoxytetrahydro-2H-pyran-4-yl)methyl)carbamate

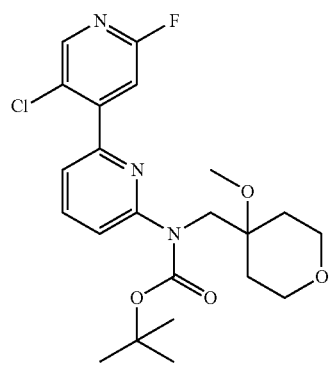 [SMILES: COC1(CN(C(=O)OC(C)(C)C)c2cccc(-c3cc(F)ncc3Cl)n2)CCOCC1]

A mixture of tert-butyl 6-bromo-pyridin-2-yl((4-methoxytetrahydro-2H-pyran-4-yl)methyl)carbamate (50 mg, 0.125 mmol), 5-chloro-2-fluoropyridin-4-ylboronic acid (43.7 mg, 0.249 mmol), PdCl$_2$(dppf).CH$_2$Cl$_2$ adduct (15.2 mg, 0.019 mmol), DME (1.5 Ml) and 2M aqueous Na$_2$CO$_3$ (0.25 Ml, 0.5 mmol) was sealed and stirred at 100° C. for 3 hours. After cooling to room temperature the mixture was diluted with EtOAc (15 Ml), filtered and concentrated in vacuo. The crude material was purified by column chromatography [silica gel, 12 g, EtOAc/hexane=5/100 to 50/50] to provide tert-butyl 5'-chloro-2'-fluoro-2,4'-bipyridin-6-yl((4-methoxytetrahydro-2H-pyran-4-yl)methyl)carbamate (32 mg, 57% yield). LCMS (m/z): 452.2 [M+H]+; retention time=1.068 min.

Step 3: Synthesis of 5'-chloro-2'-fluoro-N-((4-methoxytetrahydro-2H-pyran-4-yl)methyl)-2,4'-bipyridin-6-amine (Intermediate AC)

A solution of tert-butyl 5'-chloro-2'-fluoro-2,4'-bipyridin-6-yl((4-methoxytetrahydro-2H-pyran-4-yl)methyl)carbamate (32 mg, 0.071 mmol) and TRIFLUOROACETIC ACID (0.982 ml, 12.75 mmol) in DCM (2 ml) was stirred at room temperature for 40 min. The mixture was then concentrated to afford 22 mg of the crude material which was used in the next step without purification. LCMS (m/z): 352.2 [M+H]+; Rt=0.634 min.

Example 1a

Compound 1

N2'-(trans-4-aminocyclohexyl)-5'-chloro-N6-(3-fluorobenzyl)-2,4'-bipyridine-2',6-diamine

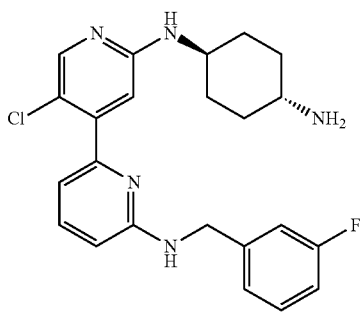

Step 1. Preparation of trans-N1-(5-chloro-4-iodopyridin-2-yl)cyclohexane-1,4-diamine A mixture of 5-chloro-2-fluoro-4-iodopyridine (1000 mg, 3.88 mmol), DMSO (7 ml), and trans-cyclohexane-1,4-diamine (2661 mg, 23.31 mmol) reaction mixture was stirred at about 85° C. for 2 hours, followed by LCMS. The crude reaction mixture mixture then was mixed with 5 ml DMSO, filtered and purified by prep LC. After lyapholization, 1.17 grams of the title compound was obtained as a TFA salt. LCMS (m/z): 352.1 (MH+), retention time=0.50 min.

Step 2. Preparation of trans-N1-(5'-chloro-6-fluoro-2,4'-bipyridin-2'-yl)cyclohexane-1,4-diamine A mixture of trans-N1-(5-chloro-4-iodopyridin-2-yl)cyclohexane-1,4-diamine (from step 1 above, 300 mg, 0.853 mmol), 2-fluoro-6-(4,4,5,5-tetramethyl-1,3,2-dioxaborolan-2-yl)pyridine (285 mg, 1.280 mmol), PdCl2(dppf).CH2Cl2 adduct (84 mg, 0.102 mmol), DME (4 ml), Ethanol (1 ml), and 2M sodium carbonate (1.706 ml, 3.41 mmol) reaction mixture was stirred at about 90° C. until done by LCMS. The reaction mixture mixture was cooled, then diluted with 25 ml of ethyl acetate and 10 ml of methanol, filtered, and concentrated to yield a crude solid. The crude solid was dissolved in DMSO, filtered and purified by prep LC. After lyapholization, 200 mg of the title compound was obtained as a TFA salt. LCMS (m/z): 321.0 (MH+), retention time=0.48 min.

Step 3. Preparation of N2'-(trans-4-aminocyclohexyl)-5'-chloro-N6-(3-fluorobenzyl)-2,4'-bipyridine-2',6-diamine To trans-N1-(5'-chloro-6-fluoro-2,4'-bipyridin-2'-yl)cyclohexane-1,4-diamine (from Step 2 above, 200 mg, 0.623 mmol) was added DMSO (2 ml) and (3-fluorophenyl)methanamine (351 mg, 2.81 mmol). The crude reaction mixture mixture was stirred at 115° C. until done, as indicated by LCMS. The excess amine was removed under reduced pressure. The resulting crude residue was dissolved in 2 ml of DMSO, filtered, purified by prep LC and lyphilized to yield a TFA salt. The TFA salt was free-based using 200 ml of ethyl acetate and washed with saturated sodium bicarbonate 35 ml (1×), water (2×), saturated brine (1×), dried over sodium sulfate, filtered and concentrated to yield a solid. The solid was dissolved in (1:1 ACN/water), filtered, and lyapholized to yield 80 mg of the title compound as free-base. LCMS (m/z): 426.1 (MH+), retention time=0.61 min.; 1H NMR (300 MHz, METHANOL-d4, 25° C.) 1.21-1.40 (m, 4 H) 1.89-2.00 (m, 2 H) 2.07 (d, J=10.56 Hz, 2 H) 2.69-2.79 (m, 1 H) 3.55-3.64 (m, 1 H) 4.57 (s, 2 H) 6.53 (d, J=8.61 Hz, 1 H) 6.59 (s, 1 H) 6.80 (d, J=7.04 Hz, 1 H) 6.90-6.97 (m, 1 H) 7.09 (d, J=10.17 Hz, 1 H) 7.14-7.20 (m, 1 H) 7.25-7.34 (m, 1 H) 7.48 (t, J=7.83 Hz, 1 H) 7.93 (s, 1 H)

Example 1b

Compound 1

N2'-(trans-4-aminocyclohexyl)-5'-chloro-N6-(3-fluorobenzyl)-2,4'-bipyridine-2',6-diamine

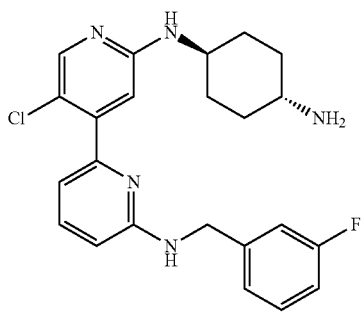

Step 1. Preparation of 6-bromo-N-(3-fluorobenzyl)pyridin-2-amine

A mixture of 2,6-dibromopyridine (7.1 g, 30.0 mmol), NMP (16 ml), (3-fluorophenyl)methanamine (4.13 g, 33.0 mmol) and Hunig's Base (5.76 ml, 33.0 mmol) was flushed with argon. The crude reaction mixture mixture was stirred at 115-120° C. for about 168 hours. LC/MS was used to monitor the reaction. The crude mixture was then cooled to room temperature, and then diluted with 250 ml of ethyl acetate, washed with saturated sodium bicarbonate (2×), water (2×), saturated, salt solution (1×), dried over sodium sulfate, filtered, and concentrated under reduced pressure to yield a residue. The residue was purified by silica gel chromatography using a 120 g column, eluting from 0%-20% ethyl acetate with hexane. The desired fractions were concentrated to yield, 7.11 grams of the titled compound as a free base, which was used in the next step without further purification. LCMS (m/z): 281.1/283.1 (MH+), retention time=1.03 min.

Step 2. Preparation of 5'-chloro-2'-fluoro-N-(3-fluorobenzyl)-2,4'-bipyridin-6-amine A mixture of 6-bromo-N-(3-fluorobenzyl)pyridin-2-amine (2.0 g, 7.11 mmol), 5-chloro-2-fluoropyridin-4-ylboronic acid (1.996 g, 11.38 mmol), PdCl$_2$(dppf).CH$_2$Cl$_2$ adduct (0.465 g, 0.569 mmol), DME (27 ml), and 2M sodium carbonate (9.25 ml, 18.50 mmol) reaction mixture was stirred at about 100° C. for 3 hours. The crude mixture was cooled to room temperature, diluted with 25 ml ethyl acetate and 20 ml methanol, filtered and concentrated to yield crude residue. The crude residue was purified by silica gel chromatography using a 120 g column, eluting from 0%-20% ethyl acetate with hexane. The desired fractions were concentrated to constant mass, to yield 1.259 grams of titled compound as free base, which was used in the next step without further purification. LCMS (m/z): 332.2 (MH+), retention time=0.92 min.

Step 3. Preparation of N2'-(trans-4-aminocyclohexyl)-5'-chloro-N6-(3-fluorobenzyl)-2,4'-bipyridine-2',6-diamine A mixture of 5'-chloro-2'-fluoro-N-(3-fluorobenzyl)-2,4'-bipyridin-6-amine (725 mg, 2.185 mmol) was added DMSO (7 ml), trans-cyclohexane-1,4-diamine (1996 mg, 17.48 mmol) and TEA (0.609 ml, 4.37 mmol) was stirred at about 100° C. for 20 hours. The reaction was monitored by LC/MS. The crude reaction mixture mixture was cooled to room temperature, diluted with 3 ml DMSO, filtered, and purified by prep HPLC. (there is a general HPLC conditions in the general experimental session). The fractions were concentrated, mixed with 500 ml ethyl acetate, and basified with saturated sodium bicarbonate 120 ml. The ethyl acetate layer was separated, and the basic water layer was extracted with 300 ml ethyl acetate. The ethyl acetate layers were combined and washed with water (3×), saturated salt solution (1×), dried with sodium sulfate, filtered and concentrated to yield a solid. The solid was dissolved in (1:1 ACN/water) filtered and lyapholized to yield 755 mg of the title compound as free-base. LCMS (m/z): 426.3 (MH+), retention time=0.59 min.; 1H NMR (300 MHz, METHANOL-d4, 25° C.) δ ppm 1.10-1.43 (m, 4 H) 1.90 (d, J=12.01 Hz, 2 H) 2.01 (d, J=12.01 Hz, 2 H) 2.70-2.84 (m, 1 H) 3.47-3.60 (m, 1 H) 4.48 (s, 2 H) 6.44 (d, J=8.50 Hz, 1 H) 6.51 (s, 1 H) 6.71 (d, J=7.33 Hz, 1 H) 6.79-6.91 (m, 1 H) 7.00 (d, J=9.96 Hz, 1 H) 7.05-7.13 (m, 1 H) 7.15-7.27 (m, 1 H) 7.40 (t, J=7.77 Hz, 1 H) 7.85 (s, 1 H)

Example 2

Compound 2

N2'-(trans-4-aminocyclohexyl)-N6-(cyclohexylmethyl)-2,4'-bipyridine-2',6-diamine

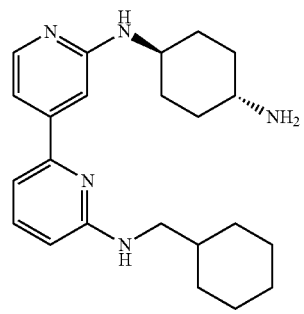

Step 1. Preparation of trans-N1-(4-bromopyridin-2-yl)cyclohexane-1,4-diamine

A mixture of 4-bromo-2-chloropyridine (1500 mg, 7.79 mmol), DMSO (15 ml), and trans-cyclohexane-1,4-diamine (4450 mg, 39.0 mmol) was stirred at 100° C. until the formation of the product, as indicated by LCMS. The reaction mixture was cooled to room temperature, filtered and purified by prep LC, and lyapholized to yield 393 mg of the title compound as a TFA salt. LCMS (m/z): 270.2/272.2 (MH+), retention time=0.31 min.

Step 2. Preparation of trans-N1-(6-fluoro-2,4'-bipyridin-2'-yl)cyclohexane-1,4-diamine A mixture of trans-N1-(4-bromopyridin-2-yl)cyclohexane-1,4-diamine (102 mg, 0.377 mmol), 2-fluoro-6-(4,4,5,5-tetramethyl-1,3,2-dioxaborolan-2-yl)pyridine (80 mg, 0.359 mmol), PdCl2(dppf).CH$_2$Cl$_2$ adduct (29.3 mg, 0.036 mmol), DME (2 ml), Ethanol (0.2 ml), and 2M sodium carbonate (0.717 ml, 1.435 mmol) reaction mixture was stirred at about 85° C. until completion, as indicated by LCMS. The crude mixture was cooled to room temperature, diluted with 5 ml of ethyl acetate and 2 ml of methanol, filtered and concentrated to yield a crude solid. The solid was dissolved in DMSO, refiltered, purified by prep LC, and lyophilized to yield 64 mg of the title compound as its TFA salt. LCMS (m/z): 287.2 (MH+), retention time=0.43 min.

Step 3. Preparation of N2'-(trans-4-aminocyclohexyl)-N6-(cyclohexylmethyl)-2,4'-bipyridine-2',6-diamine A mixture of trans-N1-(6-fluoro-2,4'-bipyridin-2'-yl)cyclohexane-1,4-diamine (15 mg, 0.052 mmol), DMSO (0.4 ml), and cyclohexylmethanamine (59.3 mg, 0.524 mmol) was heated at about 105° C. for about 24 hours, or until the product pormation was completed, as indicated by LCMS. The excess amine was removed under reduced pressure to yield a residue. The residue was mixed with 0.5 ml of DMSO, filtered and purified by prep LC. After lyophilization, 11.3 mg of the title compound was obtained as a TFA salt. LCMS (m/z): 380.3 (MH+), retention time=0.61 min. 1H NMR (400 MHz, METHANOL-d4, 45° C.) δ ppm 0.97-1.11 (m, 2 H) 1.17-1.36 (m, 3 H) 1.49-1.72 (m, 6 H) 1.71-1.80 (m, 2 H) 1.84 (d, J=12.91 Hz, 2 H) 2.11-2.28 (m, 4 H) 3.13-3.25 (m, 1 H) 3.28 (d, 2 H, App.) 3.65-3.75 (m, 1 H) 6.65 (d, J=8.61 Hz, 1 H) 7.16 (d, J=7.43 Hz, 1 H) 7.43-7.48 (m, 1 H) 7.52 (t, J=7.83 Hz, 1 H) 7.64 (s, 1 H) 7.85 (d, J=7.04 Hz, 1 H)

Example 3

Compound 3 trans-N1-(5-chloro-4-(6-(cyclohexylmethylamino) pyridin-2-yl)pyrimidin-2-yl)cyclohexane-1,4-diamine

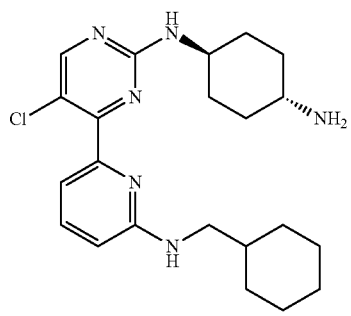 [SMILES: N[C@H]1CC[C@H](Nc2ncc(Cl)c(-c3cccc(NCC4CCCCC4)n3)n2)CC1]

Step 1. Preparation of 2,5-dichloro-4-(6-fluoropyridin-2-yl)pyrimidine

A mixture of 2,4,5-trichloropyrimidine (49.3 mg, 0.269 mmol), 2-fluoro-6-(4,4,5,5-tetramethyl-1,3,2-dioxaborolan-2-yl)pyridine (50 mg, 0.224 mmol), PdCl$_2$(dppf).CH$_2$Cl$_2$ adduct (18.31 mg, 0.022 mmol), DME (0.7 ml), and 2M sodium carbonate (0.247 ml, 0.493 mmol) reaction mixture was stirred at about 80° C. until the reaction mixture was complete, as indicated by LCMS. The reaction mixture mixture was cooled, diluted with 5 ml of ethyl acetate and 1 ml of methanol, filtered and concentrated to yield a crude solid. The crude material was purified by silica gel chromatography using a 12 g column, eluting from 0%-40% ethyl acetate with hexane. The desired fractions were concentrated to constant mass, to yield 39.5 mg of titled compound as a free base. LCMS (m/z): 244.0 (MH+), retention time=0.89 min.

Step 2. Preparation of trans-N1-(5-chloro-4-(6-fluoropyridin-2-yl)pyrimidin-2-yl)cyclohexane-1,4-diamine A mixture of 2,5-dichloro-4-(6-fluoropyridin-2-yl)pyrimidine (37 mg, 0.152 mmol), DMSO (1.5 ml) and trans-cyclohexane-1,4-diamine (87 mg, 0.758 mmol) reaction mixture was stirred at about 75° C. for about 2 hours. The reaction mixture was cooled, filter and purified by prep LC, and then lyophilized to yield 39.5 mg of the title compound as a TFA salt. LCMS (m/z): 322.2 (MH+), retention time=0.59 min.

Step 3. Preparation of trans-N1-(5-chloro-4-(6-(cyclohexylmethylamino)pyridin-2-yl)pyrimidin-2-yl)cyclohexane-1,4-diamine A mixture of trans-N1-(5-chloro-4-(6-fluoropyridin-2-yl)pyrimidin-2-yl)cyclohexane-1,4-diamine (12 mg, 0.037 mmol), cyclohexylmethanamine (42.2 mg, 0.373 mmol), and DMSO (0.35 ml) was stirred at about 105° C. for about 24 hours. The excess cyclohexylmethanamine was removed under vacuum to yield a residue. The residue was mixed with 0.5 ml DMSO, filtered, purified by prep HPLC and then lyophilized to yield 9.4 mg of the title compound as a TFA salt. LCMS (m/z): 415.3 (MH+), retention time=0.67 min.; 1H NMR (400 MHz, METHANOL-d4, 45° C.) δ ppm 0.89-1.07 (m, 2 H) 1.10-1.30 (m, 3 H) 1.30-1.54 (m, 4 H) 1.55-1.65 (m, 2 H) 1.69 (d, J=12.91 Hz, 2 H) 1.76 (d, J=12.91 Hz, 2 H) 1.96-2.14 (m, 4 H) 2.98-3.10 (m, 1 H) 3.18 (d, J=6.65 Hz, 2 H) 3.71-3.82 (m, 1 H) 7.03 (d, J=9.00 Hz, 1 H) 7.49 (br. s., 1 H) 7.83 (t, J=8.22 Hz, 1 H) 8.35 (s, 1 H)

Example 4

Compound 4

(N2'-(trans-4-(aminomethyl)cyclohexyl)-5'-chloro-N6-(3-fluorobenzyl)-2,4'-bipyridine-2',6-diamine

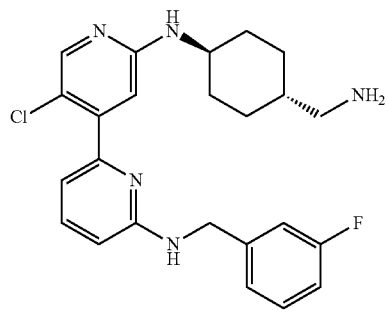

Step 1. Preparation of tert-butyl(trans-4-(5-chloro-4-iodopyridin-2-yl-amino)cyclohexyl)methylcarbamate A mixture of 5-chloro-2-fluoro-4-iodopyridine (517 mg, 2.008 mmol), tert-butyl (trans-4-aminocyclohexyl)methylcarbamate (550 mg, 2.410 mmol), DMSO (2 ml) and TEA (0.336 ml, 2.410 mmol) reaction mixture was stirred at about 95° C. for about 26 hours. The crude reaction mixture mixture was cooled to room temperature, mixed with 125 ml ethyl acetate, washed with saturated sodium bicarbonate (2×), water (3×), saturated salt solution (1×), dried sodium sulfate, filtered and concentrated under reduced pressure to yield a residue. The residue was purified by silica gel chromatography using a 40 g column, eluting from 0%-35% ethyl acetate with hexane. The desired fractions were concentrated to constant mass, yielding 656 mg of titled compound as free base. LCMS (m/z): 466.1 (MH+), retention time=0.93 min.

Step 2. Preparation of tert-butyl(trans-4-(5'-chloro-6-fluoro-2,4'-bipyridin-2'-yl-amino)cyclohexyl)methylcarbamate A mixture of tert-butyl(trans-4-(5-chloro-4-iodopyridin-2-yl-amino)cyclohexyl)methylcarbamate (510 mg, 1.095 mmol), 2-fluoro-6-(4,4,5,5-tetramethyl-1,3,2-dioxaborolan-2-yl)pyridine (440 mg, 1.971 mmol), PdCl$_2$(dppf).CH$_2$Cl$_2$ adduct (89 mg, 0.109 mmol), DME (7.5 ml), and 2M sodium carbonate (2.464 ml, 4.93 mmol) reaction mixture was stirred at about 100° C. for about 2 hours. The reaction mixture mixture was cooled to room temperature, mixed with 20 ml ethyl acetate, filtered and concentrated to yield a crude solid. The crude solid was purified by silica gel chromatography using 40 g column, eluting from 0%-45% ethyl acetate with hexane. The desired fractions were concentrated to constant mass, yielding 396 mg of titled compound as a free base. LCMS (m/z): 435.2 (MH+), retention time=0.85 min.

Step 3. Preparation of N-(trans-4-(aminomethyl)cyclohexyl)-5'-chloro-6-fluoro-2,4'-bipyridin-2'-amine A mixture of tert-butyl(trans-4-(5'-chloro-6-fluoro-2,4'-bipyridin-2'-yl-amino)cyclohexyl)methylcarbamate (390 mg, 0.897 mmol), 4M HCl in Dioxane (5604 µl, 22.42 mmol) reaction mixture was stirred at ambient temperature for 1 hr. The crude reaction mixture mixture was concentrated, and then dried under high vacuum to a constant mass giving 335 mg of the title compound as a HCL salt. LCMS (m/z): 335.1 (MH+), retention time=0.51 min.

Step 4. Preparation of N2'-(trans-4-(aminomethyl)cyclohexyl)-5'-chloro-N6-(3-fluorobenzyl)-2,4'-bipyridine-2',6-diamine A mixture of N-(trans-4-(aminomethyl)cyclohexyl)-5'-chloro-6-fluoro-2,4'-bipyridin-2'-amine (15 mg, 0.045 mmol), DMSO (0.35 ml), TEA (0.012 ml, 0.090 mmol) and (3-fluorophenyl)methanamine (50.5 mg, 0.403 mmol) reaction mixture was flushed with argon and then stirred at about 105° C. for about 40 hours. The excess (3-fluorophenyl)methanamine was removed under reduced pressure to yield a crude material, which was mixed with 0.5 ml DMSO, filtered, purified by prep LC, and then lyophilized to yield 11.2 mg of the title compound, as a TFA salt. LCMS (m/z): 440.2(MH+), retention time=0.62 min. 1H NMR (300 MHz, METHANOL-d4, 25° C.) δ ppm 1.11-1.28 (m, 2 H) 1.28-1.47 (m, 2 H) 1.67 (ddd, J=10.92, 7.40, 3.66 Hz, 1 H) 1.92 (d, J=11.72 Hz, 2 H) 2.14 (d, J=10.55 Hz, 2 H) 2.83 (d, J=6.74 Hz, 2 H) 3.57-3.69 (m, 1 H) 4.63 (s, 2 H) 6.84 (d, J=8.79 Hz, 1 H) 6.90 (s, 1 H) 6.94 (d, J=7.03 Hz, 1 H) 6.96-7.03 (m, 1 H) 7.10 (d, J=9.96 Hz, 1 H) 7.18 (d, J=7.62 Hz, 1 H) 7.29-7.39 (m, 1 H) 7.69-7.77 (m, 1 H) 8.01 (s, 1 H)

Example 5

Compound 5

(5'-chloro-N6-(3-fluorobenzyl)-N2'-(piperidin-4-yl)-2,4'-bipyridine-2',6-diamine)

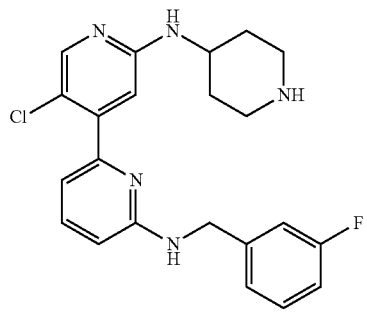 [SMILES: Fc1cccc(CNc2cccc(-c3cc(NC4CCNCC4)ncc3Cl)n2)c1]

Step 1. Preparation of tert-butyl 4-(5-chloro-4-iodopyridin-2-yl-amino)piperidine-1-carboxylate A mixture of 5-chloro-2-fluoro-4-iodopyridine (517 mg, 2.008 mmol), tert-butyl 4-aminopiperidine-1-carboxylate (603 mg, 3.01 mmol), DMSO (2 ml) and TEA (0.420 ml, 3.01 mmol) reaction mixture was stirred at 90° C. for 18 hours. The reaction mixture was cooled to room temperature, mixed with 150 ml of ethyl acetate, washed with saturated sodium bicarbonate (2×), water (3×), saturated salt solution (1×), dried sodium sulfate, filtered and concentrated to yield a crude material, which was purified by silica gel chromatography using a 40 g column, eluting from 0%-40% ethyl acetate with hexane. The desired fractions were concentrated to constant mass, giving 585 mg of the title compound as free base. LCMS (m/z): 438.1 (MH+), retention time=1.00 min.

Step 2. Preparation of tert-butyl 4-(5'-chloro-6-fluoro-2,4'-bipyridin-2'-yl-amino)piperidine-1-carboxylate A mixture of tert-butyl 4-(5-chloro-4-iodopyridin-2-yl-amino)piperidine-1-carboxylate (468 mg, 1.069 mmol), 2-fluoro-6-(4,4,5,5-tetramethyl-1,3,2-dioxaborolan-2-yl)pyridine (429 mg, 1.925 mmol), PdCl$_2$(dppf).CH$_2$Cl$_2$ adduct (87 mg, 0.107 mmol), DME (7.5 ml), and 2M sodium carbonate (2.406 ml, 4.81 mmol) reaction mixture was stirred at 100° C. for 2 hr. The reaction mixture mixture was cooled to room temperature, mixed with 20 ml of ethyl acetate, filtered and concentrated to yield a crude material. The crude material was purified by silica gel chromatography using a 40 g column, eluting from 0%-40% ethyl acetate with hexane. The desired fractions were combined and concentrated to constant mass, giving 360 mg of the title compound as free base. LCMS (m/z): 407.2 (MH+), retention time=0.85 min.

Step 3. Preparation of tert-butyl 4-(5'-chloro-6-(3-fluorobenzylamino)-2,4'-bipyridin-2'-yl-amino)piperidine-1-carboxylate A mixture of tert-butyl 4-(5'-chloro-6-fluoro-2,4'-bipyridin-2'-yl-amino)piperidine-1-carboxylate (200 mg, 0.492 mmol), DMSO (2 ml), TEA (0.137 ml, 0.983 mmol) and (3-fluorophenyl)methanamine (554 mg, 4.42 mmol) reaction mixture was flushed with argon and stirred at 100° C. for 40 hr, as the reaction mixture progress was followed by LCMS. The reaction mixture was cooled to room temperature, mixed with 150 ml of ethyl acetate, washed with saturated sodium bicarbonate (2×), water (3), saturated salt solution (1×), dried over sodium sulfate, filtered and concentrated to yield a crude material, which was purified by silica gel chromatography using a 12 g column, eluting from 0%-35% ethyl acetate with hexane. The desired fractions were collected and concentrated to constant mass, giving 225 mg of the title compound as a free base. LCMS (m/z): 512.3 (MH+), retention time=0.91 min.

Step 4. Preparation of 5'-chloro-N6-(3-fluorobenzyl)-N2'-(piperidin-4-yl)-2,4'-bipyridine-2',6-diamine A mixture of tert-butyl 4-(5'-chloro-6-(3-fluorobenzylamino)-2,4'-bipyridin-2'-yl-amino)piperidine-1-carboxy late (220 mg, 0.430 mmol), HCl 4M in Dioxane (7 mL, 28.0 mmol) was stirred at ambient temperature for 1 hr. The solvent was evaporated under reduced pressure to yield a solid which was furthe dried under high vacuum to yield 250 mg of the title compound as a HCl salt. A portion of the title compound was purified by prep LC, and then lyophilized to yield 19.0 mg of the title compound as a TFA salt. LCMS (m/z): 412.2 (MH+), retention time=0.60 min.; 1H NMR (300 MHz, METHANOL-d4, 25° C.) δ ppm 1.66-1.83 (m, 2 H) 2.25 (dd, J=14.21, 3.08 Hz, 2 H) 3.08-3.21 (m, 2 H) 3.36-3.51 (m, 2 H) 3.96-4.12 (m, 1 H) 4.65 (s, 2 H) 6.74 (s, 1 H) 6.91 (s, 1 H) 6.94 (s, 1 H) 6.98-7.06 (m, 1 H) 7.12 (d, J=9.96 Hz, 1 H) 7.19 (d, J=7.62 Hz, 1 H) 7.31-7.43 (m, 1 H) 7.77-7.85 (m, 1 H) 8.09 (s, 1 H)

Example 6

Compound 6

5'-chloro-N2'-(1-(ethylsulfonyl)piperidin-4-yl)-N6-(3-fluorobenzyl)-2,4'-bipyridine-2',6-diamine

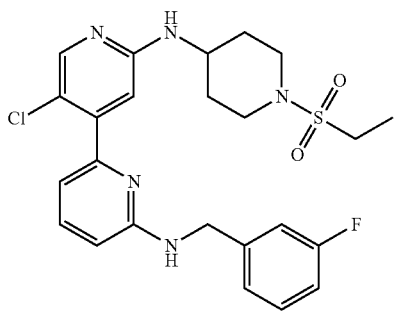 [SMILES: CCS(=O)(=O)N1CCC(Nc2cc(-c3cccc(NCc4cccc(F)c4)n3)c(Cl)cn2)CC1]

Preparation of 5'-chloro-N2'-(1-(ethylsulfonyl)piperidin-4-yl)-N6-(3-fluoro benzyl)-2,4'-bipyridine-2',6-diamine A mixture of 5'-chloro-N6-(3-fluorobenzyl)-N2'-(piperidin-4-yl)-2,4'-bipyridine-2',6-diamine (Example 6, 16 mg, 0.039 mmol), dichloromethane (0.5 ml), and TEA (0.022 ml, 0.155 mmol) was cooled to 0° C. This cooled mixture was then diluted with a solution of 0.03 ml of dichlormethane with ethanesulfonyl chloride (6.99 mg, 0.054 mmol). The reaction mixture then was warmed to ambient temperature and stirred for 1 hour, followed by LCMS. The reaction mixture solvent was removed under reduced pressure, to yield a residue which was dissolved in 0.75 ml DMSO, filtered, purified by prep LC and then lyophilized to yield 9.9 mg of the title compound, as a TFA salt. LCMS (m/z): 504.2 (MH+), retention time=0.77 min.; 1H NMR (300 MHz, METHANOL-d4, 25° C.) δ ppm 1.32 (t, J=7.33 Hz, 3 H) 1.47-1.67 (m, 2 H) 2.08 (d, J=10.84 Hz, 2 H) 2.96-3.12 (m, 4 H) 3.75 (d, J=12.89 Hz, 2 H) 3.80-3.92 (m, 1 H) 4.65 (s, 2 H) 6.83 (s, 1 H) 6.92 (d, J=9.08 Hz, 1 H) 6.95 (d, J=7.62 Hz, 1 H) 7.01 (t, J=8.64 Hz, 1 H) 7.11 (d, J=9.96 Hz, 1 H) 7.19 (d, J=7.62 Hz, 1 H) 7.30-7.41 (m, 1 H) 7.75-7.85 (m, 1 H) 8.06 (s, 1 H)

Example 7

Compound 7

N-(trans-4-(5'-chloro-6-(3-fluorobenzylamino)-2,4'-bipyridin-2'-yl-amino)cyclohexyl)-2-(dimethylamino)acetamide

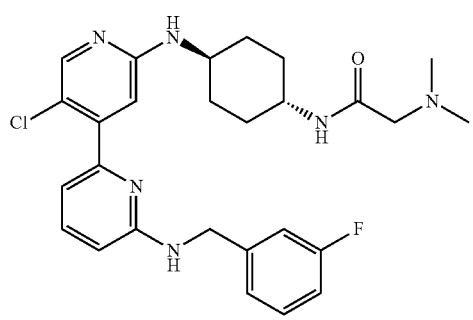 [SMILES: CN(C)CC(=O)N[C@H]1CC[C@H](Nc2cc(-c3cccc(NCc4cccc(F)c4)n3)c(Cl)cn2)CC1]

Preparation of N-(trans-4-(5'-chloro-6-(3-fluorobenzylamino)-2,4'-bipyridin-2'-yl-amino)cyclohexyl)-2-(dimethylamino)acetamide A mixture of 2-(dimethylamino)acetic acid (6.05 mg, 0.059 mmol), NMP (0.5 ml), Huenig's Base (0.023 ml, 0.132 mmol), and HATU (24.55 mg, 0.065 mmol) was stirred at ambient temperature for 5 minutes, followed by addition of N2'-(trans-4-aminocyclohexyl)-5'-chloro-N6-(3-fluorobenzyl)-2,4'-bipyridine-2',6-diamine (Example 1) (12.5 mg, 0.029 mmol). The resulting mixture was stirred at ambient temperature for 4 hours. The crude reaction mixture mixture was diluted with 0.25 ml of DMSO, filtered, purified by prep LC and then lyophilized to yield 6.8 mg of the title compound, as a TFA salt. LCMS (m/z): 511.3 (MH+), retention time=0.62 min.; 1H NMR (300 MHz, METHANOL-d4, 25° C.) δ ppm 1.32-1.53 (m, 4 H) 1.98-2.07 (m, 2 H) 2.07-2.18 (m, 2 H) 2.92 (s, 6 H) 3.60-3.68 (m, 1 H) 3.70-3.82 (m, 1 H) 3.90 (s, 2 H) 4.63 (s, 2 H) 6.83 (d, J=8.79 Hz, 1 H) 6.86 (s, 1 H) 6.93 (d, J=7.03 Hz, 1 H) 6.99 (s, 1 H) 7.10 (d, J=9.67 Hz, 1 H) 7.18 (d, J=7.62 Hz, 1 H) 7.28-7.40 (m, 1 H) 7.68-7.77 (m, 1 H) 8.01 (s, 1 H)

Example 8

Compound 8 trans-4-(5'-chloro-6-(piperidin-4-yl-amino)-2,4'-bipyridin-2'-yl-amino)cyclohexanol

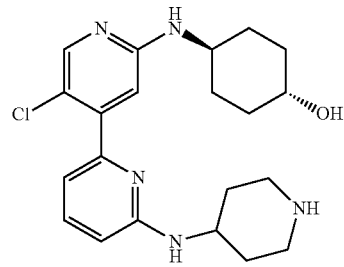 [SMILES: O[C@H]1CC[C@H](Nc2cc(-c3cccc(NC4CCNCC4)n3)c(Cl)cn2)CC1]

Step 1. Preparation of trans-4-(5-chloro-4-iodopyridin-2-yl-amino)cyclohexanol To 5-chloro-2-fluoro-4-iodopyridine (600 mg, 2.331 mmol) was added DMSO (2.2 ml), trans-4-aminocyclohexanol (1074 mg, 9.32 mmol) and TEA (0.390 ml, 2.80 mmol). The resulting reaction mixture was stirred at 75° C. for 24 hr, followed by LCMS. The reaction mixture was cooled to room temperature, mixed with 150 ml of ethyl acetate, washed with saturated sodium bicarbonate (1×), water (1×), saturated salt solution (1×), dried over sodium sulfate, filtered and concentrated to yield a crude material. The crude material was purified by silica gel chromatography using a 40 g column eluting from 15%-75% ethyl acetate with hexane. The desired fractions were combined and concentrated to constant mass, giving 750 mg of the title compound as free base, which was used in the next step without further purification. LCMS (m/z): 353.0 (MH+), retention time=0.56 min.

Step 2. Preparation of trans-4-(5'-chloro-6-fluoro-2,4'-bipyridin-2'-yl-amino)cyclohexanol A mixture of trans-4-(5-chloro-4-iodopyridin-2-yl-amino) cyclohexanol (575 mg, 1.631 mmol), 2-fluoro-6-(4,4,5,5-tetramethyl-1,3,2-dioxaborolan-2-yl)pyridine (655 mg, 2.94 mmol), PdCl$_2$(dppf).CH$_2$Cl$_2$ adduct (133 mg, 0.163 mmol), DME (15 ml), and t 2M sodium carbonate (4.48 ml, 8.97 mmol) reaction mixture was stirred at 95° C. for 2 hr, followed by LCMS. The reaction mixture was cooled to room temperature, mixed with 20 ml of ethyl acetate, 15 ml of methanol, filtered and concentrated to yield a crude product. The crude was purified by silica gel chromatography using a 40 g column, eluting from 35%-85% ethyl acetate with hexane. The desired fractions were combined and concentrated to constant mass, giving 440 mg of titled compound as free base. LCMS (m/z): 322.2 (MH+), retention time=0.53 min.

Step 3. Preparation of trans-4-(5'-chloro-6-(piperidin-4-yl-amino)-2,4'-bipyridin-2'-yl-amino)cyclohexanol A mixture of trans-4-(5'-chloro-6-fluoro-2,4'-bipyridin-2'-yl-amino)cyclohexanol (15.5 mg, 0.048 mmol), DMSO (0.4 ml), and tert-butyl 4-aminopiperidine-1-carboxylate (48.2 mg, 0.241 mmol) reaction mixture was stirred at 105° C. for 40 hr. LCMS indicated formation of the intermediate tert-butyl 4-(5'-chloro-2'-(trans-4-hydroxycyclohexylamino)-2,4'-bipyridin-6-yl-amino)piperidine-1-carboxylate (LCMS (m/z): 502.4 (MH+), retention time=0.70 min.). The Boc protecting group was removed from the intermediate by adding HCL 6M aq (140 µl, 0.840 mmol) to the crude reaction mixture mixture, followed by stirring the mixture at 90° C. for 45 minutes. The reaction mixture was cooled, 0.5 ml of DMSO was added, filtered and purified by prep LC. Lypholization of the material yielded 9.8 mg of the title compound, as a TFA salt. LCMS (m/z): 402.3 (MH+), retention time=0.41 min.; 1H NMR (300 MHz, METHANOL-d4, 25° C.) δ ppm 1.32-1.52 (m, 4 H) 1.71-1.87 (m, 2 H) 1.96-2.12 (m, 4 H) 2.27 (dd, J=14.21, 3.37 Hz, 2 H) 3.06-3.18 (m, 2 H) 3.39-3.50 (m, 2 H) 3.54-3.68 (m, 2 H) 4.05-4.17 (m, 1 H) 6.72 (d, J=8.50 Hz, 1 H) 6.90 (d, J=7.33 Hz, 1 H) 7.00 (s, 1 H) 7.56-7.64 (m, 1 H) 8.01 (s, 1 H)

Example 9

Compound 9

N-(trans-4-(aminomethyl)cyclohexyl)-5'-chloro-6-(3-fluorobenzyloxy)-2,4'-bipyridin-2'-amine

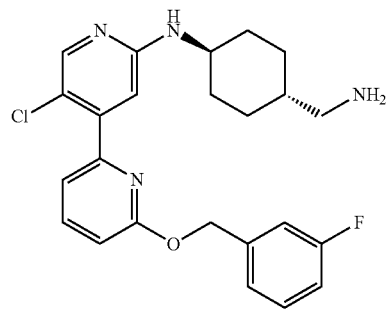 [SMILES: NC[C@H]1CC[C@H](Nc2cc(-c3cccc(OCc4cccc(F)c4)n3)c(Cl)cn2)CC1]

Step 1. Preparation of 2-bromo-6-(3-fluorobenzyloxy)pyridine

To 2-bromo-6-fluoropyridine (176 mg, 1.000 mmol) was added DMF (1.5 ml) and (3-fluorophenyl)methanol (139 mg, 1.100 mmol) and cesium carbonate (391 mg, 1.200 mmol), and the resulting mixture reaction mixture was stirred at 95° C. for 6 hr, as the progress of the reaction mixture was followed by LCMS. The reaction mixture mixture was cooled to room temperature, diluted with 120 ml of ethyl acetate, washed with saturated sodium bicarbonate (1×), water (1×), saturated salt solution (1×), dried over sodium sulfate, filtered and concentrated to yield a crude product which was purified by silica gel chromatography using a 12 g column eluting from 0%-20% ethyl acetate with hexane. The desired fractions were combined and concentrated to constant mass, giving 156 mg of the title compound as a free base. LCMS (m/z): 282.0/284.0 (MH+), retention time=1.19 min.

Step 2. Preparation of 5'-chloro-2'-fluoro-6-(3-fluorobenzyloxy)-2,4'-bipyridine A mixture of 2-bromo-6-(3-fluorobenzyloxy)pyridine (145 mg, 0.514 mmol), 5-chloro-2-fluoropyridin-4-ylboronic acid (144 mg, 0.822 mmol), PalladiumTetrakis (71.3 mg, 0.062 mmol), DME (3 ml), and 12M sodium carbonate (1.028 ml, 2.056 mmol) was reaction mixture was stirred at 100° C. for 3 hr, followed by LCMS. The reaction mixture was cooled, diluted with 10 ml of ethyl acetate, filtered and concentrated to yield a crude product, which was purified by silica gel chromatography using a 12 g column eluting from 0%-20% ethyl acetate with hexane. The desired fractions were concentrated to constant mass, giving 100 mg of titled compound as a free base. LCMS (m/z): 333.1 (MH+), retention time=1.26 min.

Step 3. Preparation of N-(trans-4-(aminomethyl)cyclohexyl)-5'-chloro-6-(3-fluorobenzyloxy)-2,4'-bipyridin-2'-amine To 5'-chloro-2'-fluoro-6-(3-fluorobenzyloxy)-2,4'-bipyridine (30 mg, 0.090 mmol) was added DMSO (0.8 ml), TEA (0.025 ml, 0.180 mmol), and tert-butyl (trans-4-aminocyclohexyl)methylcarbamate (41.2 mg, 0.180 mmol). The reaction mixture was flushed with argon and stirred at 100-105° C. for 40 hr. Formation of the intermediate product tert-butyl(trans-4-(5'-chloro-6-(3-fluorobenzyloxy)-2,4'-bipyridin-2'-yl-amino)cyclohexyl)methylcarbamate was indicated by LCMS. (LCMS (m/z): 541.4 (MH+), retention time=1.05 min.). The solvent DMSO was removed under reduce pressure. The Boc group was removed from the intermediate by adding 4M HCl in Dioxane (1.5 ml, 6.00 mmol), followed with stirring at ambient temperature for 90 minutes. The solvent was removed under reduced pressure. The crude product was dissolved in 1.0 ml of DMSO with 0.075 ml of water, filtered and purified by prep LC. After lyophilization, 28.3 mg of the title compound was obtained as a TFA salt. LCMS (m/z): 441.3 (MH+), retention time=0.76 min.; 1H NMR (300 MHz, METHANOL-d4, 25° C.) δ ppm 1.12-1.29 (m, 2 H) 1.29-1.47 (m, 2 H) 1.60-1.76 (m, J=14.76, 7.51, 3.66, 3.66 Hz, 1 H) 1.92 (d, J=12.60 Hz, 2 H) 2.16 (d, J=10.55 Hz, 2 H) 2.84 (d, J=6.74 Hz, 2 H) 3.58-3.71 (m, 1 H) 5.43 (s, 2 H) 6.92-6.99 (m, 2 H) 6.99-7.08 (m, 1 H) 7.18 (d, J=9.67 Hz, 1 H) 7.25 (d, J=7.62 Hz, 1 H) 7.30-7.42 (m, 2 H) 7.83 (t, J=7.77 Hz, 1 H) 8.01 (s, 1 H)

Example 10

Compound 10 trans-N1-benzyl-N4-(4-(6-(3-fluorobenzylamino) pyrazin-2-yl)pyridin-2-yl)cyclohexane-1,4-diamine

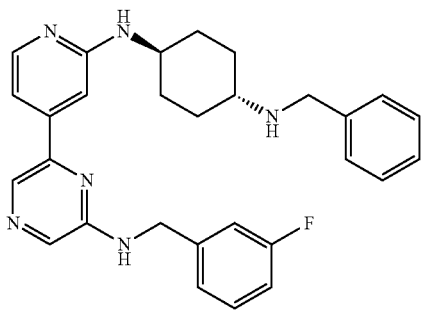 [SMILES: Fc1cccc(CNc2cncc(-c3ccnc(N[C@H]4CC[C@H](NCc5ccccc5)CC4)c3)n2)c1]

Step 1. Preparation of 6-chloro-N-(3-fluorobenzyl)pyrazin-2-amine: To 2,6-dichloropyrazine (175 mg, 1.175 mmol) was added DMSO (1.5 ml), TEA (0.196 ml, 1.410 mmol) and (3-fluorophenyl)methanamine (368 mg, 2.94 mmol) 1. The reaction mixture then was stirred at 90° C. until completion as indicated by LCMS, about 1 hour. To the reaction mixture was added 3 ml of DMSO, filtered and the residue was purified by prep LC. After lyphilization, 160 mg of the title compound was obtained as a TFA. LCMS (m/z): 238.1 (MH+), retention time=0.96 min.

Step 2. Preparation of N-(3-fluorobenzyl)-6-(2-fluoropyridin-4-yl)pyrazin-2-amine: To 6-chloro-N-(3-fluorobenzyl)pyrazin-2-amine (140 mg, 0.589 mmol) was added 2-fluoropyridin-4-ylboronic acid (125 mg, 0.884 mmol), PalladiumTetrakis (82 mg, 0.071 mmol), DME (3.3 ml), and 2M sodium carbonate (1.031 ml, 2.062 mmol). The resulting reaction mixture was stirred at 110° C. until completion as indicated by LCMS, about 3 hours. The reaction mixture was cooled to room temperature, diluted with 20 ml of ethyl acetate, filtered and concentrated to yield a crude solid. The solid was dissolved in DMSO, filtered and purified by prep LC. After lyophilization, 72 mg of the title compound was obtained as a TFA salt. LCMS (m/z): 299.1 (MH+), retention time=0.89 min.

Step 3. Preparation of trans-N1-(4-(6-(3-fluorobenzylamino)pyrazin-2-yl)pyridin-2-yl)cyclohexane-1, 4-diamine To N-(3-fluorobenzyl)-6-(2-fluoropyridin-4-yl)pyrazin-2-amine (30 mg, 0.101 mmol) was added DMSO (0.6 ml) and trans-cyclohexane-1,4-diamine (115 mg, 1.006 mmol). The reaction mixture then was stirred at 105° C. until completion as indicated by LCMS, about 40 hours. To the crude reaction mixture, after cooling to room temperature mixture was added 0.75 ml of DMSO, the resulting mixture filtered and purified by prep LC. After lyophilization, 34 mg of the title compound was obtained as a TFA salt. LCMS (m/z): 393.2 (MH+), retention time=0.54 min.

Step 4. Preparation of trans-N1-benzyl-N4-(4-(6-(3-fluorobenzylamino) pyrazin-2-yl)pyridin-2-yl)cyclohexane-1,4-diamine To trans-N1-(4-(6-(3-fluorobenzyl amino)pyrazin-2-yl)pyridin-2-yl)cyclohexane-1,4-diamine (19 mg, 0.048 mmol) was added NMP (0.6 ml), acetic acid (0.042 ml, 0.726 mmol) and benzaldehyde (10.27 mg, 0.097 mmol). The resulting reaction mixture was stirred overnight at ambient temperature. To the srirred reaction mixture was added sodium triacetoxyborohydride (41.0 mg, 0.194 mmol) and the resulting mixture was stirred overnight (24 hours) at ambient temperature. To the reaction mixture mixture then was added additional sodium triacetoxyborohydride (21.0 mg, 0.099 mmol) and the resulting mixture was stirred for an additional 2 more hours. To the crude mixture then was added 0.8 ml of DMSO, filtered and purified by prep LC. After lyophilization, 7.0 mg of the title compound was obtained as a TFA salt. LCMS (m/z): 483.2 (MH+), retention time=0.65 min.; 1H NMR (300 MHz, METHANOL-d4, 25° C.) δ ppm 1.35-1.51 (m, 2 H) 1.51-1.69 (m, 2 H) 2.04-2.36 (m, 4 H) 3.08-3.18 (m, 1 H) 3.56-3.70 (m, 1 H) 4.16 (s, 2 H) 4.60 (s, 2 H) 6.82-6.93 (m, 1 H) 7.03 (d, J=9.67 Hz, 1 H) 7.11 (d, J=7.62 Hz, 1 H) 7.19-7.29 (m, 1 H) 7.32 (d, J=6.74 Hz, 1 H) 7.35-7.46 (m, 5 H) 7.54 (s, 1 H) 7.80 (d, J=6.74 Hz, 1 H) 7.97 (s, 1 H) 8.25 (s, 1 H)

Example 11

Compound 11

N2'-(trans-4-aminocyclohexyl)-N6-(3-fluorobenzyl)-4-(trifluoromethyl)-2,4'-bipyridine-2',6-diamine

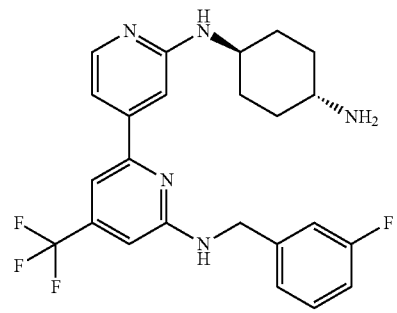 [SMILES: N[C@H]1CC[C@H](Nc2cc(-c3cc(C(F)(F)F)cc(NCc4cccc(F)c4)n3)ccn2)CC1]

Step 1. Preparation of 6-chloro-N-(3-fluorobenzyl)-4-(trifluoromethyl)pyridin-2-amine To 2,6-dichloro-4-(trifluoromethyl)pyridine (250 mg, 1.157 mmol) was added DMSO (2 ml), TEA (0.194 ml, 1.389 mmol), and (3-fluorophenyl)methanamine (290 mg, 2.315 mmol). The reaction mixture was stirred at 90° C. until completion as indicated by LCMS, about 1 hour. To the crude reaction mixture was added 1.5 ml of DMSO, filtered and purified by prep LC. After lyophilization, 158 mg of the title compound was obtained as a TFA salt. LCMS (m/z): 305.1 (MH+), rt= 1.21 min.

Step 2. Preparation of 2'-fluoro-N-(3-fluorobenzyl)-4-(trifluoromethyl)-2,4'-bipyridin-6-amine To 6-chloro-N-(3-fluorobenzyl)-4-(trifluoromethyl)pyridin-2-amine (70 mg, 0.230 mmol) was added 2-fluoropyridin-4-ylboronic acid (58.3 mg, 0.414 mmol), PdCl$_2$(dppf).CH$_2$Cl$_2$ adduct (22.52 mg, 0.028 mmol), DME (1.2 ml), and 2M sodium carbonate (0.460 ml, 0.919 mmol). The resulting reaction mixture was stirred at 105° C. until completion as indicated by LCMS, about 6 hours. The reaction mixture was cooled, 15 ml of ethyl acetate and 5 ml of methanol was added, filtered and concentrated to yield a crude solid. The solid was purified by prep LC. The product was free-based using 200 ml of ethyl acetate and washed with saturated sodium bicarbonate (1×), water (2×), saturated salt solution (1×), dried sodium sulfate, filtered and concentrated to a constant mass, yielding 35 mg of titled compound as free base. LCMS (m/z): 366.2 (MH+), retention time=1.20 min.

Step 3. preparation of N2'-(trans-4-aminocyclohexyl)-N6-(3-fluorobenzyl)-4-(trifluoromethyl)-2,4'-bipyridine-2',6-diamine To 2'-fluoro-N-(3-fluorobenzyl)-4-(trifluoromethyl)-2,4'-bipyridin-6-amine (34 mg, 0.093 mmol) was added DMSO (1.7 ml) and trans-cyclohexane-1,4-diamine (159 mg, 1.396 mmol). The resulting reaction mixture was stirred at 105° C. until completion as indicated by LCMS, about 40 hours. To the crude reaction mixture was added 0.75 ml of DMSO, filtered and purified by prep LC. After lyophilization, 28.1 mg of the title compound was obtained as a TFA salt. LCMS (m/z): 460.3 (MH+), retention time=0.72 min.; 1H NMR (300 MHz, METHANOL-d4, 25° C.) δ ppm 1.40-1.72 (m, 4 H) 2.18 (t, J=13.77 Hz, 4 H) 3.11-3.24 (m, 1H) 3.62-3.76 (m, 1 H) 4.72 (s, 2 H) 6.95 (s, 1 H) 7.12 (d, J=9.96 Hz, 1 H) 7.17-7.24 (m, 1 H) 7.27-7.37 (m, 1 H) 7.40 (s, 1 H) 7.42-7.48 (m, 1 H) 7.69 (s, 1 H) 7.87 (d, J=6.74 Hz, 1 H)

Example 12

Compound 12

N2'-(trans-4-aminocyclohexyl)-5'-chloro-5-fluoro-N6-(3-fluorobenzyl)-2,4'-bipyridine-2',6-diamine

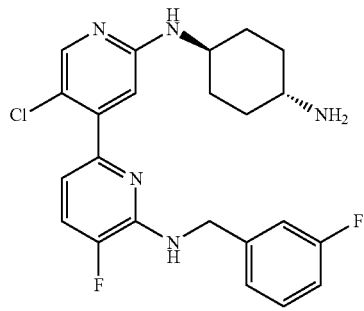 [SMILES: N[C@H]1CC[C@H](Nc2cc(-c3ccc(F)c(NCc4cccc(F)c4)n3)c(Cl)cn2)CC1]

Step 1. Preparation of 3,6-difluoro-N-(3-fluorobenzyl)pyridine-2-amine 2,3,6-trifluoropyridine (1.07 mL, 1.5 g, 11.27 mmol), 3-fluorobenzylamine (3.18 mL, 3.53 g, 28.2 mmol), and triethylamine (4.71 mL, 3.42 g, 33.8 mmol) were dissolved in NMP (39 mL) to form a mixture This mixture reaction mixture was stirred at 100° C. for 1 hr. The reaction mixture was then extracted with EtOAc (3×75 mL). The combined extracts were washed with H$_2$O (4×75 mL) followed by brine (1×75 mL). The organic layer was dried (Na$_2$SO$_4$), filtered, and the solvent removed in vacuo. The resulting residue was subjected to silica gel column chromatography. Elution using 100 hexanes to 30 EtOAc/70 hexanes yielded 2.63 g (98%) of 3,6-difluoro-N-(3-fluorobenzyl)pyridine-2-amine. LCMS (m/z): 239.1 (MH+), retention time=1.01 min.

Step 2. Preparation of 3-fluoro-N-(3-fluorobenzyl)-6-methoxypyridin-2-amine:

3,6-difluoro-N-(3-fluorobenzyl)pyridine-2-amine (0.5209 g, 2.19 mmol), was dissolved in anhydrous MeOH (6.6 mL) and placed under argon. This mixture then was treated with sodium methoxide (0.500 mL, 0.473 g, 2.19 mmol, 25% in MeOH) by slow addition. The resulting mixture was then heated in the microwave at 150° C. for four 30 min. The reaction mixture was then poured into brine (25 mL). This mixture was extracted with EtOAc (3×25 mL), the combined extracts were washed with brine (1×25 mL) and dried (Na$_2$SO$_4$). After filtration the solvent removed in vacuo. The resulting residue was subjected to silica gel column chromatography. Elution using 100 hexanes to 25 EtOAc/75 hexanes afforded 0.3408 g (62%) of 3-fluoro-N-(3-fluorobenzyl)-6-methoxypyridin-2-amine. LCMS (m/z): 251.1 (MH+), retention time=1.07 min.

Step 3. Preparation of 5-fluoro-6-(3-fluorobenzylamino)pyridine-2-ol:

3-fluoro-N-(3-fluorobenzyl)-6-methoxypyridin-2-amine (0.100 g, 0.400 mmol) was dissolved in anhydrous CH$_3$CN (1.6 mL). This mixture was treated with sodium iodide (0.301 g, 2.01 mmol) followed by trimethylsilylchloride (0.257 mL, 0.218 g, 2.01 mmol). The resulting reaction mixture was then heated at reflux for 2 hr. The reaction mixture was then treated with MeOH (1 ml), and the resulting mixture was stirred at ambient temperature for 2 hr, and then concentrated in vacuo. The resulting residue was dissolved in EtOAc (25 ml) and partitioned with H$_2$O (25 ml). The H$_2$O layer was extracted with EtOAc (2×25 ml). The organic layers were combined and washed with brine (1×25 ml). The organic layer was dried (Na$_2$SO$_4$), filtered, and the solvent removed in vacuo. The resulting residue was subjected to silica gel column chromatography. Elution using 10 EtOAc/90 hexanes to 60 EtOAc/40 hexanes gave 0.060 g (64%) of 5-fluoro-6-(3-fluorobenzylamino)pyridine-2-ol. LCMS (m/z): 237.2 (MH+), retention time=0.74 min.

Step 4. Preparation of 5-fluoro-6-(3-fluorobenzylamino)pyridine-2-yl trifluoromethanesulfonate 5-fluoro-6-(3-fluorobenzylamino)pyridine-2-ol (0.060 g, 0.254 mmol) was dissolved in anhydrous CH$_2$Cl$_2$ (2.0 mL) and placed under argon. The solution was cooled to 0° C. in an ice bath. It was then treated with triethylamine (0.096 mL, 0.070 g, 0.691 mmol) followed by dropwise addition of trifluoromethanesulfonic anhydride (0.058 mL, 0.096 g, 0.340 mmol). Once the addition was complete, the reaction mixture was stirred at 0° C. for 2 hr. The reaction mixture was then poured into saturated NaHCO$_3$ (25 mL). This mixture was extracted with EtOAc (2×25 mL). The combined extracts were washed with brine (1×25 mL), dried (Na$_2$SO$_4$), filtered, and the solvent removed in vacuo. The resulting residue was subjected to silica gel column chromatography. Elution using 5 EtOAc/95 hexanes to 60 EtOAc/40 hexanes yielded 0.081 g (87%) of 5-fluoro-6-(3-fluorobenzylamino)pyridine-2-yl trifluoromethanesulfonate. LCMS (m/z): 369.1 (MH+), retention time=1.15 min.

Step 5. Preparation of 5'-chloro-2',5-difluoro-N-(3-fluorobenzyl)-2,4'-bipyridin-6-amine 5-fluoro-6-(3-fluorobenzylamino)pyridine-2-yl trifluoromethanesulfonate (0.0811 g, 0.220 mmol), 5-chloro-2-fluoropyridin-4-ylboronic acid (0.116 g, 0.661 mmol), and sodium carbonate (0.286 mL, 0.573 mmol, 2M in $H_2O$) were dissolved in DME (2 mL). The solution was then degassed by sparging with argon for 5 min. It was then treated with $PdCl_2$ (dppf) $CH_2Cl_2$ adduct (0.036 g, 0.044 mmol). The reaction mixture was then heated in the microwave at 120° C. for 10 min. The reaction mixture was then filtered through a pad of Celite. The filtrate was concentrated in vacuo. The resulting residue was subjected to silica gel column chromatography. Elution using 5 EtOAc/95 hexanes to 60 EtOAc/40 hexanes yielded 0.044 g (57%) of 5'-chloro-2',5-difluoro-N-(3-fluorobenzyl)-2,4'-bipyridin-6-amine. LCMS (m/z): 350.0 (MH+), retention time=1.16 min.

Step 6. Preparation of N2'-(trans-4-aminocyclohexyl)-5'-chloro-5-fluoro-N6-(3-fluorobenzyl)-2,4'-bipyridine-2',6-diamine 5'-chloro-2',5-difluoro-N-(3-fluorobenzyl)-2,4'-bipyridin-6-amine (0.022 g, 0.063 mmol) was dissolved in anhydrous DMSO (0.93 mL) and charged to a microwave vial, and then treated with trans-cyclohexane-1,4-diamine (0.072 g, 0.629 mmol). The reaction mixture then was heated at 100° C. for 18 hr. The material was purified by preparative reverse-phase HPLC to yield 0.0151 g (44%) of $N^{2'}$-(trans-4-aminocyclohexyl)-5'-chloro-5-fluoro-$N^{6}$-(3-fluorobenzyl)-2,4'-bipyridine-2',6-diamine as the TFA salt. LCMS (m/z): 444.2 (MH+), retention time=0.7 min.

Example 13

Compound 13

2'-(trans-4-amonocyclohexylamino)-5'-chloro-6-(3-fluorobenzylamino)-2,4'-bipyridine-5-carbonitrile

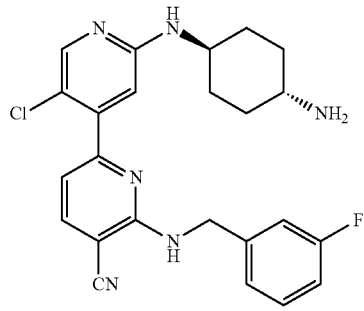 [SMILES: N#Cc1ccc(-c2cc(N[C@H]3CC[C@H](N)CC3)ncc2Cl)nc1NCc1cccc(F)c1]

Step 1. Preparation of 6-chloro-2-(3-fluorobenzylamino)nicotinonitrile 2,6-dichloronicotinonitrile (0.500 g, 2.89 mmol), (4-fluorophenyl)methanamine (0.816 mL, 0.904 g, 7.23 mmol), and triethylamine (1.21 mL, 0.877 g, 8.67 mmol) were all mixed in NMP (10 mL). The resulting solution then was heated at 50° C. for 18 hr. The reaction mixture was then poured in $H_2O$ (25 mL), and extracted with EtOAc (3×25 mL). The combined extracts were washed with $H_2O$ (4×25 mL), and brine (1×25 mL). The organic layer was separated and dried ($Na_2SO_4$), filtered, and the solvent removed in vacuo. The resulting residue was purified using silica gel column chromatography. Elution using 1 EtOAc/3 hexanes to 3 EtOAc/1 hexanes afforded 0.6024 g (80%) of 6-chloro-2-(3-fluorobenzylamino)nicotinonitrile. LCMS (m/z): 350.0 (MH+), retention time=0.96 min. $^1$H NMR (300 MHz, $CDCl_3$) δ 4.58 (d, J=5.86 Hz, 2 H) 5.48 (br. s., 1 H) 6.30 (d, J=8.50 Hz, 1 H) 6.96-7.06 (m, 2 H) 7.10 (d, J=7.62 Hz, 1 H) 7.28-7.38 (m, 1 H) 7.58 (d, J=8.79 Hz, 1 H).

Step 2. Preparation of 5'-chloro-2'-fluoro-6-(3-fluorobenzylamino)-2,4'-bipyridine-5-carbonitrile 6-chloro-2-(3-fluorobenzylamino)nicotinonitrile (0.602 g, 2.30 mmol), 5-chloro-2-fluoropyridin-4-ylboronic acid (1.21 g, 6.91 mmol), and sodium carbonate (2.99 mL, 5.99 mmol, 2M in $H_2O$) were dissolved in DME (10.5 mL). The resulting solution was then degassed by sparging with argon for 5 min. It was then treated with $PdCl_2$(dppf) $CH_2Cl_2$ adduct (0.376 g, 0.460 mmol). The resulting reaction mixture was heated in the microwave at 120° C. for 10 min. It was then filtered through a pad of Celite. The filtrate was concentrated in vacuo. The resulting residue was subjected to silica gel column chromatography. Elution using 5 EtOAc/95 hexanes to 50 EtOAc/50 hexanes yielded 0.2689 g (33%) of 5'-chloro-2'-fluoro-6-(3-fluorobenzylamino)-2,4'-bipyridine-5-carbonitrile. LCMS (m/z): 357.2 (MH+), retention time=1.02 min.

Step 3. Preparation of 2'-(trans-4-amonocyclohexylamino)-5'-chloro-6-(3-fluorobenzylamino)-2,4'-bipyridine-5-carbonitrile 5'-chloro-2'-fluoro-6-(3-fluorobenzylamino)-2,4'-bipyridine-5-carbonitrile (0.2689 g, 0.754 mmol) was dissolved in anhydrous DMSO (11.0 mL) and charged to a microwave vial. This mixture was treated with trans-cyclohexane-1,4-diamine (0.861 g, 7.54 mmol), and the reaction mixture was then heated at 100° C. for 5 hr. The reaction mixture mixture was cooled to ambient temperature, and the material was purified by preparative reverse-phase HPLC and freebased to yield 0.2539 g (75%) of 2'-(trans-4-amonocyclohexylamino)-5'-chloro-6-(3-fluorobenzylamino)-2,4'-bipyridine-5-carbonitrile. LCMS (m/z): 451.2 (MH+), retention time=0.67 min.

Example 14

Compound 14

2'-(trans-4-aminocyclohexylamino)-5'-chloro-6-(3-fluorobenzylamino)-2,4'-bipyridine-5-carboxamide

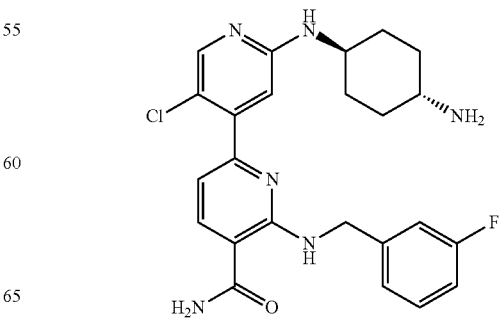

Step 1. Preparation of 2'-(trans-4-aminocyclohexylamino)-5'-chloro-6-(3-fluorobenzylamino)-2,4'-bipyridine-5-carboxamide 2'-(trans-4-amonocyclohexylamino)-5'-chloro-6-(3-fluorobenzylamino)-2,4'-bipyridine-5-carbonitrile (0.028 g, 0.055 mmol) was dissolved in DMSO (0.5 mL), and the solution was cooled to 0° C. in an ice bath. The cooled solution was treated with potassium carbonate (0.0011 g, 0.0078 mmol) followed by hydrogen peroxide (0.007 mL, 0.0069 mmol). The ice bath was removed and the reaction mixture was stirred at ambient temperature for 2 hr. More of the reagents in the same amounts were added and the reaction mixture was heated to 50° C. for 16 hr. This procedure was repeated and the reaction mixture was heated at 65° C. for an additional 4 hr. The reaction mixture was diluted with brine (10 mL), extracted with EtOAc (3×10 mL), the combined extracts were washed with brine (1×10 mL) and dried ($Na_2SO_4$), filtered and concentrated in vacuo. The material was purified by preparative reverse-phase HPLC to afford 0.0042 g (13%) of 2'-(trans-4-aminocyclohexylamino)-5'-chloro-6-(3-fluorobenzylamino)-2,4'-bipyridine-5-carboxamide as the TFA salt. LCMS (m/z): 469.1 ($MH^+$), retention time=0.56 min.

Example 15

Compound 15

2'-(trans-4-aminocyclohexylamino)-5'-chloro-6-(3-fluorobenzylamino)-2,4'-bipyridine-4-carbonitrile

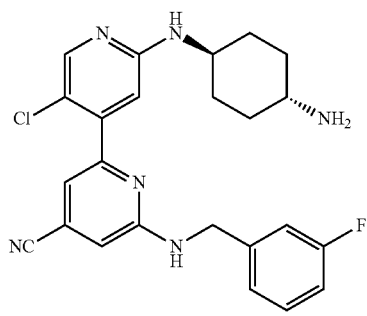 [SMILES: N#Cc1cc(NCc2cccc(F)c2)nc(-c2cc(N[C@H]3CC[C@H](N)CC3)ncc2Cl)c1]

Step 1. Preparation of 2-chloro-6-(3-fluorobenzylamino)isonicotinonitrile

To a scintillation vial containing 2,6-dichloroisonicotinonitrile (500 mg, 2.89 mmol) was added NMP (6 ml) and (3-fluorophenyl)methanamine (868 mg, 6.94 mmol). The homogenous reaction mixture was capped and heated to 110° C. in a oil bath for 1 hr. The reaction mixture was diluted with EtOAc and washed with sat $NaHCO_3$, $H_2O$ and sat NaCl. The organic layer was dried $Na_2SO_4$, filtered and concentrated. The crude residue was purified by column chromatography on silica gel (0-20% EtOAc/Hexane) to give 2-chloro-6-(3-fluorobenzylamino)isonicotinonitrile (750 mg, 95%). LCMS (m/z): 262.0 ($MH^+$), retention time=1.03 min.

Step 2. Preparation of 5'-chloro-2'-fluoro-6-(3-fluorobenzylamino)-2,4'-bipyridine-4-carbonitrile To a degassed suspension of 2-chloro-6-(3-fluorobenzylamino) isonicotinonitrile (150 mg, 0.573 mmol) and 5-chloro-2-fluoropyridin-4-ylboronic acid (151 mg, 0.860 mmol) in DME (5 ml) was added $Na_2CO_3$ (1.433 ml, 2M, 2.87 mmol) and $Pd(Ph_3P)_4$ (66.2 mg, 0.057 mmol). The reaction mixture was capped and heated to 110° C. in an oil bath for 2 hr. The reaction mixture was diluted with EtOAc and washed with sat $NaHCO_3$, and then sat NaCl. The organic layer was dried over Na2SO4, filtered and concentrated. The resulting residue was purified purified by column chromatography on silica gel (0-20% EtOAc/Hexane) to give 5'-chloro-2'-fluoro-6-(3-fluorobenzylamino)-2,4'-bipyridine-4-carbonitrile (95 mg, 47%). LCMS (m/z): 357.0 ($MH^+$), retention time=1.09 min

Step 3. Preparation of 2'-(trans-4-aminocyclohexylamino)-5'-chloro-6-(3-fluorobenzylamino)-2,4'-bipyridine-4-carbonitrile To a scintillation vial containing 5'-chloro-2'-fluoro-6-(3-fluorobenzylamino)-2,4'-bipyridine-4-carbonitrile (72 mg, 0.202 mmol) was added DMSO (3 ml) and trans-cyclohexane-1,4-diamine (230 mg, 2.018 mmol). The homogenous yellow reaction mixture was capped and heated to 105° C. in a oil bath for 3 hr. The reaction mixture was diluted with EtOAc and washed with sat $NaHCO_3$, sat NaCl. The organic layer was dried $Na_2SO_4$, filtered and concentrated. The crude solid was purified by Prep HPLC and the collected fractions were combined and diluted with EtOAc and neutralized with sat $NaHCO_3$ and then sat NaCl. The organic layer was dried over $Na_2SO_4$, filtered and concentrated to afford 2'-(trans-4-aminocyclohexylamino)-5'-chloro-6-(3-fluorobenzylamino)-2,4'-bipyridine-4-carbonitrile (73 mg, 80%). LCMS (m/z): 451.2 ($MH^+$), retention time=0.70 min. 1H NMR (400 MHz, METHANOL-d4) d ppm 1.34-1.48 (m, 2 H) 1.50-1.64 (m, 2 H) 2.06-2.22 (m, 4 H) 3.08-3.20 (m, 1 H) 3.63-3.74 (m, 1 H) 4.61 (s, 2H) 6.81 (s, 1 H) 6.87 (s, 1 H) 6.91-6.99 (m, 1 H) 7.02 (s, 1H) 7.04-7.10 (m, 1H) 7.12-7.18 (m, 1 H) 7.25-7.36 (m, 1 H) 8.00 (s, 1 H).

Examples 16 and 17

Compounds 16 and 17

2'-(trans-4-aminocyclohexylamino)-5'-chloro-6-(3-fluorobenzylamino)-2,4'-bipyridine-4-carboxamide & 2'-(trans-4-aminocyclohexylamino)-5'-chloro-6-(3-fluorobenzylamino)-2,4'-bipyridine-4-carboxylic acid

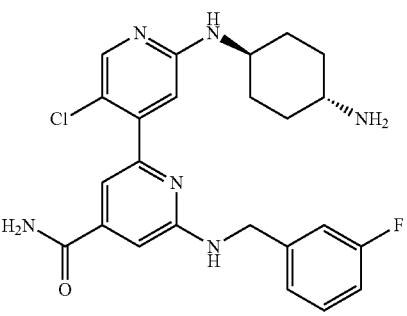

-continued

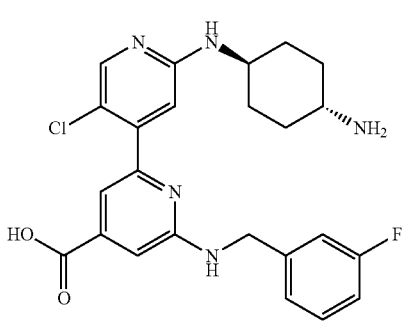

Step 4. Preparation of 2'-(trans-4-aminocyclohexylamino)-5'-chloro-6-(3-fluorobenzylamino)-2,4'-bipyridine-4-carboxamide To a scintillation vial containing 2'-(trans-4-aminocyclohexylamino)-5'-chloro-6-(3-fluorobenzylamino)-2,4'-bipyridine-4-carbonitrile (11 mg, 0.024 mmol) and $K_2CO_3$ (33.7 mg, 0.244 mmol) at 0° C. was added DMSO (1 ml) and $H_2O_2$ (10.68 μl, 0.122 mmol). The reaction mixture was capped and stirred at 0° C. for 10 min and rt for 10 min. The reaction mixture was diluted with EtOAc and washed with $H_2O$, sat NaCl. The organic layer was dried over $Na_2SO_4$, filtered and concentrated. The crude oil/solid was purified by reverse phase preparative HPLC to yield a TFA salt of 2'-(trans-4-aminocyclohexylamino)-5'-chloro-6-(3-fluorobenzylamino)-2,4'-bipyridine-4-carboxamide (3.5 mg, 25%), LCMS (m/z): 469.2 (MH$^+$), retention time=0.56 min and 2'-(trans-4-aminocyclohexylamino)-5'-chloro-6-(3-fluorobenzylamino)-2,4'-bipyridine-4-carboxylic acid (3.2 mg, 22%), LCMS (m/z): 470.2 (MH$^+$), retention time=0.61 min.

Example 18

Compound 18

5'-chloro-N2'-(trans-4-(dimethylamino)cyclohexyl)-N6-(3-fluorobenzyl)-2,4'-bipyridine-2',6-diamine

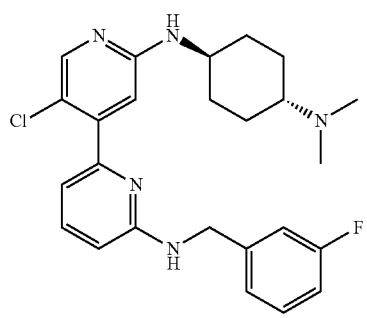 [SMILES: CN(C)[C@H]1CC[C@H](Nc2cc(-c3cccc(NCc4cccc(F)c4)n3)c(Cl)cn2)CC1]

Step 1. Preparation of 5'-chloro-N2'-(trans-4-(dimethylamino)cyclohexyl)-N6-(3-fluorobenzyl)-2,4'-bipyridine-2',6-diamine: To a scintillation vial containing N2'-(trans-4-aminocyclohexyl)-5'-chloro-N6-(3-fluorobenzyl)-2,4'-bipyridine-2',6-diamine (7 mg, 0.016 mmol) and formaldehyde (6.12 μl, 0.082 mmol) was added MeOH (0.3 ml) and Pd/C (5.25 mg, 4.93 μmol). The reaction mixture was stirred under hydrogen at room temperature for 16 hours. The reaction mixture mixture was filtered over celite and concentrated. The crude solid was purified by reverse phase preparative HPLC to yield 5'-chloro-N2'-(trans-4-(dimethylamino)cyclohexyl)-N6-(3-fluorobenzyl)-2,4'-bipyridine-2',6-diamine (2.0 mg, 24%). LCMS (m/z): 454.2 (MH$^+$), retention time=0.61 min. as a TFA salt after lyophilizing.

Example 19

Compound 19

2-(trans-4-(5'-chloro-6-(3-fluorobenzylamino)-2,4'-bipyridin-2'-yl-amino) cyclohexylamino)ethanol

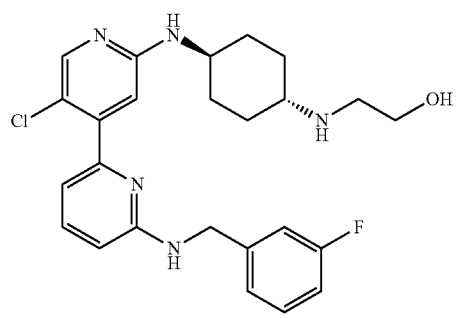 [SMILES: OCCN[C@H]1CC[C@H](Nc2cc(-c3cccc(NCc4cccc(F)c4)n3)c(Cl)cn2)CC1]

Step 1. Preparation of N2'-(trans-4-(2-(tert-butyldimethylsilyloxy)ethylamino) cyclohexyl)-5'-chloro-N6-(3-fluorobenzyl)-2,4'-bipyridine-2',6-diamine: To a scintillation vial containing N2'-(trans-4-aminocyclohexyl)-5'-chloro-N6-(3-fluorobenzyl)-2,4'-bipyridine-2',6-diamine (17 mg, 0.040 mmol) and $K_2CO_3$ (22.06 mg, 0.160 mmol) was added DMF (0.3 ml) and (2-bromoethoxy)(tert-butyl)dimethylsilane (9.55 mg, 0.040 mmol). The reaction mixture was capped and heated to 75° C. for 7 hr. The reaction mixture was diluted with DCM and washed with $H_2O$, sat NaCl. The organic layer was dried over $Na_2SO_4$, filtered and concentrated. The crude solid was purified by reverse phase preparative HPLC. Collected fractions were combined, neutralized with Saturated $NaHCO_3$ and extracted with EtOAc. The organic layer was dried over Na2SO4, filtered, concentrated and used directly in next step. LCMS (m/z): 584.3 (MH$^+$), retention time=0.87 min.

Step 2. Preparation of 2-(trans-4-(5'-chloro-6-(3-fluorobenzylamino)-2,4'-bipyridin-2'-yl-amino) cyclohexylamino)ethanol: To a scintillation vial containing N2'-(trans-4-(2-(tert-butyldimethylsilyloxy)ethylamino)cyclohexyl)-5'-chloro-N6-(3-fluorobenzyl)-2,4'-bipyridine-2',6-diamine s from step 1) was added THF (0.300 ml) and TBAF (0.160 ml, 0.319 mmol). The homogenous reaction mixture was capped, and stirred at ambient temperature for 3 hours. The reaction mixture was concentrated and purified by reverse phase preparative HPLC to yield 2-(trans-4-(5'-chloro-6-(3-fluorobenzylamino)-2,4'-bipyridin-2'-yl-amino) cyclohexylamino)ethanol (2.2 mg, 9%). LCMS (m/z): 470.3 (MH$^+$), retention time= 0.58 min as a TFA salt after lyophilizing. 1H NMR (400 MHz, METHANOL-d4) δ ppm 1.31-1.46 (m, 2 H) 1.51-1.67 (m, 1 H) 2.21 (d, J=10.56 Hz, 2H) 3.11-3.20 (m, 2 H) 3.66-3.77 (m, 1 H) 3.77-3.83 (m, 1 H) 4.62 (s, 1 H) 6.74 (s, 1H) 6.78-6.84 (m, 1H) 6.87-6.92 (m, 1 H) 6.96-7.03 (m, 1 H) 7.08-7.14 (m, 1H) 7.15-7.21 (m, 1 H) 7.31-7.38 (m, 1 H) 7.68-7.76 (m, 1 H) 8.02 (s, 1 H).

Example 20

Compound 20

5'-chloro-N6-(3-fluorobenzyl)-N2'-(trans-4-(2-(methylsulfonyl)ethylamino)cyclohexyl)-2,4'-bipyridine-2',6-diamine

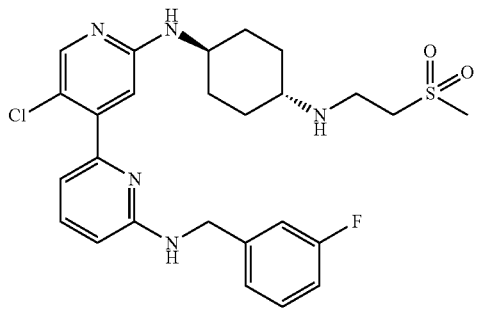 [SMILES: CS(=O)(=O)CCN[C@H]1CC[C@H](Nc2cc(-c3cccc(NCc4cccc(F)c4)n3)c(Cl)cn2)CC1]

Step 1. Preparation of 2-(methylsulfonyl)ethyl methanesulfonate: To a round-bottom flask containing 2-(methylsulfonyl)ethanol (400 mg, 3.22 mmol) at 0° C. was added DCM (10 ml) and triethylamine (4.91 μl, 0.035 mmol), followed by dropwise addition of mesyl chloride (2.96 mg, 0.026 mmol). The ice bath was removed and the reaction mixture was stirred at ambient temperature for 2 hr. The reaction mixture was diluted with DCM and washed with sat NaHCO₃ and then sat NaCl. The organic layer was dried over Na2SO4, filtered and concentrated. The resulting residue was purified via ISCO (0-60% EtOAc/Hexane) to yield 2-(methylsulfonyl) ethyl methanesulfonate (400 mg, 61%). LCMS (m/z): 203.0 (MH$^+$), retention time=0.37 min.

Step 2. Preparation of 5'-chloro-N6-(3-fluorobenzyl)-N2'-(trans-4-(2-(methylsulfonyl)ethylamino)cyclohexyl)-2,4'-bipyridine-2',6-diamine: To a scintillation vial containing N2'-(trans-4-aminocyclohexyl)-5'-chloro-N6-(3-fluorobenzyl)-2,4'-bipyridine-2',6-diamine (10 mg, 0.023 mmol) and K2CO3 (8 mg, 0.058 mmol) was added DMSO (0.5 ml) and 2-(methylsulfonyl)ethyl methanesulfonate (30 mg). The reaction mixture was capped and heated to 120° C. in an oil bath for 4 hr. The resulting solution was purified by reverse phase preparative HPLC to yield 5'-chloro-N6-(3-fluorobenzyl)-N2'-(trans-4-(2-(methylsulfonyl)ethylamino)cyclohexyl)-2,4'-bipyridine-2',6-diamine (3.7 mg, 24%). LCMS (m/z): 532.2 (MH$^+$), retention time=0.62 min as a TFA salt after lyophilizing.

Example 21

Compound 21

5'-chloro-N6-(3-fluorobenzyl)-N2'-(trans-4-(methylamino)cyclohexyl)-2,4'-bipyridine-2',6-diamine

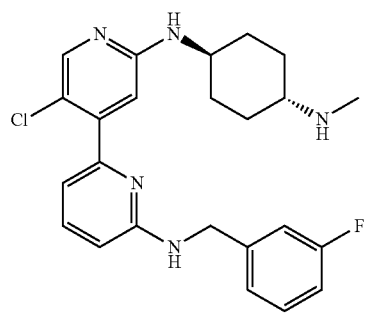 [SMILES: CN[C@H]1CC[C@H](Nc2cc(-c3cccc(NCc4cccc(F)c4)n3)c(Cl)cn2)CC1]

Step 1. Preparation of (1s,4s)-4-(5'-chloro-6-(3-fluorobenzylamino)-2,4'-bipyridin-2'-yl-amino)cyclohexyl methanesulfonate: To a round-bottom flask containing (1s,4s)-4-(5'-chloro-6-(3-fluorobenzylamino)-2,4'-bipyridin-2'-yl-amino)cyclohexanol (obtained following example 2) (85 mg, 0.199 mmol) at 0° C. was added DCM (2 ml) and triethylamine (0.042 ml, 0.299 mmol), followed by dropwise addition of Mesyl Chloride (0.020 ml, 0.259 mmol). The ice bath was removed and the reaction mixture was stirred at ambient temperature for 2 hr. The reaction mixture was diluted with DCM and washed with sat NaHCO₃, and then sat NaCl. The organic layer was dried over Na₂SO₄, filtered and concentrated to yield (1s,4s)-4-(5'-chloro-6-(3-fluorobenzylamino)-2,4'-bipyridin-2'-yl-amino)cyclohexyl methanesulfonate (90 mg, 90% yield), LCMS (m/z): 505.3 (MH$^+$), retention time=0.77 min. The resulting residue was used in next step without further purification.

Step 2. Preparation of 5'-chloro-N6-(3-fluorobenzyl)-N2'-(trans-4-(methylamino)cyclohexyl)-2,4'-bipyridine-2',6-diamine To a scintillation vial containing (1s,4s)-4-(5'-chloro-6-(3-fluorobenzylamino)-2,4'-bipyridin-2'-yl-amino)cyclohexyl methanesulfonate (20 mg, 0.040 mmol) was added MeOH (1 ml) and methyl amine (0.594 ml, 2M, 1.188 mmol). The reaction mixture was capped and heated to 70° C. in a oil bath for 16 hr. Solvent was evaporated and recharge the vial with 0.6 ml 30% methyl amine in ethanol. After heating at 70° C. for another 6 hr, the reaction mixture was concentrated and purified by reverse phase preparative HPLC to yield 5'-chloro-N6-(3-fluorobenzyl)-N2'-(trans-4-(methylamino)cyclohexyl)-2,4'-bipyridine-2',6-diamine (6.5 mg, 0.015 mmol, 37.3%), LCMS (m/z): 440.3 (MH$^+$), retention time= 0.61 min and 5'-chloro-N2'-(cyclohex-3-enyl)-N6-(3-fluorobenzyl)-2,4'-bipyridine-2',6-diamine (3.5 mg, 22%) LCMS (m/z): 409.2 (MH$^+$), retention time= 0.82 min. $^1$H NMR (400 MHz, METHANOL-d4) δ ppm 1.32-1.46 (m, 2 H) 1.47-1.62 (m, 2 H) 2.20 (d, J=11.35 Hz, 4 H) 3.01-3.11 (m, 1 H) 3.67-3.78 (m, 1 H) 4.64 (s, 2 H) 6.81 (s, 1 H) 6.88-6.97 (m, 3 H) 6.97-7.05 (m, 1 H) 7.08-7.14 (m, 1 H) 7.16-7.22 (m, 1 H) 7.31-7.41 (m, 1 H) 7.75-7.83 (m, 1 H) 8.05 (s, 1 H).

Example 22

Compound 22

5'-chloro-N6-(3-fluorobenzyl)-N2'-(trans-4-((methylamino)methyl)cyclohexyl)-2,4'-bipyridine-2',6-diamine

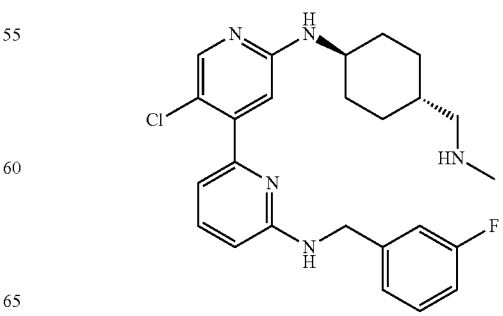

Step 1. Preparation of (trans-4-(5'-chloro-6-(3-fluorobenzylamino)-2,4'-bipyridin-2'-yl-amino)cyclohexyl)methyl methanesulfonate To a round-bottom flask containing (trans-4-(5'-chloro-6-(3-fluorobenzylamino)-2,4'-bipyridin-2'-yl-amino)cyclohexyl)methanol (obtained following example 2) (102 mg, 0.231 mmol) at 0° C. was added DCM (2 ml) and triethylamine (0.048 ml, 0.347 mmol), followed by dropwise addition of Mesyl Chloride (0.023 ml, 0.301 mmol). The ice bath was removed and the reaction mixture was stirred at rt for 2 hr. The reaction mixture was diluted with DCM and washed with sat NaHCO$_3$ and then sat NaCl. The organic layer was dried over Na$_2$SO$_4$, filtered and concentrated to yield (trans-4-(5'-chloro-6-(3-fluorobenzylamino)-2,4'-bipyridin-2'-yl-amino) cyclohexyl)methyl methanesulfonate (110 mg, 92% yield), LCMS (m/z): 519.2 (MH$^+$), retention time=0.80 min. The resulting residue was used in next step without further purification.

Step 2. Preparation of 5'-chloro-N6-(3-fluorobenzyl)-N2'-(trans-4-((methylamino) methyl)cyclohexyl)-2,4'-bipyridine-2',6-diamine: To a scintillation vial containing (trans-4-(5'-chloro-6-(3-fluorobenzylamino)-2,4'-bipyridin-2'-yl-amino)cyclohexyl)methyl methanesulfonate (15 mg, 0.029 mmol) was added MeOH (1 ml) and a solution of methyl amine (0.144 ml, 0.289 mmol) in MeOH. The reaction mixture was capped and heated to 70° C. in a oil bath for 16 hr. The resulting solution was concentrated and purified by reverse phase preparative HPLC to yield 5'-chloro-N6-(3-fluorobenzyl)-N2'-(trans-4-((methylamino) methyl)cyclohexyl)-2,4'-bipyridine-2',6-diamine (8.6 mg, 52%), LCMS (m/z): 454.2 (MH$^+$), retention time=0.64 min as a TFA salt after lyophilizing. $^1$H NMR (400 MHz, METHANOL-d4) δ ppm 1.15-1.29 (m, 2 H) 1.29-1.42 (m, 2 H) 1.67-1.80 (m, 1 H) 1.86-1.96 (m, 2 H) 2.09-2.21 (m, 2 H) 2.71 (s, 3 H) 2.90 (d, J=7.04 Hz, 2 H) 3.58-3.70 (m, 1 H) 4.63 (s, 2 H) 6.88 (s, 2 H) 6.94 (d, J=7.43 Hz, 1 H) 6.96-7.03 (m, 1 H) 7.07-7.13 (m, 1 H) 7.15-7.21 (m, 1 H) 7.29-7.39 (m, 1 H) 7.69-7.78 (m, 1 H) 8.01 (s, 1H).

Example 23

Compound 23

5'-chloro-N6-(3,5-difluorobenzyl)-N2'-(trans-4-(pyrrolidin-1-yl)cyclohexyl)-2,4'-bipyridine-2',6-diamine

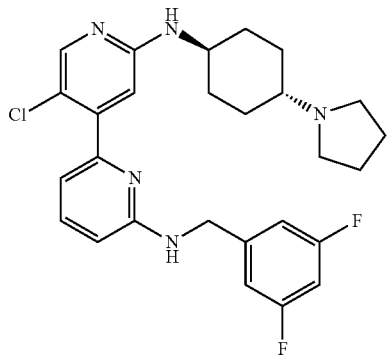 [SMILES: Fc1cc(F)cc(CNc2cccc(-c3cc(N[C@H]4CC[C@H](N5CCCC5)CC4)ncc3Cl)n2)c1]

Step 1. Preparation of 5'-chloro-N6-(3,5-difluorobenzyl)-N2'-(trans-4-(pyrrolidin-1-yl)cyclohexyl)-2,4'-bipyridine-2',6-diamine: To a scintillation vial containing N2'-(trans-4-aminocyclohexyl)-5'-chloro-N6-(3,5-difluorobenzyl)-2,4'-bipyridine-2',6-diamine (12.3 mg, 0.028 mmol) (obtained following example 2) and K$_2$CO$_3$ (15.32 mg, 0.111 mmol) was added DMSO (0.5 ml) and 1,4-dibromobutane (5.98 mg, 0.028 mmol). The reaction mixture was capped and heated at 60° C. for 7 hr. The reaction mixture was diluted with DCM and washed with H$_2$O, sat NaCl. The organic layer was dried over Na$_2$SO$_4$, filtered and concentrated. The crude solid was purified by reverse phase preparative HPLC to yield 5'-chloro-N6-(3,5-difluorobenzyl)-N2'-(trans-4-(pyrrolidin-1-yl)cyclohexyl)-2,4'-bipyridine-2',6-diamine (7.8 mg, 46.0%), LCMS (m/z): 498.3 (MH$^+$), retention time=0.65 min as a TFA salt after lyophilizing. $^1$H NMR (400 MHz, METHANOL-d4) δ ppm 1.26-1.40 (m, 2 H) 1.48-1.62 (m, 2 H) 1.85-1.98 (m, 2 H) 1.99-2.24 (m, 7 H) 2.99-3.14 (m, 4 H) 3.51-3.68 (m, 3 H) 4.54 (s, 2 H) 6.69-6.80 (m, 3 H) 6.81-6.90 (m, 3 H) 7.60-7.69 (m, 1 H) 7.94 (s, 1 H).

Example 24

Compounds 256+257

N2'-trans-4-aminocyclohexyl)-5'-chloro-N6-(((R)-2,2-dimethyltetrahydro-2H-pyran-4-yl)methyl)-2,4'-bipyridine-2',6-diamine and N2'-(trans-4-aminocyclohexyl)-5'-chloro-N6-(((S)-2,2-dimethyltetrahydro-2H-pyran-4-yl)methyl)-2,4'-bipyridine-2',6-diamine

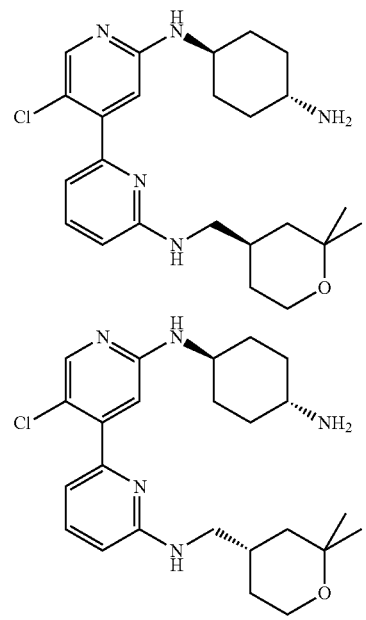

Step 1: Preparation of N2'-(trans-4-aminocyclohexyl)-5'-chloro-N6-(((R/S)-2,2-dimethyltetrahydro-2H-pyran-4-yl)methyl)-2,4'-bipyridine-2',6-diamine A mixture of (R/S)-5'-chloro-N-((2,2-dimethyltetrahydro-2H-pyran-4-yl)methyl)-2'-fluoro-2,4'-bipyridin-6-amine (35 mg, 0.100 mmol), trans-cyclohexane-1,4-diamine (91 mg, 0.800 mmol), DIPEA (20.25 mg, 0.200 mmol) in DMSO (0.35 mL) was heated at 109° C. for 16 hr. The mixture was diluted with DMSO, filtered through a syringe filter and purified by HPLC to give N2'-(trans-4-aminocyclohexyl)-5'-chloro-N6-(((R/S)-2,2-dimethyltetrahydro-2H-pyran-4-yl) methyl)-2,4'-bipyridine-2',6-diamine as its trifluoroacetic acid salt. Yield: 29 mg. LCMS (m/z): 444.2 [M+H]+; Retention time=0.51 min.

N2'-(trans-4-aminocyclohexyl)-5'-chloro-N6-(((R)-2, 2-dimethyltetrahydro-2H-pyran-4-yl)methyl)-2,4'-bipyridine-2',6-diamine and N2'-(trans-4-aminocyclohexyl)-5'-chloro-N6-(((S)-2,2-dimethyltetrahydro-2H-pyran-4-yl)methyl)-2,4'-bipyridine-2',6-diamine N2'-(trans-4-aminocyclohexyl)-5'-chloro-N6-(((R/S)-2,2-dimethyltetrahydro-2H-pyran-4-yl)methyl)-2,4'-bipyridine-2',6-diamine trifluoroacetic acid salt was dissolved in MeOH (2 mL) and filtered through VariPure™ IPE [500 mg per 6 mL tube; 0.9 mmol (nominal); part no.: PL3540-C603VP], eluted with MeOH (6 mL) and concentrated in vacuo providing N2'-(trans-4-aminocyclohexyl)-5'-chloro-N6-(((R/S)-2,2-dimethyltetrahydro-2H-pyran-4-yl)methyl)-2,4'-bipyridine-2',6-diamine as a colorless oil. Yield: 20 mg. The enantiomers were resolved by chiral HPLC [Chiralpak AD column 21×50 mm, 20 mic; 20 mg/2 mL EtOH; heptane/IP A; 85:15 (v:v); 20 mL/min, 330 psi]. Fraction 1: White solid. Yield: 7.2 mg. Retention time: 10.4 min. [Chiralpak AD-H, column 4.6×100 mm, 5 mic; 20 mg/2 mL EtOH; heptane/IPA; 85:15 (v:v); 1 mL/min]. $^1$H NMR (400 MHz, METHANOL-$d_4$) δ [ppm] 1.07-1.18 (m, 2 H) 1.20 (s, 3 H) 1.21 (s, 3 H) 1.23-1.41 (m, 4 H) 1.65-1.74 (m, 2 H) 1.90-1.99 (m, 2 H) 2.09 (m, 3 H) 2.71 (br. s., 1H) 3.19 (d, J=6.65 Hz, 2 H) 3.57-3.67 (m, 1 H) 3.67-3.74 (m, 2 H) 6.52 (d, 1 H) 6.61 (s, 1 H) 6.71 (d, 1 H) 7.42-7.50 (m, 1 H) 7.94 (s, 1 H).

Fraction 2: White solid. Yield: 6.6 mg. Retention time: 17.4 min. [Chiralpak AD-H, column 4.6×100 mm, 5 mic; 20 mg/2 mL EtOH; heptane/IP A; 85:15 (v:v); 1 mL/min]. $^1$H NMR (400 MHz, METHANOL-$d_4$) δ [ppm] 1.06-1.18 (m, 2H) 1.20 (s, 3 H) 1.21 (s, 3 H) 1.24-1.42 (m, 4 H) 1.63-1.74 (m, 2 H) 1.91-2.01 (m, 2 H) 2.04-2.19 (m, 3 H) 2.75 (br. s., 1 H) 3.19 (d, J=7.04 Hz, 2 H) 3.57-3.66 (m, 1 H) 3.66-3.74 (m, 2 H) 6.52 (d, 1 H) 6.61 (s, 1 H) 6.72 (d, 1 H) 7.43-7.50 (m, 1 H) 7.94 (s, 1 H). Absolute stereochemistry of compounds in Fraction 1 and Fraction 2 is not determined.

Example 25

Compound 269

N2'-(trans-4-aminocyclohexyl)-5'-chloro-5-fluoro-N6-((tetrahydro-2H-pyran-4-yl)methyl)-2,4'-bipyridine-2',6-diamine

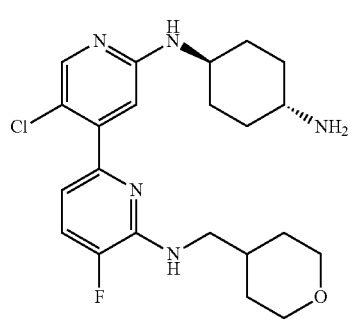 [SMILES: N[C@H]1CC[C@H](Nc2cc(-c3ccc(F)c(NCC4CCOCC4)n3)c(Cl)cn2)CC1]

A mixture of 5'-chloro-2',5-difluoro-N-((tetrahydro-2H-pyran-4-yl)methyl)-2,4'-bipyridin-6-amine (30 mg, 0.088 mmol) and trans-cyclohexane-1,4-diamine (81 mg, 0.706 mmol) in DMSO (0.3 mL) under argon in a sealed tube was heated at 103° C. for 18 hr. The mixture was allowed to cool to ambient temperature. The mixture was diluted with DMSO and filtered through a syringe filter. Purification by HPLC provided N2'-(trans-4-aminocyclohexyl)-5'-chloro-5-fluoro-N6-((tetrahydro-2H-pyran-4-yl)methyl)-2,4'-bipyridine-2',6-diamine as its trifluoroacetic acid salt. Yield: 22.3 mg. LCMS (m/z): 434.1 [M+H]+; Retention time=0.57 min.
$^1$H NMR (400 MHz, METHANOL-$d_4$) δ [ppm] 1.22 (dd, J=12.91, 4.30 Hz, 2 H) 1.31-1.65 (m, 6 H) 1.87 (ddd, J=11.05, 7.34, 3.91 Hz, 1 H) 2.07 (dd, 4 H) 3.00-3.13 (m, 1 H) 3.24-3.34 (m, 4 H) 3.50-3.64 (m, 1 H) 3.84 (dd, J=11.15, 2.93 Hz, 2 H) 6.79 (dd, 1 H) 6.93 (s, 1 H) 7.20 (dd, 1 H) 7.93 (s, 1 H).

Example 26

Compound 155

Ethyl 2-(trans-4-(5'-chloro-6-(3-fluorobenzylamino)-2,4'-bipyridin-2'-yl-amino)cyclohexylamino)oxazole-4-carboxylate

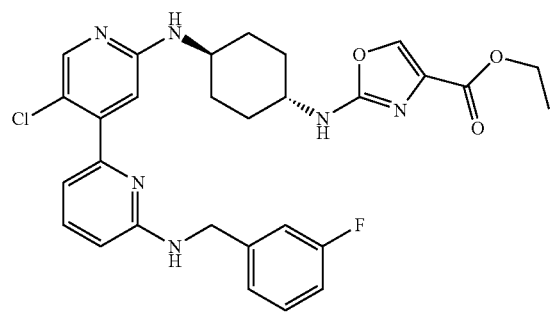 [SMILES: CCOC(=O)c1coc(N[C@H]2CC[C@H](Nc3cc(-c4cccc(NCc5cccc(F)c5)n4)c(Cl)cn3)CC2)n1]

A mixture of N2'-(trans-4-aminocyclohexyl)-5'-chloro-N6-(3-fluorobenzyl)-2,4'-bipyridine-2',6-diamine (25 mg, 0.059 mmol), ethyl 2-chlorooxazole-4-carboxylate (12.88 mg, 0.073 mmol), triethylamine (0.041 mL, 0.293 mmol) in dioxane (1 mL) was heated at 80° C. for 20 hr. The mixture was concentrated in vacuo. The resulting residue was dissolved in DMSO and purified by HPLC providing ethyl 2-(trans-4-(5'-chloro-6-(3-fluorobenzylamino)-2,4'-bipyridin-2'-yl-amino)cyclohexylamino)oxazole-4-carboxylate as its trifluoroacetic acid salt. Yield: 7.1 mg. LCMS (m/z): 565.2 [M+H]+; Retention time=0.85 min.

Example 27

Compound 156

5'-chloro-N2'-(trans-4-(6-chloropyrimidin-4-yl-amino)cyclohexyl)-N6-(3-fluorobenzyl)-2,4'-bipyridine-2',6-diamine

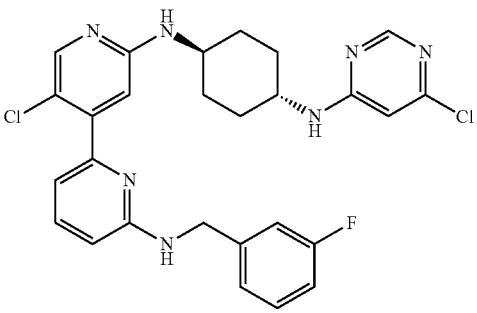 [SMILES: Fc1cccc(CNc2cccc(-c3cc(N[C@H]4CC[C@H](Nc5cc(Cl)ncn5)CC4)ncc3Cl)n2)c1]

A mixture of N2'-(trans-4-aminocyclohexyl)-5'-chloro-N6-(3-fluorobenzyl)-2,4'-bipyridine-2',6-diamine (25 mg, 0.059 mmol), 4,6-dichloropyrimidine (10.93 mg, 0.073 mmol), triethylamine (0.020 mL, 0.147 mmol) in dioxane (1 mL) was heated at 80° C. for ~16 hr. The mixture was concentrated in vacuo. The resulting residue was dissolved in DMSO and purified by HPLC providing 5'-chloro-N2'-(trans-4-(6-chloropyrimidin-4-yl-amino)cyclohexyl)-N6-(3-fluorobenzyl)-2,4'-bipyridine-2',6-diamine as its trifluoroacetic acid salt. Yield: 18 mg. LCMS (m/z): 538.1 [M+H]+; Retention time=0.82 min.

Example 28

Compound 266

N2'-(trans-4-aminocyclohexyl)-3,5,5'-trichloro-N6-((tetrahydro-2H-pyran-4-yl)methyl)-2,4'-bipyridine-2',6-diamine

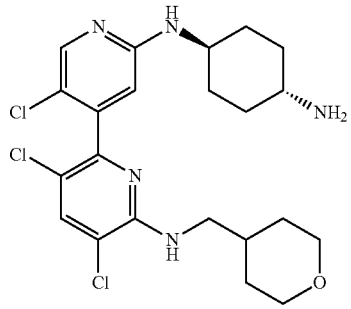 [SMILES: N[C@H]1CC[C@H](Nc2cc(-c3nc(NCC4CCOCC4)c(Cl)cc3Cl)c(Cl)cn2)CC1]

Step 1: Preparation of 6-bromo-N-((tetrahydro-2H-pyran-4-yl)methyl)pyridin-2-amine To a solution of 2-bromo-6-fluoropyridine (3 g, 17.05 mmol) in DMSO (8 mL) was added (tetrahydro-2H-pyran-4-yl)methanamine (3.10 g, 20.46 mmol) and triethylamine (5.68 mL, 40.9 mmol). The mixture was heated at 110° C. for 18 hr. The mixture was allowed to cool to ambient temperature and diluted with EtOAc. The organic layer was washed with saturated aqueous NaHCO$_3$ solution (1×), water (1×), brine (1×), dried over Na$_2$SO$_4$, filtered off and concentrated in vacuo. The resulting residue was purified by column chromatography over silica gel providing 6-bromo-N-((tetrahydro-2H-pyran-4-yl)methyl)pyridin-2-amine as a white solid. Yield: 4.24 g. LCMS (m/z): 270.9/273.0 [M+H]+; Retention time=0.78 min.

Step 2: Preparation of 6-bromo-3,5-dichloro-N-((tetrahydro-2H-pyran-4-yl)methyl)pyridin-2-amine Step 2a To a solution of 6-bromo-N-((tetrahydro-2H-pyran-4-yl)methyl)pyridin-2-amine (20 g, 74 mmol) in acetonitrile (240 mL) was added NCS (9.85 g, 74 mmol). The mixture was heated to 80° C. for 3 hr. The reaction mixture was allowed to cool to ambient temperature and concentrated in vacuo. The resulting residue was diluted with brine (200 mL) and extracted with EtOAc (3×200 mL). The combined organic layers were concentrated in vacuo. The resulting residue was purified by column chromatography [SiO$_2$, EtOAc/heptane= 0/100 to 50/50] providing 6-bromo-5-chloro-N-((tetrahydro-2H-pyran-4-yl)methyl)pyridin-2-amine (12 g) and a mixture of 6-bromo-3,5-dichloro-N-((tetrahydro-2H-pyran-4-yl)methyl)pyridin-2-amine/6-bromo-3-chloro-N-((tetrahydro-2H-pyran-4-yl)methyl)pyridin-2-amine (5 g, ratio ~2:3).

Step 2b: To a solution of a mixture of 6-bromo-3,5-dichloro-N-((tetrahydro-2H-pyran-4-yl)methyl)pyridin-2-amine/6-bromo-3-chloro-N-((tetrahydro-2H-pyran-4-yl)methyl)pyridin-2-amine (4.5 g, ratio ~2:3) in acetonitrile (40 mL) was added NCS (1.250 g, 9.36 mmol). The mixture was heated to 80° C. for 50 min. The mixture was allowed to cool to ambient temperature and concentrated in vacuo. The resulting residue was purified by column chromatography [SiO$_2$, 120 g, EtOAc/heptane] providing 6-bromo-3,5-dichloro-N-((tetrahydro-2H-pyran-4-yl)methyl)pyridin-2-amine as white solid. Yield: 2.25 g. LCMS (m/z): 340.9[M+H]+; Retention time=1.11 min.

Step 3: Preparation of 3,5,5'-trichloro-2'-fluoro-N-((tetrahydro-2H-pyran-4-yl)methyl)-2,4'-bipyridin-6-amine A mixture of 6-bromo-3,5-dichloro-N-((tetrahydro-2H-pyran-4-yl)methyl)pyridin-2-amine (1 g, 2.94 mmol), 5-chloro-2-fluoropyridin-4-ylboronic acid (0.774 g, 4.41 mmol), PdCl$_2$(dppf).CH$_2$Cl$_2$ adduct (0.240 g, 0.294 mmol) in DME (12 mL) and 2M aqueous Na$_2$CO$_3$ solution (4 mL, 2.94 mmol) in a sealed tube was heated at 90° C. for 2 hr. The mixture was allowed to cool to ambient temperature and was diluted with EtOAc (~100 mL) and saturated aqueous NaHCO$_3$. The separated organic layer was washed with saturated aqueous NaHCO$_3$ (2×), brine, dried over Na$_2$SO$_4$, filtered off and concentrated in vacuo. The resulting residue was purified by column chromatography [SiO$_2$, 80 g, EtOAc/heptane= 0/100 to 30/70 over 25 min] providing 3,5,5'-trichloro-2'-fluoro-N-((tetrahydro-2H-pyran-4-yl)methyl)-2,4'-bipyridin-6-amine as a colorless liquid. Yield: 510 mg. LCMS (m/z): 391.9 [M+H]+; Retention time=1.14 min.

Step 4: Preparation of N2'-(trans-4-aminocyclohexyl)-3,5,5'-trichloro-N6-((tetrahydro-2H-pyran-4-yl)methyl)-2,4'-bipyridine-2',6-diamine A mixture of 3,5,5'-trichloro-2'-fluoro-N-((tetrahydro-2H-pyran-4-yl)methyl)-2,4'-bipyridin-6-amine (35 mg, 0.090 mmol) and trans-cyclohexane-1,4-diamine (10.23 mg, 0.090 mmol) in DMSO (0.3 mL) under argon in a sealed tube was heated at 100° C. for 18 hr. The mixture was allowed to cool to ambient temperature. The mixture was diluted with DMSO, filtered through a syringe filter. Purification by HPLC provided N2'-(trans-4-aminocyclohexyl)-3,5,5'-trichloro-N6-((tetrahydro-2H-pyran-4-yl)methyl)-2,4'-bipyridine-2',6-diamine as its trifluoroacetic acid salt. Yield: 38 mg. LCMS (m/z): 486.0 [M+H]+; Retention time=0.70 min.

$^1$H NMR (400 MHz, METHANOL-d$_4$) δ [ppm] 1.28 (dd, J=13.11, 4.11 Hz, 2 H) 1.34-1.48 (m, 2 H) 1.49-1.69 (m, 4 H) 1.85-2.01 (m, 1 H) 2.10 (d, J=12.13 Hz, 2 H) 2.15-2.26 (m, 2 H) 3.07-3.20 (m, 1 H) 3.31-3.40 (m, 4 H) 3.65-3.75 (m, 1 H) 3.91 (dd, J=11.35, 2.74 Hz, 2 H) 6.59 (s, 1H) 7.69 (s, 1H) 8.02 (s, 1 H).

Example 29

Compound 311

N2'-(trans-4-aminocyclohexyl)-5'-chloro-N6-((4-methyltetrahydro-2H-pyran-4-yl)methyl)-2,4'-bipyridine-2',6-diamine

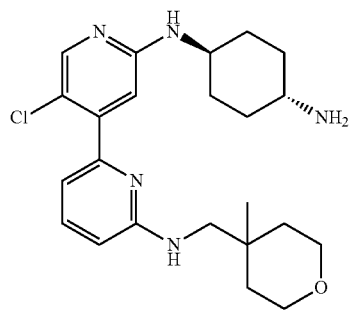 [SMILES: CC1(CNc2cccc(-c3cc(N[C@H]4CC[C@H](N)CC4)ncc3Cl)n2)CCOCC1]

Step 1: Preparation of 4-methyltetrahydro-2H-pyran-4-carbonitrile (following reference: WO2005/058860)

To a solution of tetrahydro-2H-pyran-4-carbonitrile (2 g, 18.00 mmol) in THF (10 mL) at 0-5° C. was slowly added LHMDS (21.59 mL, 21.59 mmol). The mixture was stirred for 1.5 hr 0° C. Iodomethane (3.37 mL, 54.0 mmol) was added slowly and stirring was continued for 30 min at ~0° C. and ~2 hr at ambient temperature. The mixture was cooled to 0° C. and carefully diluted with 1N aqueous HCl (30 mL) and EtOAc (5 mL) and concentrated. The resulting residue was taken up in diethylether and the separated organic layer was washed with brine, dried over $Na_2SO_4$, filtered off and concentrated in vacuo providing crude 4-methyltetrahydro-2H-pyran-4-carbonitrile as an orange oil, which was directly used in the next reaction without further purification. Yield: 1.8 g. LCMS (m/z): 126.1 [M+H]+; Retention time=0.44 min.

Step 2: Preparation of (4-methyltetrahydro-2H-pyran-4-yl)methanamine

To a solution of 4-methyltetrahydro-2H-pyran-4-carbonitrile (1.8 g, 14.38 mmol) in THF (30 mL) was added carefully 1M LAH/THF (21.57 mL, 21.57 mmol) at 0° C. The reaction mixture was stirred for 15 min at 0° C., allowed to warm to ambient temperature and stirred for ~3 hours at ambient temperature. To the reaction mixture was carefully added water (0.9 mL), 1N aqueous NaOH (2.7 mL) and water (0.9 mL) [Caution: gas development!]. The mixture was vigorously stirred for 30 min. The precipitate was filtered off and rinsed with THF. The solution was concentrated in vacuo providing crude (4-methyltetrahydro-2H-pyran-4-yl)methanamine as a yellowish solid, which was directly used in the next step without further purification. Yield: 1.54 g. LCMS (m/z): 130.1 [M+H]+; Retention time=0.21 min.

Step 3: Preparation of 6-bromo-N-((4-methyltetrahydro-2H-pyran-4-yl)methyl)pyridin-2-amine To a solution of 2-bromo-6-fluoropyridine (619 mg, 3.52 mmol) in DMSO (3 mL) was added (4-methyltetrahydro-2H-pyran-4-yl)methanamine (500 mg, 3.87 mmol) and triethylamine (498 mg, 4.93 mmol). The mixture was heated at 110° C. for 18 hr. The mixture was allowed to cool to ambient temperature and diluted with EtOAc. The organic layer was washed with saturated aqueous $NaHCO_3$ solution (1×), water (1×), brine (1×), dried over $Na_2SO_4$, filtered off and concentrated in vacuo. The resulting residue was purified by column chromatography [$SiO_2$, 24 g, EtOAc/heptane= 0/100 2 min, 0/100 to 40/60 2-25 min] providing 6-bromo-N-((4-methyltetrahydro-2H-pyran-4-yl)methyl)pyridin-2-amine as a white solid. Yield: 750 mg. LCMS (m/z): 285.0/287.0 [M+H]+; Retention time=0.88 min.

Step 4: Preparation of 5'-chloro-2'-fluoro-N-((4-methyltetrahydro-2H-pyran-4-yl)methyl)-2,4'-bipyridin-6-amine A mixture of 6-bromo-N-((4-methyltetrahydro-2H-pyran-4-yl)methyl)pyridin-2-amine (750 mg, 2.63 mmol), 5-chloro-2-fluoropyridin-4-ylboronic acid (830 mg, 4.73 mmol), $PdCl_2(dppf)$-$CH_2Cl_2$ Adduct (215 mg, 0.263 mmol) in DME (12 mL) and 2M aqueous $Na_2CO_3$ (4 mL, 8.00 mmol) in a sealed tube was heated at 103° C. for 4 hr. The mixture was allowed to cool to ambient temperature and was diluted with EtOAc (~50 mL) and saturated aqueous $NaHCO_3$ solution. The separated organic layer was washed with saturated aqueous $NaHCO_3$ solution (2×), dried over $Na_2SO_4$, filtered off and concentrated in vacuo. The resulting residue was purified by column chromatography [$SiO_2$, 40 g, 20 min, EtOAc/heptane= 0/100 for 2 min, then EtOAc/heptane= 5/95 to 50/50 over 18 min, then EtOAc/heptane= 50/50] providing 5'-chloro-2'-fluoro-N-((4-methyltetrahydro-2H-pyran-4-yl)methyl)-2,4'-bipyridin-6-amine as a colorless oil. Yield: 691 mg. LCMS (m/z): 336.2 [M+H]+; Retention time=0.66 min.

Step 5: Preparation of N2'-(trans-4-aminocyclohexyl)-5'-chloro-N6-((4-methyltetrahydro-2H-pyran-4-yl)methyl)-2,4'-bipyridine-2',6-diamine A mixture of 5'-chloro-2'-fluoro-N-((4-methyltetrahydro-2H-pyran-4-yl)methyl)-2,4'-bipyridin-6-amine (50 mg, 0.149 mmol), trans-cyclohexane-1,4-diamine (136 mg, 1.191 mmol), DIPEA (30.1 mg, 0.298 mmol) in DMSO (0.5 mL) was heated at 107° C. for 16 hr. The mixture was diluted with EtOAc and saturated aqueous $NaHCO_3$ solution. The separated aqueous layer was extracted with EtOAc (2×). The combined organic layers were dried over $Na_2SO_4$, filtered off and concentrated in vacuo. The resulting residue was dissolved in DMSO/water (1/1), filtered through a syringe filter and purified by HPLC providing N2'-(trans-4-aminocyclohexyl)-5'-chloro-N6-((4-methyltetrahydro-2H-pyran-4-yl)methyl)-2,4'-bipyridine-2',6-diamine as its trifluoroacetic acid salt. Yield: 59.5 mg. LCMS (m/z): 430.3 [M+H]+; Retention time=0.48 min.

$^1$H NMR (400 MHz, METHANOL-$d_4$) δ [ppm] 1.13 (s, 3 H) 1.33-1.49 (m, 4 H) 1.49-1.68 (m, 4 H) 2.06-2.23 (m, 4 H) 3.07-3.22 (m, 1 H) 3.37 (s, 2H) 3.60-3.69 (m, 2 H) 3.70-3.80 (m, 3 H) 6.77 (s, 1 H) 6.90 (d, J=7.04 Hz, 1 H) 7.12 (d, J=9.00 Hz, 1 H) 7.81-7.91 (m, 1 H) 8.09 (s, 1 H).

Example 30

Compound 312

N2'-(trans-4-aminocyclohexyl)-5'-chloro-5-fluoro-N6-((4-methyltetrahydro-2H-pyran-4-yl)methyl)-2,4'-bipyridine-2',6-diamine

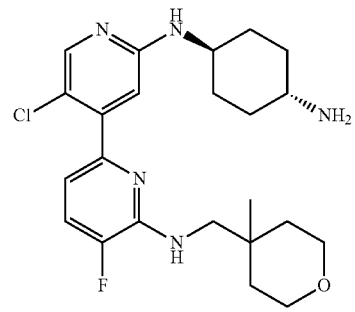 [SMILES: CC1(CNc2nc(-c3cc(N[C@H]4CC[C@H](N)CC4)ncc3Cl)ccc2F)CCOCC1]

Step 1: Preparation of 3,6-difluoro-N-((4-methyltetrahydro-2H-pyran-4-yl)methyl)pyridin-2-amine A mixture of 2,3,6-trifluoropyridine (858 mg, 6.45 mmol), (4-methyltetrahydro-2H-pyran-4-yl)methanamine (1000 mg, 7.74 mmol) and triethylamine (2.158 mL, 15.48 mmol) in NMP (16 mL) was heated at 70° C. for 1 hr. The reaction mixture was allowed to ambient temperature and was diluted with EtOAc (~100 mL), brine (~50 mL) and water (~50 mL). The separated organic layer was washed with brine (1×), 0.3N aqueous HCl (2×), saturated aqueous $NaHCO_3$ solution (1×), brine (1×), dried over $Na_2SO_4$, filtered off and concentrated in vacuo to provide crude 3,6-difluoro-N-((4-methyltetrahydro-2H-pyran-4-yl)methyl)pyridin-2-amine as a colorless oil, which was directly used in the next reaction without further purification. Yield: 1.4 g. LCMS (m/z): 243.1 [M+H]+; Retention time=0.86 min.

Step 2: Preparation of 3-fluoro-6-methoxy-N-((4-methyltetrahydro-2H-pyran-4-yl)methyl)pyridin-2-amine To a solution of 3,6-difluoro-N-((4-methyltetrahydro-2H-pyran-4-yl)methyl)pyridin-2-amine (1.4 g, 5.78 mmol) in MeOH (14 mL) was added sodium methoxide (25 wt. % in MeOH, 7 mL, 30.8 mmol). The mixture was heated in a steel bomb at 135° C. for 3 days. The mixture was cooled to ambient temperature and concentrated in vacuo. The resulting residue was taken up in water (200 mL), and the resulting precipitate was filtered off and rinsed with water. The solid was dissolved in DCM. The organic solution was washed with brine, dried over $Na_2SO_4$, filtered off and concentrated in vacuo. The resulting residue was purified by column chromatography [$SiO_2$, 80 g, 20 min, EtOAc/heptane= 0/100 for 2 min, then EtOAc/heptane= 5/95 to 25/75 over 23 min, EtOAc/heptane= 25/75] providing 3-fluoro-6-methoxy-N-((4-methyltetrahydro-2H-pyran-4-yl)methyl)pyridin-2-amine as an off-white solid. Yield: 1.22 g. LCMS (m/z): 255.1 [M+H]+; Retention time=0.89 min.

Step 3: Preparation of 5-fluoro-6-((4-methyltetrahydro-2H-pyran-4-yl)methyl)aminopyridin-2-ol To 3-fluoro-6-methoxy-N-((4-methyltetrahydro-2H-pyran-4-yl)methyl)pyridin-2-amine in acetonitrile (12 mL) was added sodium iodide (4.24 g, 28.3 mmol) and slowly TMS-Cl (3.62 mL, 28.3 mmol). The mixture was heated to reflux (oil bath: 83° C.) for 4 hr. The mixture was allowed to cool to ambient temperature and was diluted with EtOAc and saturated aqueous $NaHCO_3$ solution. The mixture was vigorously stirred for 15 min and acidified with 0.5N aqueous $NaHSO_4$ solution and stirring was continued for 5 min. The mixture was neutralized with saturated aqueous $NaHCO_3$ solution. The separated aqueous phase was extracted with EtOAc (3×). The combined organic layers were dried over sodium sulfate, filtered off and concentrated in vacuo. The resulting residue was purified by column chromatography [$SiO_2$, 40 g, 25 min, EtOAc/heptane=5/95 for 2 min, 5/95 to 50/50 over 18 min, then 50/50] providing 5-fluoro-6-((4-methyltetrahydro-2H-pyran-4-yl)methyl)aminopyridin-2-ol as colorless highly viscous oil. Yield: 420 mg. LCMS (m/z): 241.1 [M+H]+; Retention time=0.55 min.

Step 4: Preparation of 5-fluoro-6-((4-methyltetrahydro-2H-pyran-4-yl)methyl)aminopyridin-2-yl trifluoromethanesulfonate To a solution of 5-fluoro-6-((4-methyltetrahydro-2H-pyran-4-yl)methyl)aminopyridin-2-ol (420 mg, 1.748 mmol) and triethylamine (0.731 mL, 5.24 mmol) in DCM (16 mL) was added trifluoromethanesulfonic anhydride (0.443 mL, 2.62 mmol) slowly at 0° C. The mixture was stirred for 2 hr at 0° C. and poured carefully into ice-cooled saturated aqueous $NaHCO_3$ solution. The separated aqueous layer was extracted with DCM (2×). The combined organic layers were dried over $Na_2SO_4$, filtered off and concentrated in vacuo. The resulting residue was purified by column chromatography [$SiO_2$, 24 g, EtOAc/heptane= 5/95 for 2 min, then EtOAc/heptane= 5/95 to 40/60 over 13 min, then EtOAc/heptane= 40/60] providing 5-fluoro-6-((4-methyltetrahydro-2H-pyran-4-yl)methyl) aminopyridin-2-yl trifluoromethanesulfonate as colorless oil. Yield: 600 mg.

Step 5: Preparation of 5'-chloro-2',5-difluoro-N-((4-methyltetrahydro-2H-pyran-4-yl)methyl)-2,4'-bipyridin-6-amine A mixture of 5-fluoro-6-((4-methyltetrahydro-2H-pyran-4-yl)methyl)aminopyridin-2-yl trifluoromethanesulfonate (600 mg, 1.611 mmol), 5-chloro-2-fluoropyridin-4-ylboronic acid (565 mg, 3.22 mmol), $PdCl_2$(dppf)-$CH_2Cl_2$ adduct (132 mg, 0.161 mmol) in DME (8 mL) and 2M aqueous $Na_2CO_3$ (3 mL, 6.00 mmol) in a sealed tube was heated at 102° C. for 10 hr. The mixture was cooled to ambient temperature and was diluted with EtOAc (~100 mL) and saturated aqueous $NaHCO_3$ solution. The separated organic layer was washed with saturated aqueous $NaHCO_3$ solution (2×), dried over $Na_2SO_4$, filtered off and concentrated in vacuo. The resulting residue was purified by column chromatography [$SiO_2$, 40 g, EtOAc/heptane= 0/100 for 3 min, EtOAc/heptane=0/100 to 30/70 over 17 min, then EtOAc/heptane= 30/70] providing 5'-chloro-2',5-difluoro-N-((4-methyltetrahydro-2H-pyran-4-yl)methyl)-2,4'-bipyridin-6-amine as a colorless oil. Yield: 490 mg. LCMS (m/z): 354.2 [M+H]+; Retention time=1.05 min.

Step 6: Preparation of N2'-(trans-4-aminocyclohexyl)-5'-chloro-5-fluoro-N6-((4-methyltetrahydro-2H-pyran-4-yl)methyl)-2,4'-bipyridine-2',6-diamine A mixture of 5'-chloro-2',5-difluoro-N-((4-methyltetrahydro-2H-pyran-4-yl)methyl)-2,4'-bipyridin-6-amine (50 mg, 0.141 mmol), trans-cyclohexane-1,4-diamine (129 mg, 1.131 mmol), DIPEA (28.6 mg, 0.283 mmol) in DMSO (0.5 mL) was heated at 107° C. for 16 hr. The mixture was diluted with EtOAc and saturated aqueous $NaHCO_3$ solution. The separated aqueous layer was extracted with EtOAc (2×). The combined organic layers were dried over $Na_2SO_4$, filtered off and concentrated in vacuo. The resulting residue was dissolved in DMSO/water (1/1), filtered through a syringe filter and purified by HPLC providing N2'-(trans-4-aminocyclohexyl)-5'-chloro-5-fluoro-N6-((4-methyltetrahydro-2H-pyran-4-yl)methyl)-2,4'-bipyridine-2',6-diamine as its trifluoroacetic acid salt. Yield: 61.3 mg. LCMS (m/z): 448.2 [M+H]+; Retention time=0.62 min.

$^1$H NMR (400 MHz, METHANOL-$d_4$) δ [ppm] 1.06 (s, 3 H) 1.28-1.54 (m, 4 H) 1.54-1.65 (m, 4 H) 2.06-2.25 (m, 4 H) 3.09-3.22 (m, 1 H) 3.49 (s, 2 H) 3.57-3.72 (m, 3 H) 3.72-3.81 (m, 2 H) 6.86 (dd, 1 H) 6.92 (s, 1 H) 7.31 (dd, 1 H) 7.99 (s, 1 H)

Example 31

Compound 313

N2'-(trans-4-aminocyclohexyl)-5'-chloro-N6-((4-fluorotetrahydro-2H-pyran-4-yl)methyl)-2,4'-bipyridine-2',6-diamine

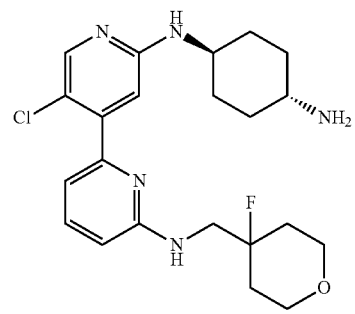 [SMILES: N[C@H]1CC[C@H](Nc2cc(-c3cccc(NCC4(F)CCOCC4)n3)c(Cl)cn2)CC1]

Step 1: Preparation of 4-fluorotetrahydro-2H-pyran-4-carbaldehyde (as described in WO2009/011836)

Step 1a: To a solution of DIPEA (6.12 mL, 35.0 mmol) in DCM (80 mL) was added trimethylsilyl trifluoromethanesulfonate (7.79 g, 35.0 mmol) followed by a solution of tetrahydro-2H-pyran-4-carbaldehyde (2 g, 17.52 mmol) in DCM (80 mL) at 0° C. Upon completion of the addition, the reaction mixture was allowed to stir at ambient temperature for 2 hr. The mixture was concentrated in vacuo and the resulting residue was treated with hexane (200 mL). The precipitate was filtered off and the solution was concentrated in vacuo providing crude trimethylsilyl ether, which was directly used in the next step without further purification.

Step 1b: To a solution of crude trimethylsilyl ether in DCM (100 mL) was added dropwise a solution of N-fluorobenzenesulfonimide (5.53 g, 17.52 mmol), dissolved in DCM (50 mL), at 0° C. The mixture was stirred for 3 hr at ambient temperature and the crude solution of 4-fluorotetrahydro-2H-pyran-4-carbaldehyde was directly used in the next reaction.

Step 2: Preparation of 6-bromo-N-((4-fluorotetrahydro-2H-pyran-4-yl)methyl)pyridin-2-amine To 6-bromopyridin-2-amine (3.03 g, 17.50 mmol) was added the crude solution of 4-fluorotetrahydro-2H-pyran-4-carbaldehyde in DCM. To the mixture was added acetic acid (1.002 mL, 17.50 mmol) and sodium triacetoxyborohydride (5.56 g, 26.3 mmol) in portions. The mixture was stirred for 2 hr at ambient temperature. The mixture was diluted carefully with saturated aqueous $NaHCO_3$ solution. The separated aqueous layer was extracted with DCM (1×). The combined organic layers were washed with water (1×), saturated aqueous $NaHCO_3$ solution (1×) and concentrated in vacuo. The solid resulting residue was dissolved in DCM (100 mL) and 3M aqueous HCl (60 mL). The separated organic layer was extracted with 3M aqueous HCl (3×20 mL). The combined acidic layers were washed with DCM (1×). Solid $NaHCO_3$ was added carefully to the acidic solution [Caution: gas development!] until pH>~8. The aqueous mixture was extracted with DCM (2×) and EtOAc (2×). The combined organic layers were concentrated in vacuo. The resulting residue was dissolved in EtOAc. The solution was washed with 0.3M aqueous HCl, and brine, dried over $Na_2SO_4$, filtered off and concentrated in vacuo. The resulting residue was purified by column chromatography [$SiO_2$, 40 g, EtOAc/heptane= 5/95 for 3 min, then EtOAc/heptane= 5/95 to 30/70 over 15 min, then EtOAc/heptane= 30/70] providing 6-bromo-N-((4-fluorotetrahydro-2H-pyran-4-yl)methyl)pyridin-2-amine as a white solid. Yield: 1.82 g. LCMS (m/z): 288.9/291.0 [M+H]+; Retention time=0.84 min.

Step 3: Preparation of 5'-chloro-2'-fluoro-N-((4-fluorotetrahydro-2H-pyran-4-yl)methyl)-2,4'-bipyridin-6-amine A mixture of 6-bromo-N-((4-fluorotetrahydro-2H-pyran-4-yl)methyl)pyridin-2-amine (1 g, 3.46 mmol), 5-chloro-2-fluoropyridin-4-ylboronic acid (1.092 g, 6.23 mmol), $PdCl_2$(dppf)-$CH_2Cl_2$ adduct (0.282 g, 0.346 mmol) in DME (13 mL) and 2M aqueous $Na_2CO_3$ (5.19 mL, 10.38 mmol) in a sealed tube was heated at 100° C. for 2 hr. The mixture was cooled to ambient temperature and was diluted with EtOAc (~50 mL) and saturated aqueous $NaHCO_3$. The separated organic layer was washed with saturated aqueous $NaHCO_3$ (2×), dried over $Na_2SO_4$, filtered off and concentrated in vacuo. The resulting residue was purified by column chromatography [$SiO_2$, 80 g, EtOAc/heptane= 5/95 for 4 min, then EtOAc/heptane= 5/95 to 50/50 over 18 min, then EtOAc/heptane= 50/50]providing 5'-chloro-2'-fluoro-N-((4-fluorotetrahydro-2H-pyran-4-yl)methyl)-2,4'-bipyridin-6-amine as a colorless oil. Yield: 1.00 g. LCMS (m/z): 340.1 [M+H]+; Retention time=0.67 min.

Step 4: Preparation of N2'-(trans-4-aminocyclohexyl)-5'-chloro-N6-((4-fluorotetrahydro-2H-pyran-4-yl)methyl)-2,4'-bipyridine-2',6-diamine A mixture of 5'-chloro-2'-fluoro-N-((4-fluorotetrahydro-2H-pyran-4-yl)methyl)-2,4'-bipyridin-6-amine (75 mg, 0.221 mmol) and trans-cyclohexane-1,4-diamine (202 mg, 1.766 mmol) in DMSO (1 mL) under argon in a sealed tube was heated at 103° C. for 18 hr. The mixture was cooled to ambient temperature and diluted with EtOAc and water. The separated organic layer was washed with saturated aqueous $NaHCO_3$ solution and concentrated in vacuo. The resulting residue was dissolved in DMSO/water (~2/1), filtered through a syringe filter. Purification by HPLC provided N2'-(trans-4-aminocyclohexyl)-5'-chloro-N6-((4-fluorotetrahydro-2H-pyran-4-yl)methyl)-2,4'-bipyridine-2',6-diamine as its trifluoroacetic acid salt. The material was dissolved in MeOH (3 mL), filtered through VariPure™ IPE [500 mg per 6 mL tube; 0.9 mmol (nominal); part no.: PL3540-C603VP], eluted with MeOH (15 mL) and concentrated in vacuo. The resulting residue was dissolved in acetonitrile/water (~3/1) and lyophilized providing N2'-(trans-4-aminocyclohexyl)-5'-chloro-N6-((4-fluorotetrahydro-2H-pyran-4-yl)methyl)-2,4'-bipyridine-2',6-diamine. Yield: 58 mg. LCMS (m/z): 434.2 [M+H]+; Retention time=0.50 min.

$^1$H NMR (400 MHz, METHANOL-$d_4$) δ [ppm] 1.32 (d, J=9.78 Hz, 4 H) 1.73-1.88 (m, 4 H) 1.91-1.99 (m, 2 H) 2.08 (d, J=9.78 Hz, 2 H) 2.67-2.78 (m, 1 H) 3.57-3.73 (m, 5 H) 3.75-3.84 (m, 2 H) 6.60 (d, J=8.61 Hz, 1 H) 6.63 (s, 1 H) 6.78 (d, J=7.43 Hz, 1 H) 7.34-7.55 (m, 1 H) 7.94 (s, 1 H).

Example 32

Compound 152

N2'-((1S,3S,4S)-4-amino-3-methylcyclohexyl)-5'-chloro-N6-(3-fluorobenzyl)-2,4'-bipyridine-2',6-diamine/N2'-((1R,3R,4R)-4-amino-3-methylcyclohexyl)-5'-chloro-N6-(3-fluorobenzyl)-2,4'-bipyridine-2',6-diamine

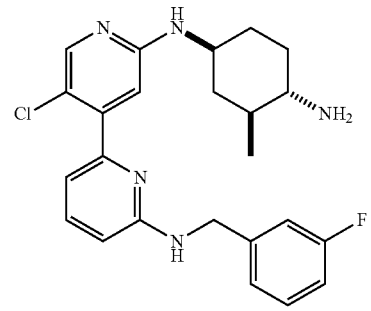

Step 1: Preparation of 4-(dibenzylamino)cyclohexanol

To a mixture of 4-aminocyclohexanol (3.51 g, 23.15 mmol) and $K_2CO_3$ (12.80 g, 93 mmol) in acetonitrile (100 mL) was added benzylbromide (5.64 mL, 47.5 mmol) and the mixture was stirred at reflux for 17 hr. The crude mixture was concentrated in vacuo and the resulting residue was dissolved in water and EtOAc. The separated aqueous layer was extracted with EtOAc (2×~100 mL). The combined organic layers were washed with brine, dried over $Na_2SO_4$, filtered off and concentrated in vacuo providing crude 4-(dibenzylamino)cyclohexanol as a viscous oil, which was directly used in the next step without further purification. Yield: 6.12 g. LCMS (m/z): 296.1 [M+H]+; Retention time=0.59 min.

Step 2: Preparation of 4-(dibenzylamino)cyclohexanone (following reference WO96/07657)

To a solution of oxalylic acid (2.03 mL, 20.31 mmol) in DCM (80 mL) at −60° C. was added dropwise DMSO (3.46 mL, 48.8 mmol). After stirring for 5 min, a solution of 4-(dibenzylamino)cyclohexanol (6 g, 20.31 mmol) in DCM (40 mL) was added slowly. The mixture was stirred for 15 min and $NEt_3$ (14.3 mL, 103 mmol) was added slowly. After stirring for 15 min the ice bath was removed and the mixture was stirred for additional 16 hr. The mixture was diluted with water (100 mL). The separated organic layer was washed with brine (1×~75 mL), dried over Na$_2$SO$_4$, filtered off and concentrated in vacuo. The resulting residue was purified by column chromatography [SiO$_2$, 120 g, EtOAc/hexane= 10/90 to 50/50] providing 4-(dibenzylamino)cyclohexanone as a white solid. Yield: 5.5 g. LCMS (m/z): 294.1 [M+H]+; Retention time=0.58 min.

Step 3: Preparation of (2S,4S)-4-(dibenzylamino)-2-methylcyclohexanone/(2R,4R)-4-(dibenzylamino)-2-methylcyclohexanone A solution of 4-(dibenzylamino)cyclohexanone (4 g, 13.63 mmol) in THF (27 mL) was added to KHMDS/toluene (32.7 mL, 16.36 mmol) at ambient temperature. The mixture was stirred for 15 min at ambient temperature. Triethylborane (1M in THF, 17.72 mL, 17.72 mmol) was added dropwise and the mixture was allowed to stir an additional 30 min. Iodomethane (1.6 mL, 25.7 mmol) was added and the mixture was stirred for 20 hr at ambient temperature. Aqueous 1M NaOH solution was added (~25 mL) and the mixture was vigorously stirred for 3 hr. The mixture was extracted with EtOAc (4×~100 mL) and the combined organic layers were washed with brine, dried over Na$_2$SO$_4$, filtered off, and concentrated in vacuo. The resulting residue was purified by column chromatography [SiO$_2$, 125 g, EtOAc/hexane= 0/100 to 20/80]. Fractions were combined and concentrated in vacuo providing (2S,4S)-4-(dibenzylamino)-2-methylcyclohexanone/(2R,4R)-4-(dibenzylamino)-2-methylcyclohexanone as a highly viscous oil, which became partially a white solid. Yield: 3.1 g. LCMS (m/z): 308.2[M+H]+; Retention time=0.65 min (major isomer). Ratio major/minor isomer: ~9:1.

Step 4: Preparation of (1R,2S,4S)-4-(dibenzylamino)-2-methylcyclohexanol/(1S,2R,4R)-4-(dibenzylamino)-2-methylcyclohexanol To a solution of (2S,4S)-4-(dibenzylamino)-2-methylcyclohexanone/(2R,4R)-4-(dibenzylamino)-2-methylcyclohexanone (3.1 g, 10.08 mmol) in THF (55 mL) at −78° C. was added L-selectride (15.13 mL, 15.13 mmol) dropwise. After stirring for 5 min at −78° C. the mixture was allowed to warm up to 0° C. Stirring was continued for 18 hr as the reaction mixture mixture was warmed from 0° C. to ambient temperature. The mixture was diluted carefully with 1N aq NaOH (15 mL) and stirred vigorously for 3 hr. The mixture was extracted with EtOAc (3×~100 mL). The combined organic layers were washed with brine (~100 mL), dried over Na$_2$SO$_4$, filtered off and concentrated in vacuo. The resulting residue was purified by column chromatography [SiO$_2$, 120 g, EtOAc/hexane= 0/100 to 20/80 over-25 min; EtOAc/hexane= 20/80 to 40/60 over 5 min] providing (1R,2S,4S)-4-(dibenzylamino)-2-methylcyclohexanol/(1S,2R,4R)-4-(dibenzylamino)-2-methylcyclohexanol as a colorless liquid. Yield: 2.83 g. LCMS (m/z): 310.3 [M+H]+; Retention time=0.66 min.

Step 5: Preparation of (1S,3S ,4S)-4-azido-N,N-dibenzyl-3-methylcyclohexanamine/(1R,3R,4R)-4-azido-N,N-dibenzyl-3-methylcyclohexanamine A mixture of DIAD (5.03 mL, 25.9 mmol) and triphenylphosphine (6.78 g, 25.9 mmol) in THF (35 mL) was allowed to form a salt. After 30 min a solution of (1R,2S,4S)-4-(dibenzylamino)-2-methylcyclohexanol/(1S,2R,4R)-4-(dibenzylamino)-2-methylcyclohexanol (2 g, 6.46 mmol) and diphenyl phosphorazidate (2.507 mL, 11.63 mmol) in THF (25 mL) was added and the mixture was stirred for 20 hr at 55° C. The mixture was cooled to ambient temperature and diluted with EtOAc and brine. The separated organic layer was dried over Na$_2$SO$_4$, filtered off and concentrated in vacuo providing crude (1S,3S ,4S)-4-azido-N,N-dibenzyl-3-methylcyclohexanamine/(1R,3R,4R)-4-azido-N,N-dibenzyl-3-methylcyclohexanamine as orange oil, which was directly used in the next step without further purification. LCMS (m/z): 335.1 [M+H]+; Retention time=0.81 min.

Step 6: Preparation of (1S,3S ,4S)—N1,N1-dibenzyl-3-methylcyclohexane-1,4-diamine/(1R,3R,4R)—N1,N1-dibenzyl-3-methylcyclohexane-1,4-diamine To a solution of (1S,3S ,4S)-4-azido-N,N-dibenzyl-3-methylcyclohexanamine/(1R,3R,4R)-4-azido-N,N-dibenzyl-3-methylcyclohexanamine (2.174 g, 6.5 mmol) in acetic acid (50 mL) was added slowly Zn-dust (0.638 g, 9.75 mmol). The mixture was stirred for 30 min at ambient temperature. Additional Zn-dust was added (150 mg) and stirring was continued for ~15 min. The mixture was diluted carefully with 1N aqueous HCl and diethylether. The separated aqueous layer was extracted with diethylether (5×~100 mL). The aqeuous layer was partially lyophilized and concentrated to dryness in vacuo. The resulting residue was diluted with 1N aqueous HCl and concentration to dryness was repeated. Dilution with 1N HCl and concentration was repeated. The resulting residue was dissolved in water/acetonitrile and lyophilized to provide crude (1S,3S ,4S)—N1,N1-dibenzyl-3-methylcyclohexane-1,4-diamine/(1R,3R,4R)—N1,N1-dibenzyl-3-methylcyclohexane-1,4-diamine as fluffy white solid. The crude material was directly used in the next step without further purification. Yield: 2.292 g. LCMS (m/z): 309.3 [M+H]+; Retention time=0.50 min.

Step 7: Preparation of tert-butyl (1S,2S,4S)-4-(dibenzylamino)-2-methylcyclohexylcarbamate/tert-butyl (1R,2R,4R)-4-(dibenzylamino)-2-methylcyclohexylcarbamate To (1S,3S ,4S)—N1,N1-dibenzyl-3-methylcyclohexane-1,4-diamine/(1R,3R,4R)—N1,N1-dibenzyl-3-methylcyclohexane-1,4-diamine (1.851 g, 6 mmol) in dioxane (200 mL) and saturated aqueous NaHCO$_3$ solution (100 mL) was added BOC-anhydride (2.438 mL, 10.50 mmol), dissolved in dioxane (~5 mL). The resulting white suspension was stirred vigorously for 18 hr. The mixture was extracted with DCM (4×300 mL) and EtOAc (1×100 mL). The combined organic layers were concentrated in vacuo. The resulting residue was dissolved in EtOAc, washed with brine, dried over Na$_2$SO$_4$, filtered of and concentrated in vacuo. The resulting residue was purified by column chromatography [SiO$_2$, 120 g, DCM/MeOH= 100/0 to 95/5]. Fractions containing product were combined, concentrated in vacuo providing tert-butyl (1S,2S,4S)-4-(dibenzylamino)-2-methylcyclohexylcarbamate/tert-butyl (1R,2R,4R)-4-(dibenzylamino)-2-methylcyclohexylcarbamate. Yield: 778 mg. LCMS (m/z): 409.2 [M+H]+; Retention time=0.84 min.

Step 8: Preparation of tert-butyl (1S,2S,4S)-4-amino-2-methylcyclohexylcarbamate/tert-butyl (1R,2R,4R)-4-amino-2-methylcyclohexylcarbamate A mixture of tert-butyl (1S,2S,4S)-4-(dibenzylamino)-2-methylcyclohexylcarbamate/tert-butyl (1R,2R,4R)-4-

(dibenzylamino)-2-methylcyclohexylcarbamate (750 mg, 1.836 mmol) and Pearlman's catalyst (290 mg, 2.73 mmol) in EtOH (35 mL) was hydrogenated in a steel bomb under H$_2$-atmosphere (pressure ~75 psi) for 16 hr. The steel bomb was flushed with Argon, Celite and methanol were added. The mixture was filtered and concentrated in vacuo. The white resulting residue was dissolved in acetonitrile/water (1:1) and lyophilized giving crude tert-butyl (1S,2S,4S)-4-amino-2-methylcyclohexylcarbamate/tert-butyl (1R,2R,4R)-4-amino-2-methylcyclohexylcarbamate, which was directly used in the next step without further purification. Yield: 412 mg. LCMS (m/z): 173.2/229.3 [M+H]+; Retention time=0.54 min.

Step 9: Preparation of N2'-((1S,3S ,4S)-4-amino-3-methylcyclohexyl)-5'-chloro-N6-(3-fluorobenzyl)-2, 4'-bipyridine-2',6-diamine/N2'-((1R,3R,4R)-4-amino-3-methylcyclohexyl)-5'-chloro-N6-(3-fluorobenzyl)-2,4'-bipyridine-2',6-diamine Step 9a: A mixture of Intermediate B (preparation of intermediate B is described in the intermediate session which is in front of the Examples) (25 mg, 0.075 mmol), tert-butyl (1S, 2S,4S)-4-amino-2-methylcyclohexylcarbamate/tert-butyl (1R,2R,4R)-4-amino-2-methylcyclohexylcarbamate (25.8 mg, 0.113 mmol), triethylamine (28 μl, 0.201 mmol) in DMSO (0.25 mL) was heated at 100° C. for 3 days. The mixture was allowed to cool to ambient temperature and diluted with EtOAc (20 mL) and saturated aqueous NaHCO$_3$ solution (10 mL). The separated aqueous layer was extracted with EtOAc (3×). The combined organic layers were dried over Na$_2$SO$_4$, filtered off and concentrated in vacuo providing crude tert-butyl (1S,2S,4S)-4-(5'-chloro-6-(3-fluorobenzylamino)-2,4'-bipyridin-2'-yl-amino)-2-methylcyclohexylcarbamate/tert-butyl (1R,2R,4R)-4-(5'-chloro-6-(3-fluorobenzylamino)-2,4'-bipyridin-2'-yl-amino)-2-methylcyclohexylcarbamate, which was directly used in the next step without further purification.

Step 9b: To a solution of crude tert-butyl (1S,2S,4S)-4-(5'-chloro-6-(3-fluorobenzylamino)-2,4'-bipyridin-2'-yl-amino)-2-methylcyclohexylcarbamate/tert-butyl (1R,2R, 4R)-4-(5'-chloro-6-(3-fluorobenzylamino)-2,4'-bipyridin-2'-yl-amino)-2-methylcyclohexylcarbamate was dissolved in MeOH (3 mL) was added 4M HCl/dioxane (9 mL, 36.0 mmol). The mixture was stirred for 1 hr and concentrated in vacuo. The resulting residue was dissolved in DMSO, filtered over a syringe filter and purified by HPLC providing N2'-((1S,3S ,4S)-4-amino-3-methylcyclohexyl)-5'-chloro-N6-(3-fluorobenzyl)-2,4'-bipyridine-2',6-diamine/N2'-((1R,3R, 4R)-4-amino-3-methylcyclohexyl)-5'-chloro-N6-(3-fluorobenzyl)-2,4'-bipyridine-2',6-diamine as the trifluoroacetic acid salt. Yield: 28.1 mg. LCMS (m/z): 440.1 [M+H]+; Retention time=0.62 min.

Example 33

Compound 224

5-(2-(trans-4-aminocyclohexylamino)-5-chloropyridin-4-yl)-3-((tetrahydro-2H-pyran-4-yl)methyl)aminopyrazine-2-carboxamide

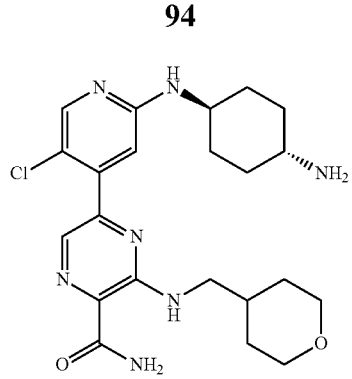

Step 1. Preparation of 5-(5-chloro-2-fluoropyridin-4-yl)-3-((tetrahydro-2H-pyran-4-yl)methyl)aminopyrazine-2-carboxamide:

3-chloro-6-(5-chloro-2-fluoropyridin-4-yl)-N-((tetrahydro-2H-pyran-4-yl)methyl)pyrazin-2-amine (0.0342 g, 0.096 mmol), CuCN (0.034 g, 0.383 mmol), and dppf (0.085 g, 0.153 mmol) were dissolved in dioxane (1.5 ml). The solution was then degassed by sparging with argon for 5 min. It was then treated with Pd2(dba)$_3$ (0.035 g, 0.038 mmol). The reaction mixture was then heated at 100° C. for 5 hr. The reaction mixture was filtered through a pad of Celite then it was concentrated in vacuo to give 0.110 g of 5-(5-chloro-2-fluoropyridin-4-yl)-3-((tetrahydro-2H-pyran-4-yl)methyl)aminopyrazine-2-carboxamide. LCMS (m/z): 366 (MH$^+$), retention time=0.89 min.

Step 2. Preparation of 5-(2-(trans-4-aminocyclohexylamino)-5-chloropyridin-4-yl)-3-((tetrahydro-2H-pyran-4-yl)methyl)aminopyrazine-2-carboxamide 5-(5-chloro-2-fluoropyridin-4-yl)-3-((tetrahydro-2H-pyran-4-yl)methyl)aminopyrazine-2-carboxamide (0.035 g, 0.096 mmol) was dissolved in DMSO (2 ml). This was treated with 1,4-diaminocyclohexane (0.109 g, 0.957 mmol). The reaction mixture was then heated at 100° C. for 4 hr. The material was purified by preparative reverse-phase HPLC to give 0.0053 g of 5-(2-(trans-4-aminocyclohexylamino)-5-chloropyridin-4-yl)-3-((tetrahydro-2H-pyran-4-yl)methyl) aminopyrazine-2-carboxamide as the TFA salt. LCMS (m/z): 460.1 (MH$^+$), retention time=0.54 min.

Example 34

Compound 231 trans-N1-(5-chloro-4-(5-methyl-6-((tetrahydro-2H-pyran-4-yl)methyl)aminopyrazin-2-yl)pyridin-2-yl)cyclohexane-1,4-diamine

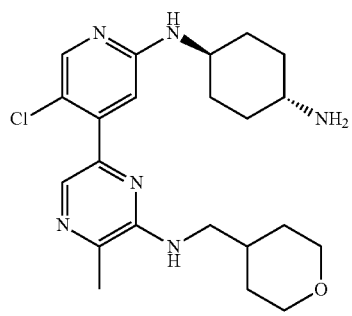

Step 1. Preparation of 6-(5-chloro-2-fluoropyridin-4-yl)-3-methyl-N-(tetrahydro-2H-pyran-4-yl-methyl)pyrazine-2-amine:

3-chloro-6-(5-chloro-2-fluoropyridin-4-yl)-N-((tetrahydro-2H-pyran-4-yl)methyl)pyrazin-2-amine (0.0275 g, 0.077 mmol), methylboronic acid (0.014 g, 0.231 mmol), and sodium carbonate (0.100 ml, 0.200 mmol, 2M aq solution) were dissolved in DME (1.0 ml). The solution was then degassed by sparging with argon for 5 min. It was then treated with PdCl$_2$(dppf).CH$_2$Cl$_2$ adduct (0.013 g, 0.015 mmol). The reaction mixture was then heated in the microwave at 105° C. for 20 min. More of the above reagents in the same amounts were added to the reaction mixture and heating in the microwave was continued at 115° C. for 20 min. The reaction mixture was allowed to cool to ambient temperature. It was then filtered through a pad of Celite. The filtrate was concentrated in vacuo to yield 0.0497 g of a mixture of 6-(5-chloro-2-fluoropyridin-4-yl)-3-methyl-N-((tetrahydro-2H-pyran-4-yl)methyl)pyrazine-2-amine and 6-(2-fluoro-5-methylpyridin-4-yl)-3-methyl-N-((tetrahydro-2H-pyran-4-yl-methyl)pyrazine-2-amine.

Step 2. Preparation of trans-N1-(5-chloro-4-(5-methyl-6-((tetrahydro-2H-pyran-4-yl)methyl)aminopyrazin-2-yl)pyridin-2-yl)cyclohexane-1,4-diamine:

The mixture of 6-(5-chloro-2-fluoropyridin-4-yl)-3-methyl-N-((tetrahydro-2H-pyran-4-yl)pyrazine-2-amine and 6-(2-fluoro-5-methylpyridin-4-yl)-3-methyl-N-((tetrahydro-2H-pyran-4-yl methyl)pyrazine-2-amine (0.025 g, 0.074 mmol) and (0.023 g, 0.074 mmol) respectively was dissolved in DMSO (1 ml). This was treated with 1,4-diaminocyclohexane (0.085 g, 0.742 mmol). The reaction mixture was then heated at 100° C. for 18 hr. The material was purified by preparative reverse-phase HPLC to give 0.0047 g of trans-N1-(5-chloro-4-(5-methyl-6-((tetrahydro-2H-pyran-4-yl)methyl)aminopyrazin-2-yl)pyridin-2-yl)cyclohexane-1,4-diamine as the TFA salt. LCMS (m/z): 431.2 (MH$^+$), retention time=0.49 min.

Example 35

Compound 240 trans-N$^1$-(5-chloro-4-(5-cyclopropyl-6-((tetrahydro-2H-pyran-4-yl)methyl)aminopyrazin-2-yl)pyridin-2-yl)cyclohexane-1,4-diamine

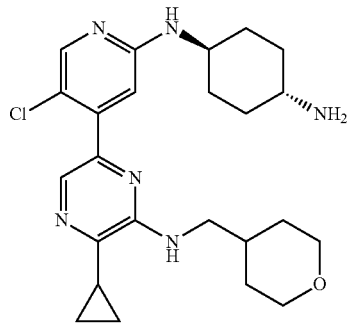 [SMILES: N[C@H]1CC[C@H](Nc2cc(-c3cnc(C4CC4)c(NCC4CCOCC4)n3)c(Cl)cn2)CC1]

Step 1. Preparation of 6-(5-chloro-2-fluoropyridin-4-tl)-3-cyclopropyl-N-((tetrahydro-2H-pyran-4-yl)methyl)pyrazin-2-amine 3-chloro-6-(5-chloro-2-fluoropyridin-4-yl)-N-((tetrahydro-2H-pyran-4-yl)methyl)pyrazin-2-amine (0.0316 g, 0.088 mmol), potassium cyclopropyltrifluoroborate (0.026 g, 0.177 mmol), and potassium phosphate (0.113 g, 0.531 mmol) were dissolved in a mixture of toluene (1 ml) and H$_2$O (0.170 ml). The solution was then degassed by sparging with argon for 5 min. At this time it was treated with PdCl$_2$(dppf).CH$_2$Cl$_2$ adduct (0.014 g, 0.018 mmol). The reaction mixture was then heated in the microwave at 115° C. for 25 min. The reaction mixture was filtered through a plug of Celite and the filtrate was concentrated in vacuo to give 0.0445 g of the crude product. The resulting residue was subjected to silica gel column chromatography. Elution using 20 EtOAc/80 heptane to 70 EtOAc/30 heptane gave 0.0271 g (84%) of 6-(5-chloro-2-fluoropyridin-4-tl)-3-cyclopropyl-N-((tetrahydro-2H-pyran-4-yl)methyl)pyrazin-2-amine. LCMS (m/z): 363.1 (MET), retention time=1.06 min.

Step 2. Preparation of trans-N$^1$-(5-chloro-4-(5-cyclopropyl-6-((tetrahydro-2H-pyran-4-yl)methyl)aminopyrazin-2-yl)pyridin-2-yl)cyclohexane-1,4-diamine:

6-(5-chloro-2-fluoropyridin-4-tl)-3-cyclopropyl-N-((tetrahydro-2H-pyran-4-yl)methyl)pyrazin-2-amine (0.0267 g, 0.074 mmol) was dissolved in DMSO (1 ml). This was treated with 1,4-diaminocyclohexane (0.084 g, 0.736 mmol). The reaction mixture was then heated at 100° C. for 4 hr. Additional 1,4-diaminocyclohexane (0.084 g, 0.736 mmol) and triethylamine (0.0204 ml, 0.028 g, 0.294 mmol) were added. Heating at 100° C. was continued for 17 hr. The reaction mixture was purified using prep HPLC. The material was purified by preparative reverse-phase HPLC to yield 0.0240 g of trans-N$^1$-(5-chloro-4-(5-cyclopropyl-6-((tetrahydro-2H-pyran-4-yl)methyl)aminopyrazin-2-yl)pyridin-2-yl)cyclohexane-1,4-diamine as the TFA salt. LCMS (m/z): 457.2 (MH$^+$), retention time=0.60 min.

Example 36

Compound 241 trans-N$^1$-(5-chloro-4-(5-ethyl-6-((tetrahydro-2H-pyran-4-yl)methyl)aminopyrazin-2-yl)pyridin-2-yl)cyclohexane-1,4-diamine

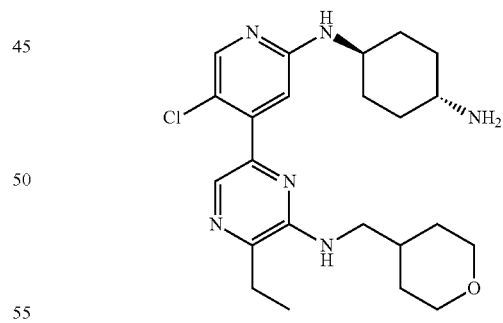

Step 1. Preparation of 6-(5-chloro-2-fluoropyridin-4-yl)-3-ethyl-N-((tetrahydro-2H-pyran-4-yl)methyl)pyrazine-2-amine:

3-chloro-6-(5-chloro-2-fluoropyridin-4-yl)-N-((tetrahydro-2H-pyran-4-yl)methyl)pyrazin-2-amine (0.0347 g, 0.097 mmol), ethylboronic acid (0.014 g, 0.194 mmol), and sodium carbonate (0.126 ml g, 0.253 mmol, 2 M aq solution) were dissolved in DME (1 ml). The solution was then degassed by sparging with argon for 5 min. At this time it was treated with PdCl$_2$(dppf).CH$_2$Cl$_2$ adduct (0.016 g, 0.019 mmol). The reaction mixture was then heated in the microwave at 115° C. for 25 min. More ethylboronic acid (0.014 g, 0.194 mmol) and PdCl$_2$(dppf).CH$_2$Cl$_2$ adduct (0.016 g, 0.019 mmol) were added. The reaction mixture was then heated in the microwave at 115° C. for 25 min. The reaction mixture was filtered through a plug of Celite and the filtrate was concentrated in vacuo to afford 0.0709 g of crude product. The material was purified using the Isco with a 4 g SiO2 column. The resulting residue was subjected to silica gel column chromatography. Elution using 20 EtOAc/80 heptane to 70 EtOAc/30 heptane gave 0.0049 g (14%) of 6-(5-chloro-2-fluoropyridin-4-yl)-3-ethyl-Af-((tetrahydro-2H-pyran-4-yl)methyl)pyrazine-2-amine. LCMS (m/z): 351.1 (MH$^+$), retention time=0.97 min.

Step 2. Preparation of trans-N$^1$-(5-chloro-4-(5-ethyl-6-((tetrahydro-2H-pyran-4-yl)methyl)aminopyrazin-2-yl)pyridin-2-yl)cyclohexane-1,4-diamine:

6-(5-chloro-2-fluoropyridin-4-yl)-3-ethyl-N-((tetrahydro-2H-pyran-4-yl)methyl)pyrazine-2-amine (0.0053 g, 0.015 mmol) was dissolved in DMSO (1 ml). This was treated with 1,4-diaminocyclohexane (0.017 g, 0.151 mmol). The reaction mixture was then heated at 100° C. for 4 hr. Additional 1,4-diaminocyclohexane (0.017 g, 0.151 mmol) and triethylamine (0.0084 ml, 0.012 g, 0.060 mmol) were added. Heating at 100° C. was continued for 17 hr. The reaction mixture was purified using prep HPLC. The material was purified by preparative reverse-phase HPLC to give 0.0040 g of trans-N$^1$-(5-chloro-4-(5-ethyl-6-((tetrahydro-2H-pyran-4-yl)methyl)aminopyrazin-2-yl)pyridin-2-yl)cyclohexane-1,4-diamine as the TFA salt. LCMS (m/z): 445.2 (MH$^+$), retention time=0.54 min.

Example 37

Compound 255 trans-N1-(5-chloro-4-(6-((tetrahydro-2H-pyran-4-yl)methyl)amino-3-(trifluoromethyl)pyrazin-2-yl)pyridin-2-yl)cyclohexane-1,4-diamine

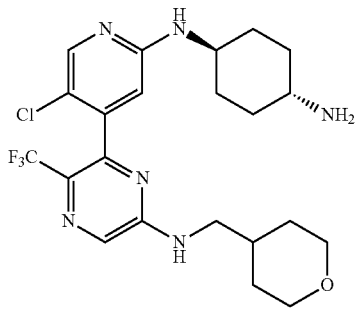 [SMILES: N[C@H]1CC[C@H](Nc2cc(-c3nc(NCC4CCOCC4)cnc3C(F)(F)F)c(Cl)cn2)CC1]

Step 1. Preparation of 6-chloro-5-iodo-N-((tetrahydro-2H-pyran-4-yl)methyl)pyrazin-2-amine 6-chloro-N-((tetrahydro-2H-pyran-4-yl)methyl)pyrazin-2-amine (0.250 g, 1.098 mmol) was dissolved in a mixture of DMSO (4.30 ml) and H$_2$O (0.105 ml). It was cooled to 0° C. in an ice bath and was then treated with N-iodosuccinimide (0.247 g, 1.098 mmol) by portion-wise addition. Once the addition was complete the reaction mixture was stirred at ambient temperature for 24 hr. Additional NIS (0.025 g, 0.111 mmol) was added. Stirring at ambient temperature was continued for 24 hr. The reaction mixture was diluted with H$_2$O (50 ml). This was extracted with EtOAc (3×50 ml). The organic layers were combined and washed with brine (1×50 ml). The organic layer was dried (Na$_2$SO$_4$), filtered, and the solvent removed in vacuo to give 0.410 g of crude product. The resulting residue was subjected to silica gel column chromatography. Elution using 30 EtOAc/70 heptane to 100 EtOAc gave 0.2144 g (55%) of 6-chloro-5-iodo-N-((tetrahydro-2H-pyran-4-yl)methyl)pyrazin-2-amine. LCMS (m/z): 353.9 (MH$^+$), retention time=0.92 min. $^1$H NMR (400 MHz, CHLOROFORM-d) d ppm 1.37 (qd, 2 H) 1.59 (s, 2 H) 1.67 (d, J=12.91 Hz, 2 H) 1.77-1.94 (m, J=14.87, 7.63, 7.63, 3.52 Hz, 1 H) 3.25 (t, J=6.46 Hz, 2 H) 3.39 (td, J=11.74, 1.96 Hz, 2 H) 4.00 (dd, J=11.15, 3.72 Hz, 2 H) 4.80 (br. s., 1 H) 7.62 (s, 1 H).

Step 2. Preparation of t-butyl-6-chloro-5-iodopyrazin-2-yl((tetrahydro-2H-pyran-4-yl)methyl)carbamate: 6-chloro-5-iodo-N-((tetrahydro-2H-pyran-4-yl)methyl)pyrazin-2-amine (0.0801 g, 0.227 mmol) was dissolved in anhydrous DMF and placed under nitrogen. It was then treated with sodium hydride (0.0109 g, 0.272 mmol, 60% dispersion in mineral oil) followed by di-t-butyldicarbonate (0.099 g, 0.453 mmol). The reaction mixture was then stirred at 50° C. for 24 hr. More NaH (0.0109 g, 0.072 mmol) and Boc$_2$O (0.099 g, 0.453 mmol) were added. The reaction mixture was then heated at 70° C. for 18 hr. The reaction mixture was cooled to ambient temperature, and then it was poured into brine (25 ml). This was extracted with EtOAc (3×25 ml). The combined extracts were washed with H$_2$O (3×25 ml) followed by brine (1×25 ml). The organic layer was dried (Na$_2$SO$_4$), filtered, and the solvent removed in vacuo to yield 0.0846 g of crude product. The resulting residue was subjected to silica gel column chromatography. Elution using 25 EtOAc/75 heptane to 75 EtOAc/25 heptane gave 0.0569 g (55%) of t-butyl-6-chloro-5-iodopyrazin-2-yl((tetrahydro-2H-pyran-4-yl)methyl)carbamate. LCMS (m/z): 454.0 (MH$^+$), retention time=1.20 min. $^1$H NMR (400 MHz, CHLOROFORM-d) d ppm 1.28-1.46 (m, 4 H) 1.46-1.64 (m, 26 H) 1.81-2.02 (m, 2 H) 3.26-3.42 (m, 3 H) 3.86 (d, J=7.04 Hz, 3 H) 3.96 (dd, J=11.54, 2.93 Hz, 3 H) 8.86 (s, 1 H).

Step 3. Preparation of 6-chloro-N-((tetrahydro-2H-pyran-4-yl)methyl)-5-(trifluoromethyl)pyrazin-2-amine t-butyl-6-chloro-5-iodopyrazin-2-yl((tetrahydro-2H-pyran-4-yl)methyl)carbamate (0.0569 g, 0.125 mmol), methyl 2-chloro-2,2-difluoroacetate (0.047 ml, 0.063 g, 0.439 mmol), potassium fluoride (0.015 g, 0.251 mmol), and copper (I) iodide (0.100 g, 0.527 mmol) were dissovled in anhydrous DMF (0.80 ml) and placed under argon. The reaction mixture was then heated at 115° C. for 17 hr. It was allowed to cool to ambient temperature. The reaction mixture was filtered through a pad of Celite. The filtrate was poured into brine (25 ml). This was extracted with EtOAc (3×25 ml). The combined extracts were washed with H$_2$O (1×25 ml) followed by brine (1×25 ml). The organic layer was dried (Na$_2$SO$_4$), filtered, and the solvent removed in vacuo to give 0.0401 g of crude product. The resulting residue was subjected to silica gel column chromatography. Elution using 25 EtOAc/75 heptane to 100 EtOAc gave 0.0569 g (55%) of 6-chloro-N-((tetrahydro-2H-pyran-4-yl)methyl)-5-(trifluoromethyl)pyrazin-2-amine. LCMS (m/z): 296.0 (MH$^+$), retention time=0.93 min. $^1$H NMR (400 MHz, CHLOROFORM-d) d ppm 1.39 (qd, J=12.33, 4.50 Hz, 2 H) 1.68 (d, J=11.35 Hz, 3 H) 1.80-2.00 (m, J=14.87, 7.63, 7.63, 3.52 Hz, 1 H) 3.32-3.47 (m, 4 H) 4.01 (dd, J=11.35, 3.52 Hz, 2 H) 5.26 (br. s., 1 H) 7.76 (s, 1 H).

Step 4. Preparation of 6-(5-chloro-2-fluoropyridin-4-yl)-N-((tetrahydro-2H-pyran-4-yl)methyl)-5-(trifluoromethyl)pyrazin-2-amine 6-chloro-N-((tetrahydro-2H-pyran-4-yl)methyl)-5-(trifluoromethyl)pyrazin-2-amine (0.020 g, 0.068 mmol), 5-chloro-2-fluoropyridin-4-ylboronic acid (0.036 g, 0.203 mmol), and sodium carbonate (0.088 ml, 0.176 mmol, 2 M in H₂O) were dissolved in DME (0.70 ml). The solution was then degassed by sparging with argon for 5 min. It was then treated with PdCl₂(dppf) CH₂Cl₂ adduct (0.011 g, 0.014 mmol). The reaction mixture was then heated in a microwave at 110° C. for 25 min. Boronic acid (~0.036 g, 0.203 mmol) and PdCl₂(dppf) CH₂Cl₂ adduct (~0.011 g, 0.014 mmol) were added. Heating in the microwave was continued at 110° C. for 25 min. The reaction mixture was then filtered through a pad of Celite. The filtrate was then concentrated in vacuo to give 0.0759 g of crude product. The resulting residue was subjected to silica gel column chromatography. Elution using 25 EtOAc/75 heptane to 100 EtOAc gave 0.0178 g (67%) of 6-(5-chloro-2-fluoropyridin-4-yl)-N-((tetrahydro-2H-pyran-4-yl)methyl)-5-(trifluoromethyl)pyrazin-2-amine. LCMS (m/z): 391.1 (MH⁺), retention time=0.96 min.

Step 5. Preparation of trans-N¹-(5-chloro-4-(6-((tetrahydro-2H-pyran-4-yl)methyl)amino-3-(trifluoromethyl)pyrazin-2-yl)pyridin-2-yl)cyclohexane-1,4-diamine 6-(5-chloro-2-fluoropyridin-4-yl)-N-((tetrahydro-2H-pyran-4-yl)methyl)-5-(trifluoromethyl)pyrazin-2-amine (0.0178 g, 0.046 mmol) was dissolved in anhydrous DMSO (1.0 ml) and charged to a microwave vial. This was treated with trans-cyclohexane-1,4-diamine (0.052 g, 0.456 mmol). The reaction mixture was then heated at 100° C. for 18 hr. The reaction mixture was allowed to cool to ambient temperature. The material was purified by preparative reverse-phase HPLC to give 0.0086 g (32%) of trans-N¹-(5-chloro-4-(6-((tetrahydro-2H-pyran-4-yl)methyl)amino-3-(trifluoromethyl)pyrazin-2-yl)pyridin-2-yl)cyclohexane-1,4-diamine as the TFA salt. LCMS (m/z): 485.3 (MH⁺), retention time=0.63 min.

Example 38

Compound 260

N2'-(trans-4-aminocyclohexyl)-3-chloro-5'-fluoro-N6-((tetrahydro-2H-pyran-4-yl)methyl)-2,4'-bipyridine-2',6-diamine

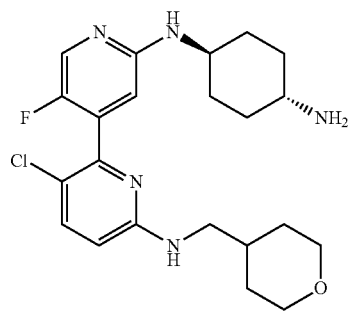 [SMILES: N[C@H]1CC[C@H](Nc2cc(-c3nc(NCC4CCOCC4)ccc3Cl)c(F)cn2)CC1]

Step 1. Preparation of 2,5-difluoropyridin-4-ylboronic acid

Diisopropylamine (1.74 ml, 1.24 g, 12.20 mmol) was dissolved in anhydrous THF (22 ml) and placed under argon. The solution was cooled to −20° C. and then treated with n-butyllithium (7.66 ml, 12.25 mmol, 1.6 M in hexanes) by slow addition over 10 min. The newly formed LDA (LDA=lithium diisopropylamide, this acronyl should be listed in the general session) was then cooled to −78° C. and treated with a solution of 2,5-difluoropyridine (1.05 ml, 1.33 g, 11.56 mmol) dissolved in anhydrous THF (3 ml) by slow addition over 30 min. Once the addition was complete the reaction mixture was allowed to stir at −78° C. for 4 hr. At this time the reaction mixture was treated with a solution of triisopropyl borate (5.90 ml, 4.78 g, 25.4 mmol) dissolved in anhydrous THF (8.6 ml) by dropwise addition. Once the addition was complete the reaction mixture was allowed to warm to ambient temperature then stirred at ambient temperature for an additional hour. The reaction mixture was then quenched by adding 4% aq NaOH (34 ml). The layers were separated and the aqueous layer was cooled in an ice bath. It was then acidified to pH=4 with 6N HCl (~10 ml) not letting the temperature go above 10° C. This was then extracted with EtOAc (3×50 ml). The extracts were then washed with brine (1×50 ml), dried (Na₂SO₄), filtered, and the solvent removed in vacuo. The resulting residue was triturated with Et2O to give 0.8084 g (44%) of 2,5-difluoropyridin-4-ylboronic acid.

Step 2. Preparation of 3-chloro-2',5'-difluoro-N-((tetrahydro-2H-pyran-4-yl)methyl)-2,4'-bipyridin-6-amine 6-bromo-5-chloro-N-((tetrahydro-2H-pyran-4-yl)methyl)pyridin-2-amine (0.500 g, 1.64 mmol), 2,5-difluoropyridin-4-ylboronic acid (0.260 g, 1.64 mmol), and sodium carbonate (2.45 ml, 4.91 mmol, 2 M in H₂O) were dissolved in DME (7.36 ml). The solution was then degassed by sparging with argon for 5 min. It was then treated with PdCl₂(dppf) CH₂Cl₂ adduct (0.267 g, 0.327 mmol). The reaction mixture was then heated in the microwave at 105° C. for 25 min. More boronic acid (0.260 g, 1.64 mmol) and PdCl₂(dppf) CH₂Cl₂ adduct (0.267 g, 0.327 mmol), and H₂O (~2 ml) were added. Heating in the microwave was continued at 110° C. for 30 min. The reaction mixture was then filtered through a pad of Celite. The filtrate was then concentrated in vacuo to give 1.2090 g of crude product. The resulting residue was subjected to silica gel column chromatography. Elution using 10 EtOAc/90 heptane to 80 EtOAc/20 heptane gave 0.3584 g (65%) of 3-chloro-2',5'-difluoro-N-((tetrahydro-2H-pyran-4-yl)methyl)-2,4'-bipyridin-6-amine. LCMS (m/z): 340.0 (MH⁺), retention time=0.90 min. 1H NMR (400 MHz, CHLOROFORM-d) d ppm 1.37 (qd, 3 H) 1.60 (br. s., 2 H) 1.68 (d, J=12.91 Hz, 3 H) 1.84 (ddd, J=11.15, 7.24, 4.30 Hz, 1 H) 3.21 (t, J=6.26 Hz, 2 H) 3.32-3.45 (m, 3 H) 4.00 (dd, J=11.15, 3.72 Hz, 2 H) 4.74 (br. s., 1 H) 6.45 (d, J=9.00 Hz, 1 H) 6.99-7.07 (m, 1 H) 7.51 (d, J=8.61 Hz, 1 H) 8.12 (s, 1 H).

Step 3. Preparation of N2'-(trans-4-aminocyclohexyl)-3-chloro-5'-fluoro-N6-((tetrahydro-2H-pyran-4-yl)methyl)-2,4'-bipyridine-2',6-diamine 3-chloro-2',5'-difluoro-N-((tetrahydro-2H-pyran-4-yl)methyl)-2,4'-bipyridin-6-amine (0.0509 g, 0.150 mmol) was dissolved in anhydrous DMSO (3.0 ml) and charged to a microwave vial. This was treated with trans-cyclohexane-1, 4-diamine (0.171 g, 1.498 mmol). The reaction mixture was then heated at 100° C. for 18 hr. More trans-cyclohexane-1,4-diamine (0.171 g, 1.498 mmol) was added and the reaction mixture was stirred at 120° C. for 18 hr. The reaction mixture was allowed to cool to ambient temperature. The material was purified by preparative reverse-phase HPLC to give 0.2410 g (30%) of N2'-(trans-4-aminocyclohexyl)-3-chloro-5'-fluoro-N6-((tetrahydro-2H-pyran-4-yl)methyl)-2,4'-bipyridine-2',6-diamine as the TFA salt. LCMS (m/z): 434.2 (MH+), retention time=0.55 min.

Example 39

Compound 282

N2'-(trans-4-aminocyclohexyl)-5'-chloro-3-fluoro-N6-((tetrahydro-2H-pyran-4-yl)methyl)-2,4'-bipyridine-2',6-diamine

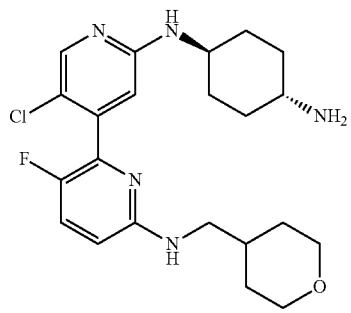

Step 1. Preparation of trans-N1-(5'-chloro-3,6-difluoro-2,4'-bipyridin-2'-yl)cyclohexane-1,4-diamine: To a solution of 5'-chloro-2',3,6-trifluoro-2,4'-bipyridine (95 mg, 0.388 mmol) in DMSO (2.5 mL) was added trans-1,4-diaminocyclohexane (177 mg, 1.55 mmol). The mixture was stirred at 90° C. for 2 hr. The cooled reaction mixture was diluted with ethyl acetate and washed with water. The organic layer was dried (Na2SO4), filtered, and concentrated to give 137 mg of crude trans-N1-(5'-chloro-3,6-difluoro-2,4'-bipyridin-2'-yl)cyclohexane-1,4-diamine which was used without further purification. LCMS (m/z): 339.0 (MH+), retention time=0.54 min Step 2. Preparation of N2'-(trans-4-aminocyclohexyl)-5'-chloro-3-fluoro-N6-((tetrahydro-2H-pyran-4-yl)methyl)-2,4'-bipyridine-2',6-diamine: To a solution of trans-N1-(5'-chloro-3,6-difluoro-2,4'-bipyridin-2'-yl)cyclohexane-1,4-diamine (79 mg, 0.388 mmol) in DMSO (1.5 ml) was added 4-aminomethyltetrahydropyran (161 mg, 1.40 mmol). The mixture was irradiated by microwave at 180° C. for 1 hr in a sealed microwave vial. The crude reaction mixture was purified by reverse phase HPLC and lyophilized to give N2'-(trans-4-aminocyclohexyl)-5'-chloro-3-fluoro-N6-((tetrahydro-2H-pyran-4-yl)methyl)-2,4'-bipyridine-2',6-diamine as its TFA salt. LCMS (m/z): 434.2 (MH+), retention time=0.57 min.; 1H NMR (400 MHz, DMSO-d6) δ ppm 1.07-1.32 (m, 2 H) 1.32-1.49 (m, 1 H) 1.59 (d, J=12.91 Hz, 1 H) 1.68-1.83 (m, 1 H) 1.96 (dd, 2 H) 2.93-3.04 (m, 1 H) 3.06 (d, J=6.65 Hz, 1 H) 3.24 (t, J=10.76 Hz, 1 H) 3.54-3.70 (m, 1 H) 3.82 (dd, J=10.96, 2.74 Hz, 1 H) 6.53 (s, 1 H) 6.57 (dd, J=9.19, 2.93 Hz, 1 H) 7.41 (t, 1 H) 7.79 (d, J=3.91 Hz, 2 H) 8.04 (s, 1 H)

Example 40

Compound 283

5'-chloro-3-fluoro-N2'-(trans-4-(2-methoxyethylamino)cyclohexyl)-N6-((tetrahydro-2H-pyran-4-yl)methyl)-2,4'-bipyridine-2',6-diamine

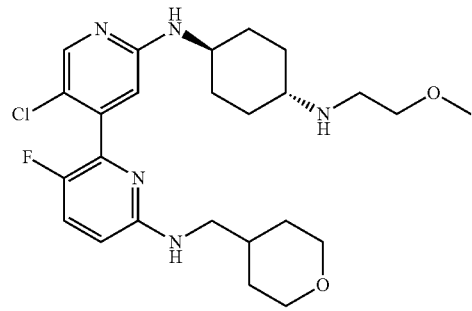 [SMILES: COCCN[C@H]1CC[C@H](Nc2cc(-c3nc(NCC4CCOCC4)ccc3F)c(Cl)cn2)CC1]

Preparation of 5'-chloro-3-fluoro-N2'-(trans-4-(2-methoxyethylamino)cyclohexyl)-N6-((tetrahydro-2H-pyran-4-yl)methyl)-2,4'-bipyridine-2',6-diamine: To a mixture of N2'-(trans-4-aminocyclohexyl)-5'-chloro-3-fluoro-N6-((tetrahydro-2H-pyran-4-yl)methyl)-2,4'-bipyridine-2',6-diamine trifluoroacetate (30 mg, 0.055 mmol) and sodium carbonate (23 mg, 0.22 mmol) in DMSO (0.75 ml) was added p-toluenesulfonic acid 2-methoxyethyl ester (15 mg, 0.066 mmol). The mixture was stirred at 85° C. for 20 hr in a sealed microwave vial. The cooled reaction mixture was filtered. The filtrate was purified by reverse phase HPLC and lyophilized to give 5.0 mg of 5'-chloro-3-fluoro-N2'-(trans-4-(2-methoxyethylamino)cyclohexyl)-N6-((tetrahydro-2H-pyran-4-yl)methyl)-2,4'-bipyridine-2',6-diamine as its TFA salt. LCMS (m/z): 492.2 (MH+), retention time=0.57 min.; 1H NMR (400 MHz, CHLOROFORM-d) δ ppm 1.10-1.46 (m, 6 H) 1.64-1.74 (m, 2 H) 1.86 (br. s., 2 H) 1.95-2.09 (m, 2 H) 2.09-2.26 (m, 2 H) 2.58 (br. s., 1 H) 2.88 (t, J=5.09 Hz, 2 H) 3.17 (t, J=6.26 Hz, 2 H) 3.29-3.45 (m, 5 H) 3.53 (t, J=5.09 Hz, 3 H) 4.00 (dd, J=11.35, 3.52 Hz, 2 H) 4.34-4.47 (m, 1 H) 4.54-4.68 (m, 1 H) 6.35-6.48 (m, 2 H) 7.31 (t, J=8.80 Hz, 1 H) 8.11 (s, 1 H).

Example 41

Compound 286

N2'-(trans-4-aminocyclohexyl)-3-bromo-5'-chloro-N6-((tetrahydro-2H-pyran-4-yl)methyl)-2,4'-bipyridine-2',6-diamine

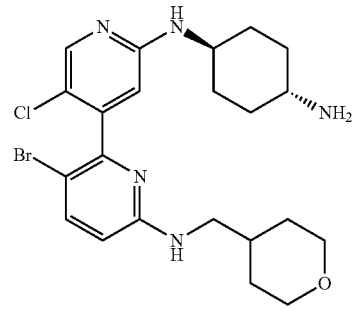

Preparation of N2'-(trans-4-aminocyclohexyl)-3-bromo-5'-chloro-N6-((tetrahydro-2H-pyran-4-yl)methyl)-2,4'-bipyridine-2',6-diamine: To a solution of 3-bromo-5'-chloro-2'-fluoro-N-((tetrahydro-2H-pyran-4-yl)methyl)-2,4'-bipyridin-6-amine (100 mg, 0.250 mmol) in DMSO (1 mL) was added trans-1,4-diaminocyclohexane (114 mg, 0.998 mmol). The mixture was stirred at 110° C. for 19 hr. The crude reaction mixture was purified by reverse phase HPLC and lyophilized to give 51 mg of N2'-(trans-4-aminocyclohexyl)-3-bromo-5'-chloro-N6-((tetrahydro-2H-pyran-4-yl)methyl)-2,4'-bipyridine-2',6-diamine as its TFA salt. LCMS (m/z): 494.2/496.1 (MH+), retention time=0.61 min; $^1$H NMR (400 MHz, DMSO-d6) d ppm 1.06-1.31 (m, 4 H) 1.31-1.49 (m, 2 H) 1.49-1.64 (m, 2 H) 1.64-1.82 (m, 1 H) 1.85-2.11 (m, 4 H) 2.93-3.12 (m, 3 H) 3.22 (t, J=10.96 Hz, 2 H) 3.61 (t, J=10.76 Hz, 1H) 3.81 (dd, J=11.35, 2.74 Hz, 2 H) 6.39 (s, 1 H) 6.48 (d, 1 H) 6.82 (br. s., 1 H) 6.94 (br. s., 1 H) 7.59 (d, J=9.00 Hz, 1 H) 7.78 (d, J=3.91 Hz, 2 H) 8.02 (s, 1H)

Example 42

Compound 288

(R)-3-(trans-4-(5'-chloro-6-((tetrahydro-2H-pyran-4-yl)methyl)amino-2,4'-bipyridin-2'-yl-amino)cyclohexylamino)-1,1,1-trifluoropropan-2-ol

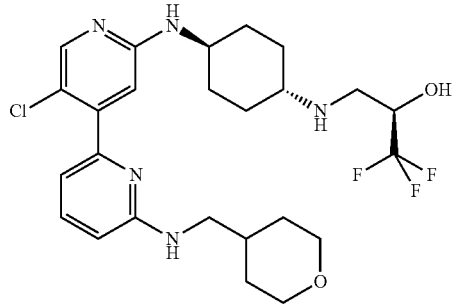 [SMILES: O[C@H](CN[C@H]1CC[C@H](Nc2cc(-c3cccc(NCC4CCOCC4)n3)c(Cl)cn2)CC1)C(F)(F)F]

Step 1. Preparation of N2'-(trans-4-aminocyclohexyl)-5'-chloro-N6-((tetrahydro-2H-pyran-4-yl)methyl)-2,4'-bipyridine-2',6-diamine: To a solution of 5'-chloro-2'-fluoro-N-((tetrahydro-2H-pyran-4-yl)methyl)-2,4'-bipyridin-6-amine (500 mg, 1.55 mmol) in DMSO (7 mL) was added trans-1,4-diaminocyclohexane (710 mg, 6.22 mmol). The mixture was stirred at 110° C. for 19 hr. The cooled reaction mixture was diluted with water and extracted with ethyl acetate. The combined extracts were washed sequentially with water and brine, dried over sodium sulfate, filtered, and concentrated to give 600 mg of N2'-(trans-4-aminocyclohexyl)-5'-chloro-N6-((tetrahydro-2H-pyran-4-yl)methyl)-2,4'-bipyridine-2',6-diamine. LCMS (m/z): 416.1 (MH+), retention time=0.48 min.

Step 2. Preparation of (R)-3-(trans-4-(5'-chloro-6-((tetrahydro-2H-pyran-4-yl)methyl)amino-2,4'-bipyridin-2'-yl-amino)cyclohexylamino)-1,1,1-trifluoropropan-2-ol: To a solution of N2'-(trans-4-aminocyclohexyl)-5'-chloro-N6-((tetrahydro-2H-pyran-4-yl)methyl)-2,4'-bipyridine-2',6-diamine (50 mg, 0.120 mmol) in 2-propanol (0.8 mL) was added (R)-(+)-3,3,3-trifluoro-1,2-epoxypropane (10.4 uL, 0.120 mmol). The mixture was stirred at 60° C. for 17 hr. The reaction mixture was concentrated. The resulting residue was purified by reverse phase HPLC and lyophilized to give 63 mg of (R)-3-(trans-4-(5'-chloro-6-((tetrahydro-2H-pyran-4-yl)methyl)amino-2,4'-bipyridin-2'-yl-amino)cyclohexylamino)-1,1,1-trifluoropropan-2-ol as its TFA salt. LCMS (m/z): 528.3 (MH+), retention time=0.53 min; $^1$H NMR (400 MHz, DMSO-d6) δ ppm 1.08-1.34 (m, 4 H) 1.36-1.56 (m, 2 H) 1.61 (d, J=12.52 Hz, 2 H) 1.70-1.90 (m, 1 H) 2.04 (d, J=9.39 Hz, 3 H) 2.13 (d, J=11.74 Hz, 1 H) 2.97-3.19 (m, 4 H) 3.24 (t, J=10.76 Hz, 3 H) 3.64 (d, J=10.96 Hz, 1 H) 3.83 (dd, J=10.96, 2.74 Hz, 2 H) 4.36-4.50 (m, 2 H) 6.54-6.68 (m, 2 H) 6.70 (d, J=7.04 Hz, 0 H) 6.94 (br. s., 0 H) 7.23 (br. s., 0 H) 7.53 (br. s., 0 H) 8.04 (s, 0 H) 8.76 (br. s., 2 H)

Example 43

Compound 289

(S)-3-(trans-4-(3,5'-dichloro-6-((tetrahydro-2H-pyran-4-yl)methyl)amino-2,4'-bipyridin-2'-yl-amino)cyclohexylamino)-1,1,1-trifluoropropan-2-ol

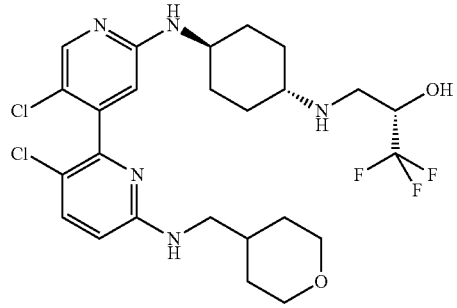 [SMILES: O[C@@H](CN[C@H]1CC[C@H](Nc2cc(-c3nc(NCC4CCOCC4)ccc3Cl)c(Cl)cn2)CC1)C(F)(F)F]

Step 1. Preparation of N2'-(trans-4-aminocyclohexyl)-3,5'-dichloro-N6-((tetrahydro-2H-pyran-4-yl)methyl)-2,4'-bipyridine-2',6-diamine: To a solution of 3,5'-dichloro-2'-fluoro-N-((tetrahydro-2H-pyran-4-yl)methyl)-2,4'-bipyridin-6-amine (500 mg, 1.40 mmol) in DMSO (8 mL) was added trans-1,4-diaminocyclohexane (641 mg, 5.61 mmol). The mixture was stirred at 95° C. for 38 hr. The cooled reaction mixture was diluted with water and extracted with ethyl acetate. The combined extracts were washed sequentially with water and brine, dried over sodium sulfate, filtered, and concentrated. The crude material was purified by flash chromatography over silica gel (dichloromethane/methanol gradient) to give 480 mg of N2'-(trans-4-aminocyclohexyl)-3,5'-dichloro-N6-((tetrahydro-2H-pyran-4-yl)methyl)-2,4'-bipyridine-2',6-diamine. LCMS (m/z): 450.2 (MH+), retention time=0.55 min.

Step 2. Preparation of (S)-3-(trans-4-(3,5'-dichloro-6-((tetrahydro-2H-pyran-4-yl)methyl)amino-2,4'-bipyridin-2'-yl-amino)cyclohexylamino)-1,1,1-trifluoropropan-2-ol: To a solution of N2'-(trans-4-aminocyclohexyl)-3,5'-dichloro-N6-((tetrahydro-2H-pyran-4-yl)methyl)-2,4'-bipyridine-2',6-diamine (54 mg, 0.120 mmol) in 2-propanol (0.4 mL) was added (S)-(−)-3,3,3-trifluoro-1,2-epoxypropane (10.4 uL, 0.120 mmol). The mixture was stirred at 70° C. for 2 hr. The reaction mixture was concentrated. The resulting residue was purified by reverse phase HPLC and lyophilized to give 32 mg of (S)-3-(trans-4-(3,5'-dichloro-6-((tetrahydro-2H-pyran-4-yl)methyl)amino-2,4'-bipyridin-2'-yl-amino)cyclohexylamino)-1,1,1-trifluoropropan-2-ol as its TFA salt. LCMS (m/z): 562.3 (MH+), retention time=0.70 min; $^1$H NMR (400 MHz, DMSO-d6) δ ppm 1.01-1.33 (m, 4 H) 1.35-1.65 (m, 4 H) 1.64-1.84 (m, 1 H) 1.93-2.23 (m, 4 H) 2.94-3.18 (m, 4 H) 3.17-3.35 (m, 3 H) 3.53-3.69 (m, 1 H) 3.81 (dd, J=11.35, 2.74 Hz, 2 H) 4.33-4.48 (m, 1 H) 6.38 (s, 1 H) 6.55 (d, 1 H) 6.82 (br. s., 1 H) 6.93 (br. s., 1 H) 7.23 (br. s., 1 H) 7.48 (d, 1 H) 8.02 (s, 1 H) 8.72 (br. s., 2 H)

Example 44

Compound 292

3-bromo-5'-chloro-N2'-(trans-4-(2-methoxyethylamino)cyclohexyl)-N6-((tetrahydro-2H-pyran-4-yl)methyl)-2,4'-bipyridine-2',6-diamine

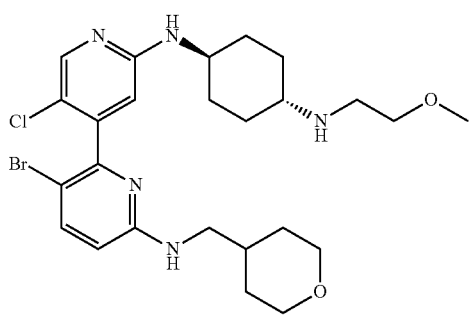

Preparation of 3-bromo-5'-chloro-N2'-(trans-4-(2-methoxyethylamino)cyclohexyl)-N6-((tetrahydro-2H-pyran-4-yl)methyl)-2,4'-bipyridine-2',6-diamine: To a mixture of N2'-(trans-4-aminocyclohexyl)-3-bromo-5'-chloro-N6-((tetrahydro-2H-pyran-4-yl)methyl)-2,4'-bipyridine-2',6-diamine (30 mg, 0.061 mmol) and sodium carbonate (19 mg, 0.18 mmol) in DMSO (0.6 ml) was added p-toluenesulfonic acid 2-methoxyethyl ester (21 mg, 0.091 mmol). The mixture was stirred at 85° C. for 20 hr in a sealed microwave vial. The cooled reaction mixture was filtered. The filtrate was concentrated and the resulting residue was purified by reverse phase HPLC and lyophilized to give 3.8 mg of 3-bromo-5'-chloro-N2'-(trans-4-(2-methoxyethylamino)cyclohexyl)-N6-((tetrahydro-2H-pyran-4-yl)methyl)-2,4'-bipyridine-2',6-diamine as its TFA salt. LCMS (m/z): 554.1 (MH+), retention time=0.61 min.

Example 45

Compound 295

3,5'-dichloro-N6-((tetrahydro-2H-pyran-4-yl)methyl)-N2'-(trans-4-((R)-3,3,3-trifluoro-2-methoxypropylamino)cyclohexyl)-2,4'-bipyridine-2',6-diamine

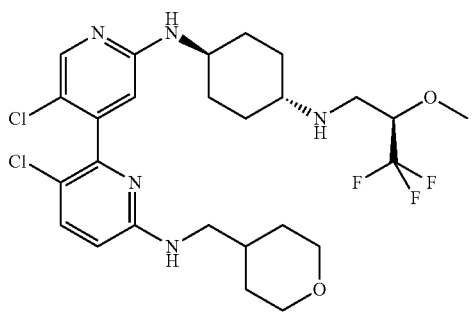 [SMILES: CO[C@H](CN[C@H]1CC[C@H](Nc2cc(-c3nc(NCC4CCOCC4)ccc3Cl)c(Cl)cn2)CC1)C(F)(F)F]

Preparation of 3,5'-dichloro-N6-((tetrahydro-2H-pyran-4-yl)methyl)-N2'-(trans-4-((R)-3,3,3-trifluoro-2-methoxypropylamino)cyclohexyl)-2,4'-bipyridine-2',6-diamine: To a solution of 3,5'-dichloro-2'-fluoro-N-((tetrahydro-2H-pyran-4-yl)methyl)-2,4'-bipyridin-6-amine (36 mg, 0.10 mmol) in DMSO (0.4 mL) was added trans-N1-((R)-3,3,3-trifluoro-2-methoxypropyl)cyclohexane-1,4-diamine (48 mg, 0.20 mmol) and 2,6-lutidine (0.023 mL, 0.20 mmol). The mixture was stirred at 120° C. for 20 hr. The cooled reaction mixture was purified by reverse phase HPLC and lyophilized to give 11.4 mg of 3,5'-dichloro-N6-((tetrahydro-2H-pyran-4-yl)methyl)-N2'-(trans-4-((R)-3,3,3-trifluoro-2-methoxypropylamino)cyclohexyl)-2,4'-bipyridine-2',6-diamine as its TFA salt. LCMS (m/z): 576.2 (MH+), retention time=0.68 min.

Example 46

Compound 297 trans-4-(3,5'-dichloro-6-((2,2-dimethyltetrahydro-2H-pyran-4-yl)methyl)amino-2,4'-bipyridin-2'-ylamino)cyclohexanol

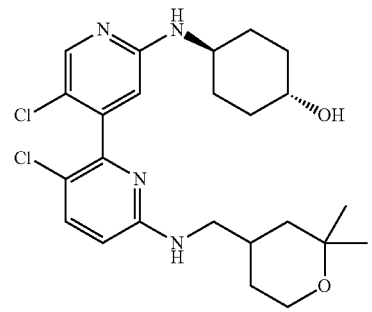 [SMILES: CC1(C)CC(CNc2ccc(Cl)c(-c3cc(N[C@H]4CC[C@H](O)CC4)ncc3Cl)n2)CCO1]

Preparation of trans-4-(3,5'-dichloro-6-((2,2-dimethyltetrahydro-2H-pyran-4-yl)methyl)amino-2,4'-bipyridin-2'-ylamino)cyclohexanol: To a solution of tert-butyl 3,5'-dichloro-2'-fluoro-2,4'-bipyridin-6-yl((2,2-dimethyltetrahydro-2H-pyran-4-yl)methyl)carbamate (30 mg, 0.062 mmol) in DMSO (0.4 mL) was added trans-4-aminocyclohexanol (36 mg, 0.31 mmol) and DIEA (0.022 mL, 0.12 mmol). The mixture was stirred at 135° C. for 3 hr. The cooled reaction mixture was diluted with water and extracted with ethyl acetate. The combined extracts were dried (Na2SO4), filtered, and concentrated. The resulting residue was re-dissolved in trifluoroacetic acid (1 mL), stirred for 15 min at ambient temperature, and then concentrated under reduced pressure. The crude resulting residue was purified by reverse phase HPLC and lyophilized to give 23 mg of trans-4-(3,5'-dichloro-6-((2,2-dimethyltetrahydro-2H-pyran-4-yl)methyl)amino-2,4'-bipyridin-2'-yl-amino)cyclohexanol as its TFA salt. LCMS (m/z): 479.3 (MH+), retention time=0.72 min; $^1$H NMR (400 MHz, DMSO-d6) δ ppm 0.96 (d, J=12.91 Hz, 2H) 1.08 (s, 6 H) 1.15-1.35 (m, 4 H) 1.54 (d, J=12.91 Hz, 2 H) 1.71-2.10 (m, 5 H) 3.00 (d, J=6.65 Hz, 2 H) 3.31-3.63 (m, 5 H) 6.47 (s, 1 H) 6.58 (d, 1 H) 7.50 (d, J=9.00 Hz, 1 H) 8.05 (s, 1 H)

Example 47

Compound 298

(2S)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol

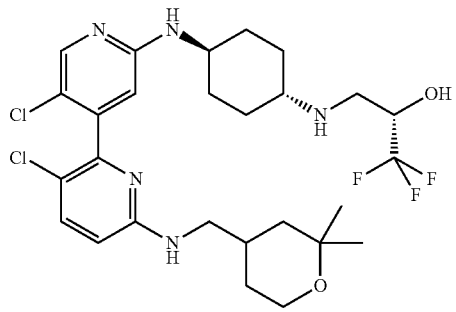 [SMILES: CC1(C)CC(CNc2ccc(Cl)c(-c3cc(N[C@H]4CC[C@H](NC[C@H](O)C(F)(F)F)CC4)ncc3Cl)n2)CCO1]

Step 1. Preparation of N2'-(trans-4-aminocyclohexyl)-3,5'-dichloro-N6-((2,2-dimethyltetrahydro-2H-pyran-4-yl)methyl)-2,4'-bipyridine-2',6-diamine: To a solution of tert-butyl 3,5'-dichloro-2'-fluoro-2,4'-bipyridin-6-yl((2,2-dimethyltetrahydro-2H-pyran-4-yl)methyl)carbamate (40 mg, 0.083 mmol) in DMSO (0.4 mL) was added trans-1,4-diaminocyclohexane (47 mg, 0.41 mmol) and DIEA (0.029 mL, 0.17 mmol). The mixture was stirred at 120° C. for 2 hr. The cooled reaction mixture was diluted with water and extracted with ethyl acetate. The combined extracts were washed sequentially with water and brine, dried over sodium sulfate, filtered, and concentrated. The resulting residue was re-dissolved in trifluoroacetic acid (1 mL), stirred for 15 min at ambient temperature, and then concentrated under reduced pressure. The resulting residue was taken up in DCM, washed with saturated aqueous sodium bicarbonate, dried (Na2SO4), filtered, and concentrated to give 39 mg of N2'-(trans-4-aminocyclohexyl)-3,5'-dichloro-N6-((2,2-dimethyltetrahydro-2H-pyran-4-yl)methyl)-2,4'-bipyridine-2',6-diamine. LCMS (m/z): 478.4 (MH+), retention time=0.64 min.

Step 2. Preparation of (S)-3-(trans-4-(3,5'-dichloro-6-((tetrahydro-2H-pyran-4-yl)methyl)amino-2,4'-bipyridin-2'-yl-amino)cyclohexylamino)-1,1,1-trifluoropropan-2-ol: To a solution of N2'-(trans-4-aminocyclohexyl)-3,5'-dichloro-N6-((2,2-dimethyltetrahydro-2H-pyran-4-yl)methyl)-2,4'-bipyridine-2',6-diamine (19 mg, 0.040 mmol) in 2-propanol (0.3 mL) was added (S)-(-)-3,3,3-trifluoro-1,2-epoxypropane (3.4 uL, 0.040 mmol). The mixture was stirred at 70° C. for 2 hr. The reaction mixture was concentrated. The resulting residue was purified by reverse phase HPLC and lyophilized to give 9.1 mg of (2S)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol as its TFA salt. LCMS (m/z): 590.5 (MH+), retention time=0.71 min; $^1$H NMR (400 MHz, DMSO-d6) δ ppm 0.81-1.32 (m, 12 H) 1.33-1.66 (m, 4 H) 1.82-1.99 (m, 1 H) 1.99-2.21 (m, 4 H) 2.89-3.04 (m, 2 H) 3.04-3.19 (m, 2 H) 3.27 (d, J=2.35 Hz, 2 H) 4.40 (br. s., 1 H) 6.38 (s, 1 H) 6.55 (d, J=9.00 Hz, 1 H) 6.77 (br. s., 1 H) 6.91 (br. s., 1 H) 7.21 (br. s., 1 H) 7.48 (d, J=9.00 Hz, 1 H) 8.03 (s, 1H)

Example 48

Compound 301

5'-chloro-N6-((tetrahydro-2H-pyran-4-yl)methyl)-N2'-(trans-4-(2-(trifluoromethoxy)ethylamino)cyclohexyl)-2,4'-bipyridine-2',6-diamine

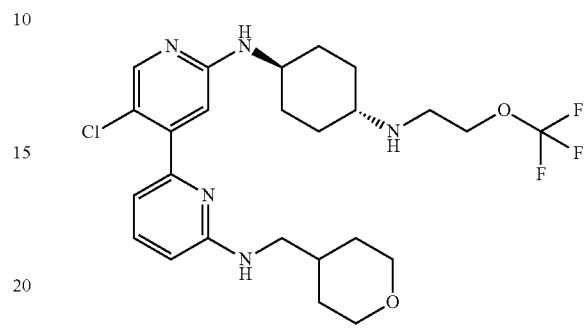

Preparation of 5'-chloro-N6-((tetrahydro-2H-pyran-4-yl)methyl)-N2'-(trans-4-(2-(trifluoromethoxy)ethylamino)cyclohexyl)-2,4'-bipyridine-2',6-diamine: To a mixture of N2'-(trans-4-aminocyclohexyl)-5'-chloro-N6-((tetrahydro-2H-pyran-4-yl)methyl)-2,4'-bipyridine-2',6-diamine (42 mg, 0.10 mmol) and triethylamine (0.028 mL, 0.20 mmol) in chloroform (0.4 ml) was added 2-(trifluoromethoxy)ethyl trifluoromethanesulfonate (39 mg, 0.15 mmol). The mixture was stirred at ambient temperature for 1 hr. The reaction mixture was concentrated under reduced pressure, purified by reverse phase HPLC, and lyophilized to give 32 mg of 5'-chloro-N6-((tetrahydro-2H-pyran-4-yl)methyl)-N2'-(trans-4-(2-(trifluoromethoxy)ethylamino)cyclohexyl)-2,4'-bipyridine-2',6-diamine as its TFA salt. LCMS (m/z): 528.4 (MH+), retention time=0.53 min.; 1H NMR (400 MHz, DMSO-d6) d ppm 1.09-1.34 (m, 4 H) 1.35-1.54 (m, 2 H) 1.55-1.69 (m, 2 H) 1.73-1.89 (m, 1 H) 1.94-2.17 (m, 4H) 3.04-3.15 (m, 1 H) 3.14-3.20 (m, 2 H) 3.20-3.30 (m, 2 H) 3.30-3.47 (m, 2 H) 3.55-3.72 (m, 1 H) 3.84 (dd, J=11.15, 2.54 Hz, 2 H) 4.35 (t, J=4.70 Hz, 2 H) 6.65 (s, 1 H) 6.67-6.83 (m, 2 H) 7.05 (br. s., 0 H) 7.46-7.68 (m, 0 H) 8.06 (s, 0 H) 8.82 (d, J=3.52 Hz, 2H)

Example 49

Compound 302

3,5'-dichloro-N6-((tetrahydro-2H-pyran-4-yl)methyl)-N2'-(trans-4-(2-(trifluoromethoxy)ethylamino)cyclohexyl)-2,4'-bipyridine-2',6-diamine

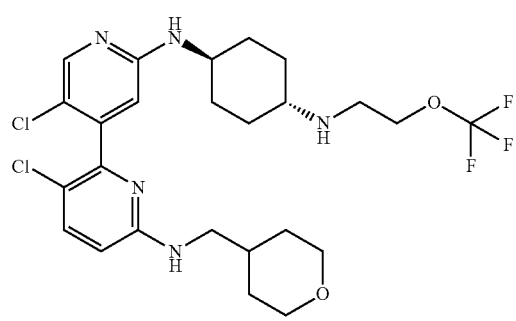 [SMILES: FC(F)(F)OCCN[C@H]1CC[C@H](Nc2cc(-c3nc(NCC4CCOCC4)ccc3Cl)c(Cl)cn2)CC1]

Preparation of 3,5'-dichloro-N6-((tetrahydro-2H-pyran-4-yl)methyl)-N2'-(trans-4-(2-(trifluoromethoxy)ethylamino)cyclohexyl)-2,4'-bipyridine-2',6-diamine: To a mixture of N2'-(trans-4-aminocyclohexyl)-3,5'-dichloro-N6-((tetrahydro-2H-pyran-4-yl)methyl)-2,4'-bipyridine-2',6-diamine (45 mg, 0.10 mmol) and triethylamine (0.028 mL, 0.20 mmol) in chloroform (0.4 ml) was added 2-(trifluoromethoxy)ethyl trifluoromethanesulfonate (39 mg, 0.15 mmol). The mixture was stirred at ambient temperature for 1 hr. The reaction mixture was concentrated under reduced pressure, purified by reverse phase HPLC, and lyophilized to give 29 mg of 3,5'-dichloro-N6-((tetrahydro-2H-pyran-4-yl)methyl)-N2'-(trans-4-(2-(trifluoromethoxy)ethylamino)cyclohexyl)-2,4'-bipyridine-2',6-diamine as its TFA salt. LCMS (m/z): 562.4 (MH+), retention time=0.67 min.; 1H NMR (400 MHz, DMSO-d6) δ ppm 1.07-1.32 (m, 4 H) 1.36-1.52 (m, 2 H) 1.58 (d, J=12.91 Hz, 2 H) 1.65-1.84 (m, 1 H) 2.07 (d, J=10.56 Hz, 4 H) 2.99-3.17 (m, 3 H) 3.23 (t, J=10.76 Hz, 2 H) 3.35 (br. s., 2 H) 3.64 (br. s., 1 H) 3.72-3.89 (m, 2 H) 4.34 (t, J=4.89 Hz, 2 H) 6.32-6.47 (m, 1 H) 6.49-6.65 (m, 1 H) 6.67-7.10 (m, 2 H) 7.49 (d, J=9.00 Hz, 1 H) 8.03 (s, 1 H) 8.75 (d, J=3.91 Hz, 1 H)

Example 50

Compound 284

N2'-(trans-4-aminocyclohexyl)-5'-chloro-N6-(((2R,6S)-2,6-dimethyltetrahydro-2H-pyran-4-yl)methyl)-2,4'-bipyridine-2',6-diamine

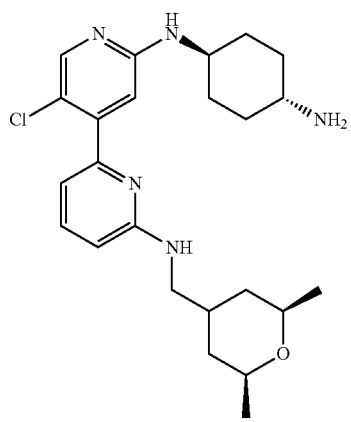 [SMILES: C[C@@H]1CC(CNc2cccc(-c3cc(N[C@H]4CC[C@H](N)CC4)ncc3Cl)n2)C[C@H](C)O1]

The mixture of 5'-chloro-N-(((2R,6S)-2,6-dimethyltetrahydro-2H-pyran-4-yl)methyl)-2'-fluoro-2,4'-bipyridin-6-amine L (30 mg, 0.08 mmol), trans-1,4-cyclohexanediamine (49 mg, 0.43 mmol) and triethylamine (26 mg, 0.25 mmol) in 1.5 ml DMSO was heated in a reaction vessel at 110° C. in an oil bath for 16 h. Formation of desired product was confirmed by LC/MS. The reaction mixture solution was diluted with ethyl acetate, washed with water, dried over sodium sulfate and concentrated. Crude compound was purified by HPLC to give desired product as TFA salt. LCMS (m/z): 444.2/446.2 (MH+), retention time=0.54 min.

Example 51

Compound 285

5'-chloro-N6-(((2R,6S)-2,6-dimethyltetrahydro-2H-pyran-4-yl)methyl)-N2'-(trans-4-(2-methoxyethylamino)cyclohexyl)-2,4'-bipyridine-2',6-diamine

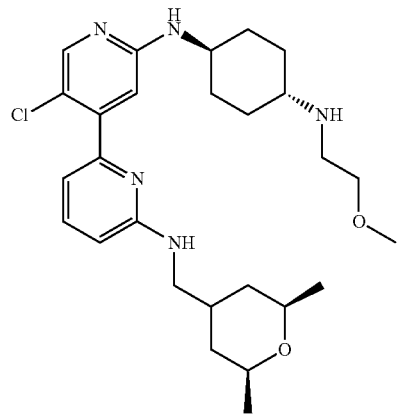 [SMILES: COCCN[C@H]1CC[C@H](Nc2cc(-c3cccc(NCC4C[C@@H](C)O[C@@H](C)C4)n3)c(Cl)cn2)CC1]

The mixture of N2'-(trans-4-aminocyclohexyl)-5'-chloro-N6-(((2R,6S)-2,6-dimethyl tetrahydro-2H-pyran-4-yl)methyl)-2,4'-bipyridine-2',6-diamine Compound 284 (20 mg, 0.045 mmol), p-toluenesulfonic acid 2-methoxyethyl ester (14 mg, 0.06 mmol) and sodium carbonate (9.6 mg, 0.09 mmol) in 1 ml DMSO was heated in a reaction vessel at 105° C. in an oil bath for 3 h. Formation of desired product was confirmed by LCMS, MH+ 502/504, 0.58 min, with ~50% conversion. Mixture was diluted with ethyl acetate, washed with water, dried over sodium sulfate, and concentrated. Crude product was purified by HPLC to give desired product as TFA salt. LCMS (m/z): 502.2/504.2, retention time=0.56 min.

Example 52

Compound 191

N2'-((1R,3R)-3-aminocyclopentyl)-5'-chloro-N6-(3-fluorobenzyl)-2,4'-bipyridine-2',6-diamine

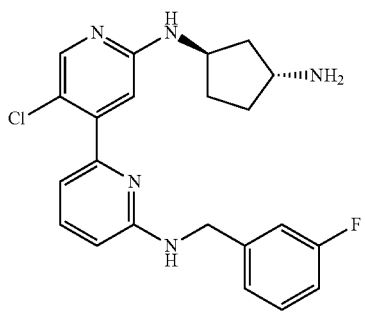 [SMILES: N[C@@H]1CC[C@@H](Nc2cc(-c3cccc(NCc4cccc(F)c4)n3)c(Cl)cn2)C1]

Step 1. Preparation of 6-bromo-N-(3-fluorobenzyl)pyridin-2-amine: To 2,6-dibromopyridine (7.1 g, 30.0 mmol) was added NMP (16 ml), (3-fluorophenyl)methanamine (4.13 g, 33.0 mmol) and Huenig's Base (5.76 ml, 33.0 mmol) flushed with argon. The crude reaction mixture was stirred at 115-120° C. for 168 hr, followed by LCMS. The crude mixture was cooled, 250 ml of ethyl acetate was added, washed with saturated sodium bicarbonate (2×), water (2×), saturated salt solution (1×), dried sodium sulfate, filtered, concentrate. The crude was purified by silica gel chromatography using 120 g column, eluting from 0%-20% ethyl acetate with hexane. The desired fractions were concentrated to constant mass, giving 7.11 grams of the title compound as a free base used without further purification. LCMS (m/z): 281.1/283.1 (MH+), retention time=1.03 min.

Step 2. Preparation of 5'-chloro-2'-fluoro-N-(3-fluorobenzyl)-2,4'-bipyridin-6-amine:
To 6-bromo-N-(3-fluorobenzyl)pyridin-2-amine (2.0 g, 7.11 mmol) was added 5-chloro-2-fluoropyridin-4-ylboronic acid (1.996 g, 11.38 mmol), PdCl2(dppf).CH2Cl2 adduct (0.465 g, 0.569 mmol), DME (27 ml) and last 2M sodium carbonate (9.25 ml, 18.50 mmol). The crude reaction was stirred at 100° C. for 3 hr, followed by LCMS. The crude mixture was cooled, 25 ml of ethyl acetate and 20 ml of methanol was added, filtered and concentrated to provide a crude product. The crude was purified by silica gel chromatography using a 120 g column, eluting from 0%-20% ethyl acetate with hexane. The desired fractions were concentrated to constant mass, giving 1.259 grams of titled compound as free base use with out further purification. LCMS (m/z): 332.2 (MH+), retention time=0.92 min.

Step 3. Preparation of (1S,3R)-3-(5'-chloro-6-(3-fluorobenzylamino)-2,4'-bipyridin-2'-yl-amino)cyclopentanol:
To 5'-chloro-2'-fluoro-N-(3-fluorobenzyl)-2,4'-bipyridin-6-amine (75 mg, 0.226 mmol), was added (1S,3R)-3-aminocyclopentanol (68.6 mg, 0.678 mmol), NMP (0.75 ml) and triethylamine (0.158 ml, 1.130 mmol). The crude reaction mixture was stirred at 100° C. for 18 hr, and the reaction progress followed by LCMS. The crude reaction mixture was cooled, filtered, and purified by prep LC. The product fractions were collected, 50 mL of 1 M NaOH and 50 mL of EtOAc were added. The aqueous layer was removed, the organic layer was washed with 50 mL of saturated salt solution, dried over sodium sulfate, and reduced to constant mass. 28 mg of the desired compound was obtained. LCMS (m/z): 413.1 (MH+), retention time=0.67 min.; 1H NMR (400 MHz, CHLOROFORM-d, 25° C.) δ ppm 1.71 (d, J=14.09 Hz, 1 H) 1.75-1.91 (m, 2 H) 1.97-2.05 (m, 1 H) 2.10-2.16 (m, 1 H) 2.61 (br. s., 1 H) 4.03-4.18 (m, 1 H) 4.39 (tt, J= 4.84, 2.59 Hz, 1 H) 4.55 (d, J= 5.09 Hz, 2 H) 5.19 (br. s., 2 H) 6.41 (d, J= 8.22 Hz, 1 H) 6.55 (s, 1 H) 6.90-7.02 (m, 2 H) 7.05-7.18 (m, 2 H) 7.24-7.34 (m, 1 H) 7.43-7.55 (m, 1 H) 8.07 (s, 1 H).

Step 4. Preparation of N2'-((1R,3R)-3-aminocyclopentyl)-5'-chloro-N6-(3-fluorobenzyl)-2,4'-bipyridine-2',6-diamine:
To (1S,3R)-3-(5'-chloro-6-(3-fluorobenzylamino)-2,4'-bipyridin-2'-yl-amino)cyclopentanol (28 mg, 0.068 mmol) was added DCM (1 ml), diisopropyl ethylamine (0.030 ml, 0.170 mmol) then mesyl chloride (5.81 µl, 0.075 mmol), stirred at ambient temperature for 1 hr, and followed by LCMS. Another 3 uL of mesyl chloride was added and the reaction mixture was stirred an additional 30 minutes at ambient temperature. DCM was removed by rotary evaporation, and crude (1S,3R)-3-(5'-chloro-6-(3-fluorobenzylamino)-2,4'-bipyridin-2'-yl-amino)cyclopentyl LCMS (m/z): 491.2 (MH+), retention time=0.76 min. was redissolved in 2 mL DMF. Sodium azide (8.82 mg, 0.136 mmol) and diisopropyl ethylamine (0.030 ml, 0.170 mmol) were added, and the reaction mixture was heated at 50° C. for 18 hours, at which point only N2'-((1R,3R)-3-azidocyclopentyl)-5'-chloro-N6-(3-fluorobenzyl)-2,4,-bipyridine-2',6-diamine was observed by LCMS (m/z): 438.2 (MH+), retention time=0.83 min. The resulting reaction mixture was partitioned between ethyl acetate and water. The aqueous layer was removed, and the organic layer was washed with water (1×) then saturated salt solution (1×), dried over sodium sulfate, and reduced to constant mass. Crude N2'-((1R,3R)-3-azidocyclopentyl)-5'-chloro-N6-(3-fluorobenzyl)-2,4'-bipyridine-2',6-diamine (20 mg, 0.046 mmol, LCMS (m/z): 438.2 (MH+), retention time=0.83 min.) was dissolved in 1 mL of methanol, and 10% palladium on charcoal (4.86 mg, 0.046 mmol) was added under argon. H2 was bubbled through the solution while stirring for 1 hr at ambient temperature, and the reaction was followed by LCMS. The crude reaction mixture was filtered over celite washed with methanol, reduced, redissolved in DMSO, filtered and purified through prep LC. The resulting product fractions were combined, then 50 mL of 1 M NaOH and 50 mL of EtOAC were added. The aqueous layer was removed, the organic layer was washed with saturated salt solution, dried over sodium sulfate, and reduced to constant mass. 8 mg of the desired compound was obtained. LCMS (m/z): 412.1 (MH+), retention time=0.58 min.; 1H NMR (300 MHz, CHLOROFORM-d, 25° C.) δ ppm 1.31-1.54 (m, 2 H) 1.71-1.86 (m, 4 H) 1.98-2.13 (m, 1H) 2.20-2.35 (m, 1 H) 3.54 (qd, J=6.35, 6.15 Hz, 1 H) 4.14 (sxt, J=6.56 Hz, 1 H) 4.55-4.67 (m, 3 H) 5.11 (t, J=5.86 Hz, 1 H) 6.40 (d, J=8.50 Hz, 1 H) 6.56 (s, 1 H) 6.88-7.02 (m, 1 H) 7.12-7.16 (m, 1 H) 7.29-7.34 (m, 1 H) 7.47-7.52 (m, 1 H) 8.09 (s, 1 H).

Example 53

Compound 205

(1S,3R)-3-(5'-chloro-6-(3-fluorobenzylamino)-2,4'-bipyridin-2'-yl-amino)-N,N-dimethylcyclopentanecarboxamide

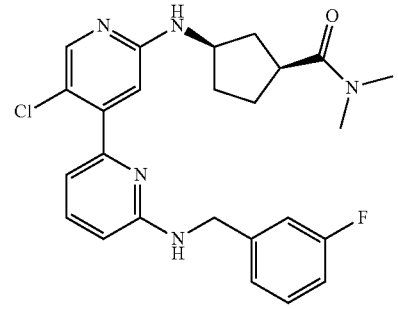 [SMILES: CN(C)C(=O)[C@H]1CC[C@@H](Nc2cc(-c3cccc(NCc4cccc(F)c4)n3)c(Cl)cn2)C1]

Step 1. Preparation of 6-bromo-N-(3-fluorobenzyl)pyridin-2-amine: To 2,6-dibromopyridine (7.1 g, 30.0 mmol) was added NMP (16 ml), (3-fluorophenyl)methanamine (4.13 g, 33.0 mmol) and Huenig's Base (5.76 ml, 33.0 mmol) flushed with argon. The crude reaction mixture was stirred at 115-120° C. for 168 hr, followed by LCMS. The crude mixture was cooled, 250 ml of ethyl acetate was added, washed with saturated sodium bicarbonate (2×), water (2×), saturated salt solution (1×), dried sodium sulfate, filtered, concentrate. The crude was purified by silica gel chromatography using 120 g column, eluting from 0%-20% ethyl acetate with hexane. The desired fractions were concentrated to constant mass, giving 7.11 grams of the titled compound as a free base used without further purification. LCMS (m/z): 281.1/283.1 (MH+), retention time=1.03 min.

Step 2. Preparation of 5'-chloro-2'-fluoro-N-(3-fluorobenzyl)-2,4'-bipyridin-6-amine: To 6-bromo-N-(3-fluorobenzyl)pyridin-2-amine (2.0 g, 7.11 mmol) was added 5-chloro-2-fluoropyridin-4-ylboronic acid (1.996 g, 11.38 mmol), PdCl2 (dppf).CH2Cl2 adduct (0.465 g, 0.569 mmol), DME (27 ml) and last 2M sodium carbonate (9.25 ml, 18.50 mmol). The crude reaction mixture was stirred at 100° C. for 3 hr, followed by LCMS. The crude mixture was cooled, 25 ml of ethyl acetate and 20 ml of methanol was added, filtered and concentrated to crude product. The crude was purified by silica gel chromatography using a 120 g column, eluting from 0%-20% ethyl acetate with hexane. The desired fractions were concentrated to constant mass, giving 1.259 grams of title compound as free base use with out further purification. LCMS (m/z): 332.2 (MH+), retention time=0.92 min.

Step 3: Preparation of (1S,3R)-3-(5'-chloro-6-(3-fluorobenzylamino)-2,4'-bipyridin-2'-yl-amino)cyclopentanecarboxylic acid: To 5'-chloro-2'-fluoro-N-(3-fluorobenzyl)-2,4'-bipyridin-6-amine (100 mg, 0.301 mmol), was added (1S,3R)-3-aminocyclopentanecarboxylic acid (117 mg, 0.904 mmol), powdered potassium hydroxide (85 mg, 1.507 mmol) and dioxane (1 ml). The reaction mixture was stirred at 100° C. for 18 hr in a sealed vessel and followed by LCMS. The crude reaction mixture was partitioned between 30 mL saturated ammonium chloride and 30 mL ethyl acetate. The organic layer was removed, dried over sodium sulfate, and reduced. This was redissolved in 1.5 mL DMSO, filtered, and purified through prep LC. The product fractions were combined and extracted with 50 mL ethyl acetate, which was dried over sodium sulfate, and concentrated to constant mass. 10 mg of the desired compound was obtained. LCMS (m/z): 441.2 (MH+), retention time=0.68 min. 1H NMR (400 MHz, CHLOROFORM-d, 25° C.) δ ppm 1.59 (m, 2 H) 1.83 (m, 2 H) 1.99 (m, 1 H) 2.72 (m, 1 H) 3.40 (br. s., 1 H) 3.78 (br. s., 1 H) 4.42 (br. s., 1 H) 5.48 (br. s., 1 H) 6.29 (d, J=8.22 Hz, 1 H) 6.50 (s, 1 H) 6.80-6.92 (m, 2 H) 6.95-7.10 (m, 2 H) 7.16-7.25 (m, 1 H) 7.38 (t, J=8.02 Hz, 1 H) 7.89 (s, 1 H).

Step 4. Preparation of (1S,3R)-3-(5'-chloro-6-(3-fluorobenzylamino)-2,4'-bipyridin-2'-yl-amino)-N,N-dimethylcyclopentanecarboxamide: To (1S,3R)-3-(5'-chloro-6-(3-fluorobenzylamino)-2,4'-bipyridin-2'-yl-amino) cyclopentanecarboxylic acid U-31332-EXP080 (10 mg, 0.023 mmol), 2M dimethyl amine in THF (0.011 ml, 0.023 mmol), N1-((ethylimino)methylene)-N3,N3-dimethylpropane-1,3-diamine hydrochloride (8.70 mg, 0.045 mmol), 3H-[1,2,3]triazolo[4,5-b]pyridin-3-ol (4.32 mg, 0.032 mmol) were added then dimethylformamide (1 ml) and diisopropyl ethylamine (0.016 ml, 0.091 mmol) were added, and the reaction mixture was stirred at ambient temperature for 18 hr and the progress followed by LCMS. The crude reaction mixture was filtered and purified by preparative LC. The product fractions were combined, 50 mL of 1M NaOH and 50 mL of ethyl acetate were added. The organic layer was removed, washed with 50 mL 1M NaOH, 50 mL saturated salt solution, dried over sodium sulfate, and reduced to constant mass. 3 mg of the desired compound was obtained. LCMS (m/z): 468.1 (MH+), retention time=0.72 min., 1H NMR (300 MHz, CHLOROFORM-d) δ ppm 1.77-2.16 (m, 6 H) 2.96 (s, 3 H) 3.07 (s, 3 H) 3.10-3.25 (m, 1 H) 4.29 (m, 1 H) 4.56 (d, J=5.27 Hz, 2 H) 5.12 (br. s., 1 H) 5.87 (br. s., 1 H) 6.38 (d, J=8.50 Hz, 1 H) 6.58 (s, 1 H) 6.91-7.01 (m, 1 H) 7.06-7.20 (m, 1 H) 7.26-7.37 (m, 2 H) 7.44-7.53 (m, 2 H) 8.09 (s, 1 H).

Example 54

Compound 235

5'-chloro-N6-(3-fluorobenzyl)-N2'-((1R,3S)-3-((methylamino)methyl)cyclopentyl)-2,4'-bipyridine-2',6-diamine

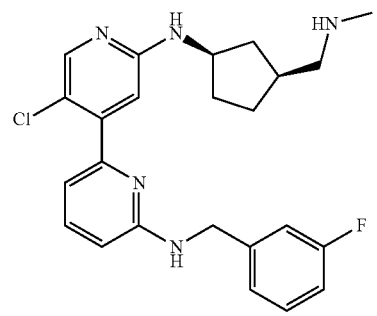 [SMILES: CNC[C@H]1CC[C@@H](Nc2cc(-c3cccc(NCc4cccc(F)c4)n3)c(Cl)cn2)C1]

Step 1. Preparation of 6-bromo-N-(3-fluorobenzyl)pyridin-2-amine: To 2,6-dibromopyridine (7.1 g, 30.0 mmol) was added NMP (16 ml), (3-fluorophenyl)methanamine (4.13 g, 33.0 mmol) and Huenig's Base (5.76 ml, 33.0 mmol) flushed with argon. The crude reaction mixture was stirred at 115-120° C. for 168 hr, followed by LCMS. The crude mixture was cooled, 250 ml of ethyl acetate was added, washed with saturated sodium bicarbonate (2×), water (2×), saturated salt solution (1×), dried sodium sulfate, filtered, concentrate. The crude was purified by silica gel chromatography using 120 g column, eluting from 0%-20% ethyl acetate with hexane. The desired fractions were concentrated to constant mass, giving 7.11 grams of the titled compound as a free base used without further purification. LCMS (m/z): 281.1/283.1 (MH+), retention time=1.03 min.

Step 2. Preparation of 5'-chloro-2'-fluoro-N-(3-fluorobenzyl)-2,4'-bipyridin-6-amine: To 6-bromo-N-(3-fluorobenzyl)pyridin-2-amine (2.0 g, 7.11 mmol) was added 5-chloro-2-fluoropyridin-4-ylboronic acid (1.996 g, 11.38 mmol), PdCl2 (dppf).CH2Cl2 adduct (0.465 g, 0.569 mmol), DME (27 ml), and 2M sodium carbonate (9.25 ml, 18.50 mmol). The crude reaction mixture was stirred at 100° C. for 3 hr, and the reaction progress followed by LCMS. The crude mixture was cooled, 25 ml of ethyl acetate and 20 ml of methanol were added, filtered and concentrated to yield a crude product. The crude was purified by silica gel chromatography using a 120 g ISCO column, eluting from 0%-20% ethyl acetate with hexane. The desired fractions were concentrated to constant mass, giving 1.259 grams of title compound as free base use with out further purification. LCMS (m/z): 332.2 (MH+), retention time=0.92 min.

Step 3. Preparation of (1R,4S)-tert-butyl 3-oxo-2-azabicyclo[2.2.1]heptane-2-carboxylate: A mixture of (1S,4R)-2-azabicyclo[2.2.1]hept-5-en-3-one (2 g, 18.33 mmol) and 10% Pd/C (0.780 g, 0.733 mmol) in MeOH (100 ml) was stirred under atmospheric pressure of H2 at ambient temperature for 2 hr, and the reaction progress was followed by LCMS. Pd/C was filtered off over Celite and the filter cake was washed with MeOH. The combined organics were concentrated to afford crude (1R,4S)-2-azabicyclo[2.2.1]heptan-3-one. LCMS (m/z): 112.1 (MH+), retention time=0.30 min. The resulting resulting residue was redissolved in DCM (100 ml), to which di-tert-butyl dicarbonate (8.51 ml, 36.7 mmol) and DMAP (1.231 g, 10.08 mmol) were added and stirred at ambient temperature for 18 hr and the reaction progress was followed by LCMS. Solvent was removed, and the crude reaction mixture was purified through column chromatography, 10-40% EtOAc: Heptane. The desired fractions were concentrated to constant mass, yielding (1R,4S)-tert-butyl 3-oxo-2-azabicyclo[2.2.1]heptane-2-carboxylate (2.99 g, 14.15 mmol) of a white solid. LCMS (m/z): 156.2 (M-tBu), retention time=0.75 min.

Step 4. Preparation of tert-butyl (1R,3S)-3-(hydroxymethyl)cyclopentylcarbamate (1R,4S)-tert-butyl 3-oxo-2-azabicyclo[2.2.1]heptane-2-carboxylate (2.99 g, 14.15 mmol) was dissolved in MeOH (40 ml) and cooled to 0° C. Sodium Borohydride (1.071 g, 28.3 mmol) was added and the reaction was stirred at 0° C. for 1 hr, and the reaction progress was followed by LCMS. MeOH was removed and the resulting residue was partitioned between EtOAc (250 mL) and H2O (250 mL). The organic layer was washed with brine (250 mL), dried over Na2SO4, and concentrated under reduced pressure. The crude material was purified by column chromatography, 50-100% EtOAc in heptane to yield tert-butyl (1R,3S)-3-(hydroxymethyl)cyclopentylcarbamate (2.92 g, 13.56 mmol) as a white solid. LCMS (m/z): 160.2 (M-tBu), retention time=0.65 min.

Step 5. Preparation of ((1S,3R)-3-aminocyclopentyl) methanol: Tert-butyl (1R,3S)-3-(hydroxymethyl)cyclopentylcarbamate (2.92 g, 13.56 mmol) was dispersed in H2O (50 ml) and refluxed at 100° C. for 18 hr, followed by LCMS. Water was removed by azeotroping with toluene (50 mL×3). Collected ((1S,3R)-3-aminocyclopentyl)methanol (1.92 g, 12.50 mmol) as a clear, viscous oil which was used without further purification. LCMS (m/z): 116.1 (MH+), retention time=0.67 min.

Step 6. Preparation of ((1S,3R)-3-(5'-chloro-6-(3-fluorobenzylamino)-2,4'-bipyridin-2'-yl-amino)cyclopentyl) methanol: To 5'-chloro-2'-fluoro-N-(3-fluorobenzyl)-2,4'-bipyridin-6-amine (100 mg, 0.301 mmol) was added DMSO (1 ml), ((1S,3R)-3-aminocyclopentyl)methanol (104 mg, 0.903 mmol) and TEA (0.21 ml, 1.51 mmol). The crude mixture was stirred at 100° C. for 20 hours, followed by LCMS. The crude reaction mixture was cooled, was diluted with EtOAc (60 mL), washed H₂O (60 mL×2), brine (60 mL), dried over Na₂SO₄, and reduced. The crude was adsorbed onto silica gel, and purified by silica gel chromatography, 40-80%) EtOAc/Heptane, 12 g ISCO silica column, resulting in ((1S,3R)-3-(5'-chloro-6-(3-fluorobenzylamino)-2,4'-bipyridin-2'-yl-amino)cyclopentyl)methanol (101 mg, 0.237 mmol). LCMS (m/z): 427.1 (MH+). retention time=0.69 min.

Step 7. Preparation of (1S,3R)-3-(5'-chloro-6-(3-fluorobenzylamino)-2,4'-bipyridin-2'-yl-amino)cyclopentanecarbaldehyde In a flame-dried argon purged 20 mL conical flask, oxalyl chloride (0.025 ml, 0.281 mmol) was dissolved in DCM (0.5 ml) and cooled to −78° C. under argon. DMSO (0.030 ml, 0.422 mmol) was dissolved in DCM (0.5 ml) and added dropwise to the previous solution (I don't see issues here). This was stirred for 30 min at −78° C. ((1S,3R)-3-(5'-chloro-6-(3-fluorobenzylamino)-2,4,-bipyridin-2'-yl-amino)cyclopentyl)methanol (60 mg, 0.141 mmol) was dissolved in DCM (0.5 ml) and added dropwise to the reaction mixture. The resulting mixture was stirred for 60 min at −78° C. TEA (0.078 ml, 0.562 mmol) was dissolved in DCM (0.5 ml) and added dropwise to the reaction mixture, after which the reaction mixture was allowed to stir and warm to ambient temp over 2 hr. The reaction mixture was diluted with EtOAc, washed with saturated NH₄Cl (30 mL×3), H20 (30 mL), brine (30 mL), dried over Na2SO4 and reduced. The resulting residue was used without further purification. LCMS (m/z): 425.2 (MH+), retention time=0.72.

Step 8. Preparation of 5'-chloro-N6-(3-fluorobenzyl)-N2'-((1R,3S)-3-((methylamino)methyl)cyclopentyl)-2,4'-bipyridine-2',6-diamine To (1S,3R)-3-(5'-chloro-6-(3-fluorobenzylamino)-2,4,-bipyridin-2,-yl-amino)cyclopentanecarbaldehyde (20 mg, 0.047 mmol) was added methyl amine in THF (0.5 ml, 1.0 mmol) and DCM (0.5 mL). Acetic acid (2.69 µl, 0.047 mmol), and sodium triacetoxyborohydride (14.96 mg, 0.071 mmol) were added and stirred for 2 hr at ambient temperature, and the reaction progress was followed by LCMS. Solvents were removed, and the crude reaction mixture redissolved in 1.5 mL of DMSO, followed by purification using preparative HPLC. Product fractions were combined and lyophilized to affore 5'-chloro-N6-(3-fluorobenzyl)-N2'-((1R,3S)-3-((methylamino)methyl)cyclopentyl)-2,4'-bipyridine-2',6-diamine (2.5 mg, 0.006 mmol) as a TFA salt. LCMS (m/z): 440.2 (MH+), retention time=0.62 min.

Example 56

Compound 212

N-2'-(trans-4-aminocyclohexyl)-5'-chloro-N6-((R)-6-oxaspiro[2.5]octan-1-yl)-2,4'-bipyridine-2',6-diamine

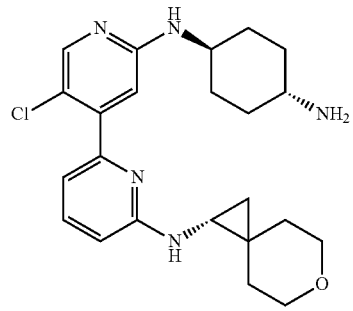

212

Step 1: Preparation of (R)-6-bromo-N-(6-oxaspiro[2.5]octan-1-yl)pyridin-2-amine: To a solution of 2,6-dibromopyridine (200 mg, 0.84 mmol) in NMP (0.42 mL) was added (R)-6-oxaspiro[2.5]octan-1-amine hydrochloride (138 mg, 0.84 mmol) and potassium carbonate (350 mg, 2.53 mmol). The mixture was heated at 110° C. for 18 hr. The mixture was allowed to cool to ambient temperature and diluted with EtOAc. The organic layer was washed with saturated aqueous sodium bicarbonate solution, water, and brine and dried over sodium sulfate, filtered off and concentrated in vacuo. The resulting residue was purified by column chromatography [SiO₂, 40 g, EtOAc/heptane= 0/100 to 30/70]. Pure fractions were combined and concentrated in vacuo giving 210 mg of titled compound. LCMS (m/z): 282.9/284.9 [M+H]+, retention time=0.85 min.

Step 2. Preparation of (R)-5'-chloro-2'-fluoro-N-(6-oxaspiro[2.5]octan-1-yl)-2,4'-bipyridin-6-amine:

A mixture of (R)-6-bromo-N-(6-oxaspiro[2.5]octan-1-yl) pyridin-2-amine (C, 100 mg, 0.35 mmol), 5-chloro-2-fluoropyridin-4-ylboronic acid (136 mg, 0.77 mmol), PdCl₂(dppf).CH₂Cl₂ adduct (23 mg, 0.028 mmol) in DME (1 mL) and 2M Na₂CO₃ (97 mg, 0.92 mmol) in a sealed tube was heated at 103° C. for 2 hr. The mixture was allowed to cool to ambient temperature and was diluted with EtOAc (~25 mL) and MeOH (~5 mL), filtered off and concentrated in vacuo. The resulting residue was purified by column chromatography [SiO₂, 12 g, EtOAc/heptane= 10/90 to 50/50]. Fractions were combined and concentrated in vacuo giving 105 mg of titled compound. LCMS (m/z): 334.0/336.0 [M+H]+, retention time=0.64 min.

Step 3. Preparation of N-2'-(trans-4-aminocyclohexyl)-5'-chloro-N6-((R)-6-oxaspiro[2.5]octan-1-yl)-2,4'-bipyridine-2',6-diamine: A mixture of (R)-5'-chloro-2'-fluoro-N-(6-oxaspiro[2.5]octan-1-yl)-2,4'-bipyridin-6-amine (15 mg, 0.045 mmol), trans-cyclohexane-1,4-diamine (10.3 mg, 0.090 mmol), in DMSO (0.2 mmol) in a sealed tube was heated at 110° C. for 18 hr. The mixture was allowed to cool to ambient temperature. To the reaction mixture was added 0.5 ml of DMSO, filtered and purified by prep LC. After lyophilisation, 5.0 mg of the titled compound as a TFA salt was obtained. LCMS (m/z): 428.3/430.3 (MH+), retention time=0.46 min.

Example 57

Compound 230

N-(4-Amino-cyclohexyl)-5'-chloro-N-(1,1-dioxo-hexahydro-1-thiopyran-4-yl-methyl)-[2,4']bipyridinyl-6,2'-diamine

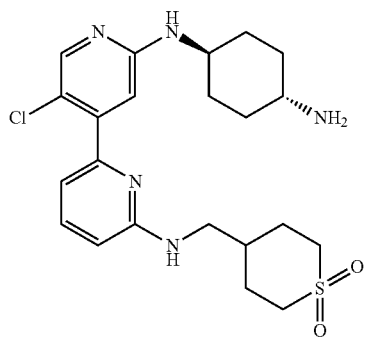

230

Step 1. Preparation of toluene-4-sulfonic acid 1,1-dioxo-hexahydro-1-thiopyran-4-yl-methyl ester: A solution of (1,1-Dioxo-hexahydro-1-thiopyran-4-yl)-methanol (500 mg, 3.04 mmol) in pyridine (10 mL) was added 4-methylbenzene-1-sulfonyl chloride (871 mg, 4.57 mmol). The mixture was stirred at ambient temperature for 18 hr. The mixture was diluted with EtOAc. The organic layer was washed with saturated aqueous sodium bicarbonate solution, water, and brine and dried over sodium sulfate, filtered off and concentrated in vacuo. The resulting residue was purified by column chromatography [SiO₂, 12 g, EtOAc/heptane= 0/100 to 30/70]. Pure fractions were combined and concentrated in vacuo giving 736 mg of title compound. LCMS (m/z): 319.1 (MH+), retention time=0.69 min.

Step 2. Preparation of (6-Bromo-pyridin-2-yl)-(1,1-dioxo-hexahydro-1-thiopyran-4-yl-methyl)-amine: A mixture of toluene-4-sulfonic acid 1,1-dioxo-hexahydro-1-thiopyran-4-yl-methyl ester (736 mg, 2.31 mmol), 6-bromopyridin-2-amine (400 mg, 2.312 mmol), potassium carbonate (639 mg, 4.62 mmol), sodium hydride (111 mg, 4.62 mmol) in a sealed tube was heated at 68° C. for 18 hr. The mixture was allowed to cool to ambient. The mixture was diluted with EtOAc. The organic layer was washed with saturated aqueous sodium bicarbonate solution, water, and brine and dried over sodium sulfate, filtered off and concentrated in vacuo. The resulting residue was purified by column chromatography [SiO₂, 12 g, EtOAc/heptane= 0/100 to 30/70]. Pure fractions were combined and concentrated in vacuo giving 240 mg of titled compound. LCMS (m/z): 318.8/320.9 (MH+), retention time=0.71 min.

Step 3. Preparation of (5'-Chloro-2'-fluoro-[2,4']bipyridinyl-6-yl)-(1,1-dioxo-hexahydro-1-thiopyran-4-yl-methyl)-amine A mixture of (6-bromo-pyridin-2-yl)-(1,1-dioxo-hexahydro-1-thiopyran-4-yl-methyl)-amine (238 mg, 0.746 mmol), 5-chloro-2-fluoropyridin-4-ylboronic acid (261 mg, 1.491 mmol), adduct (48.7 mg, 0.060 mmol) in DME (2 mL) and 2M Na₂CO₃ (205 mg, 1.938 mmol) in a sealed tube was heated at 103° C. for 2 hr. The mixture was allowed to cool to ambient temperature and was diluted with EtOAc (~25 mL) and MeOH (~5 mL), filtered off and concentrated in vacuo. The resulting residue was purified by column chromatography [SiO₂, 12 g, EtOAc/heptane= 10/90 to 50/50]. Fractions were combined and concentrated in vacuo giving 150 mg of the title compound. LCMS (m/z): 370.0/372.0 (MH+); Retention time=0.56 min.

Step 4. Preparation of N-(4-amino-cyclohexyl)-5'-chloro-N-(1,1-dioxo-hexahydro-1-thiopyran-4-yl-methyl)-[2,4']bipyridinyl-6,2'-diamine: A mixture of (R)-5'-chloro-2'-fluoro-N-(6-oxaspiro[2.5]octan-1-yl)-2,4'-bipyridin-6-amine (40 mg, 0.108 mmol), and trans-cyclohexane-1,4-diamine (124 mg, 1.082 mmol) in DMSO (0.4 mmol) was heated in a sealed tube at 100° C. for 4 hr. The mixture was allowed to cool to ambient temperature. To the cooled reaction mixture was added 0.5 ml of DMSO, filtered and purified by prep LC. After lyophilisation, 10.0 mg of the titled compound as a TFA salt was obtained. LCMS (m/z): 464.1/466.1 (MH+), retention time=0.44 min.

Example 58

Compound 317

5'-chloro-N6-(dideutero-(tetrahydro-2H-pyran-4-yl) methyl)-N2'-(trans-4-(((S)-tetrahydrofuran-2-yl)methyl)aminocyclohexyl)-2,4'-bipyridine-2',6-diamine

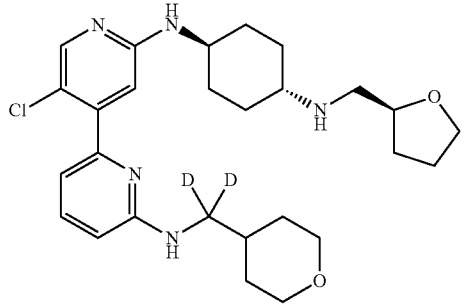 [SMILES: [2H]C([2H])(Nc1cccc(-c2cc(N[C@H]3CC[C@H](NC[C@@H]4CCCO4)CC3)ncc2Cl)n1)C1CCOCC1]

Step 1. Preparation of dideutero-(tetrahydro-2H-pyran-4-yl)methanamine: To a solution of tetrahydro-2H-pyran-4-carbonitrile (800 mg, 7.20 mmol) in THF (20 mL) was added aluminum(III) lithium deuteride at 0° C. The mixture was stirred at 0° C. for 2 hr. To the stirred reaction mixture was sequentially added 300 uL of water, 900 μL of 1 N NaOH and 300 μL of water. The mixture was filtered through a thin layer of celite to remove the solid. The filtrate was dried over sodium sulfate, filtered off and concentrated in vacuo giving 700 mg of titled compound. LCMS (m/z): 118.2 [M+H]+, retention time=0.25 min. The crude product was used directly for next step.

Step 2. Preparation of 6-bromo-N-(dideutero(tetrahydro-2H-pyran-4-yl)methyl)pyridin-2-amine: To a solution of 2,6-dibromopyridine (1051 mg, 5.97 mmol) in DMSO (5 mL) was added dideutero(tetrahydro-2H-pyran-4-yl)methanamine (700 mg, 5.97 mmol) and diisopropylethylamine (926 mg, 7.17 mmol). The mixture was heated at 80° C. for 2 hr. The mixture was allowed to cool to ambient temperature and diluted with EtOAc. The organic layer was washed with saturated aqueous sodium bicarbonate solution, water, and brine and dried over sodium sulfate, filtered off and concentrated in vacuo. The resulting residue was purified by column chromatography [$SiO_2$, 40 g, EtOAc/heptane=0/100 to 30/70]. Pure fractions were combined and concentrated in vacuo giving 780 mg of titled compound. LCMS (m/z): 272.9/274.9 [M+H]+, retention time=0.77 min.

Step 3. Preparation of 5'-chloro-N-(dideutero(tetrahydro-2H-pyran-4-yl)methyl)-2'-fluoro-2,4'-bipyridin-6-amine A mixture of 6-bromo-N-(dideutero(tetrahydro-2H-pyran-4-yl)methyl)pyridin-2-amine (500 mg, 1.83 mmol), 5-chloro-2-fluoropyridin-4-ylboronic acid (642 mg, 3.66 mmol), $PdCl_2(dppf) \cdot CH_2Cl_2$ adduct (120 mg, 0.146 mmol) in DME (1 mL) and 2M $Na_2CO_3$ (2.38 ml, 4.76 mmol) was heated in a sealed tube at 80° C. for 48 hr. The mixture was allowed to cool to ambient temperature and was diluted with EtOAc (~25 mL) and MeOH (~5 mL), filtered off and concentrated in vacuo. The resulting residue was purified by column chromatography [$SiO_2$, 12 g, EtOAc/heptane= 10/90 to 50/50]. Fractions were combined and concentrated in vacuo giving 180 mg of titled compound. LCMS (m/z): 324.0/325.8 [M+H]+, retention time=0.58 min.

Step 4. Preparation of 5'-chloro-N6-(dideutero(tetrahydro-2H-pyran-4-yl)methyl)-N2'-(trans-4-(((S)-tetrahydrofuran-2-yl)methyl)aminocyclohexyl)-2,4'-bipyridine-2',6-diamine: A mixture of 5'-chloro-N-(dideutero(tetrahydro-2H-pyran-4-yl)methyl)-2'-fluoro-2,4'-bipyridin-6-amine (30 mg, 0.093 mmol), trans-N1-(((S)-tetrahydrofuran-2-yl)methyl)cyclohexane-1,4-diamine (60 mg, 0.30 mmol), in DMSO (0.4 mmol) was heated in a sealed tube at 110° C. for 68 hr. The mixture was allowed to cool to ambient temperature. To the reaction mixture mixture was added 0.5 ml of DMSO, filtered and purified by prep LC. After lyophilisation, 10.0 mg of the titled compound as a TFA salt was obtained. LCMS (m/z): 502.3/504.3 (MH+), retention time=0.49 min.

Example 59

Compound 324

5'-chloro-5-fluoro-N2'-(trans-4-(oxetan-2-yl-methylamino)cyclohexyl)-N6-((tetrahydro-2H-pyran-4-yl)methyl)-2,4'-bipyridine-2',6-diamine

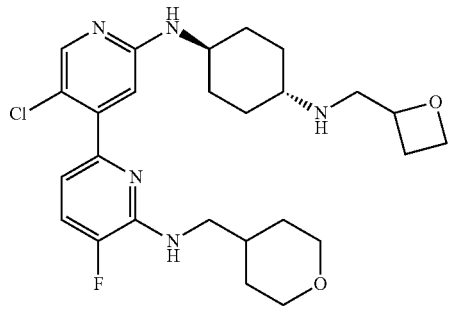 [SMILES: Fc1ccc(-c2cc(N[C@H]3CC[C@H](NCC4CCO4)CC3)ncc2Cl)nc1NCC1CCOCC1]

To a stirred solution of N2'-(trans-4-aminocyclohexyl)-5'-chloro-5-fluoro-N6-((tetrahydro-2H-pyran-4-yl)methyl)-2,4'-bipyridine-2',6-diamine (90 mg, 0.207 mmol)) in DMSO (1.0 ml) was add potassium carbonate (71.7 mg, 0.518 mmol), followed by follow oxetan-2-yl-methyl 4-methylbenzenesulfonate (151 mg, 0.622 mmol). The mixture was heated at 83° C. for 2 h. The mixture was allowed to cool to ambient temperature, then diluted with water and then extracted with EtOAc (×3). The organics were combined then washed with water (×2), saturated brine (×2), then dried ($Na_2SO_4$), filtered and evaporated under reduced pressure. The resulting residue was purified by reverse phase prep HPLC and lyophilized to yield titled compound. LCMS (m/z): 504.4/506.5 (MH+) retention time=0.60 min as a TFA salt.

Example 60

Compound 222 trans-4-(5-chloro-4-(5-chloro-6-((tetrahydro-2H-pyran-4-yl)methyl)aminopyrazin-2-yl)pyridin-2-yl-amino)cyclohexanol

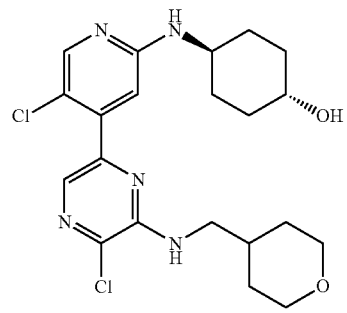 [SMILES: O[C@H]1CC[C@H](Nc2cc(-c3cnc(Cl)c(NCC4CCOCC4)n3)c(Cl)cn2)CC1]

Step 1. Preparation of 6-bromo-3-chloro-N-((tetrahydro-2H-pyran-4-yl)methyl)pyrazin-2-amine.

To a scintillation vial containing 3,5-dibromo-2-chloropyrazine (1 g, 3.67 mmol) and TEA (1.024 ml, 7.34 mmol) was added MeCN (5 ml) and (tetrahydro-2H-pyran-4-yl)methanamine (0.557 g, 3.67 mmol). The homogenous reaction mixture was capped, and heated to 80° C. in a oil bath for 4 hr. The reaction mixture was concentrated to dryness, diluted with EtOAc and sequentially washed with sat $NaHCO_3$, and sat NaCl. The organic layer was dried $Na_2SO_4$, filtered and concentrated. The crude was purified by column chromatography on silica gel (20% EtOAc/Hexane) to yield 6-bromo-3-chloro-N-((tetrahydro-2H-pyran-4-yl)methyl)pyrazin-2-amine (688 mg, 2.244 mmol, 61.1% yield), yield), LCMS (m/z): 308.0 (MH+), retention time=0.94 min, and 6-bromo-5-chloro-N-((tetrahydro-2H-pyran-4-yl)methyl)pyrazin-2-amine (55 mg, 0.179 mmol, 4.89% yield), LCMS (m/z): 308.0 (MET), retention time=0.91 min.

Step 2. Preparation of 3-chloro-6-(5-chloro-2-fluoropyridin-4-yl)-N-((tetrahydro-2H-pyran-4-yl)methyl)pyrazin-2-amine To a degassed suspension of 6-bromo-3-chloro-N-((tetrahydro-2H-pyran-4-yl)methyl)pyrazin-2-amine (358 mg, 1.168 mmol), Na2CO3 (1.518 ml, 3.04 mmol) and 5-chloro-2-fluoropyridin-4-ylboronic acid (307 mg, 1.752 mmol) in DME (5 ml) was added $PdCl_2(dppf) \cdot CH_2Cl_2$ adduct (76 mg, 0.093 mmol). The reaction mixture was capped in a flask and heated to 100° C. for 4 hr an oil bath. The reaction mixture was diluted with EtOAc and washed with $H_2O$ saturated NaCl. The organic layer was dried $Na_2SO_4$, filtered and concentrated. The crude oil/solid was purified column chromatography on silica gel (30% EtOAc/Hexane) to yield 3-chloro-6-(5-chloro-2-fluoropyridin-4-yl)-N-((tetrahydro-2H-pyran-4-yl)methyl)pyrazin-2-amine (160 mg, 0.448 mmol, 38.4% yield), LCMS (m/z): 357.0 (MH$^+$), retention time=1.02 min.

Step 3. Preparation of trans-4-(5-chloro-4-(5-chloro-6-((tetrahydro-2H-pyran-4-yl)methyl)aminopyrazin-2-yl)pyridin-2-yl-amino)cyclohexanol: To a scintillation vial containing 3-chloro-6-(5-chloro-2-fluoropyridin-4-yl)-N-((tetrahydro-2H-pyran-4-yl)methyl)pyrazin-2-amine (20 mg, 0.056 mmol) was added DMSO (1 ml) and trans-4-aminocyclohexanol (32.2 mg, 0.280 mmol). The reaction mixture was capped and heated to 120° C. in an oil bath for 3 hr. The reaction product was purified by reverse phase preparative HPLC to yield trans-4-(5-chloro-4-(5-chloro-6-((tetrahydro-2H-pyran-4-yl)methyl)aminopyrazin-2-yl)pyridin-2-yl-amino)cyclohexanol (2.2 mg, 4.86 μmol, 8.69% yield), LCMS (m/z): 452.1 (MH$^+$), retention time=0.76 min as a TFA salt after lypholyzing. 1H NMR (400 MHz, METHANOL-d4) δ ppm 1.17-1.26 (m, 4 H) 1.27-1.39 (m, 2 H) 1.58 (dd, J=13.11, 1.76 Hz, 2 H) 1.84-2.02 (m, 5 H) 3.30 (d, J=7.04 Hz, 4 H) 3.43-3.61 (m, 2 H) 3.84 (dd, J=11.35, 3.13 Hz, 2H) 6.58 (s, 1 H) 7.66 (s, 1 H) 7.90 (s, 1 H).

Example 61

Compound 223 trans-N1-(5-chloro-4-(3-chloro-6-((tetrahydro-2H-pyran-4-yl)methyl)aminopyrazin-2-yl)pyridin-2-yl)cyclohexane-1,4-diamine

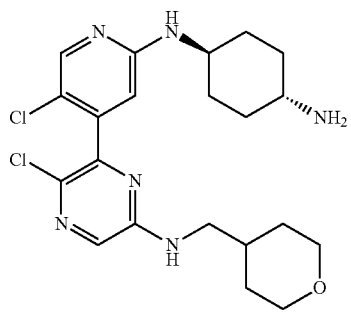 [SMILES: N[C@H]1CC[C@H](Nc2cc(-c3nc(NCC4CCOCC4)cnc3Cl)c(Cl)cn2)CC1]

Step 1. Preparation of 5-chloro-6-(5-chloro-2-fluoropyridin-4-yl)-N-((tetrahydro-2H-pyran-4-yl)methyl)pyrazin-2-amine. To a suspension of 6-bromo-5-chloro-N-((tetrahydro-2H-pyran-4-yl)methyl)pyrazin-2-amine (20 mg, 0.065 mmol), Na$_2$CO$_3$ (17.98 mg, 0.170 mmol) and 5-chloro-2-fluoropyridin-4-ylboronic acid (17.16 mg, 0.098 mmol) in DME (1 ml) was added PdCl$_2$(dppf).CH$_2$Cl$_2$ adduct (4.26 mg, 5.22 μmol). The reaction mixture was capped in a flask and heated to 100° C. for 4 hr an oil bath. The reaction mixture was diluted with EtOAc and washed with H$_2$O sat NaCl. The organic layer was dried Na$_2$SO$_4$, filtered and concentrated. The crude was purified by column chromatography on silica gel (50% EtOAc/Hexane) to yield 5-chloro-6-(5-chloro-2-fluoropyridin-4-yl)-N-((tetrahydro-2H-pyran-4-yl)methyl) pyrazin-2-amine (10 mg, 0.028 mmol, 42.9% yield). LCMS (m/z): 357.0 (MH$^+$), retention time=0.95 min.

Step 2. Preparation of trans-N1-(5-chloro-4-(3-chloro-6-((tetrahydro-2H-pyran-4-yl)methyl)aminopyrazin-2-yl)pyridin-2-yl)cyclohexane-1,4-diamine. To a scintillation vial containing 5-chloro-6-(5-chloro-2-fluoropyridin-4-yl)-N-((tetrahydro-2H-pyran-4-yl)methyl)pyrazin-2-amine (10 mg, 0.028 mmol) and TEA (7.80 μl, 0.056 mmol) was added DMSO (1 ml) and trans-cyclohexane-1,4-diamine (32.0 mg, 0.280 mmol). The resulting homogenous reaction mixture was capped and heated to 100° C. in an oil bath for 3 hr. The reaction product was purified by reverse phase preparative HPLC to yield trans-N1-(5-chloro-4-(3-chloro-6-((tetrahydro-2H-pyran-4-yl)methyl)aminopyrazin-2-yl)pyridin-2-yl)cyclohexane-1,4-diamine (7.7 mg, 0.014 mmol, 48.6% yield), LCMS (m/z): 451.1 (MH$^+$), retention time=0.63 min and a TFA salt after lypholization.

1H NMR (400 MHz, METHANOL-d4) δ ppm 1.23-1.36 (m, 3 H) 1.36-1.49 (m, 2 H) 1.51-1.71 (m, 4 H), 1.80-1.94 (m, 1 H) 2.06-2.25 (m, 4 H) 3.08-3.19 (m, 1 H) 3.23 (d, J=6.65 Hz, 2 H) 3.33-3.43 (m, 2 H) 3.66-3.77 (m, 1 H) 3.92 (dd, J=11.35, 3.13 Hz, 2 H) 6.69 (s, 1 H) 7.76 (s, 1 H) 8.05 (s, 1 H).

Example 62

Compound 225

3-chloro-6-(5-chloro-2-(trans-4-(pyrrolidin-1-yl)cyclohexylamino)pyridin-4-yl)-N-((tetrahydro-2H-pyran-4-yl)methyl)pyrazin-2-amine

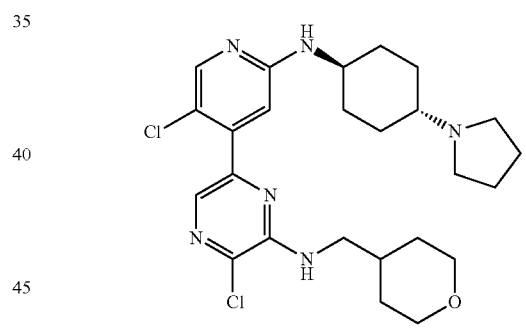

Step 1. Preparation of 3-chloro-6-(5-chloro-2-(trans-4-(pyrrolidin-1-yl)cyclohexylamino) pyridin-4-yl)-N-((tetrahydro-2H-pyran-4-yl)methyl)pyrazin-2-amine: To a scintillation vial containing trans-N1-(5-chloro-4-(5-chloro-6-((tetrahydro-2H-pyran-4-yl)methyl)aminopyrazin-2-yl)pyridin-2-yl)cyclohexane-1,4-diamine (12 mg, 0.027 mmol) and K2CO3 (3.67 mg, 0.027 mmol) was added DMF (1 ml) and 1,4-dibromobutane (3.15 μl, 0.027 mmol). The reaction mixture was capped and heated to 60° C. for 3 hr. The crude solution was concentrated and purified by reverse phase preparative HPLC to yield 3-chloro-6-(5-chloro-2-(trans-4-(pyrrolidin-1-yl)cyclohexylamino)pyridin-4-yl)-N-((tetrahydro-2H-pyran-4-yl)methyl)pyrazin-2-amine (3.8 mg, 6.13 μmol, 23.07% yield), LCMS (m/z): 505.2 (MH$^+$), retention time=0.64 min, and a TFA salt after lypholization.

1H NMR (400 MHz, METHANOL-d4) δ ppm 1.26-1.47 (m, 4 H) 1.56-1.73 (m, 4 H) 2.01 (m, 3 H) 2.10-2.32 (m, 6 H) 3.09-3.23 (m, 3 H) 3.36-3.44 (m, 4 H) 3.60-3.78 (m, 3 H) 3.89-3.98 (m, 2 H) 6.76 (s, 1 H) 7.76 (s, 1 H) 8.03 (s, 1 H).

Example 63

Compound 226

6-(2-(trans-4-aminocyclohexylamino)-5-chloropyridin-4-yl)-N2-((tetrahydro-2H-pyran-4-yl)methyl)pyrazine-2,3-diamine

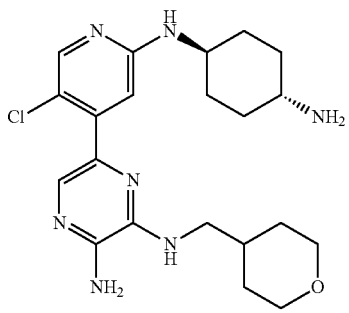 [SMILES: Nc1ncc(-c2cc(N[C@H]3CC[C@H](N)CC3)ncc2Cl)nc1NCC1CCOCC1]

Step 1. Preparation of 6-bromo-N2-((tetrahydro-2H-pyran-4-yl)methyl)pyrazine-2,3-diamine: To a scintillation vial containing 3,5-dibromopyrazin-2-amine (500 mg, 1.977 mmol) and TEA (0.551 ml, 3.95 mmol) was added MeCN (6 ml) and (tetrahydro-2H-pyran-4-yl)methanamine (300 mg, 1.977 mmol). The homogenous reaction mixture mixture was capped and heated to 80° C. in a oil bath for 36 hr. The reaction mixture was concentrated to dryness, diluted with EtOAc and washed with sat $NaHCO_3$, sat NaCl. The organic layer was dried $Na_2SO_4$, filtered and concentrated. The crude was purified by column chromatography on silica gel (30% EtOAc/Hexane) to yield 6-bromo-N2-((tetrahydro-2H-pyran-4-yl)methyl)pyrazine-2,3-diamine (351 mg, 1.222 mmol, 61.8% yield).

Step 2. Preparation of 6-(5-chloro-2-fluoropyridin-4-yl)-N2-((tetrahydro-2H-pyran-4-yl)methyl)pyrazine-2,3-diamine To a degassed suspension of 6-bromo-N2-((tetrahydro-2H-pyran-4-yl)methyl)pyrazine-2,3-diamine (100 mg, 0.348 mmol), $Na_2CO_3$ (96 mg, 0.905 mmol) and 5-chloro-2-fluoropyridin-4-ylboronic acid (92 mg, 0.522 mmol) in DME (3 ml) was added $PdCl_2(dppf).CH_2Cl_2$ adduct (22.75 mg, 0.028 mmol). The reaction mixture was capped in a flask and heated to 100° C. for 4 hr an oil bath. The reaction mixture was diluted with EtOAc and washed with $H_2O$, sat NaCl. The organic layer was dried Na2SO4, filtered and concentrated. The crude was purified by column chromatography on silica gel (100% EtOAc/Hexane) to yield 6-(5-chloro-2-fluoropyridin-4-yl)-N2-((tetrahydro-2H-pyran-4-yl)methyl)pyrazine-2,3-diamine (34 mg, 0.101 mmol, 28.9% yield).). LCMS (m/z): 338.2 (MH$^+$), retention time=0.65 min.

Step 3. Preparation of 6-(2-(trans-4-aminocyclohexylamino)-5-chloropyridin-4-yl)-N2-((tetrahydro-2H-pyran-4-yl)methyl)pyrazine-2,3-diamine: To a scintillation vial containing 6-(5-chloro-2-fluoropyridin-4-yl)-N2-((tetrahydro-2H-pyran-4-yl)methyl)pyrazine-2,3-diamine (17 mg, 0.050 mmol) was added DMSO (1.3 ml) and trans-cyclohexane-1,4-diamine $R_2$ (57.5 mg, 0.503 mmol). The homogenous reaction mixture was capped and heated to 100° C. in a oil bath for 16 hr. The reaction mixture was purified by reverse phase preparative HPLC to yield 6-(2-(trans-4-aminocyclohexylamino)-5-chloropyridin-4-yl)-N2-((tetrahydro-2H-pyran-4-yl)methyl)pyrazine-2,3-diamine (13.7 mg, 0.025 mmol, 49.9% yield), LCMS (m/z): 432.1 (MH$^+$), retention time=0.41 min as a TFA salt after lyophilizing. 1H NMR (400 MHz, METHANOL-d4) d ppm 1.30-1.50 (m, 4 H) 1.51-1.65 (m, 2 H) 1.69-1.78 (m, 2 H) 1.93-2.06 (m, 1 H) 2.07-2.24 (m, 4 H) 3.10-3.19 (m, 1 H) 3.36-3.45 (m, 2 H) 3.48 (d, J=6.65 Hz, 2 H) 3.64-3.75 (m, 1 H) 3.96 (dd, J=11.35, 3.13 Hz, 2 H) 7.04-7.10 (m, 1 H) 7.64 (s, 1 H) 8.01 (s, 1 H).

Example 64

Compound 233 trans-N1-(5-chloro-4-(3-methyl-6-((tetrahydro-2H-pyran-4-yl)methyl)aminopyrazin-2-yl)pyridin-2-yl)cyclohexane-1,4-diamine

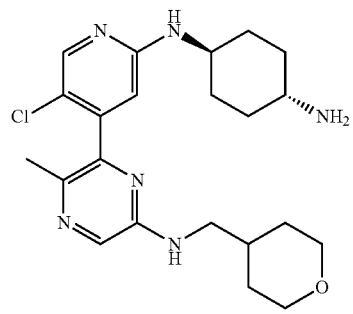 [SMILES: Cc1ncc(NCC2CCOCC2)nc1-c1cc(N[C@H]2CC[C@H](N)CC2)ncc1Cl]

Step 1. Preparation of 6-(5-chloro-2-fluoropyridin-4-yl)-5-methyl-N-((tetrahydro-2H-pyran-4-yl)methyl)pyrazin-2-amine: To a degassed suspension of 5-chloro-6-(5-chloro-2-fluoropyridin-4-yl)-N-((tetrahydro-2H-pyran-4-yl)methyl)pyrazin-2-amine (10 mg, 0.028 mmol), $Na_2CO_3$ (0.036 ml, 2 M, 0.072 mmol) and methylboronic acid (5 mg, 0.084 mmol) in DME (1 ml) was added PdCl2(dppf).CH2Cl2 adduct (6 mg, 7.35 µmol). The reaction was capped and heated to 105° C. for 4 hr an oil bath. The reaction was diluted with EtOAc and washed with $H_2O$, sat NaCl. The organic layer was dried $Na_2SO_4$, filtered and concentrated. The crude was purified by column chromatography on silica gel (50% EtOAc/Hexane) to yield 6-(5-chloro-2-fluoropyridin-4-yl)-5-methyl-N-((tetrahydro-2H-pyran-4-yl)methyl)pyrazin-2-amine (7 mg, 0.021 mmol, 74.2% yield). LCMS (m/z): 337.2 (MH$^+$), retention time=0.81 min.

Step 2. Preparation of trans-N1-(5-chloro-4-(3-methyl-6-((tetrahydro-2H-pyran-4-yl)methyl)aminopyrazin-2-yl)pyridin-2-yl)cyclohexane-1,4-diamine To a scintillation vial containing 6-(5-chloro-2-fluoropyridin-4-yl)-5-methyl-N-((tetrahydro-2H-pyran-4-yl)methyl)pyrazin-2-amine (7 mg, 0.021 mmol) was added DMSO and trans-cyclohexane-1,4-diamine (23.73 mg, 0.208 mmol). The homogenous reaction mixture was capped and heated to 100° C. in an oil bath for 4 hr. The crude solution was purified by reverse phase preparative HPLC to yield trans-N1-(5-chloro-4-(3-methyl-6-((tetrahydro-2H-pyran-4-yl)methyl)aminopyrazin-2-yl)pyridin-2-yl)cyclohexane-1,4-diamine (1.1 mg, 2.018 µmol, 9.71% yield), LCMS (m/z): 431.2 (MH$^+$), retention time=0.47 min as a TFA salt after lyophilizing.

Example 65

Compound 316

5'-chloro-N6-((6,6-dimethyl-1,4-dioxan-2-yl)methyl)-N2'-(trans-4-((R)-1-methoxypropan-2-ylamino)cyclohexyl)-2,4'-bipyridine-2',6-diamine

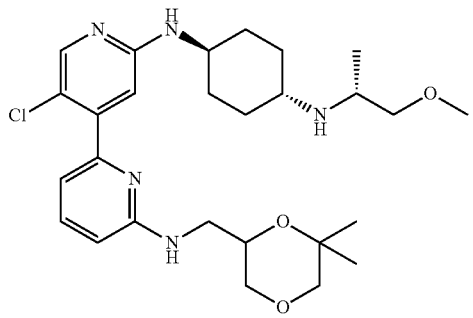 [SMILES: COC[C@@H](C)N[C@H]1CC[C@H](Nc2cc(-c3cccc(NCC4COCC(C)(C)O4)n3)c(Cl)cn2)CC1]

Step 1. Preparation of 1-(allyloxy)-2-methylpropan-2-ol

To allylic alcohol (57.4 mL, 844 mmol) at 0° C. was added NaH (60% in mineral oil, 2.43 g, 101 mmol). After 20 min 2,2-dimethyloxirane (15 mL, 169 mmol) was added and the solution was refluxed overnight. Saturated NH$_4$Cl solution was added and extracted three times with ether. The organic layers were combined, dried over Na$_2$SO$_4$ and concentrated to remove ether. The resulting residue was distilled (allylic alcohol was distilled first then the product was collected at 42 torr, bp 58-60° C.) to give the product as a colorless oil (12.3 g, 56%). $^1$H NMR (400 MHz, CDCl3) δ ppm 5.87-5.96 (1H, m), 5.26-5.31 (1H, m), 5.18-5.21 (1H, m), 4.03-4.05 (2H, m), 3.28 (2H, s), 2.31 (1H, br s), 1.23, (3H, s), 1.22 (3H, s).

Step 2. Preparation of 2-methyl-1-(oxiran-2-ylmethoxy)propan-2-ol 1-(Allyloxy)-2-methylpropan-2-ol (1.50 g, 11.5 mmol) was dissolved in DCM (50 mL) and cooled to 0° C. mCPBA (77%> max, 9.94 g) was added. The suspension was stirred at 0° C. for 6.5 hr. and then saturated NaHCO$_3$ solution (~20 ml) and Na$_2$S$_2$O$_3$ solution (~20 ml) were added. The resulting mixture was stirred at 0° C. for 15 min and the two layers were separated. The aqueous layer was extracted twice with DCM. The organic layers were combined, dried over Na$_2$SO$_4$ and concentrated. The resulting residue was purified on a silica gel column (heptane:EtOAc 1:0 to 1:2) to give the product as a colorless oil (620 mg, 37%). $^1$H NMR (400 MHz, CDCl3) δ ppm 3.64 (1H, ddd, J=12.0, 5.2, 2.8 Hz), 3.24-3.29 (1H, m), 3.17-3.21 (1H, m), 3.11-3.14 (1H, m), 2.97-3.00 (1H, m), 2.88 (1H, br s), 2.60-2.64 (1H, m), 2.44-2.47 (1H, m), 1.02 (6H, s).

Step 3. Preparation of (6,6-dimethyl-1,4-dioxan-2-yl)methanol 2-methyl-1-(oxiran-2-ylmethoxy)propan-2-ol (620 mg, 4.24 mmol) and 10-CSA (300 mg, 1.29 mmol) were dissolved in DCM (30 mL) and stirred at ambient temperature for 24 hr. Saturated NaHCO$_3$ solution was added and the two layers were separated. The aqueous phase was extracted four times with DCM. The organic layers were combined, dried over Na$_2$SO$_4$ and concentrated. The resulting residue was purified on a silica gel column (heptane:EtOAc 1:0 to 1:2) to give the desired product as a colorless oil (400 mg, 64%>). Some starting material was recovered. $^1$H NMR (400 MHz, CDCl3) δ ppm 3.90-3.96 (1H, m), 3.76 (1H, dd, J=11.2, 2.8 Hz), 3.56 (1H, dd, J=11.6, 4.0 Hz), 3.46-3.50 (2H, m), 3.29 (1H, t, J=11.2 Hz), 3.24 (1H, dd, J=11.6, 1.2 Hz), 2.69 (1H, br s), 1.35 (3H, s), 1.13 (3H, s).

Step 4. Preparation of (6,6-dimethyl-1,4-dioxan-2-yl)methyl methanesulfonate TEA (0.52 mL, 3.74 mmol) and (6,6-dimethyl-1,4-dioxan-2-yl)methanol (390 mg, 2.67 mmol) were dissolved in DCM (10 mL). Methanesulfonyl chloride (0.249 mL, 3.20 mmol) was slowly added at 0° C. After the addition was completed the solution was warmed to ambient temperature and stirred for 1 hr. Saturated NaHCO$_3$ solution was added and the two layers were separated. The aqueous layer was extracted three times with DCM. The organic layers were combined, dried over Na$_2$SO$_4$ and concentrated. The resulting residue was purified on a silica gel column (heptane:EtOAc 4:1 to 1:1) to give the product as a colorless oil (584 mg, 98%). $^1$H NMR (400 MHz, CDCl3) δ ppm 4.00-4.09 (3H, m), 3.74 (1H, dd, J=11.2, 2.8 Hz), 3.42 (1H, d, J=11.6 Hz), 3.16-3.23 (2H, m), 2.99 (3H, s), 1.27 (3H, s), 1.05 (3H, s).

Step 5. 6-bromo-N-((6,6-dimethyl-1,4-dioxan-2-yl)methyl)pyridin-2-amine

6-Bromopyridin-2-amine (722 mg, 4.17 mmol) was dissolved in 8 mL of anhydrous DMF and cooled to 0° C. NaH (60% in mineral oil, 195 mg, 4.87 mmol) was added. After 10 min the solution was warmed to ambient temperature and stirred for 45 min until bubbling ceased. The solution was cooled to 0° C. again and (6,6-dimethyl-1,4-dioxan-2-yl)methyl methanesulfonate (520 mg, 2.32 mmol) in 2 mL of DMF was added. After the addition was completed the solution was warmed to ambient temperature and stirred overnight. It was diluted with EtOAc and washed four times with water. The aqueous layers were combined and extracted once with EtOAc. The organic layers were combined, dried over Na2SO4 and concentrated. The resulting residue was purified on prep HPLC and the collected fractions were combined, concentrated, basified with Na2CO3 and extracted with EtOAc three times. The organic layers were combined, dried over Na2SO4 and concentrated to give the product as a light yellow oil (270 mg, 39%). LC-MS (m/z): 301.0/303.0 (M+H), retention time=0.86 min.

Example 66

Compound 307

5'-chloro-N6-((5,5-dimethyl-1,4-dioxan-2-yl)methyl)-N2'-(trans-4-((R)-1-methoxypropan-2-ylamino)cyclohexyl)-2,4'-bipyridine-2',6-diamine

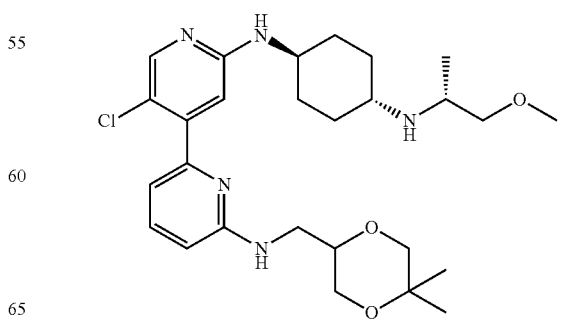

Step 1. Preparation of 2-(allyloxy)-2-methylpropan-1-ol 2,2-Dimethyloxirane (15.0 mL, 169 mmol) was dissolved in allylic alcohol (57.4 mL) and cooled to 0° C. Perchloric acid (70%, 7.26 mL, 84 mmol) was slowly added. The solution was then warmed to ambient temperature and stirred for 1.5 hr. Saturated NaHCO$_3$ solution was added and extracted three times with ether. The organic layers were combined, dried over Na$_2$SO$_4$ and concentrated to remove ether. The resulting residue was distilled (allylic alcohol was distilled first then the product was collected at 38 torr, bp 74-76° C.) to give the product as a colorless oil (9.70 g, 44%). $^1$H NMR (400 MHz, CDCl3) δ ppm 5.87-5.97 (1H, m), 5.25-5.31 (1H, m), 5.12-5.16 (1H, m), 3.92-3.94 (2H, m), 3.45 (2H, m), 1.19 (6H, s).

Step 2. Preparation of 2-methyl-2-(oxiran-2-ylmethoxy)propan-1-ol 2-(allyloxy)-2-methylpropan-1-ol (2.37 g, 18.2 mmol) was dissolved in DCM (70 mL) and cooled to 0° C. mCPBA (77% max, 15.71 g) was added. The suspension was stirred at 0° C. for 6.5 hr before saturated NaHCO$_3$ solution and Na$_2$S$_2$O$_3$ solution were added. It was stirred at 0° C. for 15 min and the two layers were separated. The aqueous layer was extracted twice with DCM. The organic layers were combined, dried over Na2SO4 and concentrated. The resulting residue was purified on a silica gel column (heptane:EtOAc 1:0 to 1:2) to give the product as a colorless oil (910 mg, 34%). $^1$H NMR (400 MHz, CDCl3) δ ppm 3.65 (1H, dd, J= 11.2, 2.8 Hz), 3.47 (1H, br s), 3.31-3.41 (3H, m), 3.07-3.09 (1H, m), 2.74 (1H, t, J= 4.8 Hz), 2.63-2.65 (1H, m), 1.12 (6H, s).

Step 3. Preparation of (5,5-dimethyl-1,4-dioxan-2-yl)methanol

2-Methyl-2-(oxiran-2-ylmethoxy)propan-1-ol (870 mg, 5.95 mmol) and 10-CSA (207 mg, 15%>) were dissolved in DCM (70 mL) and stirred at ambient temperature for 24 hr. More 10-CSA (100 mg) was added and the solution was stirred overnight. Saturated NaHCO3 solution was added. The two layers were separated and the aqueous layer was extracted twice with DCM. The organic layers were combined, dried over Na2SO4 and concentrated to give the product as a colorless oil (750 mg, 86%). $^1$H NMR (400 MHz, CDCl3) δ ppm 3.69-3.74 (1H, m), 3.52-3.64 (5H, m), 3.43 (1H, dd, J= 11.6, 0.8 Hz), 2.57 (1H, br s), 1.32 (3H, s), 1.13 (3H, s).

Step 4. Preparation of (5,5-dimethyl-1,4-dioxan-2-yl)methyl methanesulfonate (5,5-Dimethyl-1,4-dioxan-2-yl)methanol (740 mg, 5.06 mmol) and TEA (0.988 mL, 7.09 mmol) were dissolved in DCM (20 mL). At 0° C. MsCl (0.473 mL, 6.07 mmol) was added dropwise. After the addition the solution was warmed to ambient temperature and stirred for 1 hr. Saturated NaHCO3 solution was added and the two layers were separated. The aqueous layer was extracted three times with DCM. The organic layers were combined, dried over Na2SO4 and concentrated. The resulting residue was purified on a silica gel column (heptane:EtOAc 4:1 to 1:1) to give the product as a colorless oil (805 mg, 71%). $^1$H NMR (400 MHz, CDCl3) δ ppm 4.18-4.19 (2H, m), 3.71-3.76 (1H, m), 3.66 (1H, t, J= 10.8 Hz), 3.52-3.57 (2H, m), 3.37 (1H, d, J= 11.6 Hz), 3.03 (3H, s), 1.28 (3H, s), 1.09 (3H, s).

Step 5. Preparation of 6-bromo-N-((5,5-dimethyl-1,4-dioxan-2-yl)methyl)pyridin-2-amine 6-Bromopyridin-2-amine (771 mg, 4.46 mmol) was dissolved in 10 mL of anhydrous DMF and cooled to 0° C. NaH (60% in mineral oil, 214 mg, 5.35 mmol) was added. After 10 min the solution was warmed to ambient temperature and stirred for 15 min until bubbling ceased, to give a dark green solution. (5,5-Dimethyl-1,4-dioxan-2-yl)methyl methanesulfonate (500 mg, 2.23 mmol) in 2 mL of DMF was added. After the addition was completed the solution was stirred at ambient temperature for 20 min, then heated at 60° C. for 1.5 hr. It was diluted with EtOAc and washed four times with water. The aqueous layers were combined and extracted once with EtOAc. The organic layers were combined, dried over Na2SO4 and concentrated. The resulting residue was purified on a silica gel column (heptane:EtOAc 1:0 to 1:1) to give the product contaminated with the starting aminopyridine. Another purification on silica gel column (DCM:ether 20:1) gave the pure product (306 mg, 46%). LC-MS (m/z): 301.0/303.0 (M+H), retention time=0.89 min.

Example 67

Compound 291

Synthesis of 5'-chloro-N2'-(trans-4-((R)-1-methoxypropan-2-yl-amino)cyclohexyl)-N6-((tetrahydro-2H-pyran-4-yl)methyl)-2,4'-bipyridine-2',6-diamine

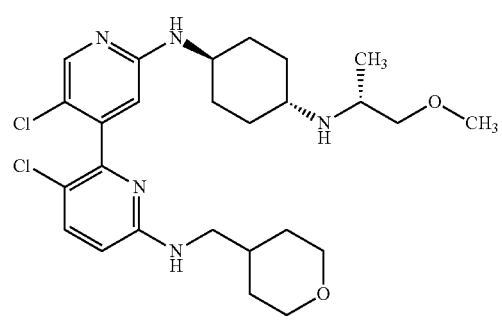 [SMILES: COC[C@@H](C)N[C@H]1CC[C@H](Nc2cc(-c3nc(NCC4CCOCC4)ccc3Cl)c(Cl)cn2)CC1]

Step 1. To sodium hydride (0.488 g, 12.21 mmol) in 5 mL of THF was added via syringe (S)-(+)-3-methoxy-2-propanol (1.000 ml, 11.10 mmol) in 25 mL of THF at ambient temperature. The mixture was stirred for 20 min. and followed by addition of p-toluenesulfonyl chloride (2.327 g, 12.21 mmol). The white cloudy solution was stirred at ambient temperature for 18 hrs. The reaction mixture was diluted with saturated aq. NaHCO$_3$ and extracted with EtOAc. The organic extracts were combined, washed with brine, dried with sodium sulfate and concentrated in vacuo to give 2 g of colorless liquid. The crude mixture was purified by Analogix system (silica gel column 40 g, gradient: 100% n-heptane to 30% EtOAc in Heptane; 30 min.). The pure fractions were concentrated in vacuo to give 1.22 g of colorless oil. LC-MS (m/z): 245 (M+H), retention time=0.83 min.

Step 2. To the tosylate obtained from step 1 (0.6 g, 2.45 mmol) in DMSO (6 ml) at ambient temperature was added trans-cyclohexane-1,4-diamine (0.84 g, 7.37 mmol). The light brown mixture was heated to 99° C. in a capped glass vial for 1 hr. LC/MS showed nearly complete consumption of the starting material. The mixture was diluted with water and extracted with DCM. The organic extracts were combined, washed with brine, dried with sodium sulfate and concentrated in vacuo to give 0.39 g of light brown liquid. This was used in the next step without further purification. LC-MS (m/z): 187 (M+H), Retention time=0.14 min.

Step 3. A mixture of Intermediate G (60 mg, 0.168 mmol), the above cyclohexadiamine (100 mg, 0.537 mmol) and 2,6-LUTIDINE (0.039 ml, 0.0.337 mmol) in DMSO (1 ml) was heated in a capped vial on a heating block for 18 hrs. LC/MS showed containing about 50%> product. The reaction mixture was purified by HPLC (ACN in water with gradient 10%-50% in 16 minutes) and lyophilized to give 25 mg of light yellow powder. LC-MS (m/z): 522/524 (M+H), retention time=0.62 min. $^1$H NMR (400 MHz, CDCl3) δ ppm 1.24-1.47 (m, 5 H) 1.50-1.79 (m, 2 H) 1.79-2.01 (m, 4 H) 2.11-2.31 (m, 4 H) 3.16-3.26 (m, 2H) 3.28-3.45 (m, 5 H) 3.45-3.66 (m, 4 H) 6.82 (d, J=9.39 Hz, 1 H) 7.05 (br. s., 1 H) 7.59 (s, 1 H) 7.78 (d, J=9.39 Hz, 1 H) 7.95 (s, 1 H) 8.76 (br. s., 1 H)

Example 68

Compound 197

5'-chloro-N6-(3-fluorobenzyl)-N2'-(trans-4-((methylamino)methyl)cyclohexyl)-2,4'-bipyridine-2',6-diamine

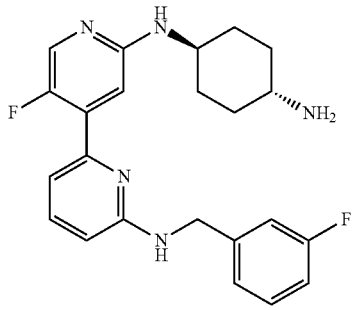

Step 1. Preparation of 2'-chloro-5'-fluoro-N-(3-fluorobenzyl)-2,4'-bipyridin-6-amine: To a solution of 6-bromo-N-(3-fluorobenzyl)pyridin-2-amine (636 mg, 2.262 mmol) and 2-chloro-5-fluoropyridin-4-yl-boronic acid (555 mg, 3.17 mmol) in DME (4 ml) and 2M Na$_2$CO$_3$ aq (2 ml) was added PdCl$_2$(dppf).CH$_2$Cl$_2$ adduct (92 mg, 0.113 mmol). This was then heated at 110° C. for 16 hours. The reaction mixture was allowed to cool and then the DME was evaporated under reduced pressure. The resulting residue was partitioned between EtOAc and water. The organics were combined, then washed with H$_2$O (×3), saturated aq. brine (×3), then dried (Na$_2$SO$_4$), filtered and evaporated under reduced pressure. The resulting residue was purified by flash column chromatography (silica gel; 20% EtOAc/hexane) to give 2'-chloro-5'-fluoro-N-(3-fluorobenzyl)-2,4'-bipyridin-6-amine (84 mg).

Step 2. Preparation of 5'-chloro-N6-(3-fluorobenzyl)-N2'-(trans-4-((methylamino)methyl)cyclohexyl)-2,4'-bipyridine-2',6-diamine: To a scintillation vial were added 2'-chloro-5'-fluoro-N-(3-fluorobenzyl)-2,4'-bipyridin-6-amine (34 mg, 0.102 mmol), trans-cyclohexane-1,4-diamine (52.7 mg, 0.461 mmol), 1,3-bis(2,6-di-isopropylphenyl)imidazol-2-ylidene(1,4-naphthoquinone)palladium(0) (13.39 mg, 10.25 μmol), KOH (51.8 mg, 0.922 mmol) and Dioxane (0.6 mL). The resulting mixture was stirred with heating at 70° C. for 16 h and then concentrated in vacuo. The resulting residue was dissolved in EtOAc and washed with H$_2$O (×2) followed by saturated brine (×2), then dried (Na$_2$SO$_4$), filtered and evaporated under reduced pressure. The resulting residue was purified by reverse phase preparative HPLC and then lyophallized to yield 5'-chloro-N6-(3-fluorobenzyl)-N2'-(trans-4-((methylamino)methyl)cyclohexyl)-2,4'-bipyridine-2',6-diamine (7.9 mg), LCMS (m/z): 410.3 (MH$^+$), retention time=0.60 min as a TFA salt. $^1$H-NMR (400 MHz, METHANOL-d4, 25° C.) 1.40-1.70 (m, 4 H) 2.05-2.25 (m, 4 H) 3.10-3.25 (m, 1 H) 3.55-3.64 (m, 1 H) 4.57 (s, 2 H) 6.76 (d, J=8.4 Hz, 1 H) 6.93-7.00 (m, 1 H) 7.11 (d, J=10.4 Hz, 1 H) 7.20 (m, 2 H) 7.28-7.36 (m, 1H) 7.52 (d, J=6.4 Hz, 1H) 7.61 (t, J=8.0 Hz, 1 H) 7.96 (d, J=4.8 Hz, 1 H).

Example 69

Compound 180

N2'-(trans-4-aminocyclohexyl)-N6-(3-fluorobenzyl)-5'-methoxy-2,4'-bipyridine-2',6-diamine Step 1. Preparation of 2'-chloro-N-(3-fluorobenzyl)-5'-methoxy-2,4'-bipyridin-6-amine: To a solution of 6-bromo-N-(3-fluorobenzyl)pyridin-2-amine (555 mg, 1.974 mmol) and 2-chloro-5-methoxypyridin-4-ylboronic acid (518 mg, 2.76 mmol) in DME (4 ml) and 2M Na$_2$CO$_3$ aq (2 ml) was added PdCl$_2$(dppf).CH$_2$Cl$_2$ adduct (81 mg, 0.099 mmol). This was then heated at 110° C. for 5 h. The reaction mixture was allowed to cool and then the DME was evaporated under reduced pressure. The resulting residue was partitioned between EtOAc and water. The organics were combined, then washed with H$_2$O (×3), saturated aq. brine (×3), then dried (Na$_2$SO$_4$), filtered and evaporated under reduced pressure. The resulting residue was purified by flash column chromatography (silica gel; 15% to 25% EtOAc/hexane) to give 2'-chloro-N-(3-fluorobenzyl)-5'-methoxy-2,4'-bipyridin-6-amine (53 mg).

Step 2. Preparation of N2'-(trans-4-aminocyclohexyl)-N6-(3-fluorobenzyl)-5'-methoxy-2,4'-bipyridine-2',6-diamine:
To a scintillation vial was added 2'-chloro-N-(3-fluorobenzyl)-5'-methoxy-2,4'-bipyridin-6-amine (30 mg, 0.087 mmol), trans-cyclohexane-1,4-diamine (45 mg, 0.394 mmol), 1,3-bis(2,6-di-isopropylphenyl)imidazol-2-ylidene (1,4-naphthoquinone)palladium(0) (11.4 mg, 8.73 μmol), KOH (45 mg, 0.802 mmol) and Dioxane (0.3 mL). The resulting mixture was stirred at 100° C. for 18 h. The mixture was concentrated in vacuo and then diluted with water. The resultant solid was filtered and washed with water (×3). The solid was then purified by reverse phase preparative HPLC and then lyophilized to yield N2'-(trans-4-aminocyclohexyl)-N6-(3-fluorobenzyl)-5'-methoxy-2,4'-bipyridine-2',6-diamine (6.5 mg), LCMS (m/z): 422.3 (MH$^+$), retention time=0.54 min as a TFA salt. $^1$H-NMR (400 MHz, METHANOL-d4, 25° C.) 1.40-1.66 (m, 4 H) 2.05-2.25 (m, 4 H) 3.10-3.25 (m, 1 H) 3.55-3.64 (m, 1 H) 3.86 (s, 3 H) 4.57 (s, 2 H) 6.69 (d, J=8.4 Hz, 1 H) 6.92-7.00 (m, 1 H) 7.10 (d, J=10.0 Hz, 1 H) 7.17 (d, J=7.6 Hz, 1 H) 7.28-7.33 (m, 2 H) 7.48-7.52 (m, 2 H) 7.53-7.58 (m, 1 H).

Example 70

Compound 211

N2'-(trans-4-aminocyclohexyl)-N6-(3-fluorobenzyl)-5'-methyl-2,4'-bipyridine-2',6-diamine

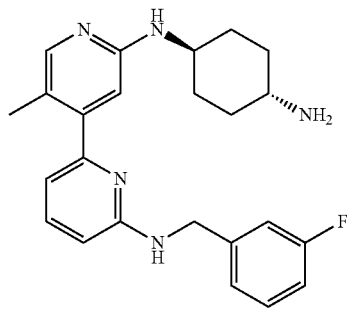 [SMILES: Cc1cnc(N[C@H]2CC[C@H](N)CC2)cc1-c1cccc(NCc2cccc(F)c2)n1]

Step 1. Preparation of 2'-fluoro-N-(3-fluorobenzyl)-5'-methyl-2,4'-bipyridin-6-amine: To a solution of 6-bromo-N-(3-fluorobenzyl)pyridin-2-amine (85 mg, 0.302 mmol) and 2-fluoro-5-methyl-4-(4,4,5,5-tetramethyl-1,3,2-dioxaborolan-2-yl)pyridine (102 mg, 0.430 mmol) in DME (2 mL) and 2M $Na_2CO_3$ aq (1 mL) was added $PdCl_2(dppf).CH_2Cl_2$ adduct (21 mg, 0.026 mmol). This was then heated at 110° C. for 16 h. The reaction mixture was allowed to cool and then the DME was evaporated under reduced pressure. The resulting residue was partitioned between EtOAc and water. The organics were combined, then washed with $H_2O$ (×3), saturated aq. brine (×3), then dried ($Na_2SO_4$), filtered and evaporated under reduced pressure. The resulting residue was purified by flash column chromatography (silica gel; 15% to 25% EtOAc/hexane) to give 2'-fluoro-N-(3-fluorobenzyl)-5'-methyl-2,4'-bipyridin-6-amine (43 mg).

Step 2. Preparation of N2'-(trans-4-aminocyclohexyl)-N6-(3-fluorobenzyl)-5'-methyl-2,4'-bipyridine-2',6-diamine: To a solution of 2'-fluoro-N-(3-fluorobenzyl)-5'-methyl-2,4'-bipyridin-6-amine (18 mg, 0.058 mmol) and trans-cyclohexane-1,4-diamine (39.6 mg, 0.347 mmol), in NMP (0.3 mL) was added DIPEA (20 µL, 0.115 mmol). The mixture was heated at 130° C. for 48 h. The mixture was allowed to cool then diluted with water and then extracted with EtOAc (×3). The combined organics were washed with saturated brine (×2), then dried ($Na_2SO_4$), filtered and evaporated under reduced pressure. The resulting residue was purified by reverse phase preparative HPLC and then lyophilized to yield N2'-(trans-4-aminocyclohexyl)-N6-(3-fluorobenzyl)-5'-methyl-2,4'-bipyridine-2',6-diamine (4.2 mg), LCMS (m/z): 406.3 ($MH^+$), retention time=0.53 min as a TFA salt.

Example 71

Compound 280

Racemic 3,5'-dichloro-N6-((tetrahydro-2H-pyran-4-yl)methyl)-N2'-(trans-4-(tetrahydrofuran-3-yl-amino)cyclohexyl)-2,4'-bipyridine-2',6-diamine

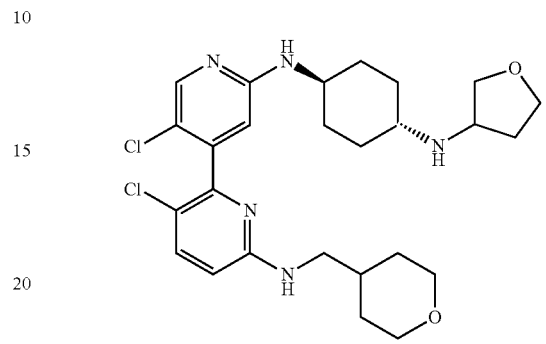

Step 1. Preparation of racemic benzyl trans-4-(tetrahydrofuran-3-yl-amino)cyclohexylcarbamate To a stirred solution of benzyl trans-4-aminocyclohexylcarbamate (396 mg, 1.595 mmol) in $CH_2Cl_2$ (9 ml) was added dihydrofuran-3(2H)-one (151 mg, 1.754 mmol) followed by acetic acid (150 µL, 2.62 mmol) and sodium triacetoxyborohydride (439 mg, 2.073 mmol) under Argon. Stirred at 25° C. for 16 h, then concentrated in vacuo. The resulting residue was partitioned between EtOAc and 1M NaOH. The organics were combined, then washed with 1M NaOH (×2), water (×2), saturated brine (×2), then dried ($Na_2SO_4$), filtered and evaporated under reduced pressure to give racemic benzyl trans-4-(tetrahydrofuran-3-yl-amino)cyclohexylcarbamate (495 mg). The resulting residue was used in next step without further purification.

Step 2. Preparation of racemic tert-butyl trans-4-aminocyclohexyl(tetrahydrofuran-3-yl)carbamate To a stirred solution of racemic benzyl trans-4-(tetrahydrofuran-3-yl-amino)cyclohexylcarbamate (495 mg, 1.555 mmol) in $CH_2Cl_2$ (5 ml) was added BOC-Anhydride (0.397 ml, 1.710 mmol) and the resulting mixture was stirred at 25° C. under Argon for 21 hours. The mixture was evaporated under reduced pressure and purified by flash column chromatography (silica gel; 15% to 25% EtOAc/hexane). A solution of the resultant Boc protected intermediate (135 mg, 0.323 mmol) in MeOH (5 mL) was hydrogenated under an atmosphere of hydrogen in the presence of 10% Pd/C (24 mg, 0.226 mmol) for 18 h. The mixture was then filtered through Celite and the filtrate evaporated under reduced pressure to give racemic tert-butyl trans-4-aminocyclohexyl(tetrahydrofuran-3-yl)carbamate (100 mg). The resulting residue was used in next step without further purification Step 3. Preparation of racemic 3,5'-dichloro-N6-((tetrahydro-2H-pyran-4-yl)methyl)-N2'-(trans-4-(tetrahydrofuran-3-yl-amino)cyclohexyl)-2,4'-bipyridine-2',6-diamine To a scintillation vial was added 3,5'-dichloro-2'-fluoro-N-((tetrahydro-2H-pyran-4-yl)methyl)-2,4'-bipyridin-6-amine (25 mg, 0.070 mmol), racemic tert-butyl trans-4-aminocyclohexyl(tetrahydrofuran-3-yl)carbamate (21.95 mg, 0.077 mmol), DIPEA (24.51 µl, 0.140 mmol) and NMP (0.2 ml). This was heated at 110° C. for 48 h. The mixture was diluted with EtOAc and washed with water (×2), saturated brine (×2), then dried (Na$_2$SO$_4$), filtered and evaporated under reduced pressure. The resulting residue was dissolved in CH$_2$Cl$_2$ (0.4 mL) and treated with TFA (100 µl, 1.298 mmol). After 30 minutes, the mixture was concentrated in vacuo and the resulting residue was purified by reverse phase preparative HPLC and then lyophilized to yield racemic 3,5'-dichloro-N6-((tetrahydro-2H-pyran-4-yl)methyl)-N2'-(trans-4-(tetrahydrofuran-3-yl-amino)cyclohexyl)-2,4'-bipyridine-2',6-diamine (10.8 mg), LCMS (m/z): 520.1/522.0 (bis-chloro isotopic signature for MH$^+$), retention time=0.59 min as a TFA salt.

Example 72

Compound 320

3,5'-dichloro-N2'-(trans-4-(((R)-2,2-dimethyl-1,3-dioxolan-4-yl)methyl)aminocyclohexyl)-N6-((tetrahydro-2H-pyran-4-yl)methyl)-2,4'-bipyridine-2',6-diamine

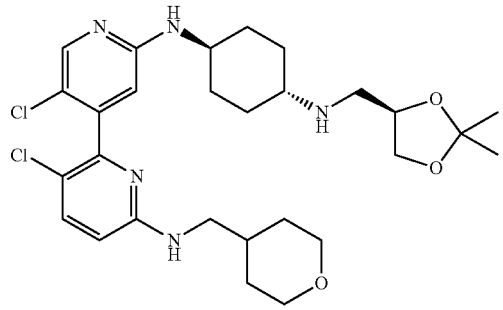 [SMILES: CC1(C)OC[C@@H](CN[C@H]2CC[C@H](Nc3cc(-c4nc(NCC5CCOCC5)ccc4Cl)c(Cl)cn3)CC2)O1]

To a stirred solution of N2'-(trans-4-aminocyclohexyl)-3,5'-dichloro-N6-((tetrahydro-2H-pyran-4-yl)methyl)-2,4'-bipyridine-2',6-diamine (68 mg, 0.151 mmol) in DMF (0.2 ml) was added DIPEA (80 µL, 0.458 mmol) followed by (S)-(2,2-dimethyl-1,3-dioxolan-4-yl)methyl 4-methylbenzenesulfonate (42 mg, 0.147 mmol). The mixture was heated at 75° C. for 19 hours. The mixture was allowed to cool, then diluted with water and then extracted with EtOAc (×3). The organics were combined then washed with water (×2), saturated brine (×2), then dried (Na$_2$SO$_4$), filtered and evaporated under reduced pressure. The resulting residue was purified by reverse phase prep HPLC and lyophilized to yield 3,5'-dichloro-N2'-(trans-4-(((R)-2,2-dimethyl-1,3-dioxolan-4-yl)methyl)aminocyclohexyl)-N6-((tetrahydro-2H-pyran-4-yl)methyl)-2,4'-bipyridine-2',6-diamine (4.4 mg), LCMS (m/z): 564.4/566.3 (bis-chloro isotopic signature for MH$^+$) retention time=0.65 min as a TFA salt.

Example 73

Compounds 323 and 327

3,5'-dichloro-N2'-(trans-4-((R)-1-methoxypropan-2-yl-amino)cyclohexyl)-N6-(((S)-tetrahydro-2H-pyran-3-yl)methyl)-2,4'-bipyridine-2',6-diamine and 3,5'-dichloro-N2'-(trans-4-((R)-1-methoxypropan-2-yl-amino)cyclohexyl)-N6-(((R)-tetrahydro-2H-pyran-3-yl)methyl)-2,4'-bipyridine-2',6-diamine

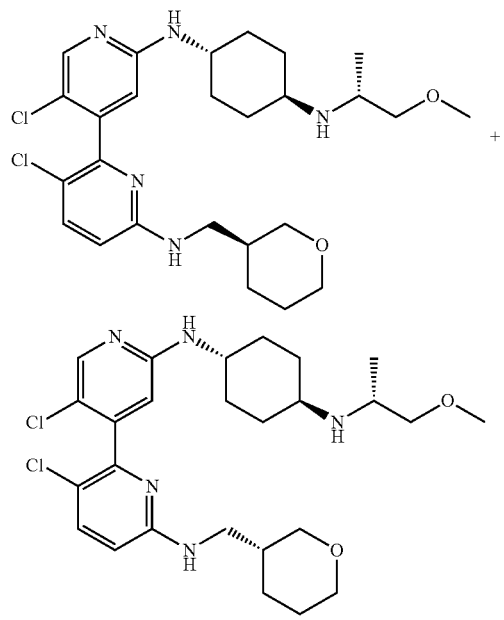

Step 1. Preparation of racemic (tetrahydro-2H-pyran-3-yl)methyl 4-methylbenzenesulfonate: To a stirred solution of (tetrahydro-2H-pyran-3-yl)methanol (1.0 g, 8.61 mmol) and DMAP (0.053 g, 0.430 mmol) in CH$_2$Cl$_2$ (5.0 mL) and pyridine (6.96 mL, 86 mmol) was added Tosyl-Cl (1.805 g, 9.47 mmol). (11:23 am). After 16 h the mixture was evaporated under reduced pressure and the resulting residue partitioned between EtOAc and water. The organics were separated, then washed with 0.1M HCl (×3), H$_2$O (×1), saturated aq. NaHCO$_3$ (×2), H$_2$O (×1), saturated brine (×1), then dried (Na$_2$SO$_4$), filtered and evaporated under reduced pressure to give racemic (tetrahydro-2H-pyran-3-yl)methyl 4-methylbenzenesulfonate (2.034 g). The resulting residue was used in next step without further purification.

Step 2. Preparation of racemic tert-butyl 6-bromo-5-chloropyridin-2-yl((tetrahydro-2H-pyran-3-yl)methyl)carbamate: To a cooled (0° C.), stirred solution of tert-butyl 6-bromo-5-chloropyridin-2-ylcarbamate (1.00 g, 3.25 mmol) in DMF (13.0 mL) was added 60% dispersion NaH (0.156 g, 3.90 mmol) under Argon. Stirred at 0° C. for 30 mins then added racemic (tetrahydro-2H-pyran-3-yl)methyl 4-methylbenzenesulfonate (1.143 g, 4.23 mmol). The mixture was then allowed to warm to 25° C. and stirring continued for 19 h. The reaction mixture then was diluted with saturated NH$_4$Cl and then extracted with EtOAc (×3). Organics washed with water (×2), saturated brine (×2), then dried (Na$_2$SO$_4$), filtered and evaporated under reduced pressure. The resulting residue was purified by flash column chromatography (silica gel; 5% to 15% EtOAc/heptanes) to give racemic tert-butyl 6-bromo-5-chloropyridin-2-yl((tetrahydro-2H-pyran-3-yl)methyl)carbamate (938 mg).

Step 3. Preparation of tert-butyl 3,5'-dichloro-2'-fluoro-2,4'-bipyridin-6-yl((tetrahydro-2H-pyran-3-yl)methyl)carbamate: To a scintillation vial was added racemic tert-butyl 6-bromo-5-chloropyridin-2-yl((tetrahydro-2H-pyran-3-yl)methyl)carbamate (832 mg, 2.051 mmol), 5-chloro-2-fluoropyridin-4-ylboronic acid (719 mg, 4.10 mmol) and PdCl$_2$(dppf).CH$_2$Cl$_2$ adduct (167 mg, 0.205 mmol) followed by DME (3 mL) and 2M Na$_2$CO$_3$ aq (2 mL). The mixture was heated at 90° C. for 20 h, then allowed to cool and added water and then extracted with EtOAc (×3). The organics were washed with water (×2), saturated brine (×2), then dried (Na$_2$SO$_4$), filtered and evaporated under reduced pressure. The resulting residue was purified by flash column chromatography (silica gel; 5%> to 15% EtOAc/heptanes) to give racemic tert-butyl 3,5'-dichloro-2'-fluoro-2,4'-bipyridin-6-yl ((tetrahydro-2H-pyran-3-yl)methyl)carbamate (374 mg)

Step 4. Preparation of 3,5'-dichloro-N2'-(trans-4-((R)-1-methoxypropan-2-yl-amino)cyclohexyl)-N6-(((S)-tetrahydro-2H-pyran-3-yl)methyl)-2,4'-bipyridine-2',6-diamine and 3,5'-dichloro-N2'-(trans-4-((R)-1-methoxypropan-2-yl-amino)cyclohexyl)-N6-(((R)-tetrahydro-2H-pyran-3-yl)methyl)-2,4'-bipyridine-2',6-diamine:

To a scintillation vial was added racemic tert-butyl 3,5'-dichloro-2'-fluoro-2,4'-bipyridin-6-yl((tetrahydro-2H-pyran-3-yl)methyl)carbamate (114 mg, 0.250 mmol), trans-N1-((R)-1-methoxypropan-2-yl)cyclohexane-1,4-diamine (70 mg, 0.376 mmol) and DIPEA (0.088 ml, 0.501 mmol) followed by NMP (0.1 ml). The mixture was heated at 110° C. for 60 hr then concentrated in vacuo. The resulting residue was purified by reverse phase prep HPLC and lyophilized. The resulting white solid was free based by dissolving in EtOAc and then washing with 1M NaOH (×3), water (×2), saturated brine (×2), then dried (Na$_2$SO$_4$), filtered and evaporated under reduced pressure. The resulting residue was then purified by chiral separation chromatography to yield 3,5'-dichloro-N2'-(trans-4-((R)-1-methoxypropan-2-yl-amino)cyclohexyl)-N6-(((S)-tetrahydro-2H-pyran-3-yl)methyl)-2,4'-bipyridine-2',6-diamine (mg), LCMS (m/z): 522.1/523.9 (MH$^+$), t$_R$=0.675 min. and 3,5'-dichloro-N2'-(trans-4-((R)-1-methoxypropan-2-yl-amino)cyclohexyl)-N6-(((R)-tetrahydro-2H-pyran-3-yl)methyl)-2,4'-bipyridine-2',6-diamine (mg) LCMS 522.1/523.9 (m/z): (MH$^+$), retention time=0.675 min.

Example 74

Compounds 321 and 325

3,5'-dichloro-N2'-(trans-4-((R)-1-methoxypropan-2-yl-amino)cyclohexyl)-N6-(((S)-tetrahydro-2H-pyran-2-yl)methyl)-2,4'-bipyridine-2',6-diamine and 3,5'-dichloro-N2'-(trans-4-((R)-1-methoxypropan-2-yl-amino)cyclohexyl)-N6-(((R)-tetrahydro-2H-pyran-2-yl)methyl)-2,4'-bipyridine-2',6-diamine

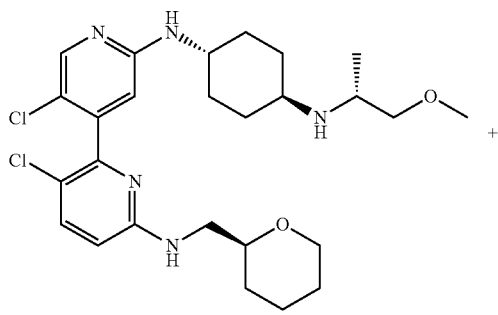

+

-continued

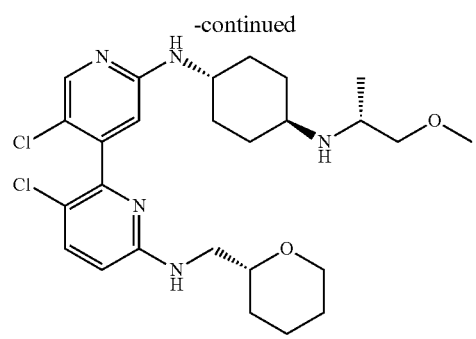

The compounds were prepared according to Example 73, except using tetrahydro-2H-pyran-2-yl)methanol to give 3,5'-dichloro-N2'-(trans-4-((R)-1-methoxypropan-2-yl-amino)cyclohexyl)-N6-(((S)-tetrahydro-2H-pyran-2-yl)methyl)-2,4'-bipyridine-2',6-diamine LCMS (m/z): 522.1/524.1 (MH$^+$), retention time=0.708 min and 3,5'-dichloro-N2'-(trans-4-((R)-1-methoxypropan-2-yl-amino)cyclohexyl)-N6-(((R)-tetrahydro-2H-pyran-2-yl)methyl)-2,4'-bipyridine-2',6-diamine LCMS (m/z): 522.1/524.1 (MH$^+$), retention time=0.708 min.

Example 75

Compound 208 trans-4-(5-chloro-4-(6-((tetrahydro-2H-pyran-4-yl)methyl)aminopyrazin-2-yl)pyridin-2-yl-amino)cyclohexanol

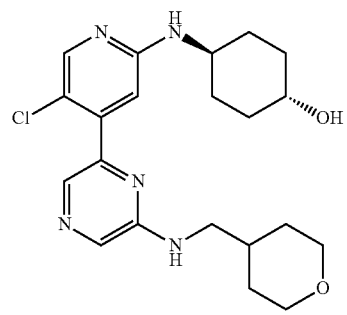

Step 1: Preparation of 6-chloro-N-((tetrahydro-2H-pyran-4-yl)methyl)pyrazin-2-amine A mixture of 2,6-dichloropyrazine (950 mg, 6.38 mmol), DMSO (14 ml), TEA (1.067 ml, 7.65 mmol) and (tetrahydro-2H-pyran-4-yl)methanamine (771 mg, 6.70 mmol) was stirred at 75° C. for 6 hours, and the reaction progress was followed by LCMS. The crude reaction mixture was cooled to ambient temperature, diluted with 300 ml of ethyl acetate, washed with 1M NaOH soln.(1×), water (1×), saturated salt soln. (1×), dried with sodium sulfate, filtered, and concentrated to constant mass, giving 1185 mg of titled compound as free base, used without further purification. LCMS (m/z): 228.0 (MH+), retention time=0.73 min.

Step 2. Preparation of 6-(5-chloro-2-fluoropyridin-4-yl)-N-((tetrahydro-2H-pyran-4-yl)methyl)pyrazin-2-amine A mixture of 6-chloro-N-((tetrahydro-2H-pyran-4-yl)methyl)pyrazin-2-amine (1390 mg, 6.10 mmol), 5-chloro-2-fluoropyridin-4-ylboronic acid (2141 mg, 12.21 mmol), PdCl2(dppf).CH2Cl2 adduct (399 mg, 0.488 mmol), DME (24 ml) and 2M sodium carbonate (9.16 ml, 18.31 mmol) was stirred at 110-115° C. for 90 min and the reaction progress was followed by LCMS. The reaction mixture was cooled, 30 ml of ethyl acetate and 20 ml of methanol were added, filtered and concentrated to crude product. The crude was purified by silica gel chromatography using 80 g column eluting with 20-75% ethyl acetate in heptane. The desired fractions were concentrated to constant mass, giving 980 mg of titled compound as free base. LCMS (m/z): 323.0 (MH+), retention time=0.81 min.

Step 3. Preparation of trans-4-(5-chloro-4-(6-((tetrahydro-2H-pyran-4-yl)methyl)aminopyrazin-2-yl)pyridin-2-yl-amino)cyclohexanol A mixture of 6-(5-chloro-2-fluoropyridin-4-yl)-N-((tetrahydro-2H-pyran-4-yl)methyl)pyrazin-2-amine (375 mg, 1.162 mmol), DMSO (3.5 ml) and trans-4-aminocyclohexanol (1204 mg, 10.46 mmol) was stirred at 100° C. for 18 hours and the progress was followed by LCMS. The reaction mixture was let cool, added 300 ml of ethyl acetate, washed with saturated sodium bicarbonate solution (3×), water (2×), saturated salt solution (1×), dried with sodium sulfate, filtered and concentrated to crude solid. The crude material was purified by silica gel chromatography using 40 g column, eluting slowly from (80%> ethyl acetate 20% heptane with 2% MeOH) to 100% ethyl acetate with 2% MeOH. The desired fractions are concentrated to a constant mass, lyophilized from 1:1 ACN/water (does not fully dissolve), re-lyophilized from 80 ml of (60/40) ACN/water solution with sonicating to dissolve solid, giving 270 mg of title compound as free base. LCMS (m/z): 418.3 (MH+), retention time=0.52 min.; 1H NMR (300 MHz, METHANOL-d4, 25° C.) δ ppm 1.19-1.55 (m, 6H) 1.71 (d, J=12.89 Hz, 2H) 1.85-2.15 (m, 5 H) 3.28-3.32 (dMeOH, 2H App.) 3.40 (td, J=11.72, 1.76 Hz, 2H) 3.50-3.73 (m, 2H) 3.94 (dd, J=11.28, 3.08 Hz, 2 H) 6.66 (s, 1 H) 7.86 (s, 2H) 7.99 (s, 1 H)

Example 76

Compound 215 and 216

1-((R)-3-((2'-(trans-4-aminocyclohexylamino)-5'-chloro-2,4'-bipyridin-6-yl-amino)methyl)piperidin-1-yl)ethanone and 1-((R)-3-((2'-(trans-4-aminocyclohexylamino)-2,4'-bipyridin-6-yl-amino)methyl)piperidin-1-yl)ethanone

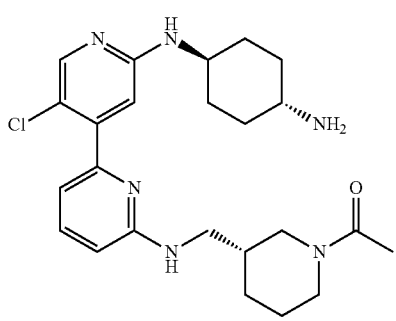

215

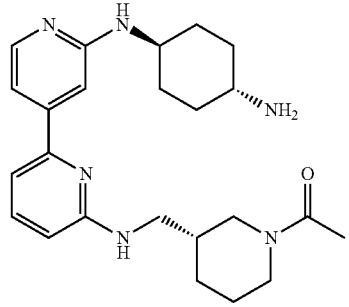

216

Step 1. Preparation of (R)-tert-butyl 3-((2'-(trans-4-aminocyclohexylamino)-5'-chloro-2,4'-bipyridin-6-yl-amino)methyl)piperidine-1-carboxylate A mixture of trans-N1-(5'-chloro-6-fluoro-2,4'-bipyridin-2'-yl)cyclohexane-1,4-diamine (Example 1a, step 2) (50 mg, 0.156 mmol), DMSO (0.75 ml), (R)-tert-butyl 3-(aminomethyl)piperidine-1-carboxylate (167 mg, 0.779 mmol) and TEA (0.033 ml, 0.234 mmol) was stirred at 100-105° C. for 40 hours and the reaction progress was followed by LCMS. The reaction mixture was let cool, added 0.75 ml of DMSO, filtered and purified by prep LC, and lyophilized to yield 36 mg of titled compound as a TFA salt. LCMS (m/z): 515.4 (MH+), retention time=0.64 min.;

Step 2. Preparation of benzyl trans-4-(5'-chloro-6-((S)-piperidin-3-yl-methylamino)-2,4'-bipyridin-2'-yl-amino)cyclohexylcarbamate A mixture of (R)-tert-butyl 3-((2'-(trans-4-aminocyclohexylamino)-5'-chloro-2,4'-bipyridin-6-yl-amino)methyl)piperidine-1-carboxylate (36 mg, 0.070 mmol), DCM (1.2 ml), TEA (0.019 ml, 0.140 mmol) and benzyl 2,5-dioxopyrrolidin-1-yl carbonate (26.1 mg, 0.105 mmol) was stirred at ambient temperature for 2 hours and the reaction progress was followed by LCMS. To this crude reaction mixture was added 25 ml of ethyl acetate, washed with 2M sodium carbonate, water (2×) and saturated salt solution (1×), dried with sodium sulfate, filtered, concentrated to crude intermediate. To the crude intermediate was added 4M HCl in Dioxane (2 ml, 8.00 mmol) and stirred at ambient temperature for 1 hour. The crude reaction mixture was concentrated to constant mass, dissolved in 1 ml of DMSO and purified by prep LC. After lyophilization, 15 mg of the title compound, was obtained as a TFA salt. LCMS (m/z): 549.4 (MH+), retention time=0.67 min.

Step 3. Preparation of 1-((R)-3-((2'-(trans-4-aminocyclohexylamino)-5'-chloro-2,4'-bipyridin-6-yl-amino)methyl)piperidin-1-yl)ethanone and 1-((R)-3-((2'-(trans-4-aminocyclohexylamino)-2,4'-bipyridin-6-yl-amino)methyl)piperidin-1-yl)ethanone A mixture of benzyl trans-4-(5'-chloro-6-((S)-piperidin-3-yl-methylamino)-2,4'-bipyridin-2'-yl-amino)cyclohexylcarbamate (15 mg, 0.027 mmol), DCM (2 mL), TEA (0.011 mL, 0.082 mmol) and acetic anhydride (3.09 µL, 0.033 mmol) was stirred at ambient temperature for 2 hours and the reaction progress was followed by LCMS. The solvent was concentrated off. The reaction mixture flask was flushed with argon, 10% palladium on activated carbon (5 mg, 4.70 μmol) was added and followed by careful addition of MeOH (0.8 mL). The resulting mixture was stirred under hydrogen for 45 minutes at ambient temperature and monitored by LCMS. To the crude reaction mixture was added 2 ml of DCM, filtered and the solvent was concentrated off. The resulting residue was dissolved in 1.0 ml of DMSO, filtered and purified by prep HPLC to give two fractions corresponding to the two title compounds respectively. After lyophilization, 4.0 mg of 1-((R)-3-((2'-(trans-4-aminocyclohexylamino)-5'-chloro-2,4'-bipyridin-6-yl-amino)methyl)piperidin-1-yl)ethanone, was obtained as a TFA salt. LCMS (m/z): 457.2 (MH+), retention time=0.46 min. In addition, 1.0 mg of 1-((R)-3-((2'-(trans-4-aminocyclohexylamino)-2,4'-bipyridin-6-yl-amino)methyl)piperidin-1-yl)ethanone, as TFA salt was also obtained. LCMS (m/z): 423.2 (MH+), retention time=0.45 min. This reaction yielded two products which are separated and purified by HPLC.

Example 77

Compound 249

6-(2-(trans-4-(aminomethyl)cyclohexylamino)-5-chloropyridin-4-yl)-N-methyl-N-((tetrahydro-2H-pyran-4-yl)methyl)pyrazin-2-amine

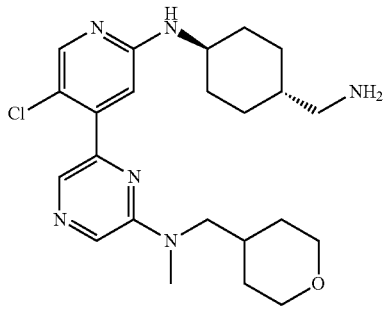 [SMILES: CN(CC1CCOCC1)c1cncc(-c2cc(N[C@H]3CC[C@H](CN)CC3)ncc2Cl)n1]

Step 1. Preparation of 6-chloro-N-methyl-N-((tetrahydro-2H-pyran-4-yl)methyl)pyrazin-2-amine A mixture of 2,6-dichloropyrazine (298 mg, 2.000 mmol), DMSO (6 ml), TEA (0.418 ml, 3.00 mmol) and N-methyl-1-(tetrahydro-2H-pyran-4-yl)methanamine (264 mg, 2.040 mmol) was stirred at 70° C. for 16 hours, and the reaction progress was followed by LCMS. The crude reaction mixture was let cool to room temperature, diluted with 150 ml of ethyl acetate, washed with 1M NaOH soln. (1×), water (2×), saturated salt soln. (1×), dried with sodium sulfate, filtered, and concentrated to constant mass, giving 475 mg of the title compound as free base, which was used without further purification. LCMS (m/z): 242.0 (MH+), retention time=0.85 min.

Step 2. Preparation of 6-(5-chloro-2-fluoropyridin-4-yl)-N-methyl-N-((tetrahydro-2H-pyran-4-yl)methyl)pyrazin-2-amine To 6-chloro-N-methyl-N-((tetrahydro-2H-pyran-4-yl)methyl)pyrazin-2-amine (450 mg, 1.862 mmol) was added 5-chloro-2-fluoropyridin-4-ylboronic acid (588 mg, 3.35 mmol), PdCl2(dppf).CH2Cl2 adduct (182 mg, 0.223 mmol), DME (8 ml) and 2M sodium carbonate (2.79 ml, 5.59 mmol). The resulting reaction mixture was stirred at 110-115° C. for 90 minutes, and the reaction progress was followed by LCMS. The reaction mixture was cooled, 20 ml of ethyl acetate and 10 ml of methanol were added, filtered and concentrated to crude product. The crude was purified by silica gel chromatography using 24 g column eluting with 20-75% ethyl acetate in heptane. The desired fractions were concentrated to constant mass, giving 499 mg of titled compound as free base. LCMS (m/z): 337.1 (MH+), retention time=0.90 min.

Step 3. Preparation of 6-(2-(trans-4-(aminomethyl)cyclohexylamino)-5-chloropyridin-4-yl)-N-methyl-N-((tetrahydro-2H-pyran-4-yl)methyl)pyrazin-2-amine A mixture of 6-(5-chloro-2-fluoropyridin-4-yl)-N-methyl-N-((tetrahydro-2H-pyran-4-yl)methyl)pyrazin-2-amine (15 mg, 0.045 mmol), DMSO (0.4 ml), and tert-butyl(trans-4-aminocyclohexyl)methylcarbamate (92 mg, 0.401 mmol) was stirred at 100-105° C. for 18 hours, and the reaction progress was followed by LCMS. To the crude intermediate was added 6 M aq.HCl (120 μl, 0.720 mmol) and heated at 80° C. for 40 minutes, and the reaction progress was followed by LCMS. The reaction mixture was let cool, added 0.5 ml of DMSO, filtered and purified by prep LC. After lyophilization, 15.6 mg of the title compound, as a TFA salt was obtained. LCMS (m/z): 445.2 (MH+), retention time=0.59 min.; 1H NMR (300 MHz, METHANOL-d4, 25° C.) δ ppm 1.12-1.47 (m, 6H) 1.59 (d, J=12.60 Hz, 2H) 1.67 (ddd, J=7.18, 3.81, 3.66 Hz, 1H) 1.92 (d, J=12.31 Hz, 2 H) 2.01-2.11 (m, 1 H) 2.16 (d, J=11.43 Hz, 2 H) 2.83 (d, J=7.03 Hz, 2 H) 3.17 (s, 3H) 3.33-3.45 (m, 2 H) 3.56 (d, J=7.33 Hz, 2 H) 3.60-3.72 (m, 1 H) 3.93 (dd, J=11.14, 2.93 Hz, 2 H) 6.92 (s, 1 H) 8.02 (d, J=2.64 Hz, 2 H) 8.11 (s, 1 H).

Example 78

Compound 244

N-(trans-4-(5-chloro-4-(6-((tetrahydro-2H-pyran-4-yl)methyl)aminopyrazin-2-yl)pyridin-2-yl-amino)cyclohexyl)acetamide

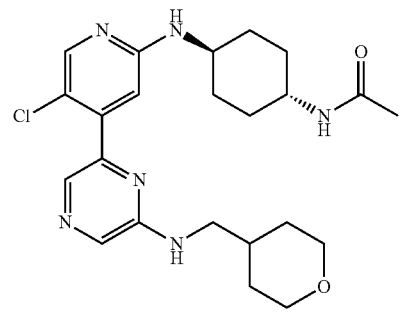 [SMILES: CC(=O)N[C@H]1CC[C@H](Nc2cc(-c3cncc(NCC4CCOCC4)n3)c(Cl)cn2)CC1]

Step 1: Preparation of N-(trans-4-(5-chloro-4-(6-((tetrahydro-2H-pyran-4-yl)methyl)aminopyrazin-2-yl)pyridin-2-yl-amino)cyclohexyl)acetamide A mixture of trans-N1-(5-chloro-4-(6-((tetrahydro-2H-pyran-4-yl)methyl)aminopyrazin-2-yl)pyridin-2-yl)cyclohexane-1,4-diamine (example 85) (14 mg, 0.034 mmol), DCM (0.5 ml), THF (0.500 ml), TEA (0.014 ml, 0.101 mmol) and acetic anhydride (3.48 µl, 0.037 mmol) was stirred at ambient temperature for 1 hour, and the reaction progress was followed by LCMS. The solvent was concentrated off, added 1.0 ml of DMSO, filtered and purified by prep LC. After lyophilization 6.3 mg of title compound was obtained as a TFA salt. LCMS (m/z): 445.2 (MH+), retention time=0.59 min.; $^1$H NMR (300 MHz, METHANOL-d4, 25° C.) δ ppm 1.21-1.55 (m, 6 H) 1.70 (d, J=12.89 Hz, 2 H) 1.92 (s, 3 H) 1.93-2.06 (m, 3 H) 2.10 (br. s., 2 H) 3.28-3.32 (dMeOH, 2H App.) 3.34-3.47 (m, 2 H) 3.55-3.73 (m, 2 H) 3.94 (dd, J=11.28, 3.08 Hz, 2 H) 7.00 (s, 1 H) 7.94 (s, 2 H) 8.01 (s, 1 H).

Example 79

Compound 254

3,5'-dichloro-N2'-(trans-4-(2-(methylsulfonyl)ethylamino)cyclohexyl)-N6-((tetrahydro-2H-pyran-4-yl)methyl)-2,4'-bipyridine-2',6-diamine

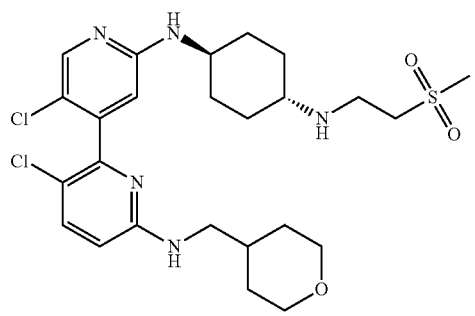 [SMILES: CS(=O)(=O)CCN[C@H]1CC[C@H](Nc2cc(-c3nc(NCC4CCOCC4)ccc3Cl)c(Cl)cn2)CC1]

Step 1. Preparation of 3,5'-dichloro-N2'-(trans-4-(2-(methylsulfonyl)ethylamino)cyclohexyl)-N6-((tetrahydro-2H-pyran-4-yl)methyl)-2,4'-bipyridine-2',6-diamine A mixture of N2'-(trans-4-aminocyclohexyl)-3,5'-dichloro-N6-((tetrahydro-2H-pyran-4-yl)methyl)-2,4'-bipyridine-2',6-diamine (Example 87) (40 mg, 0.089 mmol), potassium carbonate (30.7 mg, 0.222 mmol), DMSO (0.4 ml) and 2-(methylsulfonyl)ethyl methanesulfonate (Example 20, step 1) (26.9 mg, 0.133 mmol) was stirred at 100° C. and the reaction progress was followed by LCMS. After 4 hours, to the crude reaction mixture was added 2-(methylsulfonyl) ethyl methanesulfonate (26.9 mg, 0.133 mmol) and stirred at 100° C. for an additional 4 hours. The reaction mixture was cooled to room temperature, 0.5 mL of DMSO added, filtered and purified by prep. LC. After lyophilization to TFA salt, 16.9 mg of title compound was obtained. LCMS (m/z): 556.2 (MH+), retention time=0.61 min.; 1H NMR (300 MHz, METHANOL-d4, 25° C.) δ ppm 1.18-1.53 (m, 4 H) 1.53-1.72 (m, 4 H) 1.86 (dddd, J=14.83, 7.58, 3.96, 3.81 Hz, 1 H) 2.24 (d, J=10.55 Hz, 4H) 3.11 (s, 3H) 3.19 (d, J=6.74 Hz, 2H) 3.25 (br. s., 1 H) 3.38 (td, J=11.72, 1.76 Hz, 2 H) 3.56 (s, 4 H) 3.72 (t, J=11.28 Hz, 1 H) 3.92 (dd, J=11.28, 2.78 Hz, 2 H) 6.61 (d, J=9.08 Hz, 1 H) 6.67-6.77 (m, 1 H) 7.50 (d, J=9.08 Hz, 1 H) 8.05 (s, 1 H).

Example 80

Compound 258

3,5'-dichloro-N2'-(trans-4-(2-methoxyethylamino) cyclohexyl)-N6-((tetrahydro-2H-pyran-4-yl)methyl)-2,4'-bipyridine-2',6-diamine

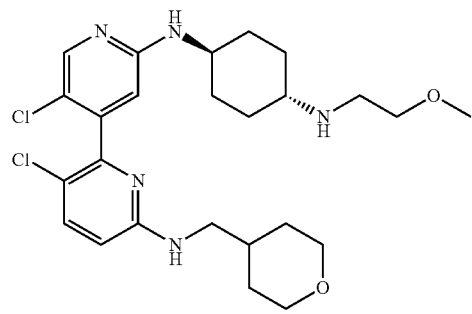 [SMILES: COCCN[C@H]1CC[C@H](Nc2cc(-c3nc(NCC4CCOCC4)ccc3Cl)c(Cl)cn2)CC1]

Step 1: Preparation of 3,5'-dichloro-N2'-(trans-4-(2-methoxyethylamino)cyclohexyl)-N6-((tetrahydro-2H-pyran-4-yl)methyl)-2,4'-bipyridine-2',6-diamine A mixture of N2'-(trans-4-aminocyclohexyl)-3,5'-dichloro-N6-((tetrahydro-2H-pyran-4-yl)methyl)-2,4'-bipyridine-2',6-diamine (example 87) (40 mg, 0.089 mmol), potassium carbonate (30.7 mg, 0.222 mmol), DMSO (0.4 ml) and 1-bromo-2-methoxyethane (18.52 mg, 0.133 mmol) was stirred at 80° C. for 2 hours and the reaction progress was followed by LCMS. To the crude reaction mixture was added BOC-Anhydride (0.041 mL, 0.178 mmol) and stirred at ambient temperature for 2 hr. The BOC intermediate was purified by prep. LC and lyophilized to TFA salt, which was then mixed with 4M HCL (1 mL, 4.00 mmol) and stirred at ambient temperature for 1 hour. The solvent was concentrated off, the resulting residue dissolved in 1 ml DMSO, filtered and purified by prep. LC. After lyophilization to TFA salt, 5.3 mg of the title compound was obtained. LCMS (m/z): 508.2 (MH+), retention time=0.63 min, Example 81

Compound 259

2-(trans-4-(3,5'-dichloro-6-((tetrahydro-2H-pyran-4-yl)methyl)amino-2,4'-bipyridin-2'-yl-amino)cyclohexylamino)ethanol

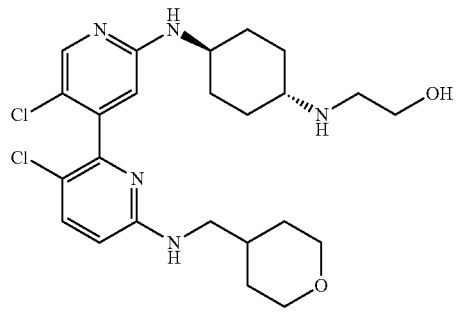 [SMILES: OCCN[C@H]1CC[C@H](Nc2cc(-c3nc(NCC4CCOCC4)ccc3Cl)c(Cl)cn2)CC1]

Step 1. Preparation of 2-(trans-4-(3,5'-dichloro-6-((tetrahydro-2H-pyran-4-yl)methyl)amino-2,4'-bipyridin-2'-yl-amino)cyclohexylamino)ethanol A mixture of N2'-(trans-4-aminocyclohexyl)-3,5'-dichloro-N6-((tetrahydro-2H-pyran-4-yl)methyl)-2,4'-bipyridine-2',6-diamine (example 87) (40 mg, 0.089 mmol), potassium carbonate (30.7 mg, 0.222 mmol), DMSO (0.4 ml) and 2-bromoethanol (16.65 mg, 0.133 mmol) was stirred at 80° C. for 2 hours and the reaction progress was followed by LCMS To this crude reaction mixture was added BOC-Anhydride (0.041 mL, 0.178 mmol) and stirred at ambient temperature for 2 hr. The BOC intermediate was purified by prep LC, and lyophilized to a TFA salt. Then was added 4M HCl in Dioxane (1 mL, 4.00 mmol) and stirred at ambient temperature for 1 hour. The solvent was concentrated off, the resulting residue dissolved in DMSO, purified by prep. LC. After lyophilization to TFA salt, 6.1 mg of the title compound was obtained. LCMS (m/z): 494.2 (MH+), retention time=0.60 min.; 1H NMR (300 MHz, METHANOL-d4, 25° C.) δ ppm 1.18-1.51 (m, 4 H) 1.50-1.73 (m, 4 H) 1.78-1.95 (m, J=14.80, 7.62, 7.47, 3.66, 3.66 Hz, 1 H) 2.23 (d, J=11.43 Hz, 4 H) 3.09-3.24 (m, 5 H) 3.38 (td, J=11.79, 1.61 Hz, 2 H) 3.64-3.77 (m, 1H) 3.77-3.84 (m, 2 H) 3.92 (dd, J=11.28, 3.08 Hz, 2 H) 6.59 (d, J=9.08 Hz, 1 H) 6.66 (s, 1 H) 7.49 (d, J=8.79 Hz, 1 H) 8.03 (s, 1 H)

Example 82

Compound 265

N2'-(trans-4-aminocyclohexyl)-3-chloro-N6-((tetrahydro-2H-pyran-4-yl)methyl)-2,4'-bipyridine-2',6-diamine

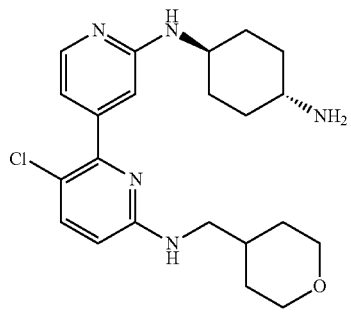 [SMILES: N[C@H]1CC[C@H](Nc2cc(-c3nc(NCC4CCOCC4)ccc3Cl)ccn2)CC1]

Step 1. Preparation of 3-chloro-2'-fluoro-N-((tetrahydro-2H-pyran-4-yl)methyl)-2,4'-bipyridin-6-amine A mixture of 6-bromo-5-chloro-N-((tetrahydro-2H-pyran-4-yl)methyl)pyridin-2-amine (intermediate E) (630 mg, 2.062 mmol), 2-fluoropyridin-4-ylboronic acid (639 mg, 4.54 mmol), PdCl₂(dppf).CH₂Cl₂ adduct (168 mg, 0.206 mmol), DME (9 ml) and 2M sodium carbonate (3.09 ml, 6.18 mmol) was stirred at 105° C. for 2 hours, and the reaction progress was followed by LCMS. The reaction mixture was let cool to room temperature, diluted with 30 ml of ethyl acetate, 10 ml of methanol, filtered and concentrated. The crude material was purified by silica gel chromatography using 40 g column and eluting with 5-45% ethyl acetate in heptane. The desired fractions were concentrated to constant mass giving, 516 mg of the title compound as free base. LCMS (m/z): 332.0 (MH+), retention time=0.88 min

Step 2. Preparation of N2'-(trans-4-aminocyclohexyl)-3-chloro-N6-((tetrahydro-2H-pyran-4-yl)methyl)-2,4'-bipyridine-2',6-diamine:

A mixture of 3-chloro-2'-fluoro-N-((tetrahydro-2H-pyran-4-yl)methyl)-2,4'-bipyridin-6-amine (250 mg, 0.777 mmol), DMSO (2 ml), and trans-cyclohexane-1,4-diamine (798 mg, 6.99 mmol) was stirred at 105° C. for 20 hours and the reaction progress was followed by LCMS. The crude reaction mixture was cooled to room temperature, diluted with 250 ml of ethyl acetate, washed with saturated sodium bicarbonate (1×), water (2×), filtered and the solvent was concentrated off. The crude was dissolved in 5 ml DMSO, filtered and purified by prep. LC. After lypholization to TFA salt, 180 mg of the title compound was obtained. LCMS (m/z): 416.2 (MH+), retention time=0.52 min.; 1H NMR (300 MHz, METHANOL-d4, 25° C.) δ ppm 1.20-1.41 (m, 2 H) 1.46-1.74 (m, 6 H) 1.85 (ddd, J=10.99, 7.33, 4.25 Hz, 1 H) 2.06-2.30 (m, 4 H) 3.19 (br. s., 1 H) 3.26 (d, J=7.03 Hz, 2 H) 3.33-3.46 (m, 2 H) 3.59-3.76 (m, 1 H) 3.93 (dd, J=1.14, 3.22 Hz, 2 H) 6.60 (d, J=8.79 Hz, 1 H) 7.23 (d, J=6.74 Hz, 1 H) 7.39 (s, 1 H) 7.49 (d, J=8.79 Hz, 1 H) 7.88 (d, J=6.74 Hz, 1 H)

Example 83

Compound 268

3,5'-dichloro-N6-((tetrahydro-2H-pyran-4-yl)methyl)-N2'-(trans-4-(((R)-tetrahydrofuran-2-yl)methyl)aminocyclohexyl)-2,4'-bipyridine-2',6-diamine

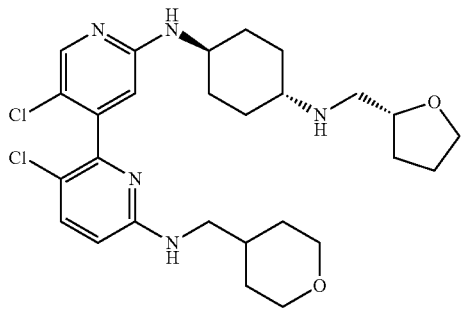 [SMILES: Clc1cnc(N[C@H]2CC[C@H](NC[C@H]3CCCO3)CC2)cc1-c1nc(NCC2CCOCC2)ccc1Cl]

Step 1. Preparation of (R)-(tetrahydrofuran-2-yl)methyl methanesulfonate

A mixture of (R)-(tetrahydrofuran-2-yl)methanol (600 mg, 5.87 mmol), DCM (35 ml), TEA (0.983 ml, 7.05 mmol) was diluted with methanesulfonyl chloride (0.467 ml, 5.99 mmol), via a dropwise addition. The reaction mixture was stirred at ambient temperature for 5 hours and the reaction progress was followed by LCMS. The crude reaction mixture was washed with saturated sodium bicarbonate (1×), water (2×), filtered and concentrated to a constant mass, giving 980 mg of the title compound, which was used without further purification. LCMS (m/z): 181.0 (MH+), retention time=0.40 min

Step 2. Preparation of 3,5'-dichloro-N6-((tetrahydro-2H-pyran-4-yl)methyl)-N2'-(trans-4-(((R)-tetrahydrofuran-2-yl)methyl)aminocyclohexyl)-2,4'-bipyridine-2',6-diamine To N2'-(trans-4-aminocyclohexyl)-3,5'-dichloro-N6-((tetrahydro-2H-pyran-4-yl)methyl)-2,4'-bipyridine-2',6-diamine (example 87) (40 mg, 0.089 mmol) was added potassium carbonate (30.7 mg, 0.222 mmol), DMSO (0.4 ml) and (R)-(tetrahydrofuran-2-yl)methyl methanesulfonate (24.01 mg, 0.133 mmol), and the resulting reaction mixture was stirred at 100° C. for 4 hours and the reaction progress was followed by LCMS. After about 4 hours (R)-(tetrahydrofuran-2-yl)methyl methanesulfonate (24.01 mg, 0.133 mmol) was added and the resulting mixture was stirred at 100° C. for 4 hours more. The reaction mixture was cooled to room temperature, 0.5 mL of DMSO added, filtered and purified by prep. LC. After lypholization to a TFA salt, 9.1 mg of the title compound was obtained. LCMS (m/z): 534.3 (MH+), retention time=0.62 min.

Example 84

Compound 272

3,5'-dichloro-N2'-(trans-4-((2-methoxyethyl)(methyl)amino)cyclohexyl)-N6-((tetrahydro-2H-pyran-4-yl)methyl)-2,4'-bipyridine-2',6-diamine

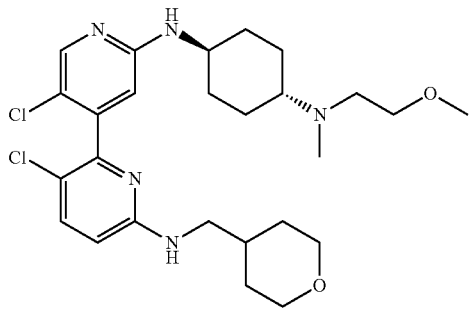 [SMILES: COCCN(C)[C@H]1CC[C@H](Nc2cc(-c3nc(NCC4CCOCC4)ccc3Cl)c(Cl)cn2)CC1]

Step 1. Preparation of (1s,4s)-4-(3,5'-dichloro-6-((tetrahydro-2H-pyran-4-yl)methyl)amino-2,4'-bipyridin-2'-yl-amino)cyclohexanol To 3,5'-dichloro-2'-fluoro-N-((tetrahydro-2H-pyran-4-yl)methyl)-2,4'-bipyridin-6-amine (intermediate G) (712 mg, 1.999 mmol) was added DMSO (4.5 ml), TEA (1.114 ml, 8.00 mmol) and (1s,4s)-4-aminocyclohexanol (607 mg, 4 mmol), and the reaction mixture was stirred at 95-100° C. for 96 hours and the reaction progress was followed by LCMS. The reaction mixture was cooled, 250 ml of ethyl acetate was added, washed with saturated sodium bicarbonate (1×) water (2×) and concentrated to constant mass. The crude was purified by silica gel chromatography using 40 g column eluting with 25-95% ethyl acetate in heptane. The desired fractions were concentrated to constant mass, giving 380 mg of title compound as free base. LCMS (m/z): 451.1 (MH+), retention time=0.65 min Step 2. Preparation of (1s,4s)-4-(3,5'-dichloro-6-((tetrahydro-2H-pyran-4-yl)methyl)amino-2,4'-bipyridin-2'-yl-amino)cyclohexyl methanesulfonate To (1s,4s)-4-(3,5'-dichloro-6-((tetrahydro-2H-pyran-4-yl)methyl)amino-2,4'-bipyridin-2'-yl-amino)cyclohexanol (375 mg, 0.831 mmol) was added DCM (8 ml), and TEA (0.174 ml, 1.246 mmol) and the resulting mixture was cooled in an ice bath to 0° C. Then with stirring was added methanesulfonyl chloride (0.071 ml, 0.914 mmol). The reaction mixture was allowed to warm to ambient temperature and stirred for 2 hours, and the reaction progress was followed by LCMS. To the crude reaction mixture was added 250 ml of ethyl acetate, washed with saturated sodium bicarbonate (1×) water (2×) and concentrated to constant mass giving, 441 mg of title compound as free base, used without further purification. LCMS (m/z): 529.3 (MH+), retention time=0.75 min.

Step 3. Preparation of 3,5'-dichloro-N2'-(trans-4-((2-methoxyethyl)(methyl)amino)cyclohexyl)-N6-((tetrahydro-2H-pyran-4-yl)methyl)-2,4'-bipyridine-2',6-diamine To (1s,4s)-4-(3,5'-dichloro-6-((tetrahydro-2H-pyran-4-yl)methyl)amino-2,4'-bipyridin-2'-yl-amino)cyclohexyl methanesulfonate (48 mg, 0.091 mmol) was added t-Butanol (0.22 ml) and 2-methoxy-N-methylethanamine (202 mg, 2.266 mmol). The reaction mixture was stirred at 95-100° C. for 5 hours and the reaction progress was followed by LCMS. The reaction mixture was cooled to room temperature, 12 ml of ethyl acetate was added then washed with saturated sodium bicarbonate (1×) water (2×) and the solvent concentrated off. The resulting residue was dissolved in 1 ml of DMSO, filtered and purified by prep LC. After lypholization to TFA salt, 8.61 mg of the title compound was obtained. LCMS (m/z): 522.2 (MH+), retention time=0.63 min.; 1H NMR (300 MHz, METHANOL-d4, 25° C.) δ ppm 1.18-1.56 (m, 4 H) 1.59-1.79 (m, 4 H) 1.79-1.95 (m, 1 H) 2.02-2.35 (m, 4 H) 2.87 (s, 3 H) 3.19 (d, J=6.74 Hz, 2 H) 3.24 (d, J=3.52 Hz, 1 H) 3.32-3.41 (m, 3 H) 3.42 (s, 3 H) 3.46-3.58 (m, 1 H) 3.63-3.78 (m, 3 H) 3.92 (dd, J=11.14, 2.93 Hz, 2 H) 6.60 (d, J=9.08 Hz, 1 H) 6.70 (s, 1 H) 7.49 (d, J=9.08 Hz, 1 H) 8.04 (s, 1 H)

Example 85

Compound 203 trans-N1-(5-chloro-4-(6-((tetrahydro-2H-pyran-4-yl)methyl)aminopyrazin-2-yl)pyridin-2-yl)cyclohexane-1,4-diamine

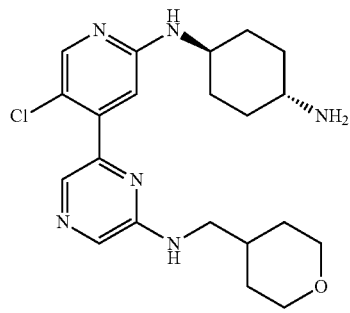 [SMILES: N[C@H]1CC[C@H](Nc2cc(-c3cncc(NCC4CCOCC4)n3)c(Cl)cn2)CC1]

Step 1. Preparation of trans-N1-(5-chloro-4-(6-((tetrahydro-2H-pyran-4-yl)methyl)aminopyrazin-2-yl)pyridin-2-yl)cyclohexane-1,4-diamine To 6-(5-chloro-2-fluoropyridin-4-yl)-N-((tetrahydro-2H-pyran-4-yl)methyl)pyrazin-2-amine (example 75 step 2) (20 mg, 0.062 mmol) was added DMSO (0.6 ml) and trans-cyclohexane-1,4-diamine (63.7 mg, 0.558 mmol). The reaction mixture then was stirred at 100-105° C. for 18 hours and the reaction progress was followed by LCMS. The reaction mixture was let cool, diluted with 0.5 ml of DMSO, filtered and purified by prep LC. After lypholization to TFA salt, 13.7 mg of the title compound was obtained. LCMS (m/z): 417.3

(MH+), retention time=0.46 min.; 1H NMR (300 MHz, METHANOL-d4, 25° C.) δ ppm 1.22-1.78 (m, 8 H) 1.81-2.01 (m, 1 H) 2.03-2.28 (m, 4 H) 3.05-3.21 (m, 1 H) 3.28-3.32 (dMeOH, 2 H App.) 3.39 (td, J=11.72, 1.76 Hz, 2 H) 3.62-3.79 (m, 1H) 3.94 (dd, J=11.14, 3.22 Hz, 2 H) 6.95 (s, 1 H) 7.92 (d, J=2.93 Hz, 2 H) 8.05 (s, 1 H).

Example 86

Compound 243 trans-N1-(5-chloro-4-(6-((tetrahydro-2H-pyran-4-yl)methyl)aminopyrazin-2-yl)pyridin-2-yl)-N4-(2-methoxyethyl)cyclohexane-1,4-diamine

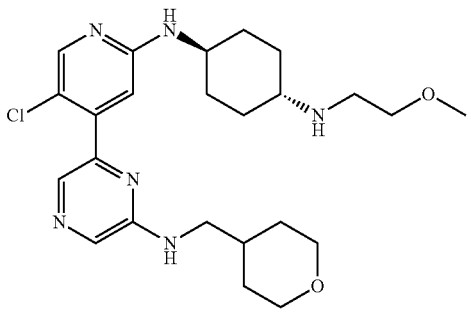 [SMILES: COCCN[C@H]1CC[C@H](Nc2cc(-c3cncc(NCC4CCOCC4)n3)c(Cl)cn2)CC1]

Step 1. Preparation of trans-N1-(5-chloro-4-(6-((tetrahydro-2H-pyran-4-yl)methyl)aminopyrazin-2-yl)pyridin-2-yl)-N4-(2-methoxyethyl)cyclohexane-1,4-diamine To trans-N1-(5-chloro-4-(6-((tetrahydro-2H-pyran-4-yl)methyl)aminopyrazin-2-yl)pyridin-2-yl)cyclohexane-1,4-diamine (Example 85) (16 mg, 0.038 mmol) was added DMSO (0.4 ml), potassium carbonate (15.91 mg, 0.115 mmol) and 1-bromo-2-methoxyethane (7.47 mg, 0.054 mmol). The reaction mixture then was stirred at 70° C. for 6 hours and the reaction progress was followed by LCMS. The reaction mixture was cooled to room temperature, 0.5 ml of DMSO was added, filtered and purified by prep LC. After lypholization to TFA salt, 2.7 mg of the title compound was obtained. LCMS (m/z): 475.2 (MH+), retention time=0.51 min.

Example 87

Compound 253

N2'-(trans-4-aminocyclohexyl)-3,5'-dichloro-N6-((tetrahydro-2H-pyran-4-yl)methyl)-2,4'-bipyridine-2',6-diamine

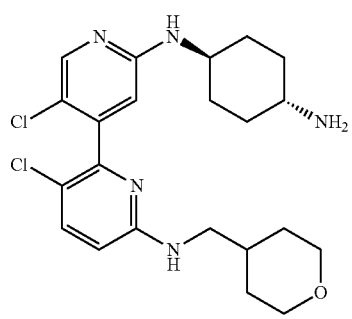 [SMILES: N[C@H]1CC[C@H](Nc2cc(-c3nc(NCC4CCOCC4)ccc3Cl)c(Cl)cn2)CC1]

Step 1. Preparation of N2'-(trans-4-aminocyclohexyl)-3,5'-dichloro-N6-((tetrahydro-2H-pyran-4-yl)methyl)-2,4'-bipyridine-2',6-diamine To 3,5'-dichloro-2'-fluoro-N-((tetrahydro-2H-pyran-4-yl)methyl)-2,4'-bipyridin-6-amine (Intermediate G) (250 mg, 0.702 mmol) was added DMSO (3 ml) and trans-cyclohexane-1,4-diamine (952 mg, 6.32 mmol). The reaction mixture was stirred at 100° C. for 20 hours and the reaction progress was followed by LCMS. The reaction mixture was cooled, diluted with 250 ml ethyl acetate, washed with saturated sodium bicarbonate (1×), water (3×) and concentrated to constant mass, giving 320 mg of product as a free base, which was used without further purification. A portion of the title compound, 25 mg was purified by prep LC and lyophilized to give 17.6 mg of the title compound as a TFA salt. LCMS (m/z): 450.2 (MH+), retention time=0.58 min.; 1H NMR (300 MHz, METHANOL-d4, 25° C.) δ ppm 1.16-1.76 (m, 8 H) 1.76-1.98 (m, 1 H) 2.04-2.27 (m, 4 H) 3.06-3.16 (m, 1 H) 3.19 (d, J=6.74 Hz, 2 H) 3.37 (t, J=11.87 Hz, 2 H) 3.62-3.77 (m, 1 H) 3.92 (dd, J=1.28, 3.08 Hz, 2 H) 6.61 (d, J=8.79 Hz, 1 H) 6.73 (s, 1 H) 7.50 (d, J=9.08 Hz, 1 H) 8.04 (s, 1 H).

Example 88

Compound 178

5'-chloro-N6-(3-fluorobenzyl)-N2'-methyl-2,4'-bipyridine-2',6-diamine

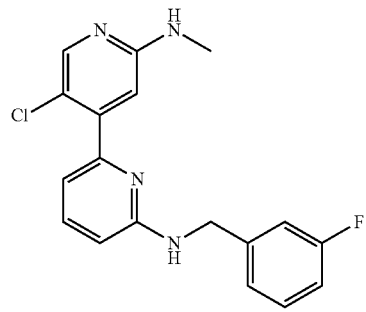 [SMILES: CNc1cc(-c2cccc(NCc3cccc(F)c3)n2)c(Cl)cn1]

Step 1. Preparation of 5'-chloro-N6-(3-fluorobenzyl)-N2'-methyl-2,4'-bipyridine-2',6-diamine A mixture of 5'-chloro-2'-fluoro-N-(3-fluorobenzyl)-2,4'-bipyridin-6-amine (Intermediate B) (15 mg, 0.045 mmol) was added DMSO (0.4 ml) and methyl amine 40% in water (200 µl, 2.293 mmol) in a microwave tube was micro waved at 145° C. for 900 seconds and the reaction progress was followed by LCMS. Most of the amine was removed under vacuum, 0.5 ml of DMSO was added, filtered and purified by prep LC. After lypholization 13.9 mg of the title compound was obtained as a TFA salt. LCMS (m/z): 343.0 (MH+), retention time=0.67 min.; 1H NMR (300 MHz, METHANOL-d4, 25° C.) δ ppm 2.97 (s, 3 H) 4.62 (s, 2 H) 6.81 (d, J=8.50 Hz, 1 H) 6.91-7.02 (m, 3 H) 7.09 (d, J=9.96 Hz, 1 H) 7.17 (d, J=7.62 Hz, 1 H) 7.27-7.39 (m, 1 H) 7.69 (dd, J=8.50, 7.33 Hz, 1 H) 8.03 (s, 1 H).

Example 89

Compound 332

5'-chloro-5-fluoro-N6-((4-methyltetrahydro-2H-pyran-4-yl)methyl)-N2'-(trans-4-((1,1-dioxo-hexahydro-1-thiopyran-4-yl)-3-ylamino)cyclohexyl)-2,4'-bipyridine-2',6-diamine

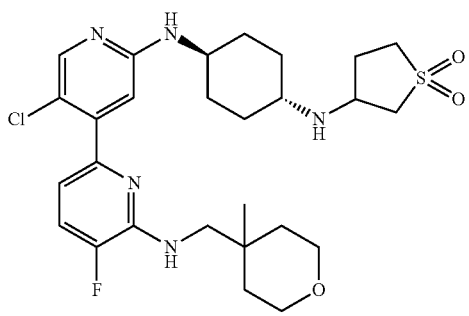 [SMILES: CC1(CNc2nc(-c3cc(N[C@H]4CC[C@H](NC5CCS(=O)(=O)C5)CC4)ncc3Cl)ccc2F)CCOCC1]

To a solution of N2'-(trans-4-aminocyclohexyl)-5'-chloro-5-fluoro-N6-((4-methyltetrahydro-2H-pyran-4-yl)methyl)-2,4'-bipyridine-2',6-diamine (40 mg, 0.089 mmol) in DMF (0.5 ml) was added potassium carbonate (49.4 mg, 0.357 mmol), 3-chloro-1,1-dioxo-tetrahydro-1-thiophene (83 mg, 0.536 mmol) and sodium iodide (40.2 mg, 0.268 mmol). The reaction mixture was stirred at 100° C. for 42 hours. The cooled reaction mixture was diluted with water and extracted with ethyl acetate. The combined extracts were washed sequentially with water and brine, dried over sodium sulfate, filtered, and concentrated. The residue was purified by reverse phase HPLC and lyophilized to give 3.8 mg off-white powder of the title compound as its TFA salt. LCMS (m/z): 566.2 (MH+), retention time=0.64 min.

Example 90

Compound 333

5'-chloro-5-fluoro-N2'-(trans-4-((2-methyl-1,3-dioxolan-2-yl)methyl)aminocyclohexyl)-N6-((tetrahydro-2H-pyran-4-yl)methyl)-2,4'-bipyridine-2',6-diamine

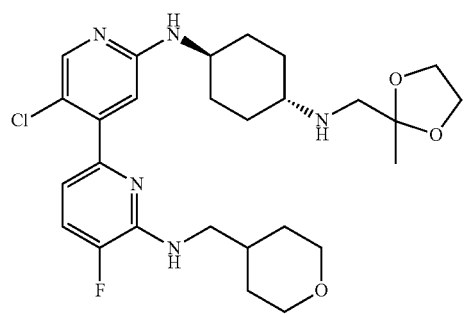 [SMILES: CC1(CN[C@H]2CC[C@H](Nc3cc(-c4ccc(F)c(NCC5CCOCC5)n4)c(Cl)cn3)CC2)OCCO1]

To a solution of N2'-(trans-4-aminocyclohexyl)-5'-chloro-5-fluoro-N6-((4-methyltetrahydro-2H-pyran-4-yl)methyl)-2,4'-bipyridine-2',6-diamine (21 mg, 0.048 mmol) in DCM (1.0 ml) was added 2-methyl-1,3-dioxolane-2-carbaldehyde (synthesized following the procedure reported in *Org. Lett.*, 2009,11, 3542-3545), sodium triacetoxyborohydride (20.51 mg, 0.097 mmol). The reaction mixture was stirred at ambient temperature for 2 hours. The reaction mixture was diluted with water and extracted with ethyl acetate. The combined extracts were washed sequentially with water and brine, dried over sodium sulfate, filtered, and concentrated. The residue was purified by reverse phase HPLC and lyophilized to give 12 mg off-white powder of the title compound as its TFA salt. LCMS (m/z): 534.1 (MH+), retention time=0.62 min.

Example 91

Compound 349

(4-((5'-chloro-2'-(trans-4-((R)-1-methoxypropan-2-ylamino)cyclohexylamino)-2,4'-bipyridin-6-ylamino)methyl)tetrahydro-2H-pyran-4-yl)methanol

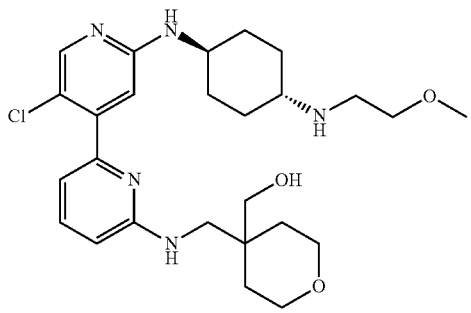 [SMILES: COCCN[C@H]1CC[C@H](Nc2cc(-c3cccc(NCC4(CO)CCOCC4)n3)c(Cl)cn2)CC1]

Step 1. Synthesis of methyl 4-cyanotetrahydro-2H-pyran-4-carboxylate

To 1-bromo-2-(2-bromoethoxy)ethane (2.57 g, 11.10 mmol) in DMSO (6 mL, by mistake, should use DMF) at room temperature was added methylcyanoacetate (1 g, 10.09 mmol) and DBU (3.35 ml, 22.20 mmol) sequentially. The brown mixture was heated to 85° C. in a capped glass vial for 3 hours. The resulting solution was dark brown.

The reaction mixture was poured into water and extracted with EtOAc. The organic extracts were combined, washed with water, brine, dried with sodium sulfate and concentrated in vacuo to give 0.944 g of brown oil. This crude material was used in the next step without further purification.

Step 2. Synthesis of (4-(aminomethyl)tetrahydro-2H-pyran-4-yl)methanol

To the crude product from step 1 (0.944 g, 5.58 mmol) in THF (5 ml) (a dark brown solution) at 0° C. was added LAH (5.58 ml, 5.58 mmol) dropwise via a syringe. The brown mixture was warmed to room temperature and stirred for 18 hours. The resulting mixture was yellow cloudy. LC/MS showed containing desired product. To the reaction was added sodium sulfate decahydrate solid at 0° C. The mixture was stirred at room temperature for 20 min., then filtered and washed with DCM. The yellow filtrate was concentrated in vacuo to give 0.74 g of orange oil. This crude material was used in the next step without further purification.

Step 3. Synthesis of (4-((6-bromopyridin-2-ylamino)methyl)tetrahydro-2H-pyran-4-yl)methanol To 2-bromo-6-fluoropyridine (0.448 g, 2.55 mmol) in NMP (4 ml) at room temperature was added TRIETHY- LAMINE (0.852 ml, 6.12 mmol) and the crude product obtained in step 2 (370 mg, 2.55 mmol) sequentially. The yellow mixture was heated to 75° C. in a capped glass vial for 3 hours. LC/MS showed about 20% conversion to the product. Continued heating at 110° C. for 16 hrs. The reaction mixture was cooled to room temperature, poured into water and extracted with EtOAc. The organic extracts were combined, washed with water, brine, dried with sodium sulfate and concentrated in vacuo to give 0.5 g of brown oil. The crude mixture was purified by Analogix system (silica gel column 24 g, gradient: 0 min, 100% n-hexane; 2-127 min, 10% EtOAc in Hex; 7-13 min. 20% EtOAc in Hex; 13-16 min. 30% EtOAc in Hex; 16-30 min. 50% EtOAc in Hex; 30-35 min. 100% EtOAc). The pure fractions were combined and concentrated in vacuo to give 0.13 g of desired product as a white crystal. LCMS (m/z): 301/303 (MH+), retention time=0.67 min.

Step 4. Synthesis of (4-((5'-chloro-2'-fluoro-2,4'-bipyridin-6-ylamino)methyl)tetrahydro-2H-pyran-4-yl)methanol Following the same procedure as in Example 1b using (4-((6-bromopyridin-2-ylamino)methyl)tetrahydro-2H-pyran-4-yl)methanol (from step 3) and 5-chloro-2-fluoropyridin-4-ylboronic acid, the desired product was obtained. LCMS (m/z): 352 (MH+), retention time=0.54 min.

Step 5. Synthesis of (4-((5'-chloro-2'-(trans-4-((R)-1-methoxypropan-2-ylamino)cyclohexylamino)-2,4'-bipyridin-6-ylamino)methyl)tetrahydro-2H-pyran-4-yl)methanol Following the same procedure as in Example 1b using (4-((5'-chloro-2'-fluoro-2,4'-bipyridin-6-ylamino)methyl) tetrahydro-2H-pyran-4-yl)methanol (from step 4) and trans-N1-((R)-1-methoxypropan-2-yl)cyclohexane-1,4-diamine, the desired product was obtained. LCMS (m/z): 518.2 (MH+), retention time=0.47 min.

Example 92

Compound 348

3,5'-dichloro-N6-((tetrahydro-2H-pyran-4-yl)methyl)-N2'-(trans-4-(1,1-dioxo-tetrahydro-2H-thiopyran-4-ylamino)cyclohexyl)-2,4'-bipyridine-2',6-diamine

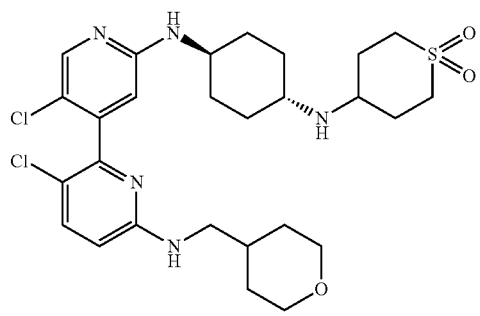 [SMILES: O=S1(=O)CCC(N[C@H]2CC[C@H](Nc3cc(-c4nc(NCC5CCOCC5)ccc4Cl)c(Cl)cn3)CC2)CC1]

Compound N2'-(4-aminocyclohexyl)-3,5'-dichloro-N6-((tetrahydro-2H-pyran-4-yl)methyl)-2,4'-bipyridine-2',6-diamine (0.100 g, 0.222 mmol) (synthesized in the same manner as in Example 1b), 2,3,5,6-tetrahydro-4H-thiopyran-4-one 1,1-dioxide (0.036 g, 0.244 mmol), and triethylamine (0.251 ml, 0.182 g, 1.798 mmol) were dissolved in anhydrous CH$_2$Cl$_2$ (1.0 ml) and placed under argon. This solution was then treated with sodium triacetoxyborohydride (0.094 g, 0.444 mmol). The reaction was then stirred at room temperature for 18 hours. At this time a LC-MS was run. The reaction was about 25% complete. Additional 2,3,5,6-tetrahydro-4H-thiopyran-4-one 1,1-dioxide (~4 equivalents) and sodium triacetoxy borohydride (~8 equivalents) were added and the reaction continued for additional 27 hours. The reaction was about 60% complete as indicated by LC/MS. The reaction was quenched with sat NaHCO$_3$ (15 ml). This was extracted with EtOAc (3×15 ml). The combined extracts were washed with brine (1×15 ml), dried (Na$_2$SO$_4$), filtered and the solvent removed in vacuo. The material was purified using the HPLC and lyophilized to give 19.7 mg off-white powder of the title compound as its TFA salt. LCMS (m/z): 582/584 (MH+), retention time=0.58 min.

Example 93

Compound 310

4-((5'-chloro-2'-(trans-4-((R)-1-methoxypropan-2-ylamino)cyclohexylamino)-2,4'-bipyridin-6-ylamino) methyl)tetrahydro-2H-pyran-4-carbonitrile

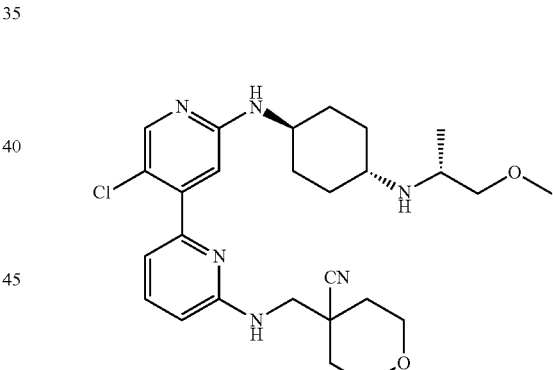

This compound was synthesized following the procedure of Example 1b using Intermediates AB (40 mg, 0.115 mmol) and N1-((R)-1-methoxypropan-2-yl)cyclohexane-trans-1,4-diamine (synthesized in step 2 of Example 67, 107 mg, 0.577 mmol). The product was obtained as an off white powder (30.2 mg, 35.5% yield). LCMS (m/z): 513.2 [M+H]+; retention time=0.531 min. $^1$H NMR (400 MHz, CHLOROFORM-d) δ ppm 1.04 (d, J=6.26 Hz, 2 H) 1.12-1.37 (m, 3 H) 1.84-2.06 (m, 3 H) 2.10-2.25 (m, 2 H) 2.44-2.69 (m, 1 H) 2.91-3.11 (m, 1 H) 3.20-3.39 (m, 3 H) 3.43-3.60 (m, 1 H) 3.61-3.83 (m, 3 H) 3.90-4.08 (m, 2 H) 4.41 (d, J=8.22 Hz, 1 H) 4.67-4.93 (m, 1 H) 6.37-6.62 (m, 2 H) 6.97 (d, J=7.43 Hz, 1 H) 7.26 (s, 1 H) 7.39-7.58 (m, 1 H).

Example 94

Synthesis of Compound 340

Synthesis of 4-((5'-chloro-5-fluoro-2'-(trans-4-((R)-1-methoxypropan-2-yl-amino)cyclohexylamino)-2,4'-bipyridin-6-ylamino)methyl)tetrahydro-2H-pyran-4-carbonitrile

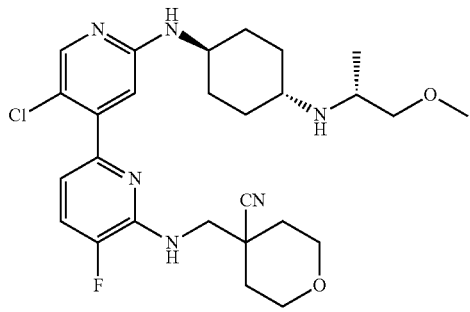 [SMILES: COC[C@@H](C)N[C@H]1CC[C@H](Nc2cc(-c3ccc(F)c(NCC4(C#N)CCOCC4)n3)c(Cl)cn2)CC1]

This compound was synthesized following the procedure of Example 1b using intermediates AA (50 mg, 0.137 mmol) and N1-((R)-1-methoxypropan-2-yl)cyclohexane-trans-1,4-diamine (synthesized in step 2 of Example 67, 128 mg, 0.685 mmol). The product was obtained as an off white powder 35 mg (33.6% yield). LCMS (m/z): 531.2 [M+H]+; retention time=0.595 min.

Examples in Table 1 were prepared using methods analogous to those described above. The method column in Table 1 indicates the synthetic procedure, from a specific example, used to synthesize a given compound. Thus for example, Compound 7 is synthesized by the procedure outlined in Example 7, while compound 25 is synthesized by the procedure outlined in Example 1a, and the like.

TABLE 1

| Compound # | Structure | M + H (m/z) | retention time (min.) | method |
|---|---|---|---|---|
| 1 | 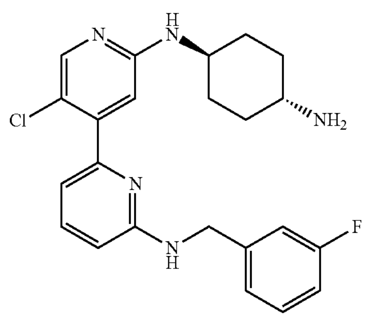 [SMILES: N[C@H]1CC[C@H](Nc2cc(-c3cccc(NCc4cccc(F)c4)n3)c(Cl)cn2)CC1] | 426.2 | 0.7 | Example 1a |
| 2 | 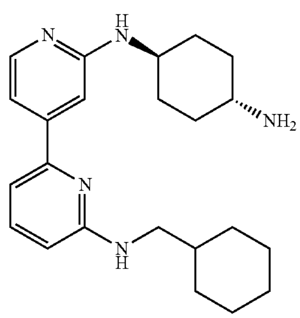 [SMILES: N[C@H]1CC[C@H](Nc2cc(-c3cccc(NCC4CCCCC4)n3)ccn2)CC1] | 380.3 | 0.61 | Example 2 |
| 3 | 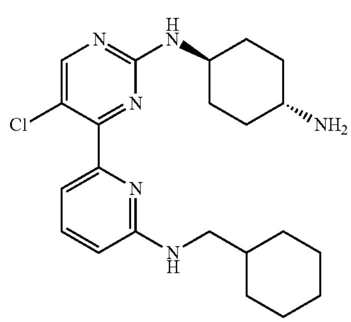 [SMILES: N[C@H]1CC[C@H](Nc2ncc(Cl)c(-c3cccc(NCC4CCCCC4)n3)n2)CC1] | 415.3 | 0.67 | Example 3 |

TABLE 1-continued

| Compound # | Structure | M + H (m/z) | retention time (min.) | method |
|---|---|---|---|---|
| 4 | 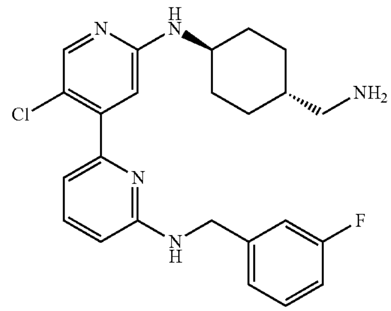 [SMILES: NC[C@H]1CC[C@H](Nc2cc(-c3cccc(NCc4cccc(F)c4)n3)c(Cl)cn2)CC1] | 440.2 | 0.62 | Example 4 |
| 5 | 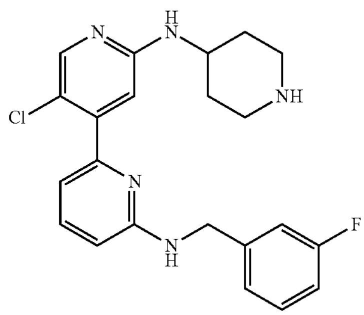 [SMILES: Fc1cccc(CNc2cccc(-c3cc(NC4CCNCC4)ncc3Cl)n2)c1] | 412.2 | 0.6 | Example 5 |
| 6 | 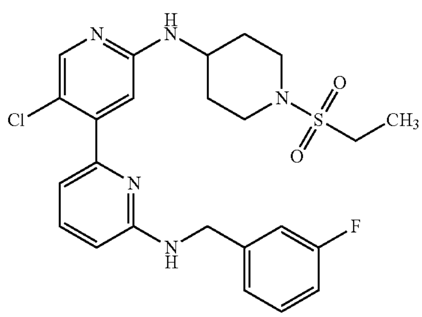 [SMILES: CCS(=O)(=O)N1CCC(Nc2cc(-c3cccc(NCc4cccc(F)c4)n3)c(Cl)cn2)CC1] | 504.2 | 0.77 | Example 6 |
| 7 | 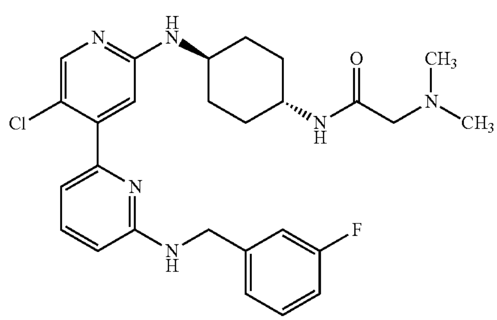 [SMILES: CN(C)CC(=O)N[C@H]1CC[C@H](Nc2cc(-c3cccc(NCc4cccc(F)c4)n3)c(Cl)cn2)CC1] | 511.3 | 0.62 | Example 7 |
| 8 | 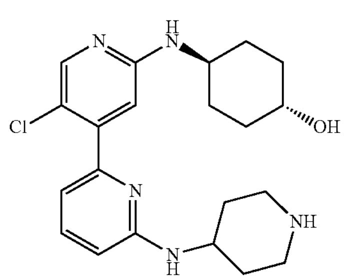 [SMILES: O[C@H]1CC[C@H](Nc2cc(-c3cccc(NC4CCNCC4)n3)c(Cl)cn2)CC1] | 402.3 | 0.41 | Example 8 |

TABLE 1-continued

| Compound # | Structure | M + H (m/z) | retention time (min.) | method |
|---|---|---|---|---|
| 9 | 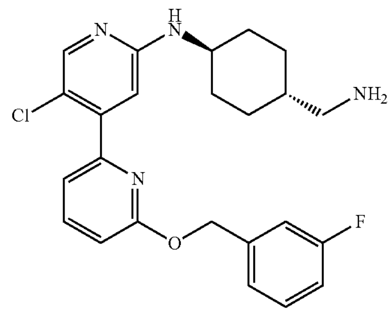 [SMILES: NC[C@H]1CC[C@H](Nc2cc(-c3cccc(OCc4cccc(F)c4)n3)c(Cl)cn2)CC1] | 441.3 | 0.76 | Example 9 |
| 10 | 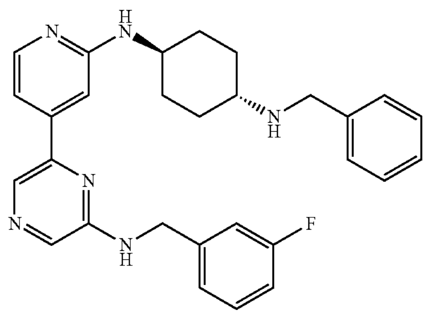 [SMILES: Fc1cccc(CNc2cncc(-c3ccnc(N[C@H]4CC[C@H](NCc5ccccc5)CC4)c3)n2)c1] | 483.2 | 0.65 | Example 10 |
| 11 | 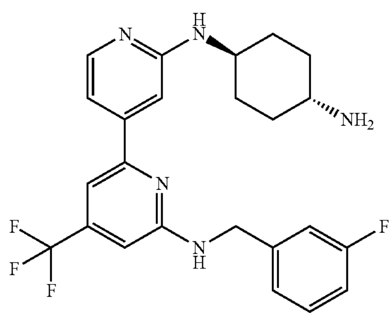 [SMILES: N[C@H]1CC[C@H](Nc2cc(-c3cc(C(F)(F)F)cc(NCc4cccc(F)c4)n3)ccn2)CC1] | 460.3 | 0.72 | Example 11 |
| 12 | Chiral | 444.2 | 0.7 | Example 12 |
| 13 | Chiral | 451.2 | 0.67 | Example 13 |

TABLE 1-continued
| Compound # | Structure | | M + H (m/z) | retention time (min.) | method |
|---|---|---|---|---|---|
| 14 | 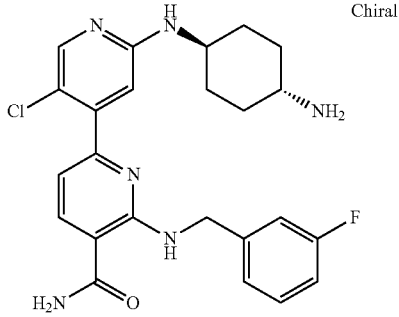 [SMILES: NC(=O)c1ccc(-c2cc(N[C@H]3CC[C@H](N)CC3)ncc2Cl)nc1NCc1cccc(F)c1] | Chiral | 469.1 | 0.56 | Example 14 |
| 15 | 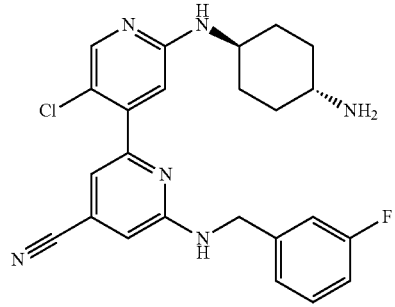 [SMILES: N#Cc1cc(NCc2cccc(F)c2)nc(-c2cc(N[C@H]3CC[C@H](N)CC3)ncc2Cl)c1] | | 451.2 | 0.7 | Example 15 |
| 16 | 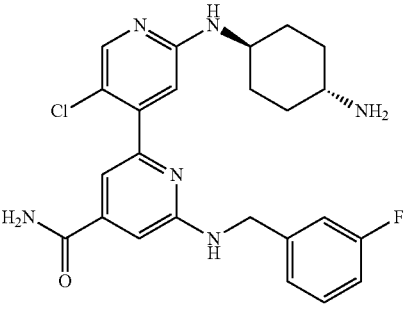 [SMILES: NC(=O)c1cc(NCc2cccc(F)c2)nc(-c2cc(N[C@H]3CC[C@H](N)CC3)ncc2Cl)c1] | | 469.2 | 0.56 | Example 16 |
| 17 | 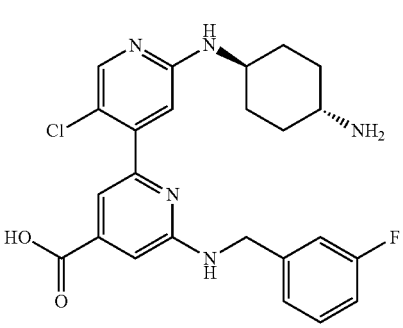 [SMILES: N[C@H]1CC[C@H](Nc2cc(-c3cc(C(=O)O)cc(NCc4cccc(F)c4)n3)c(Cl)cn2)CC1] | | 470.2 | 0.61 | Example 17 |

TABLE 1-continued

| Compound # | Structure | M + H (m/z) | retention time (min.) | method |
|---|---|---|---|---|
| 18 | 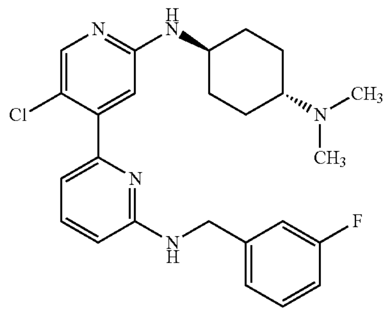 [SMILES: CN(C)[C@H]1CC[C@H](Nc2cc(-c3cccc(NCc4cccc(F)c4)n3)c(Cl)cn2)CC1] | 454.2 | 0.61 | Example 18 |
| 19 | 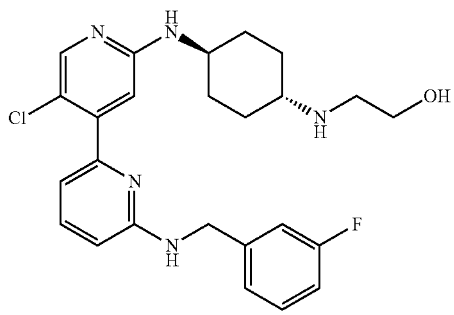 [SMILES: OCCN[C@H]1CC[C@H](Nc2cc(-c3cccc(NCc4cccc(F)c4)n3)c(Cl)cn2)CC1] | 470.3 | 0.58 | Example 19 |
| 20 | 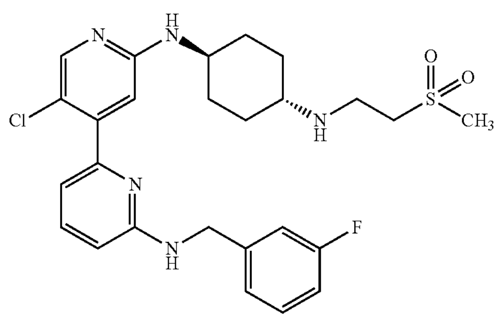 [SMILES: CS(=O)(=O)CCN[C@H]1CC[C@H](Nc2cc(-c3cccc(NCc4cccc(F)c4)n3)c(Cl)cn2)CC1] | 532.2 | 0.62 | Example 20 |
| 21 | 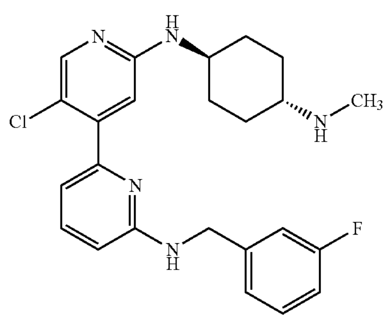 [SMILES: CN[C@H]1CC[C@H](Nc2cc(-c3cccc(NCc4cccc(F)c4)n3)c(Cl)cn2)CC1] | 440.3 | 0.61 | Example 21 |
| 22 | 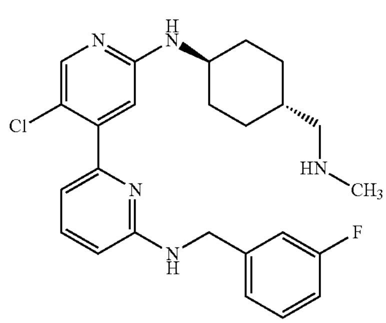 | 454.2 | 0.64 | Example 22 |

TABLE 1-continued

| Compound # | Structure | M + H (m/z) | retention time (min.) | method |
|---|---|---|---|---|
| 23 | 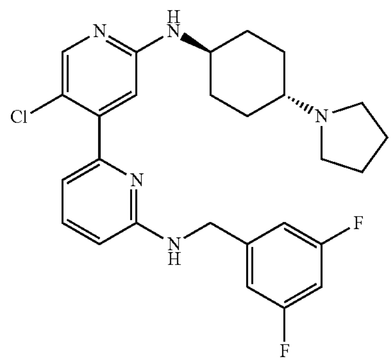 [SMILES: Fc1cc(F)cc(CNc2cccc(-c3cc(N[C@H]4CC[C@H](N5CCCC5)CC4)ncc3Cl)n2)c1] | 498.3 | 0.65 | Example 23 |
| 24 | 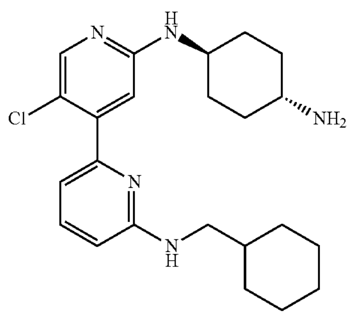 [SMILES: N[C@H]1CC[C@H](Nc2cc(-c3cccc(NCC4CCCCC4)n3)c(Cl)cn2)CC1] | 414.3 | 0.72 | Example 1a |
| 25 | 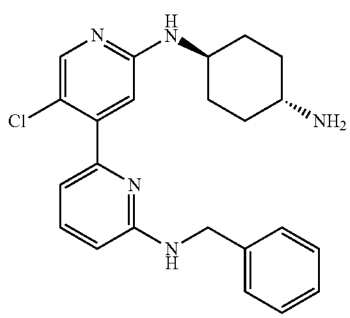 [SMILES: N[C@H]1CC[C@H](Nc2cc(-c3cccc(NCc4ccccc4)n3)c(Cl)cn2)CC1] | 408.2 | 0.61 | Example 1a |
| 26 | 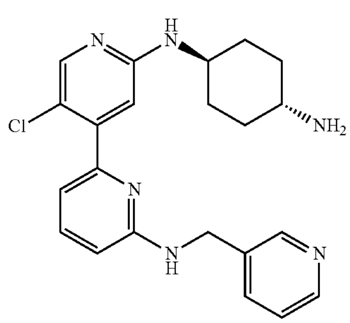 [SMILES: N[C@H]1CC[C@H](Nc2cc(-c3cccc(NCc4cccnc4)n3)c(Cl)cn2)CC1] | 409.2 | 0.41 | Example 1a |

TABLE 1-continued
| Compound # | Structure | M + H (m/z) | retention time (min.) | method |
|---|---|---|---|---|
| 27 | 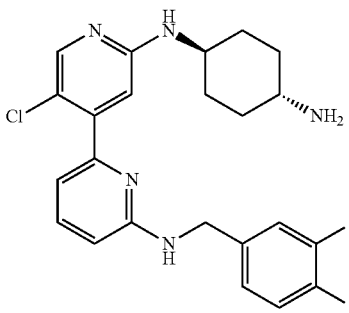 | 444.2 | 0.63 | Example 1a |
| 27 | 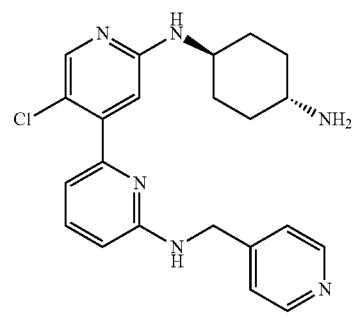 [SMILES: N[C@H]1CC[C@H](Nc2cc(-c3cccc(NCc4ccncc4)n3)c(Cl)cn2)CC1] | 444.2 | 0.63 | Example 1a |
| 29 | 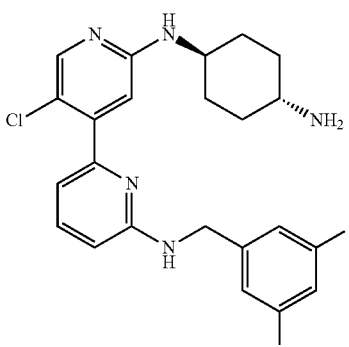 | 444.3 | 0.64 | Example 1a |
| 30 | 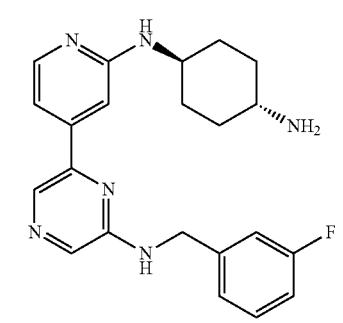 [SMILES: N[C@H]1CC[C@H](Nc2cc(-c3cncc(NCc4cccc(F)c4)n3)ccn2)CC1] | 393.2 | 0.54 | Example 10 |

TABLE 1-continued

| Compound # | Structure | M + H (m/z) | retention time (min.) | method |
|---|---|---|---|---|
| 31 | 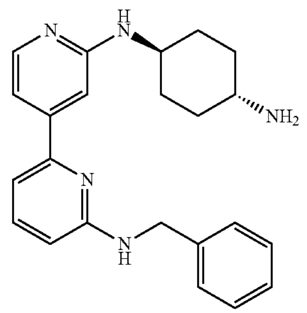 [SMILES: N[C@H]1CC[C@H](Nc2cc(-c3cccc(NCc4ccccc4)n3)ccn2)CC1] | 374.3 | 0.56 | Example 2 |
| 32 | 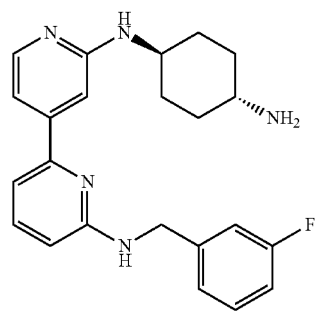 [SMILES: N[C@H]1CC[C@H](Nc2cc(-c3cccc(NCc4cccc(F)c4)n3)ccn2)CC1] | 392.3 | 0.59 | Example 2 |
| 33 | 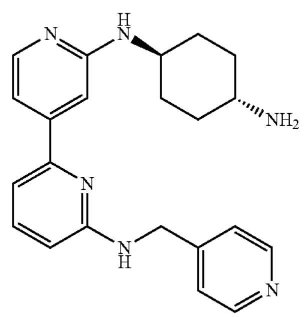 [SMILES: N[C@H]1CC[C@H](Nc2cc(-c3cccc(NCc4ccncc4)n3)ccn2)CC1] | 375.3 | 0.36 | Example 2 |
| 34 | 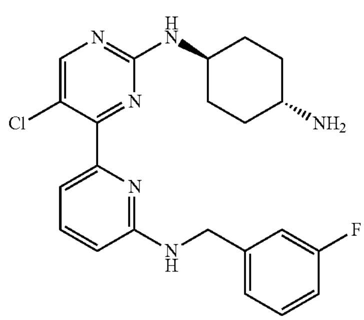 [SMILES: N[C@H]1CC[C@H](Nc2ncc(Cl)c(-c3cccc(NCc4cccc(F)c4)n3)n2)CC1] | 427.3 | 0.61 | Example 3 |
| 35 | 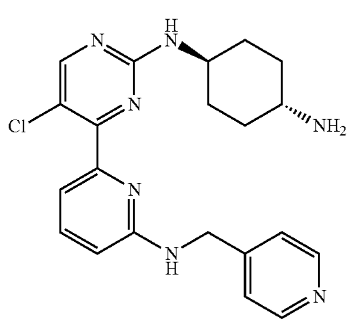 [SMILES: N[C@H]1CC[C@H](Nc2ncc(Cl)c(-c3cccc(NCc4ccncc4)n3)n2)CC1] | 410.3 | 0.41 | Example 3 |

TABLE 1-continued

| Compound # | Structure | M + H (m/z) | retention time (min.) | method |
|---|---|---|---|---|
| 36 | 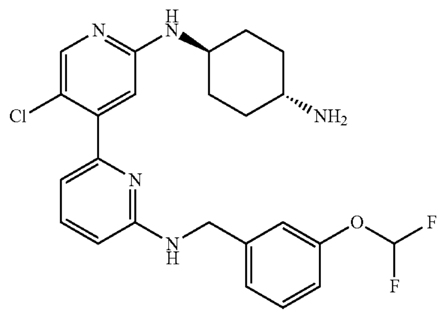 [SMILES: N[C@H]1CC[C@H](Nc2cc(-c3cccc(NCc4cccc(OC(F)F)c4)n3)c(Cl)cn2)CC1] | 474.2 | 0.66 | Example 1a |
| 37 | 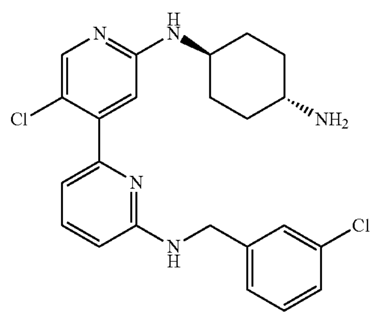 | 442.2 | 0.66 | Example 1a |
| 38 | 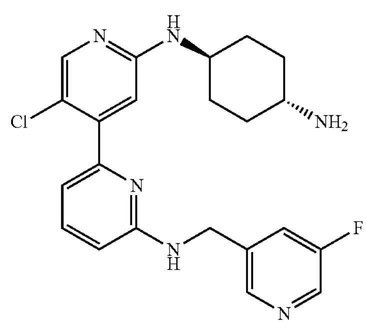 [SMILES: N[C@H]1CC[C@H](Nc2cc(-c3cccc(NCc4cncc(F)c4)n3)c(Cl)cn2)CC1] | 427.2 | 0.49 | Example 1a |
| 39 | 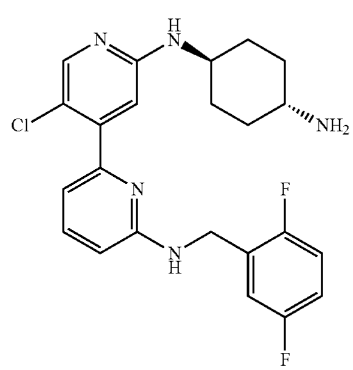 [SMILES: N[C@H]1CC[C@H](Nc2cc(-c3cccc(NCc4cc(F)ccc4F)n3)c(Cl)cn2)CC1] | 444.2 | 0.64 | Example 1a |

TABLE 1-continued
| Compound # | Structure | M + H (m/z) | retention time (min.) | method |
|---|---|---|---|---|
| 40 | 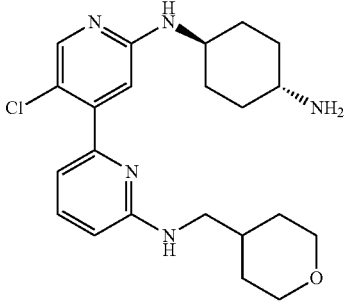 [SMILES: N[C@H]1CC[C@H](Nc2cc(-c3cccc(NCC4CCOCC4)n3)c(Cl)cn2)CC1] | 416.3 | 0.46 | Example 1a |
| 41 | 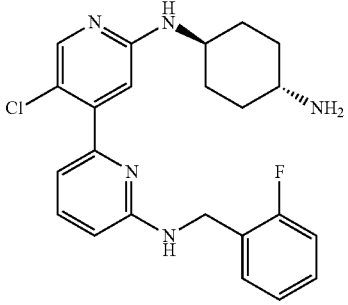 [SMILES: N[C@H]1CC[C@H](Nc2cc(-c3cccc(NCc4ccccc4F)n3)c(Cl)cn2)CC1] | 426.3 | 0.61 | Example 1a |
| 42 | 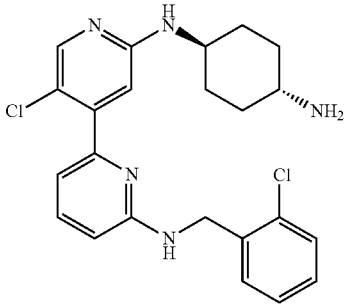 [SMILES: N[C@H]1CC[C@H](Nc2cc(-c3cccc(NCc4ccccc4Cl)n3)c(Cl)cn2)CC1] | 442.2 | 0.65 | Example 1a |
| 43 | 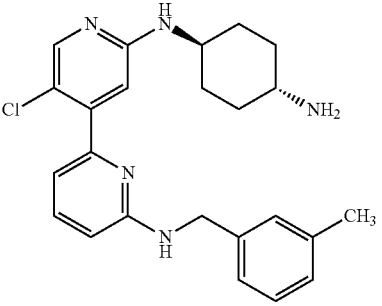 [SMILES: Cc1cccc(CNc2cccc(-c3cc(N[C@H]4CC[C@H](N)CC4)ncc3Cl)n2)c1] | 422.3 | 0.63 | Example 1a |
| 44 | 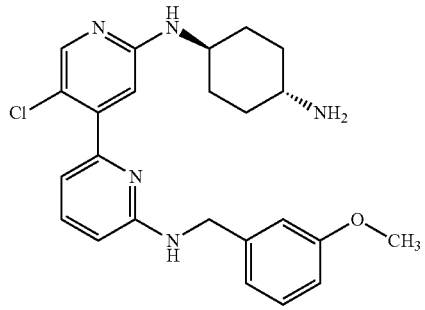 [SMILES: COc1cccc(CNc2cccc(-c3cc(N[C@H]4CC[C@H](N)CC4)ncc3Cl)n2)c1] | 438.3 | 0.59 | Example 1a |

TABLE 1-continued

| Compound # | Structure | M + H (m/z) | retention time (min.) | method |
|---|---|---|---|---|
| 45 | 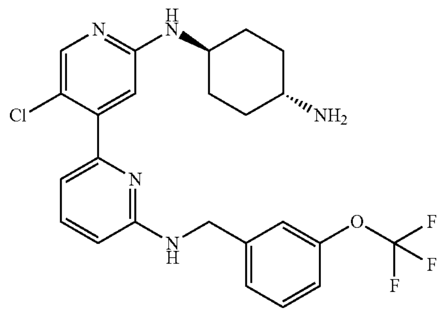 [SMILES: N[C@H]1CC[C@H](Nc2cc(-c3cccc(NCc4cccc(OC(F)(F)F)c4)n3)c(Cl)cn2)CC1] | 492.2 | 0.72 | Example 1a |
| 46 | 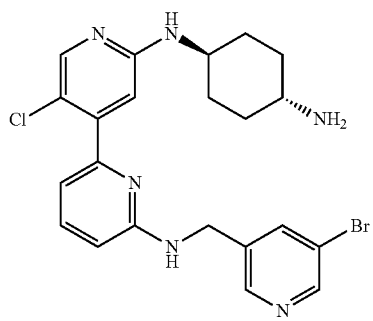 [SMILES: N[C@H]1CC[C@H](Nc2cc(-c3cccc(NCc4cncc(Br)c4)n3)c(Cl)cn2)CC1] | 487.1/ 489.2 | 0.53 | Example 1a |
| 47 | 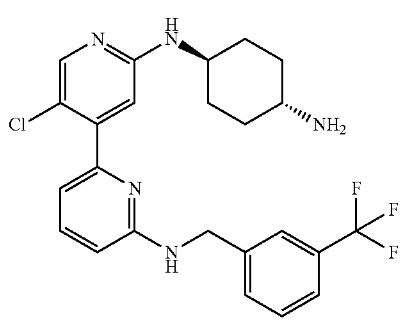 [SMILES: N[C@H]1CC[C@H](Nc2cc(-c3cccc(NCc4cccc(C(F)(F)F)c4)n3)c(Cl)cn2)CC1] | 476.3 | 0.69 | Example 1a |
| 48 | 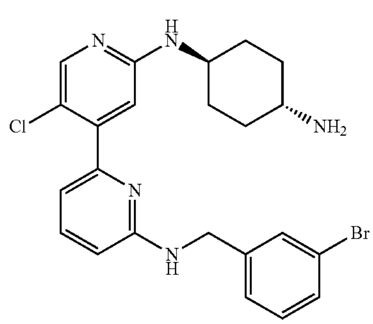 [SMILES: N[C@H]1CC[C@H](Nc2cc(-c3cccc(NCc4cccc(Br)c4)n3)c(Cl)cn2)CC1] | 486.2/ 488.2 | 0.67 | Example 1a |

TABLE 1-continued

| Compound # | Structure | M + H (m/z) | retention time (min.) | method |
|---|---|---|---|---|
| 49 | 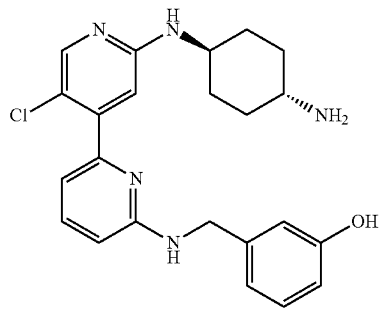 [SMILES: N[C@H]1CC[C@H](Nc2cc(-c3cccc(NCc4cccc(O)c4)n3)c(Cl)cn2)CC1] | 424.2 | 0.5 | Example 1a |
| 50 | 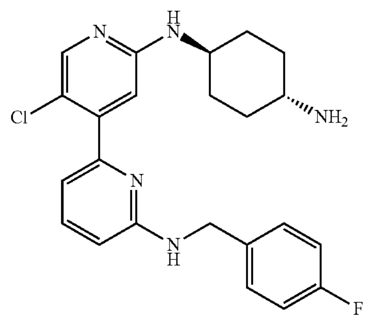 [SMILES: N[C@H]1CC[C@H](Nc2cc(-c3cccc(NCc4ccc(F)cc4)n3)c(Cl)cn2)CC1] | 426.2 | 0.6 | Example 1a |
| 51 | 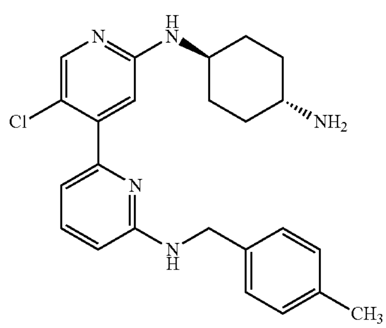 [SMILES: Cc1ccc(CNc2cccc(-c3cc(N[C@H]4CC[C@H](N)CC4)ncc3Cl)n2)cc1] | 422.2 | 0.63 | Example 1a |
| 52 | 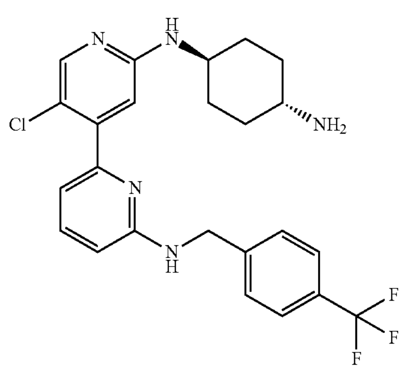 [SMILES: N[C@H]1CC[C@H](Nc2cc(-c3cccc(NCc4ccc(C(F)(F)F)cc4)n3)c(Cl)cn2)CC1] | 476.3 | 0.7 | Example 1a |

TABLE 1-continued

| Compound # | Structure | M + H (m/z) | retention time (min.) | method |
|---|---|---|---|---|
| 53 | 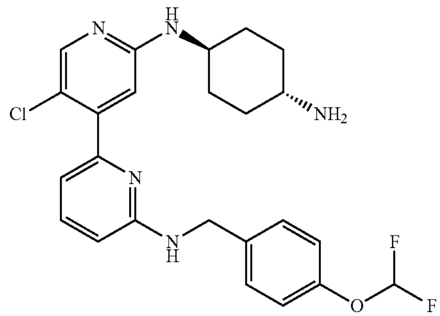 [SMILES: N[C@H]1CC[C@H](Nc2cc(-c3cccc(NCc4ccc(OC(F)F)cc4)n3)c(Cl)cn2)CC1] | 474.2 | 0.64 | Example 1a |
| 54 | 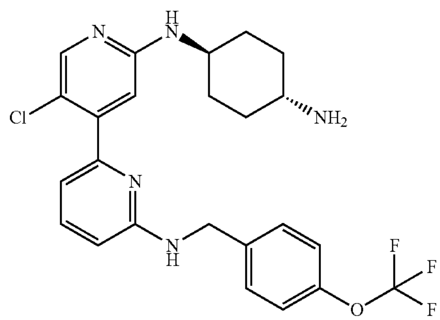 [SMILES: N[C@H]1CC[C@H](Nc2cc(-c3cccc(NCc4ccc(OC(F)(F)F)cc4)n3)c(Cl)cn2)CC1] | 492.2 | 0.73 | Example 1a |
| 55 | 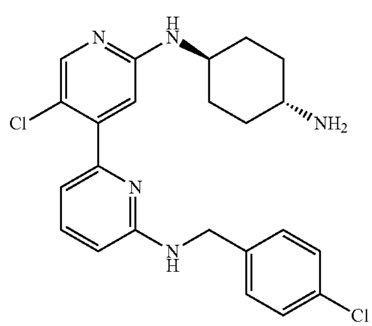 [SMILES: N[C@H]1CC[C@H](Nc2cc(-c3cccc(NCc4ccc(Cl)cc4)n3)c(Cl)cn2)CC1] | 442.2 | 0.66 | Example 1a |
| 56 | 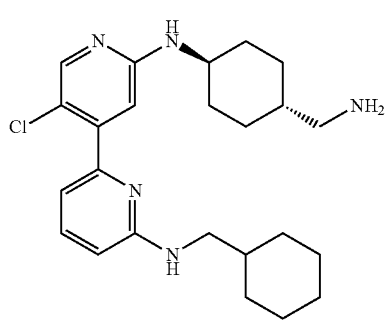 [SMILES: NC[C@H]1CC[C@H](Nc2cc(-c3cccc(NCC4CCCCC4)n3)c(Cl)cn2)CC1] | 428.3 | 0.66 | Example 4 |

TABLE 1-continued

| Compound # | Structure | M + H (m/z) | retention time (min.) | method |
|---|---|---|---|---|
| 57 | 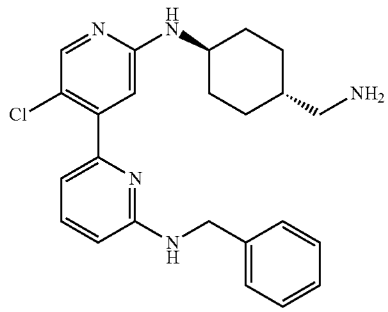 [SMILES: NC[C@H]1CC[C@H](Nc2cc(-c3cccc(NCc4ccccc4)n3)c(Cl)cn2)CC1] | 422.3 | 0.6 | Example 4 |
| 58 | 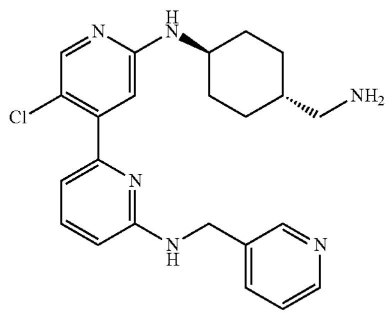 [SMILES: NC[C@H]1CC[C@H](Nc2cc(-c3cccc(NCc4cccnc4)n3)c(Cl)cn2)CC1] | 423.3 | 0.41 | Example 4 |
| 59 | 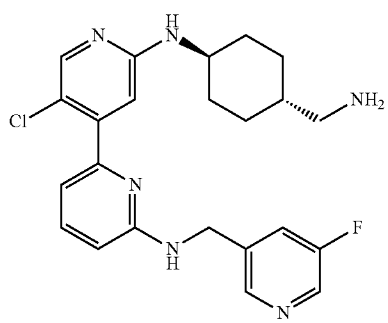 [SMILES: NC[C@H]1CC[C@H](Nc2cc(-c3cccc(NCc4cncc(F)c4)n3)c(Cl)cn2)CC1] | 441.3 | 0.5 | Example 4 |
| 60 | 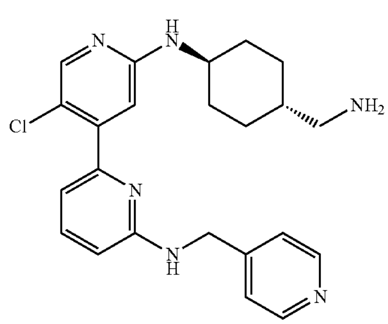 | 423.3 | 0.41 | Example 4 |

TABLE 1-continued

| Compound # | Structure | M + H (m/z) | retention time (min.) | method |
|---|---|---|---|---|
| 61 | 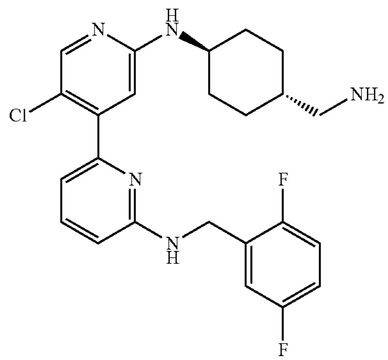 [SMILES: NC[C@H]1CC[C@H](Nc2cc(-c3cccc(NCc4cc(F)ccc4F)n3)c(Cl)cn2)CC1] | 458.3 | 0.65 | Example 4 |
| 62 | 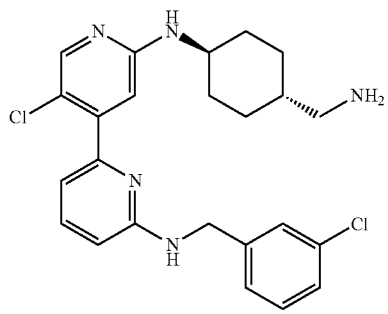 [SMILES: NC[C@H]1CC[C@H](Nc2cc(-c3cccc(NCc4cccc(Cl)c4)n3)c(Cl)cn2)CC1] | 456.3 | 0.67 | Example 4 |
| 63 | 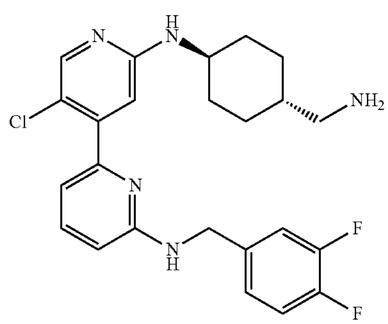 [SMILES: NC[C@H]1CC[C@H](Nc2cc(-c3cccc(NCc4ccc(F)c(F)c4)n3)c(Cl)cn2)CC1] | 458.3 | 0.65 | Example 4 |
| 64 | 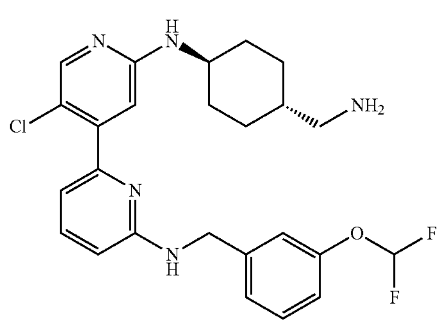 [SMILES: NC[C@H]1CC[C@H](Nc2cc(-c3cccc(NCc4cccc(OC(F)F)c4)n3)c(Cl)cn2)CC1] | 488.3 | 0.67 | Example 4 |

TABLE 1-continued

| Compound # | Structure | M + H (m/z) | retention time (min.) | method |
|---|---|---|---|---|
| 65 | 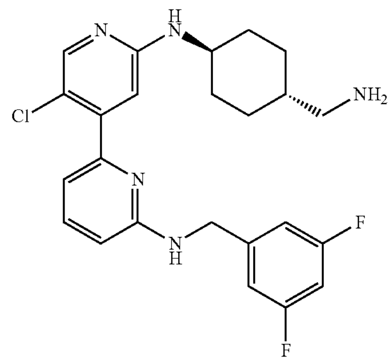 [SMILES: NC[C@H]1CC[C@H](Nc2cc(-c3cccc(NCc4cc(F)cc(F)c4)n3)c(Cl)cn2)CC1] | 458.3 | 0.66 | Example 4 |
| 66 | 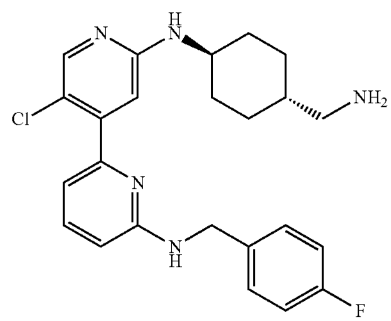 [SMILES: NC[C@H]1CC[C@H](Nc2cc(-c3cccc(NCc4ccc(F)cc4)n3)c(Cl)cn2)CC1] | 440.3 | 0.62 | Example 4 |
| 67 | 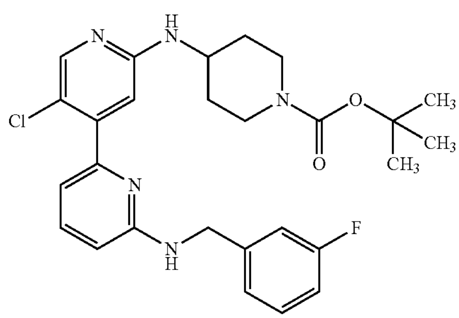 [SMILES: CC(C)(C)OC(=O)N1CCC(Nc2cc(-c3cccc(NCc4cccc(F)c4)n3)c(Cl)cn2)CC1] | 512.3 | 0.91 | Example 5 |
| 68 | 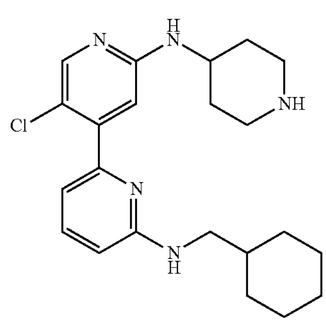 [SMILES: Clc1cnc(NC2CCNCC2)cc1-c1cccc(NCC2CCCCC2)n1] | 400.3 | 0.64 | Example 5 |

TABLE 1-continued

| Compound # | Structure | M + H (m/z) | retention time (min.) | method |
|---|---|---|---|---|
| 69 | 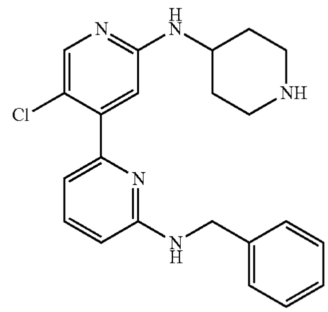 [SMILES: Clc1cnc(NC2CCNCC2)cc1-c1cccc(NCc2ccccc2)n1] | 394.3 | 0.58 | Example 5 |
| 70 | 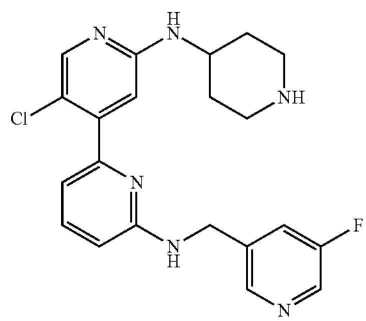 [SMILES: Fc1cncc(CNc2cccc(-c3cc(NC4CCNCC4)ncc3Cl)n2)c1] | 413.2 | 0.47 | Example 5 |
| 71 | 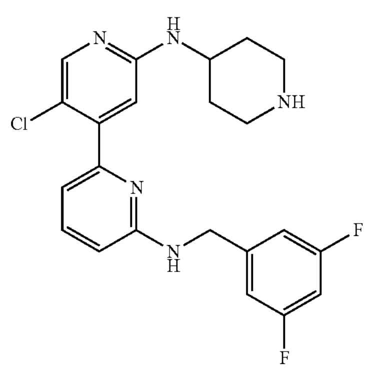 [SMILES: Fc1cc(F)cc(CNc2cccc(-c3cc(NC4CCNCC4)ncc3Cl)n2)c1] | 430.2 | 0.63 | Example 5 |
| 72 | 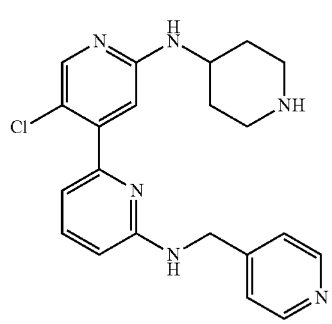 [SMILES: Clc1cnc(NC2CCNCC2)cc1-c1cccc(NCc2ccncc2)n1] | 395.2 | 0.39 | Example 5 |

TABLE 1-continued

| Compound # | Structure | M + H (m/z) | retention time (min.) | method |
|---|---|---|---|---|
| 73 | 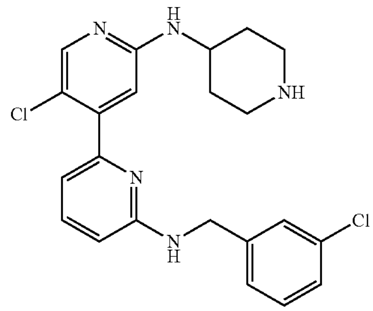 [SMILES: Clc1cccc(CNc2cccc(-c3cc(NC4CCNCC4)ncc3Cl)n2)c1] | 428.2 | 0.65 | Example 5 |
| 74 | 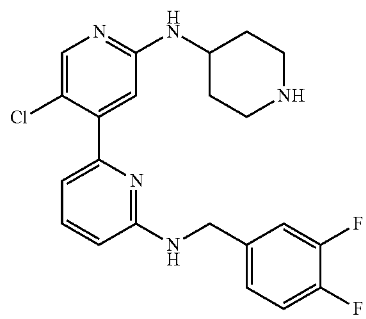 [SMILES: Fc1ccc(CNc2cccc(-c3cc(NC4CCNCC4)ncc3Cl)n2)cc1F] | 430.2 | 0.62 | Example 5 |
| 75 | 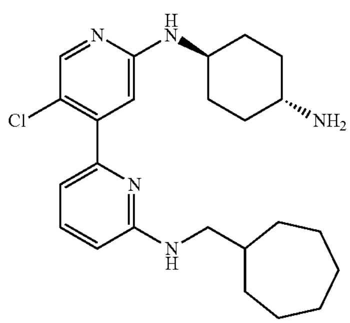 [SMILES: N[C@H]1CC[C@H](Nc2cc(-c3cccc(NCC4CCCCCC4)n3)c(Cl)cn2)CC1] | 428.4 | 0.68 | Example 1a |
| 76 | 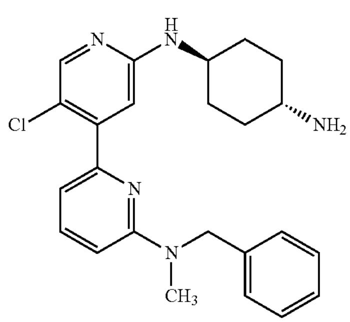 [SMILES: CN(Cc1ccccc1)c1cccc(-c2cc(N[C@H]3CC[C@H](N)CC3)ncc2Cl)n1] | 422.3 | 0.7 | Example 1a |

TABLE 1-continued

| Compound # | Structure | M + H (m/z) | retention time (min.) | method |
|---|---|---|---|---|
| 77 | 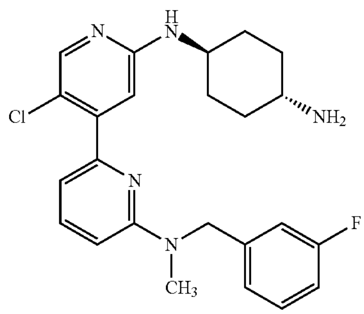 [SMILES: CN(Cc1cccc(F)c1)c1cccc(-c2cc(N[C@H]3CC[C@H](N)CC3)ncc2Cl)n1] | 440.2 | 0.73 | Example 1a |
| 78 | 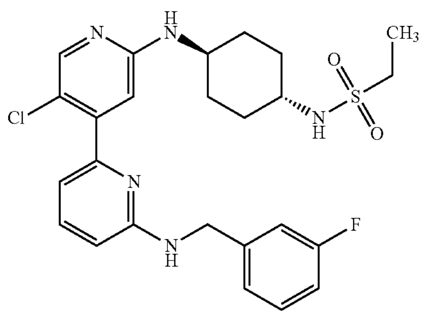 [SMILES: CCS(=O)(=O)N[C@H]1CC[C@H](Nc2cc(-c3cccc(NCc4cccc(F)c4)n3)c(Cl)cn2)CC1] | 518.3 | 0.74 | Example 6 |
| 79 | 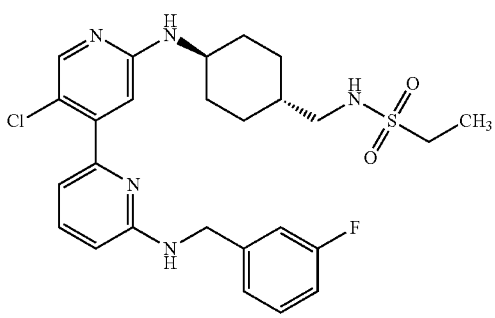 [SMILES: CCS(=O)(=O)NC[C@H]1CC[C@H](Nc2cc(-c3cccc(NCc4cccc(F)c4)n3)c(Cl)cn2)CC1] | 532.3 | 0.77 | Example 6 |
| 80 | 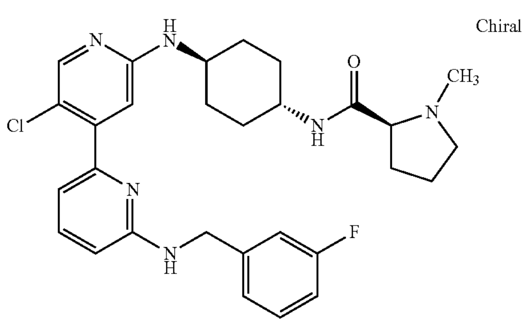 [SMILES: CN1CCC[C@H]1C(=O)N[C@H]1CC[C@H](Nc2cc(-c3cccc(NCc4cccc(F)c4)n3)c(Cl)cn2)CC1] | 537.3 | 0.63 | Example 7 |
| 81 | 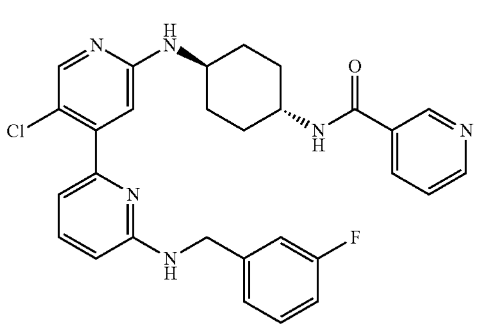 [SMILES: O=C(N[C@H]1CC[C@H](Nc2cc(-c3cccc(NCc4cccc(F)c4)n3)c(Cl)cn2)CC1)c1cccnc1] | 531.3 | 0.64 | Example 7 |

TABLE 1-continued

| Compound # | Structure | M + H (m/z) | retention time (min.) | method |
|---|---|---|---|---|
| 82 | 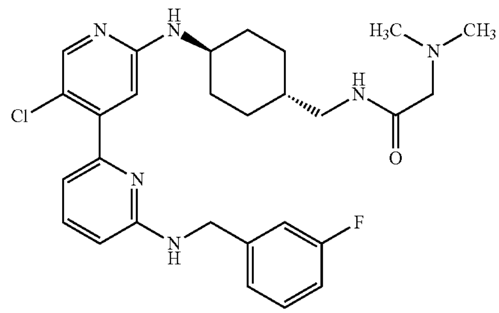 [SMILES: CN(C)CC(=O)NC[C@H]1CC[C@H](Nc2cc(-c3cccc(NCc4cccc(F)c4)n3)c(Cl)cn2)CC1] | 525.3 | 0.64 | Example 7 |
| 83 | Chiral | 551.3 | 0.65 | Example 7 |
| 84 | 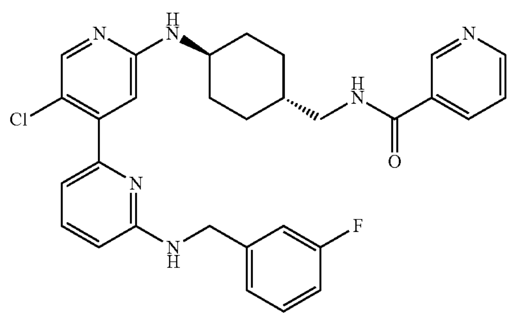 [SMILES: O=C(NC[C@H]1CC[C@H](Nc2cc(-c3cccc(NCc4cccc(F)c4)n3)c(Cl)cn2)CC1)c1cccnc1] | 545.3 | 0.66 | Example 7 |
| 85 | 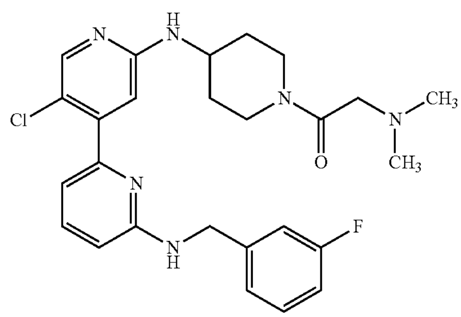 [SMILES: CN(C)CC(=O)N1CCC(Nc2cc(-c3cccc(NCc4cccc(F)c4)n3)c(Cl)cn2)CC1] | 497.3 | 0.62 | Example 7 |

TABLE 1-continued
| Compound # | Structure | M + H (m/z) | retention time (min.) | method |
|---|---|---|---|---|
| 86 | 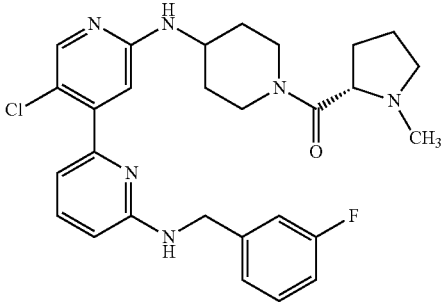 [SMILES: CN1CCC[C@H]1C(=O)N1CCC(Nc2cc(-c3cccc(NCc4cccc(F)c4)n3)c(Cl)cn2)CC1] | 523.3 | 0.63 | Example 7 |
| 87 | 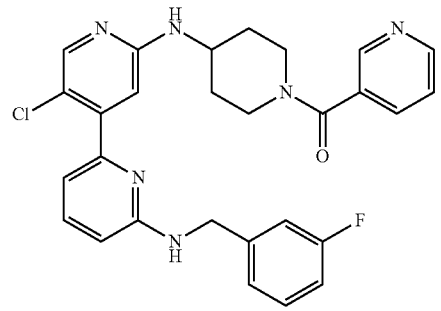 [SMILES: O=C(c1cccnc1)N1CCC(Nc2cc(-c3cccc(NCc4cccc(F)c4)n3)c(Cl)cn2)CC1] | 517.3 | 0.64 | Example 7 |
| 88 | 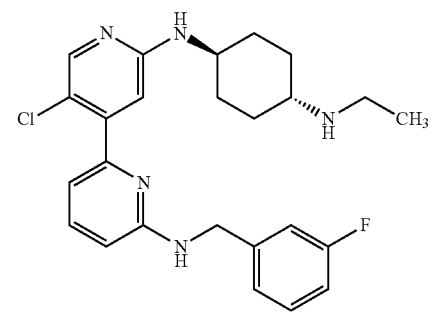 [SMILES: CCN[C@H]1CC[C@H](Nc2cc(-c3cccc(NCc4cccc(F)c4)n3)c(Cl)cn2)CC1] | 454.3 | 0.62 | Examples 1, 10 |
| 89 | 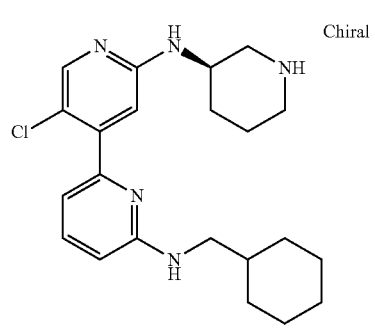 [SMILES: Clc1cnc(N[C@@H]2CCCNC2)cc1-c1cccc(NCC2CCOCC2)n1] Chiral | 400.3 | 0.65 | Example 5 |

TABLE 1-continued

| Compound # | Structure | M + H (m/z) | retention time (min.) | method |
|---|---|---|---|---|
| 90 | Chiral | 402.2 | 0.47 | Example 5 |
| 91 | Chiral | 412.2 | 0.61 | Example 5 |
| 92 | Chiral | 430.2 | 0.64 | Example 5 |
| 93 | Chiral | 395.2 | 0.41 | Example 5 |

TABLE 1-continued

| Compound # | Structure | M + H (m/z) | retention time (min.) | method |
|---|---|---|---|---|
| 94 | Chiral | 430.2 | 0.63 | Example 5 |
| 95 | Chiral | 400.3 | 0.65 | Example 5 |
| 96 | Chiral | 402.2 | 0.47 | Example 5 |
| 97 | Chiral | 412.2 | 0.61 | Example 5 |

TABLE 1-continued

| Compound # | Structure | | M + H (m/z) | retention time (min.) | method |
|---|---|---|---|---|---|
| 98 | 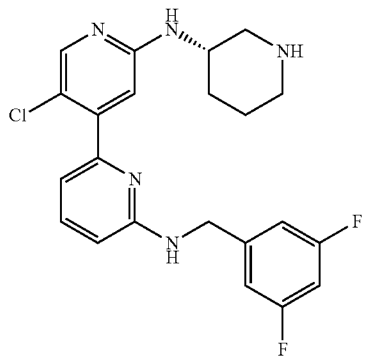 | Chiral | 430.2 | 0.64 | Example 5 |
| 99 | 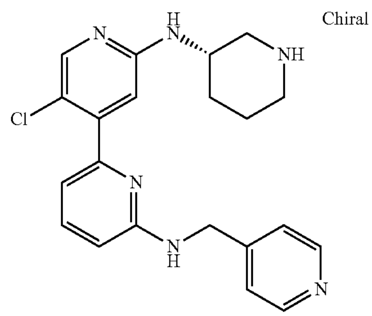 [SMILES: Clc1cnc(N[C@H]2CCCNC2)cc1-c1cccc(NCc2ccncc2)n1] | Chiral | 395.2 | 0.41 | Example 5 |
| 100 | 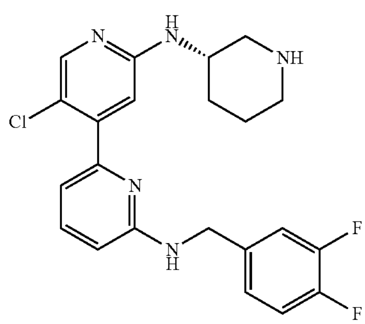 | Chiral | 430.2 | 0.64 | Example 5 |
| 101 | 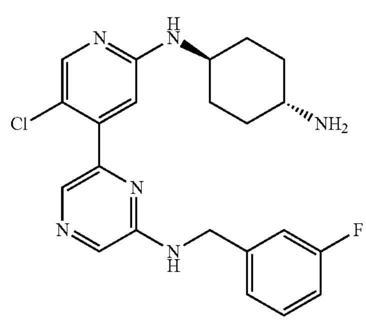 | | 427.2 | 0.6 | Example 10 |

TABLE 1-continued

| Compound # | Structure | M + H (m/z) | retention time (min.) | method |
|---|---|---|---|---|
| 102 | 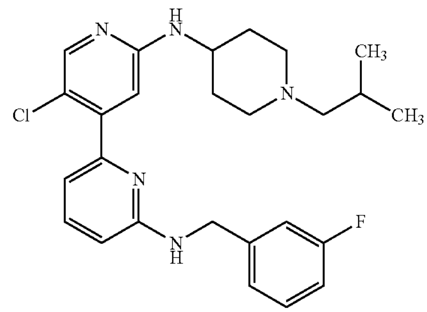 [SMILES: CC(C)CN1CCC(Nc2cc(-c3cccc(NCc4cccc(F)c4)n3)c(Cl)cn2)CC1] | 468.3 | 0.67 | Examples 5, 10 |
| 103 | 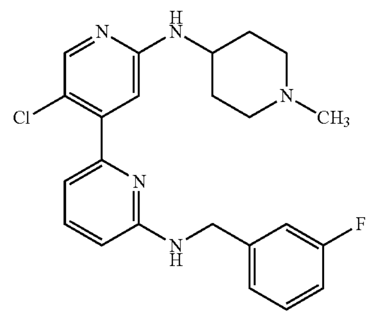 [SMILES: CN1CCC(Nc2cc(-c3cccc(NCc4cccc(F)c4)n3)c(Cl)cn2)CC1] | 426.2 | 0.61 | Examples 5, 10 |
| 104 | Chiral | 402.3 | 0.46 | Example 1a |
| 105 | 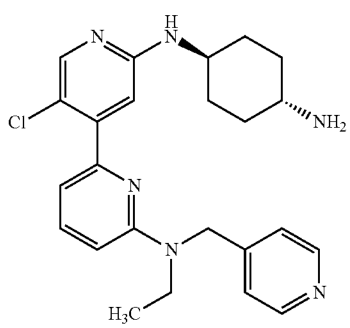 [SMILES: CCN(Cc1ccncc1)c1cccc(-c2cc(N[C@H]3CC[C@H](N)CC3)ncc2Cl)n1] | 437.3 | 0.53 | Example 1a |
| 106 | Chiral | 402.3 | 0.46 | Example 1a |

TABLE 1-continued

| Compound # | Structure | M + H (m/z) | retention time (min.) | method |
|---|---|---|---|---|
| 107 | | 416.3 | 0.47 | Example 1a |
| 105 | 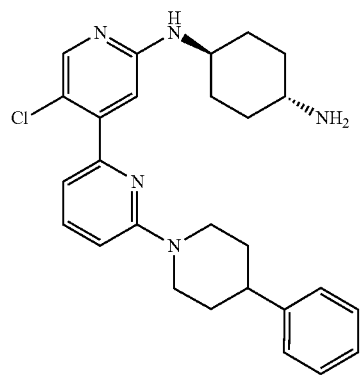 [SMILES: N[C@H]1CC[C@H](Nc2cc(-c3cccc(N4CCC(c5ccccc5)CC4)n3)c(Cl)cn2)CC1] | 462.3 | 0.78 | Example 1a |
| 106 | 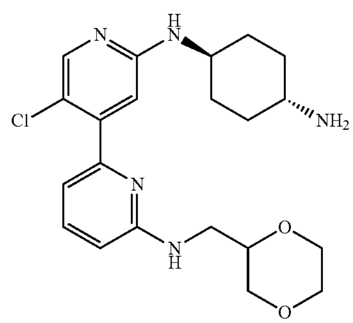 [SMILES: N[C@H]1CC[C@H](Nc2cc(-c3cccc(NCC4COCCO4)n3)c(Cl)cn2)CC1] | 418.3 | 0.43 | Example 1a |
| 107 | | 427.3 | 0.75 | Example 9 |

TABLE 1-continued

| Compound # | Structure | M + H (m/z) | retention time (min.) | method |
|---|---|---|---|---|
| 108 | 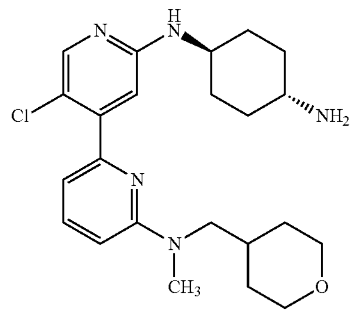 [SMILES: CN(CC1CCOCC1)c1cccc(-c2cc(N[C@H]3CC[C@H](N)CC3)ncc2Cl)n1] | 430.3 | 0.54 | Example 1a |
| 109 | 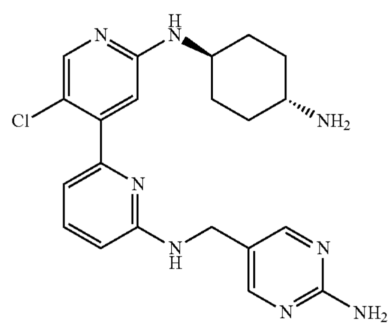 [SMILES: Nc1ncc(CNc2cccc(-c3cc(N[C@H]4CC[C@H](N)CC4)ncc3Cl)n2)cn1] | 425.3 | 0.39 | Example 1a |
| 110 | 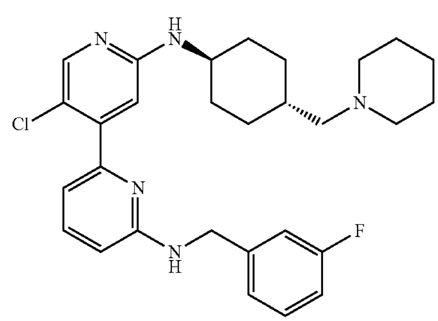 [SMILES: Fc1cccc(CNc2cccc(-c3cc(N[C@H]4CC[C@H](CN5CCCCC5)CC4)ncc3Cl)n2)c1] | 508.2 | 0.68 | Example 1b, intermediate B |
| 111 | 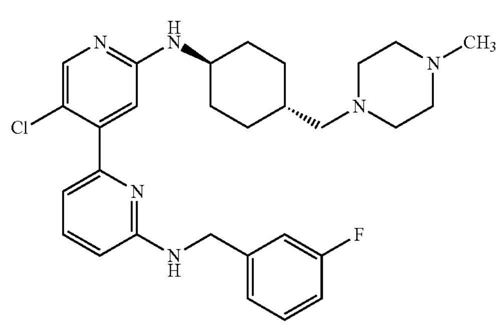 [SMILES: CN1CCN(C[C@H]2CC[C@H](Nc3cc(-c4cccc(NCc5cccc(F)c5)n4)c(Cl)cn3)CC2)CC1] | 523.3 | 0.6 | Example 1b, intermediate B |

TABLE 1-continued

| Compound # | Structure | M + H (m/z) | retention time (min.) | method |
|---|---|---|---|---|
| 112 | 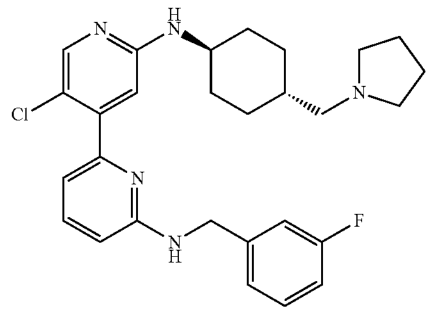 [SMILES: Fc1cccc(CNc2cccc(-c3cc(N[C@H]4CC[C@H](CN5CCCC5)CC4)ncc3Cl)n2)c1] | 494.2 | 0.67 | Example 1b, intermediate B |
| 113 | 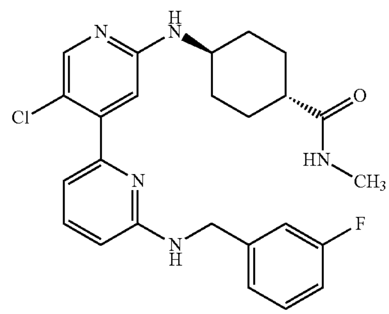 [SMILES: CNC(=O)[C@H]1CC[C@H](Nc2cc(-c3cccc(NCc4cccc(F)c4)n3)c(Cl)cn2)CC1] | 468.2 | 0.67 | Example 1b, intermediate B |
| 114 | 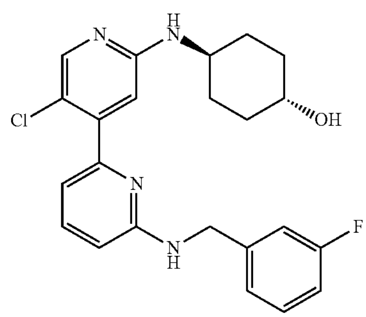 [SMILES: O[C@H]1CC[C@H](Nc2cc(-c3cccc(NCc4cccc(F)c4)n3)c(Cl)cn2)CC1] | 427.2 | 0.66 | Example 1b, intermediate B |
| 115 | 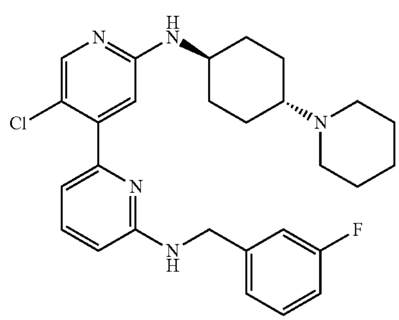 [SMILES: Fc1cccc(CNc2cccc(-c3cc(N[C@H]4CC[C@H](N5CCCCC5)CC4)ncc3Cl)n2)c1] | 494.2 | 0.64 | Example 1b, intermediate B |
| 116 | 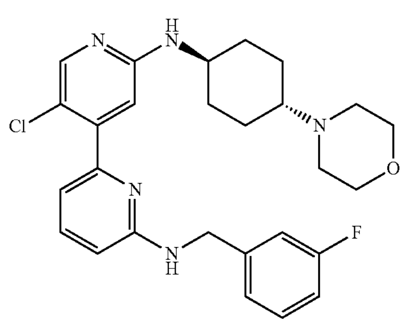 [SMILES: Fc1cccc(CNc2cccc(-c3cc(N[C@H]4CC[C@H](N5CCOCC5)CC4)ncc3Cl)n2)c1] | 496.2 | 0.62 | Example 1b, intermediate B |

TABLE 1-continued

| Compound # | Structure | M + H (m/z) | retention time (min.) | method |
|---|---|---|---|---|
| 117 | 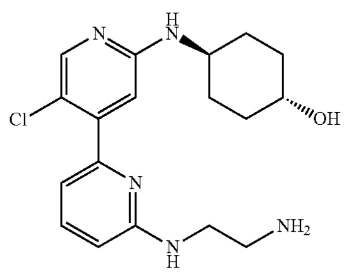 [SMILES: NCCNc1cccc(-c2cc(N[C@H]3CC[C@H](O)CC3)ncc2Cl)n1] | 362.3 | 0.38 | Example 8 |
| 118 | 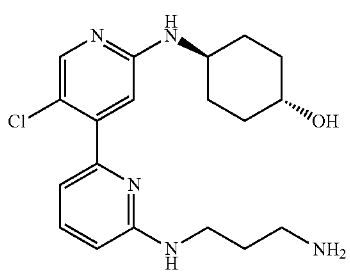 [SMILES: NCCCNc1cccc(-c2cc(N[C@H]3CC[C@H](O)CC3)ncc2Cl)n1] | 376.3 | 0.37 | Example 8 |
| 119 | 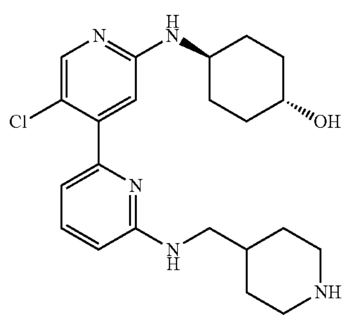 [SMILES: O[C@H]1CC[C@H](Nc2cc(-c3cccc(NCC4CCNCC4)n3)c(Cl)cn2)CC1] | 416.3 | 0.39 | Example 8 |
| 120 | 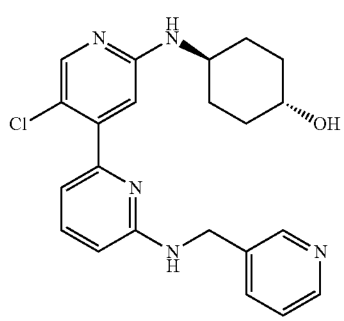 [SMILES: O[C@H]1CC[C@H](Nc2cc(-c3cccc(NCc4cccnc4)n3)c(Cl)cn2)CC1] | 410.2 | 0.42 | Example 8 |
| 121 | Chiral | 416.3 | 0.43 | Example 8 |

TABLE 1-continued

| Compound # | Structure | M + H (m/z) | retention time (min.) | method |
|---|---|---|---|---|
| 122 | 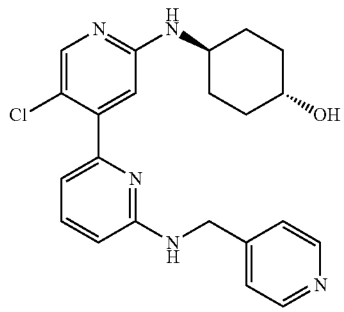 [SMILES: O[C@H]1CC[C@H](Nc2cc(-c3cccc(NCc4ccncc4)n3)c(Cl)cn2)CC1] | 410.2 | 0.42 | Example 8 |
| 123 | Chiral | 416.3 | 0.41 | Example 8 |
| 124 | 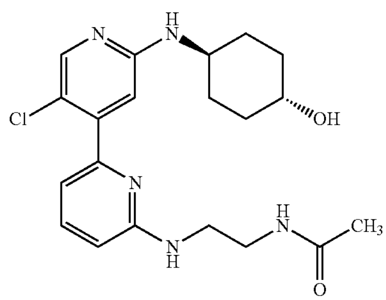 [SMILES: CC(=O)NCCNc1cccc(-c2cc(N[C@H]3CC[C@H](O)CC3)ncc2Cl)n1] | 404.2 | 0.39 | Example 8 |
| 125 | Chiral | 403.1 | 0.49 | Example 8 |
| 126 | 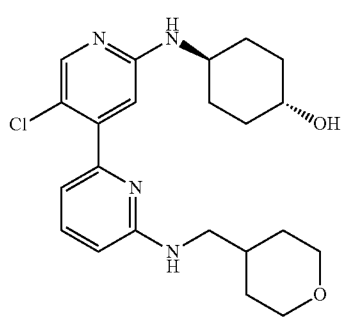 [SMILES: O[C@H]1CC[C@H](Nc2cc(-c3cccc(NCC4CCOCC4)n3)c(Cl)cn2)CC1] | 417.1 | 0.48 | Example 8 |

| Compound # | Structure | M + H (m/z) | retention time (min.) | method |
|---|---|---|---|---|
| 127 | Chiral | 403.1 | 0.49 | Example 8 |
| 128 | 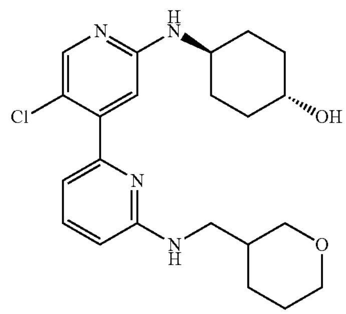 [SMILES: O[C@H]1CC[C@H](Nc2cc(-c3cccc(NCC4CCCOC4)n3)c(Cl)cn2)CC1] | 417.1 | 0.5 | Example 8 |
| 129 | 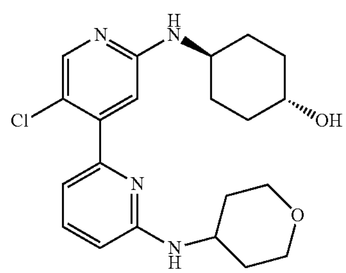 [SMILES: O[C@H]1CC[C@H](Nc2cc(-c3cccc(NC4CCOCC4)n3)c(Cl)cn2)CC1] | 403.3 | 0.47 | Example 8 |
| 130 | 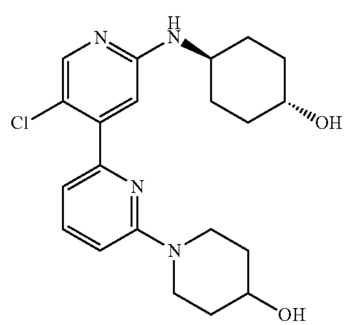 [SMILES: OC1CCN(c2cccc(-c3cc(N[C@H]4CC[C@H](O)CC4)ncc3Cl)n2)CC1] | 403.3 | 0.49 | Example 8 |
| 131 | 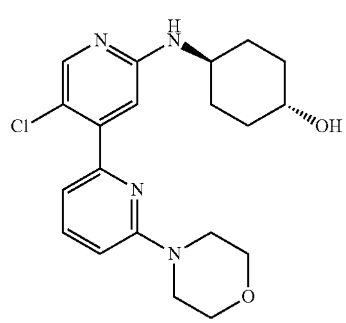 [SMILES: O[C@H]1CC[C@H](Nc2cc(-c3cccc(N4CCOCC4)n3)c(Cl)cn2)CC1] | 389.2 | 0.58 | Example 8 |

TABLE 1-continued
| Compound # | Structure | M + H (m/z) | retention time (min.) | method |
|---|---|---|---|---|
| 132 | 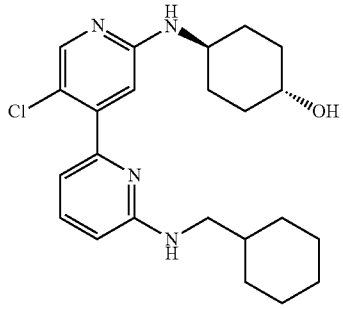 [SMILES: O[C@H]1CC[C@H](Nc2cc(-c3cccc(NCC4CCCCC4)n3)c(Cl)cn2)CC1] | 415.2 | 0.7 | Example 8 |
| 133 | 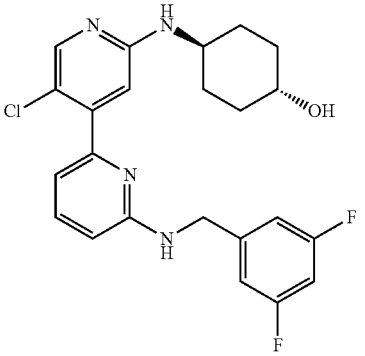 [SMILES: O[C@H]1CC[C@H](Nc2cc(-c3cccc(NCc4cc(F)cc(F)c4)n3)c(Cl)cn2)CC1] | 445.2 | 0.71 | Example 8 |
| 134 | 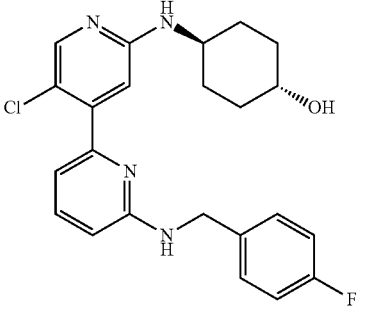 [SMILES: O[C@H]1CC[C@H](Nc2cc(-c3cccc(NCc4ccc(F)cc4)n3)c(Cl)cn2)CC1] | 427.2 | 0.66 | Example 8 |
| 135 | 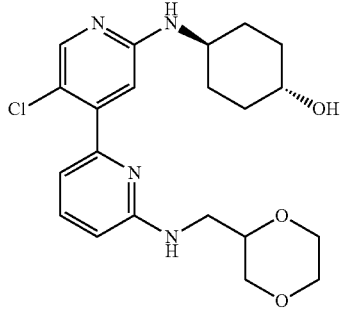 [SMILES: O[C@H]1CC[C@H](Nc2cc(-c3cccc(NCC4COCCO4)n3)c(Cl)cn2)CC1] | 419.3 | 0.47 | Example 8 |

TABLE 1-continued

| Compound # | Structure | M + H (m/z) | retention time (min.) | method |
|---|---|---|---|---|
| 136 | 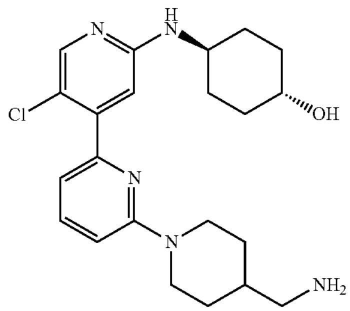 [SMILES: NCC1CCN(c2cccc(-c3cc(N[C@H]4CC[C@H](O)CC4)ncc3Cl)n2)CC1] | 416.3 | 0.45 | Example 8 |
| 137 | Chiral | 451.2 | 0.67 | Example 14 |
| 138 | Chiral | 469.1 | 0.56 | Example 15 |
| 139 | 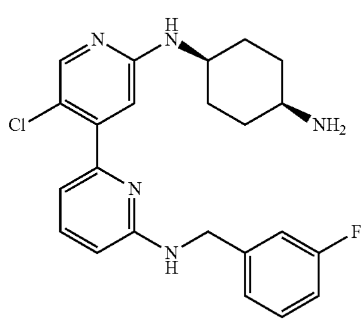 [SMILES: N[C@H]1CC[C@@H](Nc2cc(-c3cccc(NCc4cccc(F)c4)n3)c(Cl)cn2)CC1] | 426.3 | 0.61 | Example 1b |

TABLE 1-continued
| Compound # | Structure | M + H (m/z) | retention time (min.) | method |
|---|---|---|---|---|
| 140 | 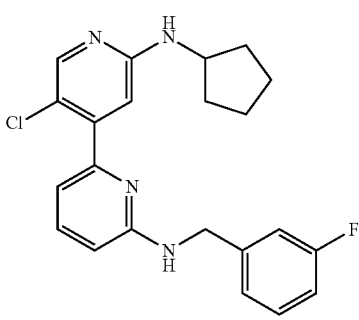 [SMILES: Fc1cccc(CNc2cccc(-c3cc(NC4CCCC4)ncc3Cl)n2)c1] | 397.3 | 0.81 | Example 1b |
| 141 | 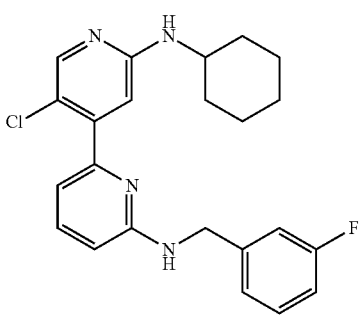 [SMILES: Fc1cccc(CNc2cccc(-c3cc(NC4CCCCC4)ncc3Cl)n2)c1] | 411.3 | 0.86 | Example 1b |
| 142 | 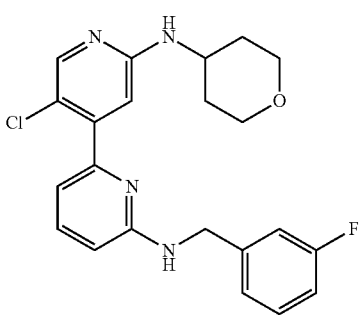 [SMILES: Fc1cccc(CNc2cccc(-c3cc(NC4CCOCC4)ncc3Cl)n2)c1] | 413.2 | 0.71 | Example 1b |
| 143 | 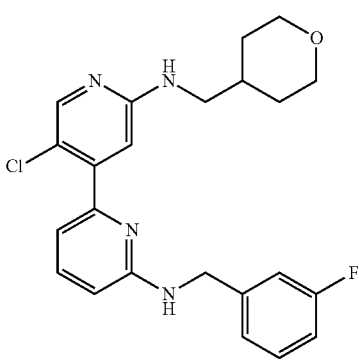 [SMILES: Fc1cccc(CNc2cccc(-c3cc(NCC4CCOCC4)ncc3Cl)n2)c1] | 427.2 | 0.72 | Example 1b |

TABLE 1-continued
| Compound # | Structure | M + H (m/z) | retention time (min.) | method |
|---|---|---|---|---|
| 144 | 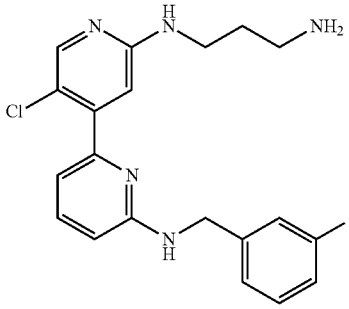 | 386.2 | 0.57 | Example 1b |
| 145 | 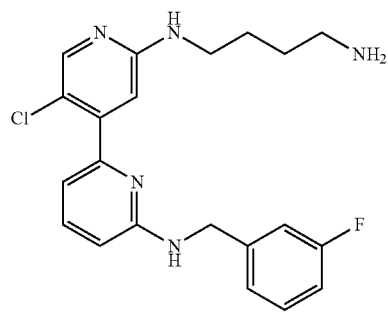 [SMILES: NCCCCNc1cc(-c2cccc(NCc3cccc(F)c3)n2)c(Cl)cn1] | 400.3 | 0.58 | Example 1b |
| 146 | 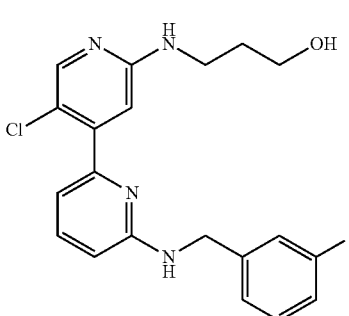 | 387.2 | 0.62 | Example 1b |
| 147 | 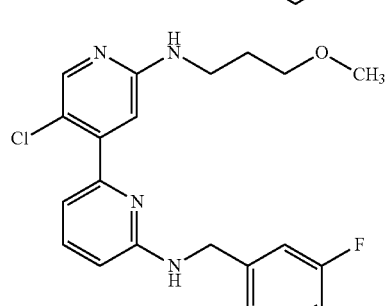 | 401.2 | 0.71 | Example 1b |
| 148 | 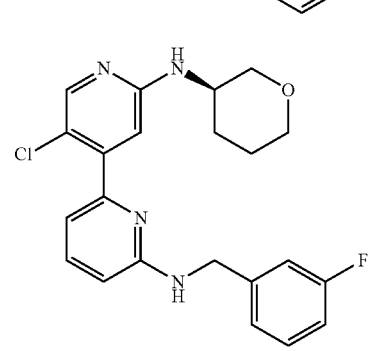 Chiral | 413.2 | 0.7 | Example 1b |

TABLE 1-continued

| Compound # | Structure | | M + H (m/z) | retention time (min.) | method |
|---|---|---|---|---|---|
| 149 | 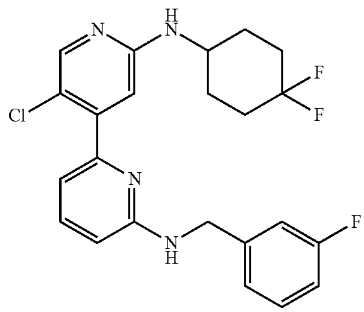 [SMILES: Fc1cccc(CNc2cccc(-c3cc(NC4CCC(F)(F)CC4)ncc3Cl)n2)c1] | | 447.3 | 0.87 | Example 1b |
| 150 | 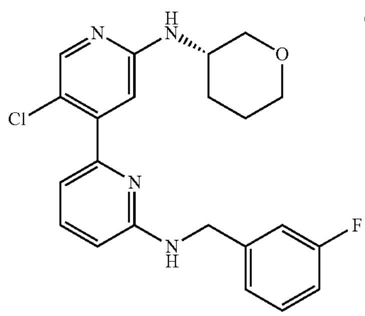 | Chiral | 413.2 | 0.69 | Example 1b |
| 151 | 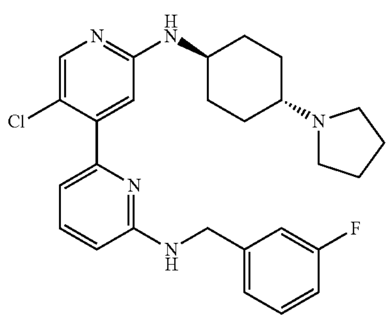 [SMILES: Fc1cccc(CNc2cccc(-c3cc(N[C@H]4CC[C@H](N5CCCC5)CC4)ncc3Cl)n2)c1] | | 481.2 | 0.63 | Example 1b |
| 152 | 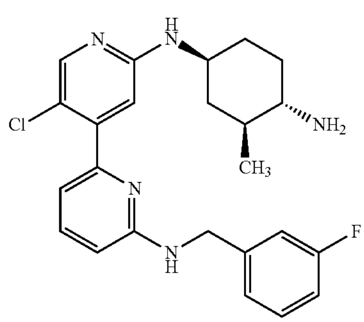 [SMILES: C[C@H]1C[C@@H](Nc2cc(-c3cccc(NCc4cccc(F)c4)n3)c(Cl)cn2)CC[C@@H]1N] | | 404.1 | 0.62 | Example 32 |

TABLE 1-continued

| Compound # | Structure | M + H (m/z) | retention time (min.) | method |
|---|---|---|---|---|
| 153 | 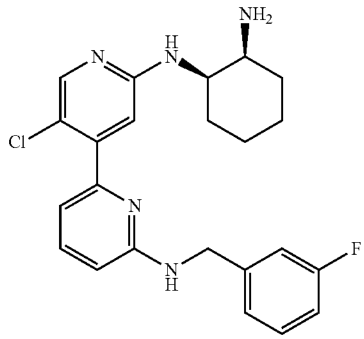 [SMILES: N[C@H]1CCCC[C@H]1Nc1cc(-c2cccc(NCc3cccc(F)c3)n2)c(Cl)cn1] | 426.1 | 0.67 | Example 1b |
| 154 | 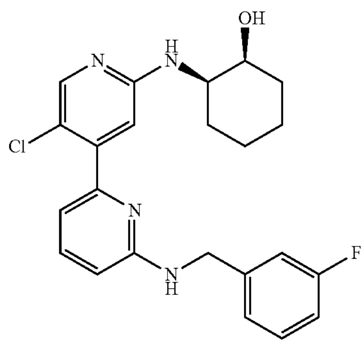 [SMILES: O[C@H]1CCCC[C@H]1Nc1cc(-c2cccc(NCc3cccc(F)c3)n2)c(Cl)cn1] | 471 | 0.75 | Example 1b |
| 155 | 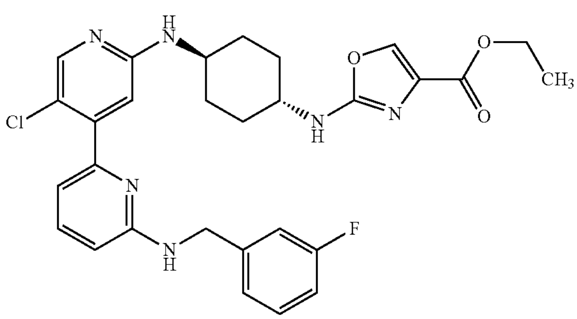 [SMILES: CCOC(=O)c1coc(N[C@H]2CC[C@H](Nc3cc(-c4cccc(NCc5cccc(F)c5)n4)c(Cl)cn3)CC2)n1] | 565.2 | 0.85 | Example 26 |
| 156 | 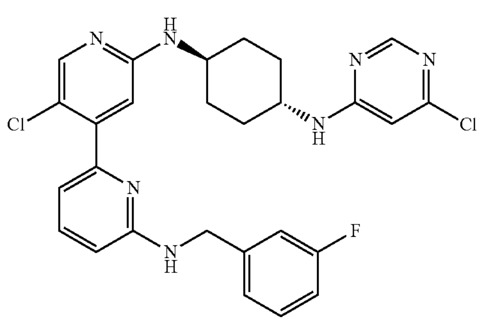 [SMILES: Fc1cccc(CNc2cccc(-c3cc(N[C@H]4CC[C@H](Nc5cc(Cl)ncn5)CC4)ncc3Cl)n2)c1] | 538.1 | 0.82 | Example 27 |

TABLE 1-continued

| Compound # | Structure | M + H (m/z) | retention time (min.) | method |
|---|---|---|---|---|
| 157 | 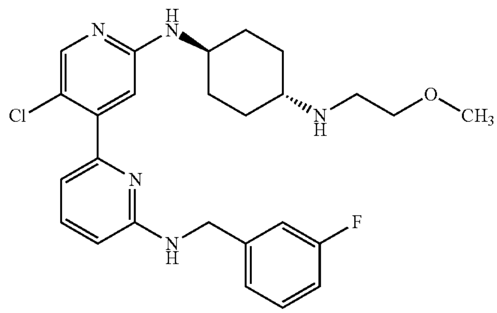 [SMILES: COCCN[C@H]1CC[C@H](Nc2cc(-c3cccc(NCc4cccc(F)c4)n3)c(Cl)cn2)CC1] | 484.2 | 0.63 | Example 19 |
| 158 | 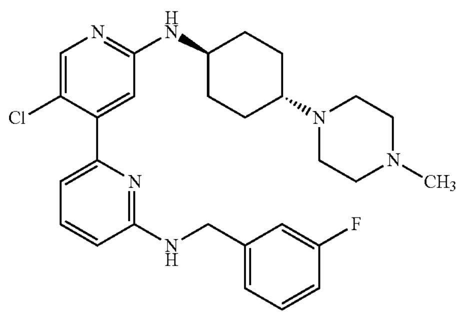 [SMILES: CN1CCN([C@H]2CC[C@H](Nc3cc(-c4cccc(NCc5cccc(F)c5)n4)c(Cl)cn3)CC2)CC1] | 509.2 | 0.58 | Example 1b |
| 159 | 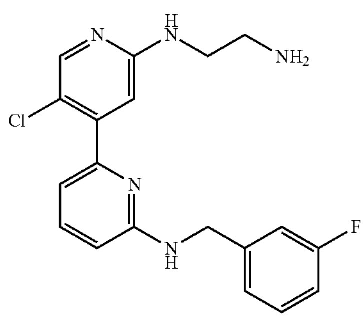 [SMILES: NCCNc1cc(-c2cccc(NCc3cccc(F)c3)n2)c(Cl)cn1] | 372.2 | 0.7 | Example 1b |
| 160 | 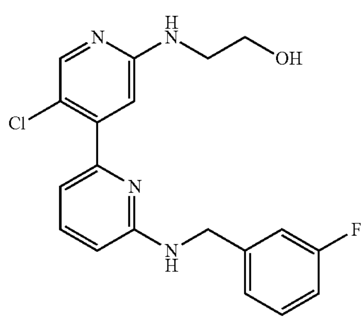 [SMILES: OCCNc1cc(-c2cccc(NCc3cccc(F)c3)n2)c(Cl)cn1] | 373.2 | 0.75 | Example 1b |
| 161 | 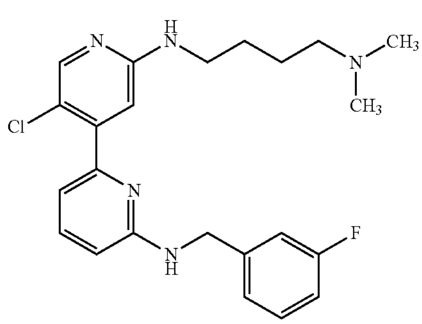 [SMILES: CN(C)CCCCNc1cc(-c2cccc(NCc3cccc(F)c3)n2)c(Cl)cn1] | 428.3 | 0.73 | Example 1b |

TABLE 1-continued

| Compound # | Structure | M + H (m/z) | retention time (min.) | method |
|---|---|---|---|---|
| 162 | 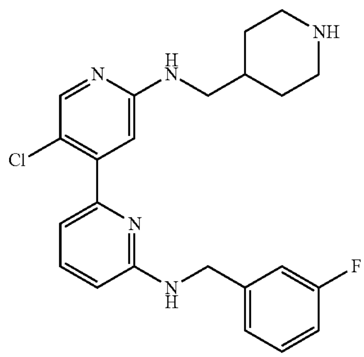 [SMILES: Fc1cccc(CNc2cccc(-c3cc(NCC4CCNCC4)ncc3Cl)n2)c1] | 426.3 | 0.73 | Example 1b, Example 8 |
| 163 | 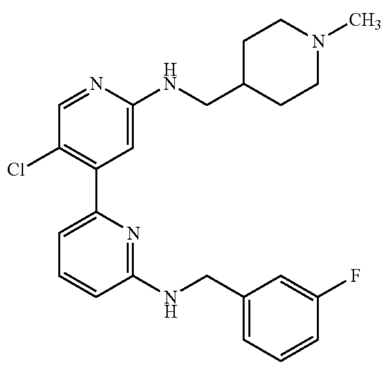 [SMILES: CN1CCC(CNc2cc(-c3cccc(NCc4cccc(F)c4)n3)c(Cl)cn2)CC1] | 440.3 | 0.73 | Example 1b |
| 164 | Chiral | 426.3 | 0.74 | Example 1b, Example 8 |
| 165 | 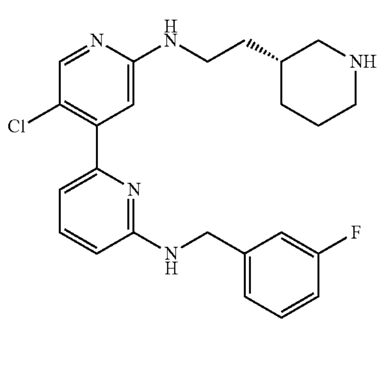 [SMILES: Fc1cccc(CNc2cccc(-c3cc(NCC[C@H]4CCCNC4)ncc3Cl)n2)c1] | 440.3 | 0.77 | Example 1b, Example 8 |

TABLE 1-continued

| Compound # | Structure | M + H (m/z) | retention time (min.) | method |
|---|---|---|---|---|
| 166 | Chiral | 426.3 | 0.76 | Example 1b, Example 8 |
| 167 | Chiral | 440.3 | 0.77 | Example 1b, Example 8 |
| 168 | 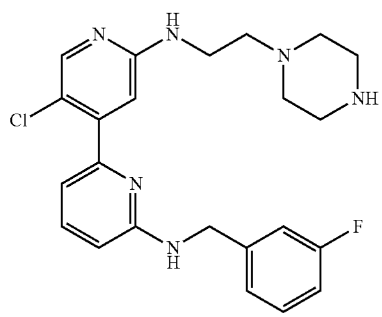 [SMILES: Fc1cccc(CNc2cccc(-c3cc(NCCN4CCNCC4)ncc3Cl)n2)c1] | 441.3 | 0.72 | Example 1b, Example 8 |
| 169 | 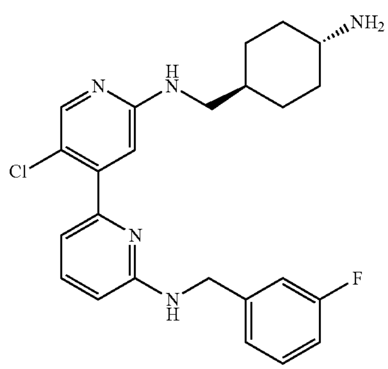 [SMILES: N[C@H]1CC[C@H](CNc2cc(-c3cccc(NCc4cccc(F)c4)n3)c(Cl)cn2)CC1] | 440.3 | 0.76 | Example 1b, Example 8 |

TABLE 1-continued

| Compound # | Structure | M + H (m/z) | retention time (min.) | method |
|---|---|---|---|---|
| 170 | 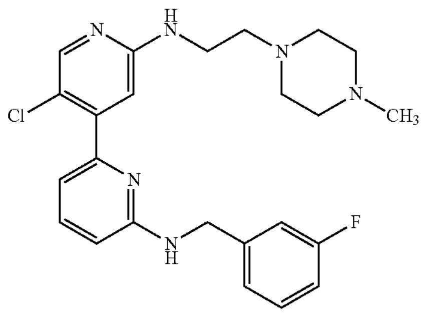 [SMILES: CN1CCN(CCNc2cc(-c3cccc(NCc4cccc(F)c4)n3)c(Cl)cn2)CC1] | 455.3 | 0.71 | Example 1b |
| 171 | 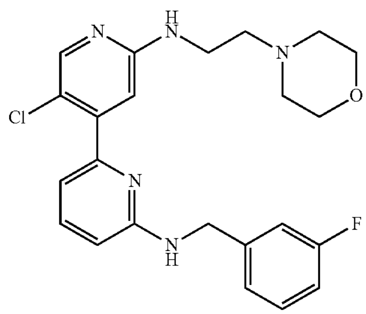 [SMILES: Fc1cccc(CNc2cccc(-c3cc(NCCN4CCOCC4)ncc3Cl)n2)c1] | 442.2 | 0.75 | Example 1b |
| 172 | 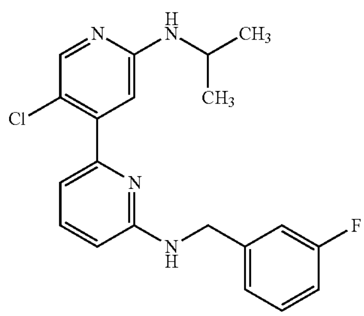 [SMILES: CC(C)Nc1cc(-c2cccc(NCc3cccc(F)c3)n2)c(Cl)cn1] | 371.2 | 0.85 | Example 1b |
| 173 | 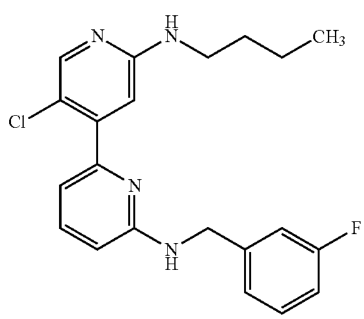 | 385.2 | 0.91 | Example 1b |
| 174 | 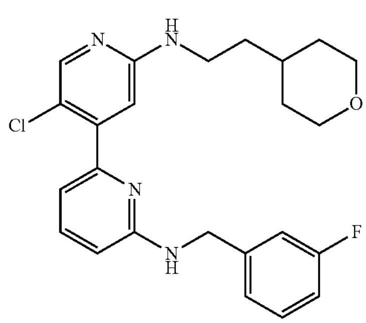 [SMILES: Fc1cccc(CNc2cccc(-c3cc(NCCC4CCOCC4)ncc3Cl)n2)c1] | 441.3 | 0.86 | Example 1b |

TABLE 1-continued

| Compound # | Structure | M + H (m/z) | retention time (min.) | method |
|---|---|---|---|---|
| 175 | 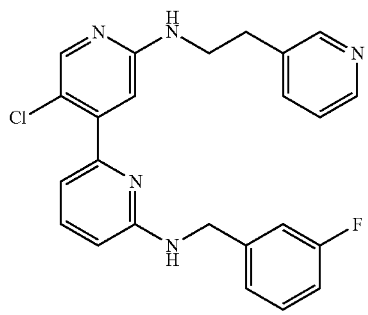 [SMILES: Fc1cccc(CNc2cccc(-c3cc(NCCc4cccnc4)ncc3Cl)n2)c1] | 434.2 | 0.74 | Example 1b |
| 176 | 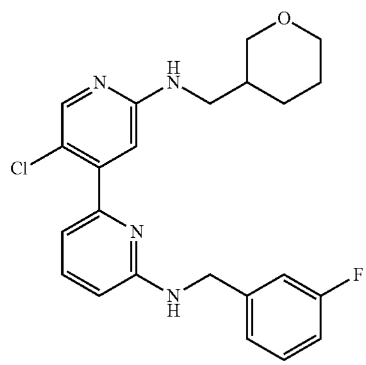 [SMILES: Fc1cccc(CNc2cccc(-c3cc(NCC4CCCOC4)ncc3Cl)n2)c1] | 427.2 | 0.85 | Example 1b |
| 177 | 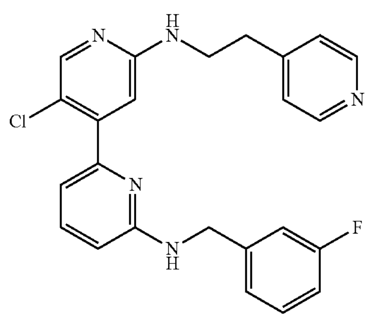 [SMILES: Fc1cccc(CNc2cccc(-c3cc(NCCc4ccncc4)ncc3Cl)n2)c1] | 434.2 | 0.73 | Example 1b |
| 178 | 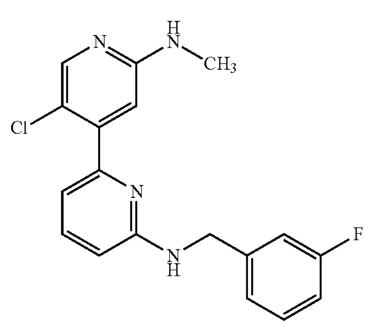 [SMILES: CNc1cc(-c2cccc(NCc3cccc(F)c3)n2)c(Cl)cn1] | 343 | 0.67 | Example 88 |

TABLE 1-continued

| Compound # | Structure | M + H (m/z) | retention time (min.) | method |
|---|---|---|---|---|
| 179 | 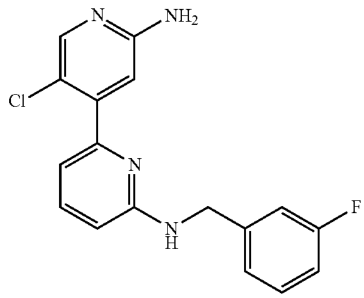 [SMILES: Nc1cc(-c2cccc(NCc3cccc(F)c3)n2)c(Cl)cn1] | 329 | 0.65 | Example 88 |
| 180 | 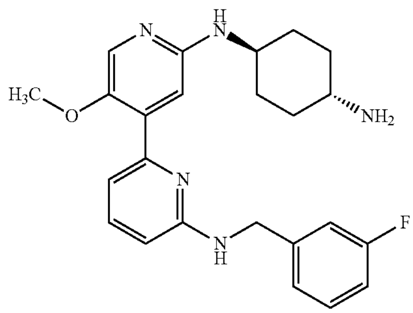 [SMILES: COc1cnc(N[C@H]2CC[C@H](N)CC2)cc1-c1cccc(NCc2cccc(F)c2)n1] | 422.3 | 0.54 | Example 69 |
| 181 | 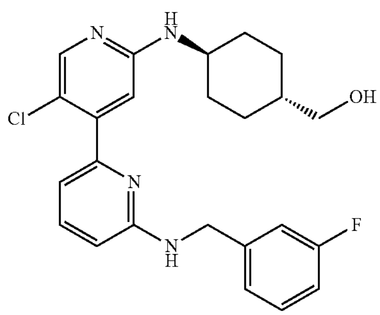 [SMILES: OC[C@H]1CC[C@H](Nc2cc(-c3cccc(NCc4cccc(F)c4)n3)c(Cl)cn2)CC1] | 441.2 | 0.71 | Example 1b |
| 182 | 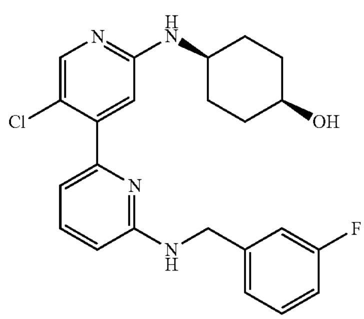 [SMILES: O[C@H]1CC[C@@H](Nc2cc(-c3cccc(NCc4cccc(F)c4)n3)c(Cl)cn2)CC1] | 427.1 | 0.69 | Example 1b |
| 183 | Chiral | 413.2 | 0.68 | Example 1b |

TABLE 1-continued

| Compound # | Structure | M + H (m/z) | retention time (min.) | method |
|---|---|---|---|---|
| 184 | Chiral | 413.2 | 0.68 | Example 1b |
| 185 | 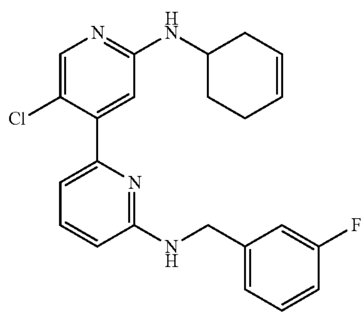 [SMILES: Fc1cccc(CNc2cccc(-c3cc(NC4CC=CCC4)ncc3Cl)n2)c1] | 409.3 | 0.83 | Example 21 |
| 186 | 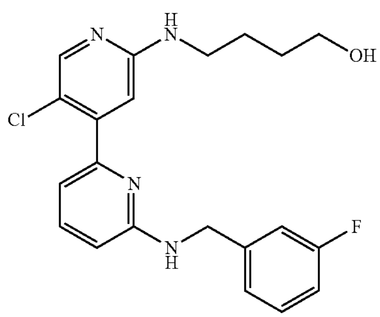 [SMILES: OCCCCNc1cc(-c2cccc(NCc3cccc(F)c3)n2)c(Cl)cn1] | 401.2 | 0.65 | Example 1b |
| 187 | 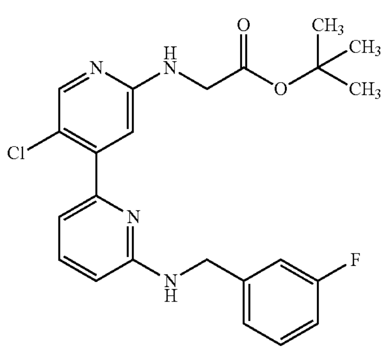 [SMILES: CC(C)(C)OC(=O)CNc1cc(-c2cccc(NCc3cccc(F)c3)n2)c(Cl)cn1] | 443.2 | 0.87 | Example 1b |

TABLE 1-continued

| Compound # | Structure | M + H (m/z) | retention time (min.) | method |
|---|---|---|---|---|
| 188 | 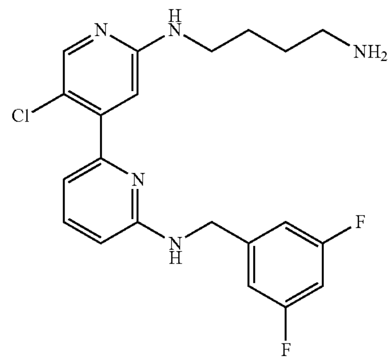 [SMILES: NCCCCNc1cc(-c2cccc(NCc3cc(F)cc(F)c3)n2)c(Cl)cn1] | 418.2 | 0.61 | Example 1b |
| 189 | 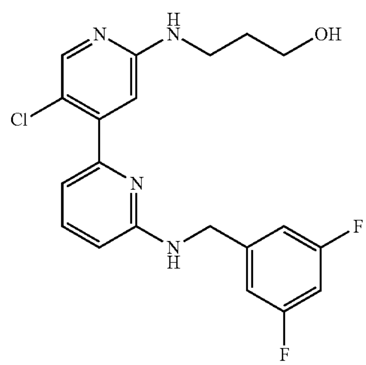 [SMILES: OCCCNc1cc(-c2cccc(NCc3cc(F)cc(F)c3)n2)c(Cl)cn1] | 405.2 | 0.68 | Example 1b |
| 190 | 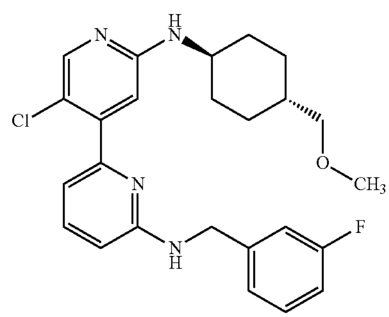 [SMILES: COC[C@H]1CC[C@H](Nc2cc(-c3cccc(NCc4cccc(F)c4)n3)c(Cl)cn2)CC1] | 455.3 | 0.8 | Example 1b |
| 191 | Chiral | 412.1 | 0.58 | Example 52 |

TABLE 1-continued

| Compound # | Structure | M + H (m/z) | retention time (min.) | method |
|---|---|---|---|---|
| 192 | (Chiral) | 412.1 | 0.58 | Example 52 |
| 193 | 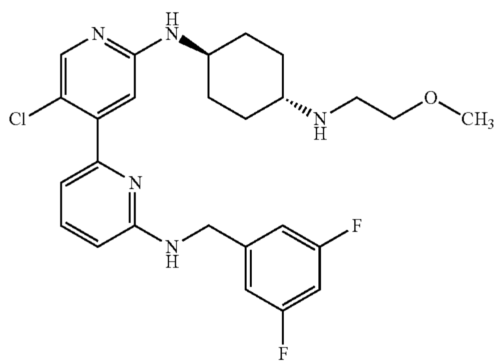 [SMILES: COCCN[C@H]1CC[C@H](Nc2cc(-c3cccc(NCc4cc(F)cc(F)c4)n3)c(Cl)cn2)CC1] | 502.1 | 0.65 | Example 19 |
| 194 | 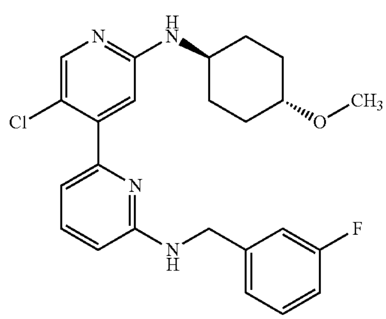 [SMILES: CO[C@H]1CC[C@H](Nc2cc(-c3cccc(NCc4cccc(F)c4)n3)c(Cl)cn2)CC1] | 441.1 | 0.75 | Example 1b |
| 195 | 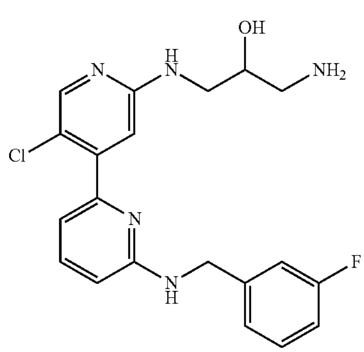 [SMILES: NCC(O)CNc1cc(-c2cccc(NCc3cccc(F)c3)n2)c(Cl)cn1] | 402.1 | 0.55 | Example 1b |

TABLE 1-continued

| Compound # | Structure | M + H (m/z) | retention time (min.) | method |
|---|---|---|---|---|
| 196 | 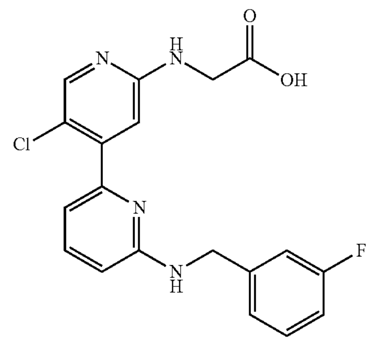 [SMILES: O=C(O)CNc1cc(-c2cccc(NCc3cccc(F)c3)n2)c(Cl)cn1] | 387.1 | 0.64 | Examples 1, 5 |
| 197 | 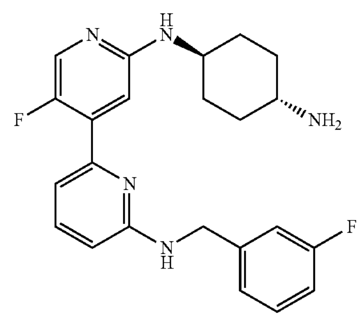 [SMILES: N[C@H]1CC[C@H](Nc2cc(-c3cccc(NCc4cccc(F)c4)n3)c(F)cn2)CC1] | 410.3 | 0.6 | Example 68 |
| 198 | 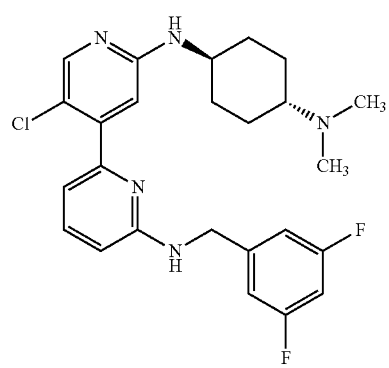 [SMILES: CN(C)[C@H]1CC[C@H](Nc2cc(-c3cccc(NCc4cc(F)cc(F)c4)n3)c(Cl)cn2)CC1] | 472.3 | 0.66 | Examples 1, 10 |
| 199 | 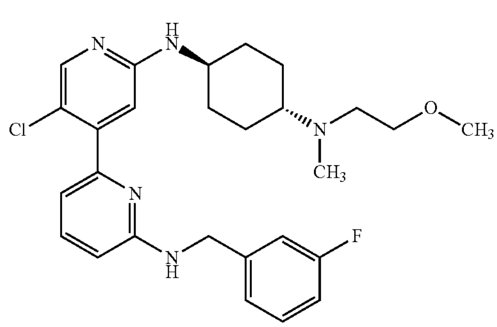 [SMILES: COCCN(C)[C@H]1CC[C@H](Nc2cc(-c3cccc(NCc4cccc(F)c4)n3)c(Cl)cn2)CC1] | 409.1 | 0.64 | Example 21 |

TABLE 1-continued

| Compound # | Structure | M + H (m/z) | retention time (min.) | method |
|---|---|---|---|---|
| 200 | 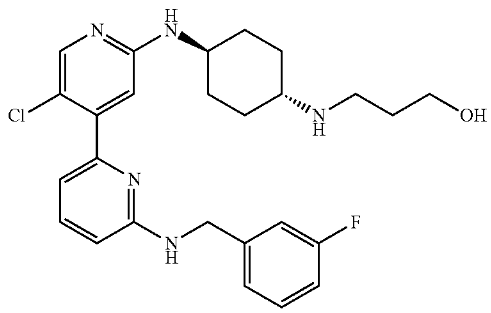 [SMILES: OCCCN[C@H]1CC[C@H](Nc2cc(-c3cccc(NCc4cccc(F)c4)n3)c(Cl)cn2)CC1] | 484.3 | 0.59 | Example 19 |
| 201 | Chiral | 441.1 | 0.73 | Example 53 |
| 202 | Chiral | 441.1 | 0.73 | Example 53 |
| 203 | 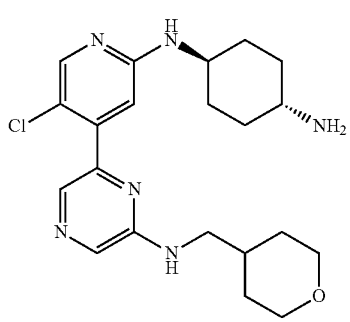 [SMILES: N[C@H]1CC[C@H](Nc2cc(-c3cncc(NCC4CCOCC4)n3)c(Cl)cn2)CC1] | 417.3 | 0.46 | Example 85 |

TABLE 1-continued

| Compound # | Structure | M + H (m/z) | retention time (min.) | method |
|---|---|---|---|---|
| 204 | Chiral | 454.2 | 0.69 | Example 53 |
| 205 | Chiral | 468.1 | 0.72 | Example 53 |
| 206 | Chiral | 549.4 | 0.67 | Example 76 |
| 207 | Chiral | 549.4 | 0.68 | Example 76 |

TABLE 1-continued

| Compound # | Structure | M + H (m/z) | retention time (min.) | method |
|---|---|---|---|---|
| 208 | 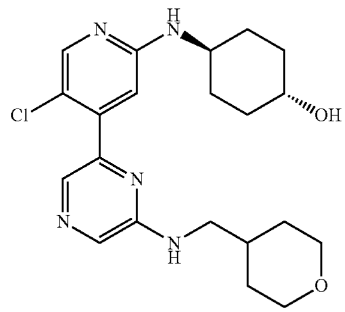 [SMILES: O[C@H]1CC[C@H](Nc2cc(-c3cncc(NCC4CCOCC4)n3)c(Cl)cn2)CC1] | 418.3 | 0.52 | Example 75 |
| 209 | 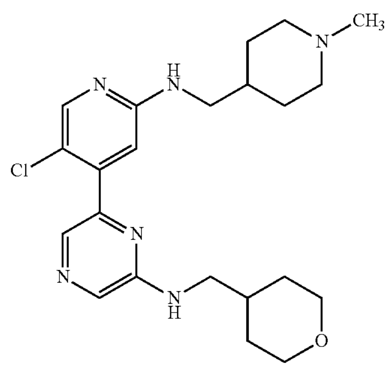 [SMILES: CN1CCC(CNc2cc(-c3cncc(NCC4CCOCC4)n3)c(Cl)cn2)CC1] | 431.3 | 0.47 | Example 85 |
| 210 | 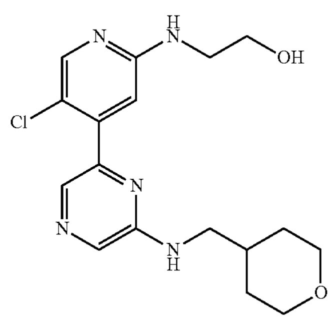 [SMILES: OCCNc1cc(-c2cncc(NCC3CCOCC3)n2)c(Cl)cn1] | 364.2 | 0.47 | Example 85 |
| 211 | 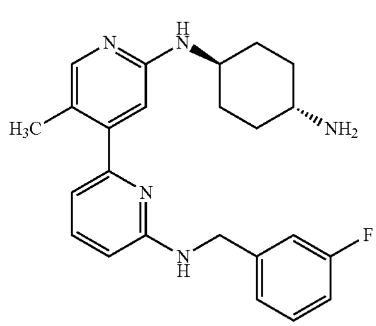 [SMILES: Cc1cnc(N[C@H]2CC[C@H](N)CC2)cc1-c1cccc(NCc2cccc(F)c2)n1] | 406.3 | 0.53 | Example 70 |

TABLE 1-continued

| Compound # | Structure | M + H (m/z) | retention time (min.) | method |
|---|---|---|---|---|
| 212 | 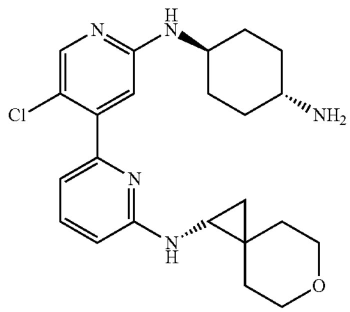 | 282.9/ 284.9 | 0.85 | Example 56 |
| 213 | Chiral | 494.2 | 0.85 | Example 53 |
| 214 | Chiral | 454.2 | 0.71 | Example 53 |
| 215 | Chiral | 457.2 | 0.46 | Example 76 |

TABLE 1-continued

| Compound # | Structure | | M + H (m/z) | retention time (min.) | method |
|---|---|---|---|---|---|
| 216 | 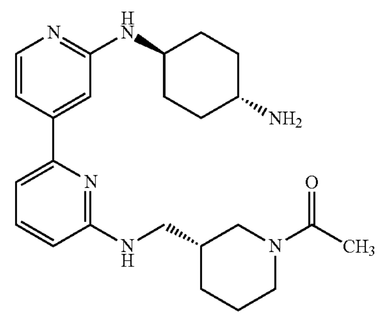 | Chiral | 423.2 | 0.45 | Example 76 |
| 217 | 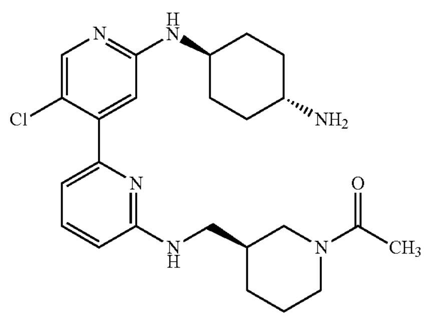 | Chiral | 457.2 | 0.47 | Example 76 |
| 218 | 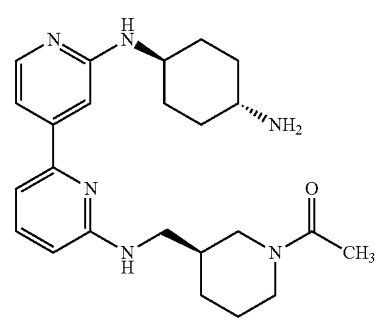 | Chiral | 423.3 | 0.45 | Example 76 |
| 219 | 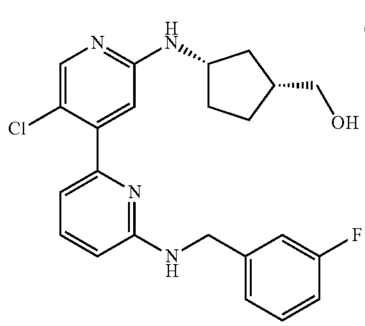 | Chiral | 427.1 | 0.7 | Example 54 |

TABLE 1-continued

| Compound # | Structure | M + H (m/z) | retention time (min.) | method |
|---|---|---|---|---|
| 220 | (Chiral) | 427.1 | 0.7 | Example 54 |
| 221 | 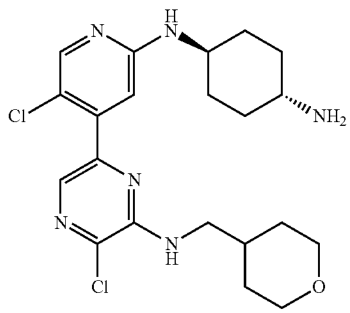 [SMILES: N[C@H]1CC[C@H](Nc2cc(-c3cnc(Cl)c(NCC4CCOCC4)n3)c(Cl)cn2)CC1] | 451.2 | 0.62 | Example 60 |
| 222 | 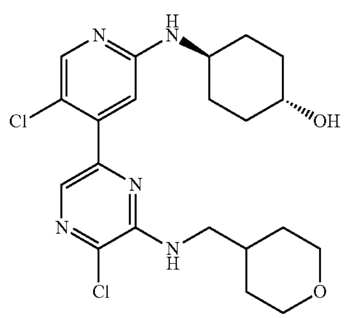 [SMILES: O[C@H]1CC[C@H](Nc2cc(-c3cnc(Cl)c(NCC4CCOCC4)n3)c(Cl)cn2)CC1] | 452.1 | 0.76 | Example 60 |
| 223 | 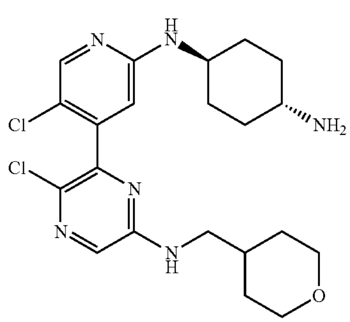 [SMILES: N[C@H]1CC[C@H](Nc2cc(-c3nc(NCC4CCOCC4)cnc3Cl)c(Cl)cn2)CC1] | 451.1 | 0.63 | Example 61 |

TABLE 1-continued

| Compound # | Structure | M + H (m/z) | retention time (min.) | method |
|---|---|---|---|---|
| 224 | 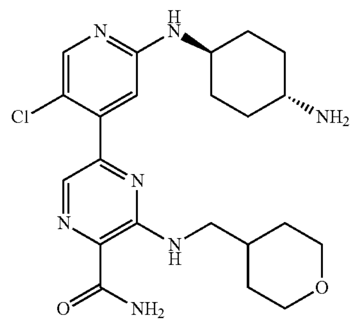 [SMILES: NC(=O)c1ncc(-c2cc(N[C@H]3CC[C@H](N)CC3)ncc2Cl)nc1NCC1CCOCC1] | 460 | 0.54 | Example 33 |
| 225 | 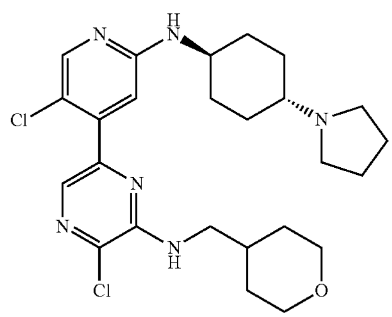 [SMILES: Clc1cnc(N[C@H]2CC[C@H](N3CCCC3)CC2)cc1-c1cnc(Cl)c(NCC2CCOCC2)n1] | 505.2 | 0.64 | Example 62 |
| 226 | 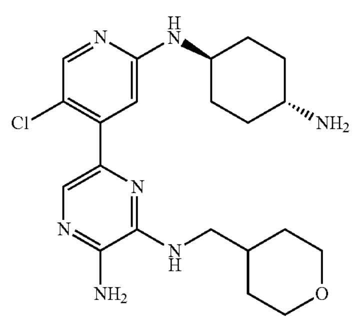 [SMILES: Nc1ncc(-c2cc(N[C@H]3CC[C@H](N)CC3)ncc2Cl)nc1NCC1CCOCC1] | 432.1 | 0.41 | Example 63 |
| 227 | 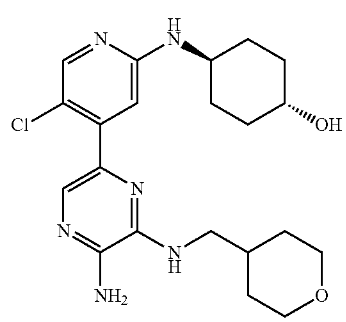 [SMILES: Nc1ncc(-c2cc(N[C@H]3CC[C@H](O)CC3)ncc2Cl)nc1NCC1CCOCC1] | 433.1 | 0.45 | Example 63 |

TABLE 1-continued

| Compound # | Structure | M + H (m/z) | retention time (min.) | method |
|---|---|---|---|---|
| 228 | 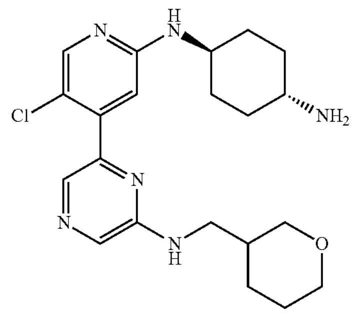 [SMILES: N[C@H]1CC[C@H](Nc2cc(-c3cncc(NCC4CCCOC4)n3)c(Cl)cn2)CC1] | 417.2 | 0.51 | Example 77 |
| 229 | 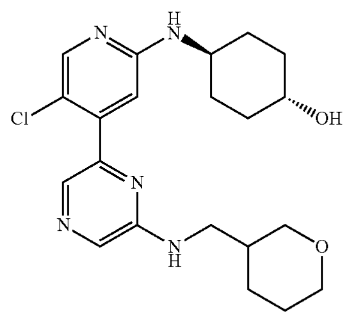 [SMILES: O[C@H]1CC[C@H](Nc2cc(-c3cncc(NCC4CCCOC4)n3)c(Cl)cn2)CC1] | 418.2 | 0.56 | Example 77 |
| 230 | 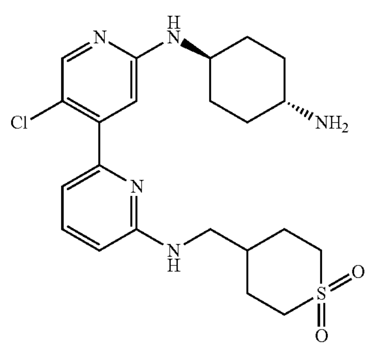 [SMILES: N[C@H]1CC[C@H](Nc2cc(-c3cccc(NCC4CCS(=O)(=O)CC4)n3)c(Cl)cn2)CC1] | 464.1/ 466.1 | 0.44 | Example 57 |
| 231 | 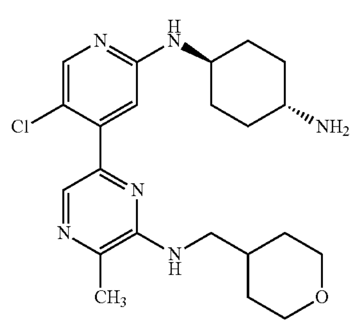 [SMILES: Cc1ncc(-c2cc(N[C@H]3CC[C@H](N)CC3)ncc2Cl)nc1NCC1CCOCC1] | 431.2 | 0.49 | Example 34 |

TABLE 1-continued

| Compound # | Structure | M + H (m/z) | retention time (min.) | method |
|---|---|---|---|---|
| 232 | 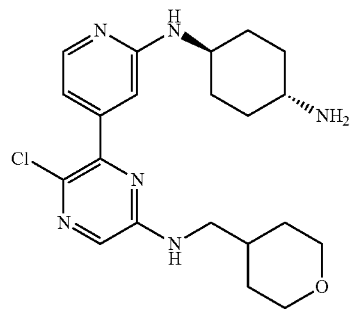 [SMILES: N[C@H]1CC[C@H](Nc2cc(-c3nc(NCC4CCOCC4)cnc3Cl)ccn2)CC1] | 417.2 | 0.47 | Example 61 |
| 233 | 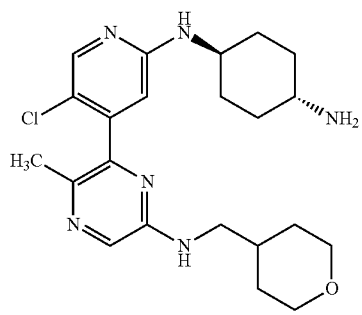 [SMILES: Cc1ncc(NCC2CCOCC2)nc1-c1cc(N[C@H]2CC[C@H](N)CC2)ncc1Cl] | 431.2 | 0.47 | Example 64 |
| 234 | 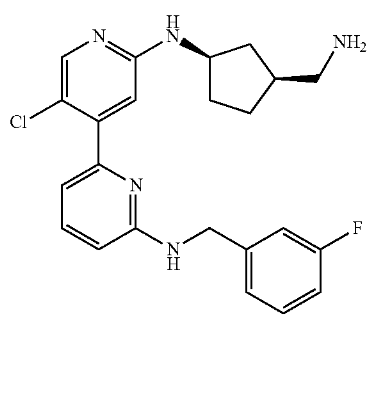 | 426.2 | 0.62 | Example 54 |
| 235 | 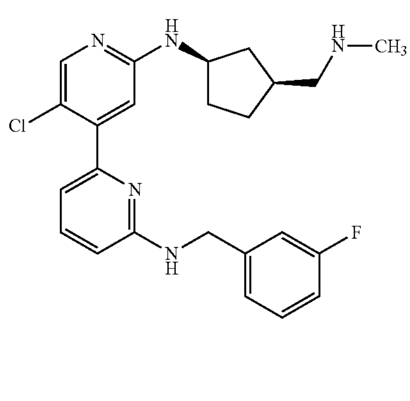 | 440.2 | 0.62 | Example 54 |

TABLE 1-continued

| Compound # | Structure | | M + H (m/z) | retention time (min.) | method |
|---|---|---|---|---|---|
| 236 | (structure) | Chiral | 454.2 | 0.64 | Example 54 |
| 237 | (structure) | Chiral | 426.2 | 0.62 | Example 54 |
| 238 | (structure) | Chiral | 440.2 | 0.61 | Example 54 |
| 239 | (structure) | Chiral | 454.2 | 0.62 | Example 54 |

TABLE 1-continued

| Compound # | Structure | M + H (m/z) | retention time (min.) | method |
|---|---|---|---|---|
| 240 | 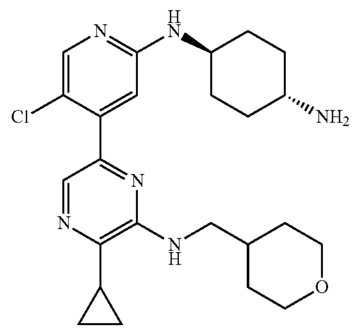 [SMILES: N[C@H]1CC[C@H](Nc2cc(-c3cnc(C4CC4)c(NCC4CCOCC4)n3)c(Cl)cn2)CC1] | 457.2 | 0.6 | Example 35 |
| 241 | 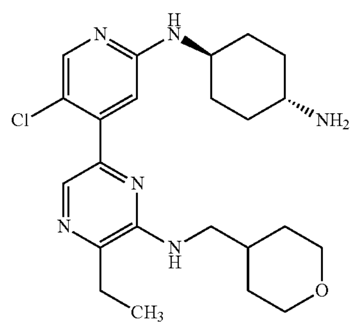 [SMILES: CCc1ncc(-c2cc(N[C@H]3CC[C@H](N)CC3)ncc2Cl)nc1NCC1CCOCC1] | 445.2 | 0.54 | Example 36 |
| 242 | 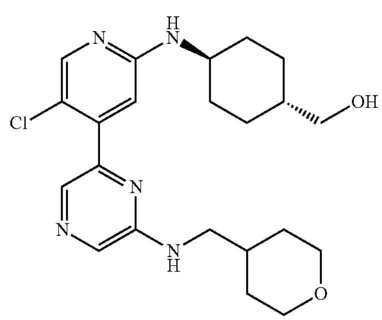 [SMILES: OC[C@H]1CC[C@H](Nc2cc(-c3cncc(NCC4CCOCC4)n3)c(Cl)cn2)CC1] | 432.2 | 0.56 | Example 75 |
| 243 | 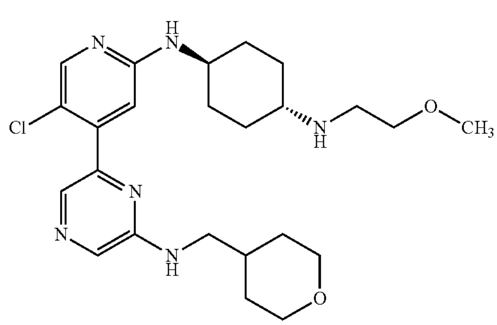 [SMILES: COCCN[C@H]1CC[C@H](Nc2cc(-c3cncc(NCC4CCOCC4)n3)c(Cl)cn2)CC1] | 475.2 | 0.51 | Example 86 |

TABLE 1-continued

| Compound # | Structure | M + H (m/z) | retention time (min.) | method |
|---|---|---|---|---|
| 244 | 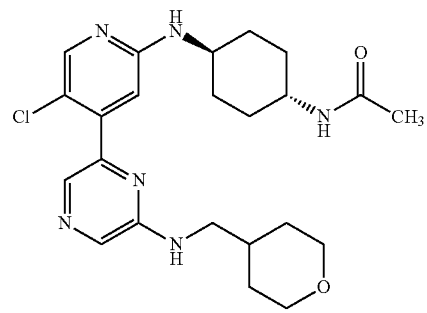 [SMILES: CC(=O)N[C@H]1CC[C@H](Nc2cc(-c3cncc(NCC4CCOCC4)n3)c(Cl)cn2)CC1] | 459.2 | 0.54 | Example 78 |
| 245 | 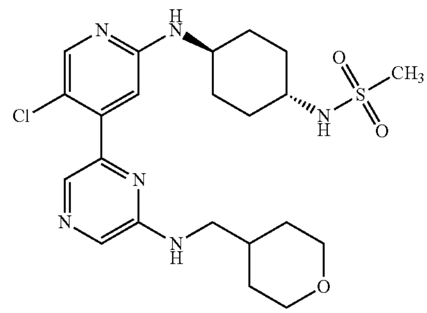 [SMILES: CS(=O)(=O)N[C@H]1CC[C@H](Nc2cc(-c3cncc(NCC4CCOCC4)n3)c(Cl)cn2)CC1] | 495.2 | 0.57 | Examples 6, 85 |
| 246 | 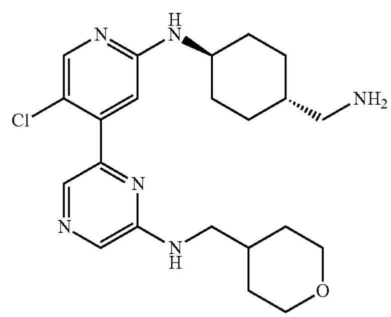 [SMILES: NC[C@H]1CC[C@H](Nc2cc(-c3cncc(NCC4CCOCC4)n3)c(Cl)cn2)CC1] | 431.2 | 0.51 | Examples 77, 85 |
| 247 | 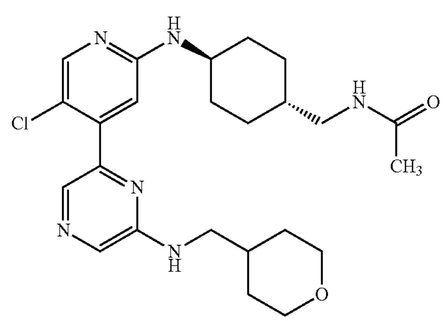 [SMILES: CC(=O)NC[C@H]1CC[C@H](Nc2cc(-c3cncc(NCC4CCOCC4)n3)c(Cl)cn2)CC1] | 473.2 | 0.57 | Example 78 |
| 248 | 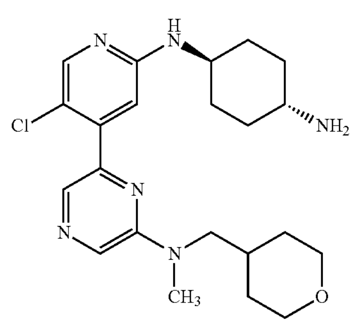 [SMILES: CN(CC1CCOCC1)c1cncc(-c2cc(N[C@H]3CC[C@H](N)CC3)ncc2Cl)n1] | 431.2 | 0.58 | Example 77 |

TABLE 1-continued
| Compound # | Structure | M + H (m/z) | retention time (min.) | method |
|---|---|---|---|---|
| 249 | 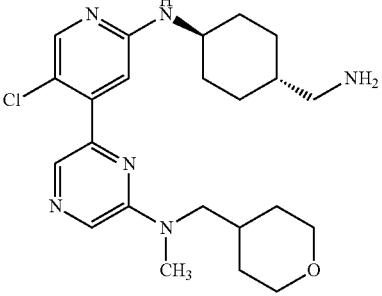 | 445.2 | 0.59 | Example 77 |
| 250 | 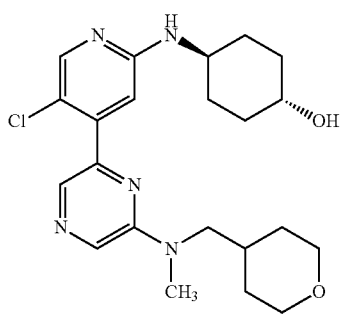 [SMILES: CN(CC1CCOCC1)c1cncc(-c2cc(N[C@H]3CC[C@H](O)CC3)ncc2Cl)n1] | 432.2 | 0.64 | Example 77 |
| 251 | 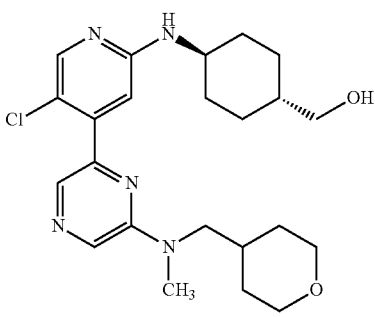 [SMILES: CN(CC1CCOCC1)c1cncc(-c2cc(N[C@H]3CC[C@H](CO)CC3)ncc2Cl)n1] | 446.2 | 0.66 | Example 77 |
| 252 | 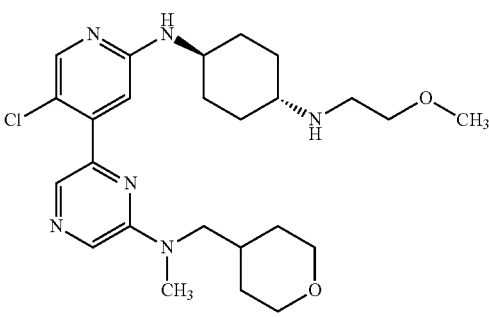 [SMILES: COCCN[C@H]1CC[C@H](Nc2cc(-c3cncc(N(C)CC4CCOCC4)n3)c(Cl)cn2)CC1] | 489.3 | 0.57 | Example 77, 86 |

TABLE 1-continued

| Compound # | Structure | M + H (m/z) | retention time (min.) | method |
|---|---|---|---|---|
| 253 | 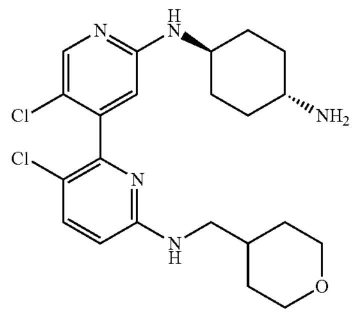 [SMILES: N[C@H]1CC[C@H](Nc2cc(-c3nc(NCC4CCOCC4)ccc3Cl)c(Cl)cn2)CC1] | 450.2 | 0.58 | Example 87 |
| 254 | 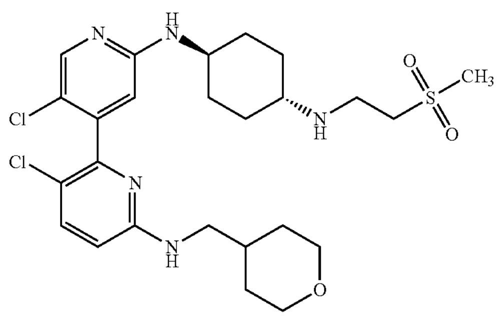 [SMILES: CS(=O)(=O)CCN[C@H]1CC[C@H](Nc2cc(-c3nc(NCC4CCOCC4)ccc3Cl)c(Cl)cn2)CC1] | 556.2 | 0.61 | Example 79 |
| 255 | 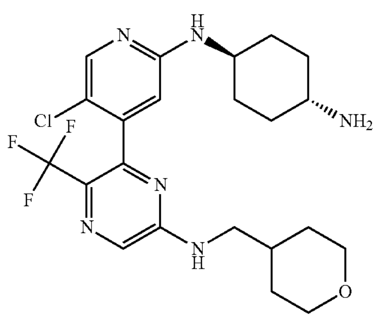 [SMILES: N[C@H]1CC[C@H](Nc2cc(-c3nc(NCC4CCOCC4)cnc3C(F)(F)F)c(Cl)cn2)CC1] | 485.3 | 0.63 | Example 37 |
| 256 | Chiral | 444.2 | 0.51 (C18 column), 10.35 (chiral column) | Example 24 |

TABLE 1-continued

| Compound # | Structure | M + H (m/z) | retention time (min.) | method |
|---|---|---|---|---|
| 257 | Chiral | 444.2 | 0.51 (C18 column), 17.44 (chiral column) | Example 24 |
| 258 | 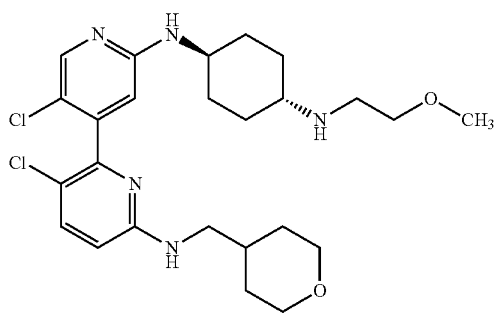 [SMILES: COCCN[C@H]1CC[C@H](Nc2cc(-c3nc(NCC4CCOCC4)ccc3Cl)c(Cl)cn2)CC1] | 508.2 | 0.63 | Example 80 |
| 259 | 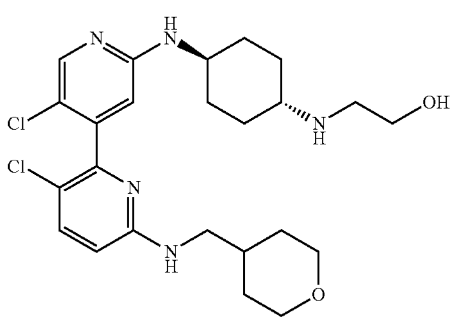 [SMILES: OCCN[C@H]1CC[C@H](Nc2cc(-c3nc(NCC4CCOCC4)ccc3Cl)c(Cl)cn2)CC1] | 494.2 | 0.6 | Example 81 |
| 260 | 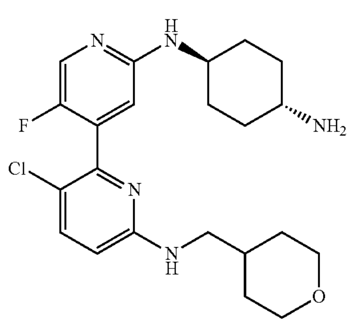 [SMILES: N[C@H]1CC[C@H](Nc2cc(-c3nc(NCC4CCOCC4)ccc3Cl)c(F)cn2)CC1] | 434.2 | 0.55 | Example 38 |

TABLE 1-continued

| Compound # | Structure | | M + H (m/z) | retention time (min.) | method |
|---|---|---|---|---|---|
| 261 | 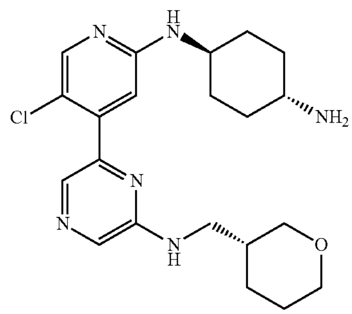 | Chiral | 417.2 | 0.49 | Example 77 |
| 262 | 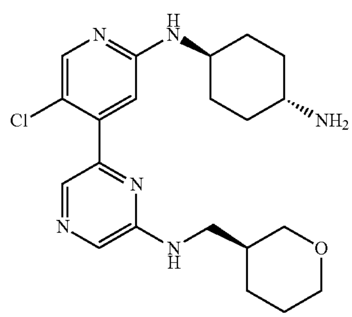 | Chiral | 417.2 | 0.49 | Example 77 |
| 263 | 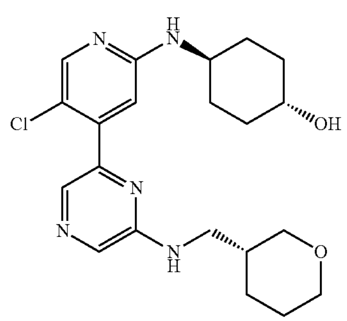 | Chiral | 418.2 | 0.54 | Example 77 |
| 264 | 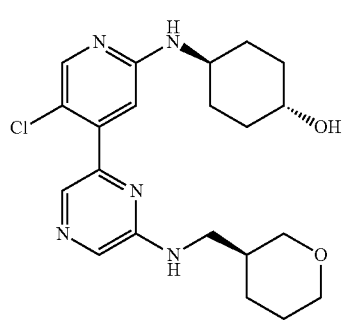 | Chiral | 418.2 | 0.54 | Example 77 |

| Compound # | Structure | M + H (m/z) | retention time (min.) | method |
|---|---|---|---|---|
| 265 | 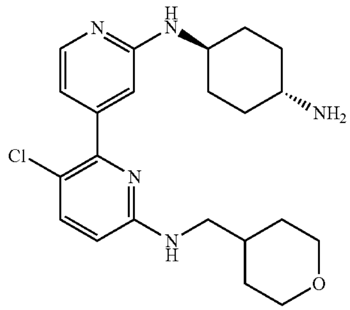 [SMILES: N[C@H]1CC[C@H](Nc2cc(-c3nc(NCC4CCOCC4)ccc3Cl)ccn2)CC1] | 416.2 | 0.52 | Example 82 |
| 266 | 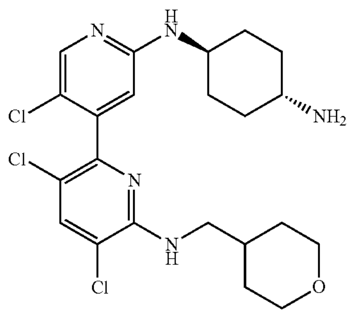 [SMILES: N[C@H]1CC[C@H](Nc2cc(-c3nc(NCC4CCOCC4)c(Cl)cc3Cl)c(Cl)cn2)CC1] | 486 | 0.7 | Example 28 |
| 267 | 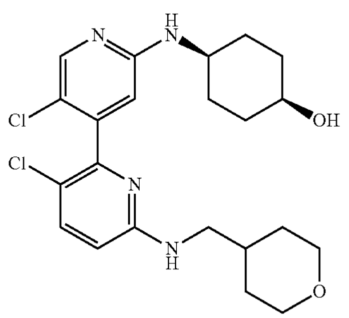 [SMILES: O[C@H]1CC[C@@H](Nc2cc(-c3nc(NCC4CCOCC4)ccc3Cl)c(Cl)cn2)CC1] | 451.1 | 0.65 | Example 84 |
| 268 | Chiral | 534.3 | 0.62 | Example 83 |
| 269 | 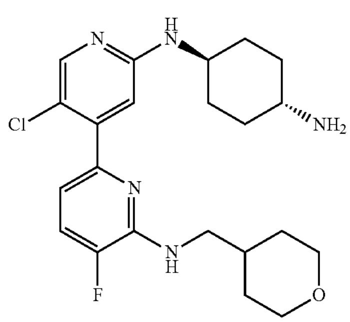 [SMILES: N[C@H]1CC[C@H](Nc2cc(-c3ccc(F)c(NCC4CCOCC4)n3)c(Cl)cn2)CC1] | 434.1 | 0.57 | Example 25 |

TABLE 1-continued

| Compound # | Structure | M + H (m/z) | retention time (min.) | method |
|---|---|---|---|---|
| 270 | Chiral | 534.3 | 0.64 | Example 84 |
| 271 | 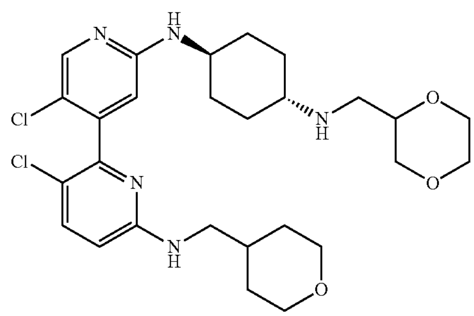 [SMILES: Clc1cnc(N[C@H]2CC[C@H](NCC3COCCO3)CC2)cc1-c1nc(NCC2CCOCC2)ccc1Cl] | 550.3 | 0.62 | Example 84 |
| 272 | 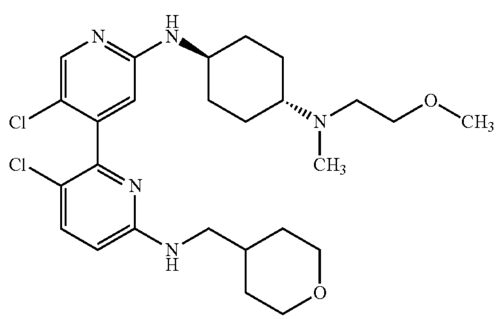 [SMILES: COCCN(C)[C@H]1CC[C@H](Nc2cc(-c3nc(NCC4CCOCC4)ccc3Cl)c(Cl)cn2)CC1] | 522.2 | 0.63 | Example 84 |
| 273 | Chiral | 500.3 | 0.58 | Example 82, 83 |

TABLE 1-continued

| Compound # | Structure | M + H (m/z) | retention time (min.) | method |
|---|---|---|---|---|
| 274 | 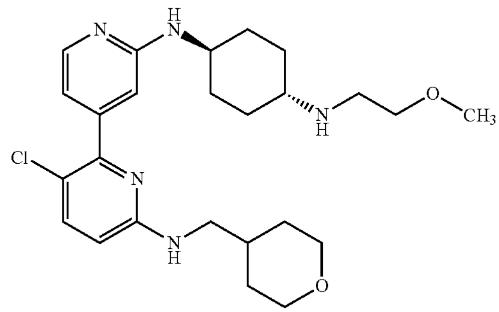 [SMILES: COCCN[C@H]1CC[C@H](Nc2cc(-c3nc(NCC4CCOCC4)ccc3Cl)ccn2)CC1] | 474.3 | 0.56 | Example 80, 82 |
| 275 | 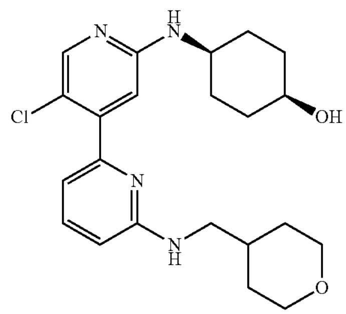 [SMILES: O[C@H]1CC[C@@H](Nc2cc(-c3cccc(NCC4CCOCC4)n3)c(Cl)cn2)CC1] | 417.2 | 0.5 | Example 84, Intermediate D |
| 276 | 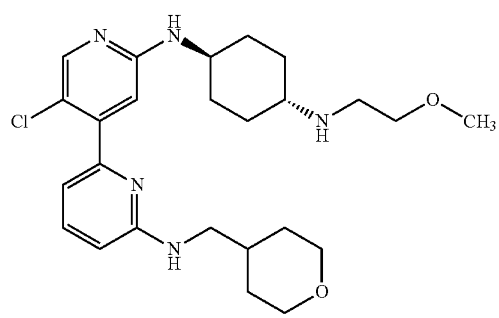 [SMILES: COCCN[C@H]1CC[C@H](Nc2cc(-c3cccc(NCC4CCOCC4)n3)c(Cl)cn2)CC1] | 474.3 | 0.48 | Example 80, Intermediate D |
| 277 | Chiral | 500.3 | 0.5 | Example 83, Intermediate D |

TABLE 1-continued

| Compound # | Structure | M + H (m/z) | retention time (min.) | method |
|---|---|---|---|---|
| 278 | 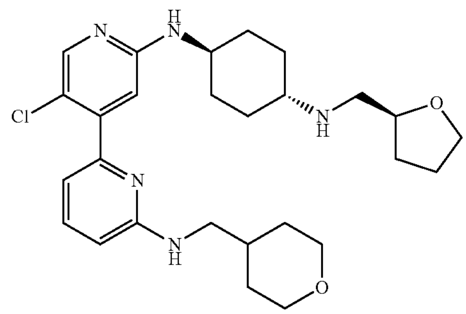 | Chiral 500.1 | 0.49 | Example 84, Intermediate D |
| 279 | 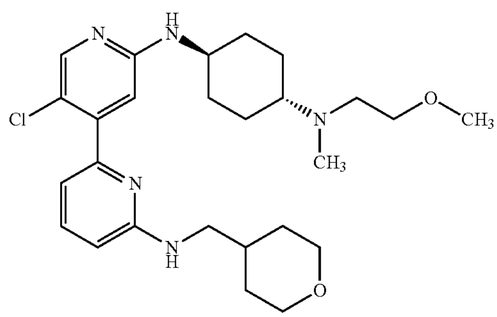 [SMILES: COCCN(C)[C@H]1CC[C@H](Nc2cc(-c3cccc(NCC4CCOCC4)n3)c(Cl)cn2)CC1] | 488.1 | 0.48 | Example 84, Intermediate D |
| 280 | 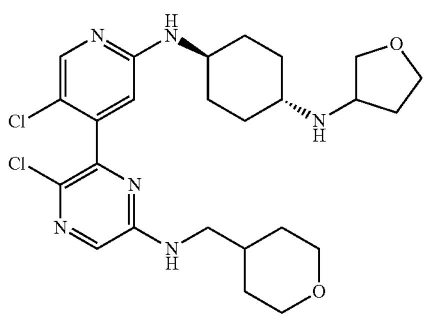 [SMILES: Clc1cnc(N[C@H]2CC[C@H](NC3CCOC3)CC2)cc1-c1nc(NCC2CCOCC2)cnc1Cl] | 520.1/ 522 | 0.59 | Example 71 |
| 281 | 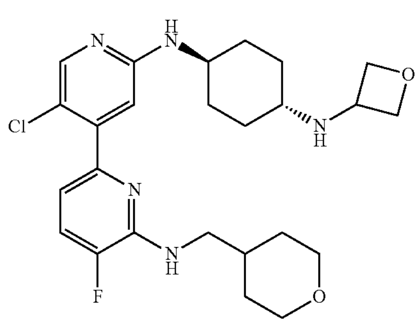 [SMILES: Fc1ccc(-c2cc(N[C@H]3CC[C@H](NC4COC4)CC3)ncc2Cl)nc1NCC1CCOCC1] | | | Example 71 |

TABLE 1-continued

| Compound # | Structure | M + H (m/z) | retention time (min.) | method |
|---|---|---|---|---|
| 282 | Chiral | 339 | 0.54 | Example 39 |
| 283 | Chiral | 492.2 | 0.57 | Example 40 |
| 284 | 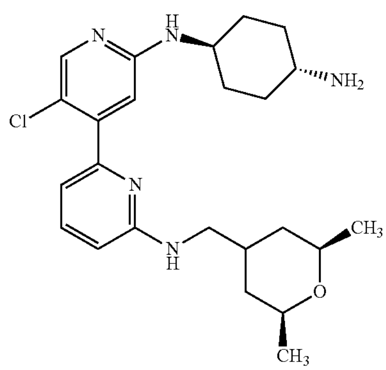 [SMILES: C[C@@H]1CC(CNc2cccc(-c3cc(N[C@H]4CC[C@H](N)CC4)ncc3Cl)n2)C[C@H](C)O1] | 444.2/ 446.2 | 0.54 | Example 50 |
| 285 | 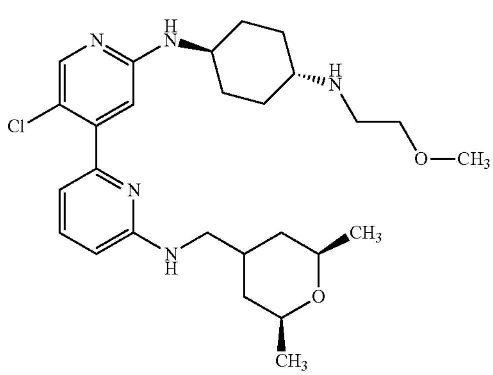 [SMILES: COCCN[C@H]1CC[C@H](Nc2cc(-c3cccc(NCC4C[C@@H](C)O[C@@H](C)C4)n3)c(Cl)cn2)CC1] | 502.2/ 504.2 | 0.56 | Example 50 |

TABLE 1-continued

| Compound # | Structure | | M + H (m/z) | retention time (min.) | method |
|---|---|---|---|---|---|
| 286 | 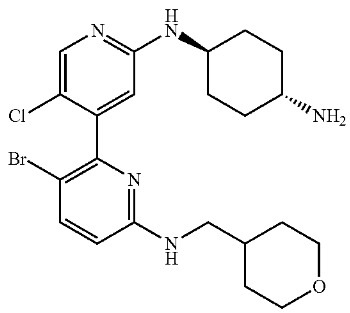 | Chiral | 494.2/ 496.1 | 0.61 | Example 41 |
| 287 | 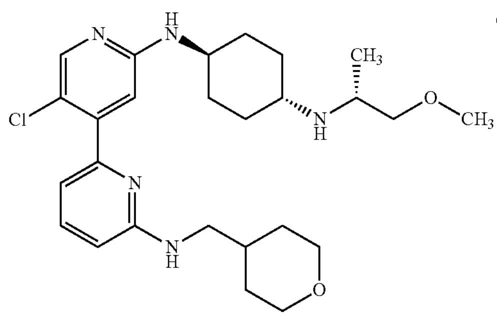 | Chiral | 488 | 0.51 | Example 67, Intermediate D |
| 288 | 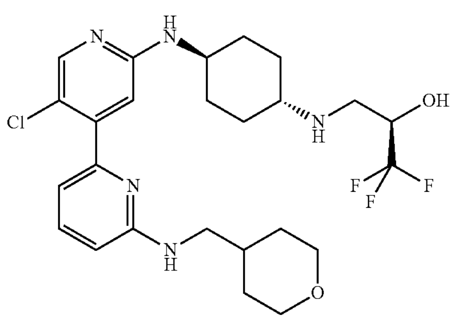 | Chiral | 528.3 | 0.53 | Example 42 |
| 289 | 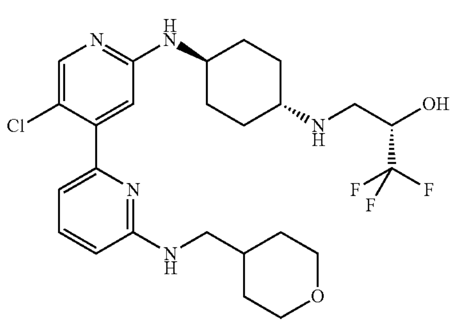 | Chiral | 528.3 | 0.53 | Example 42 |

TABLE 1-continued

| Compound # | Structure | | M + H (m/z) | retention time (min.) | method |
|---|---|---|---|---|---|
| 290 | 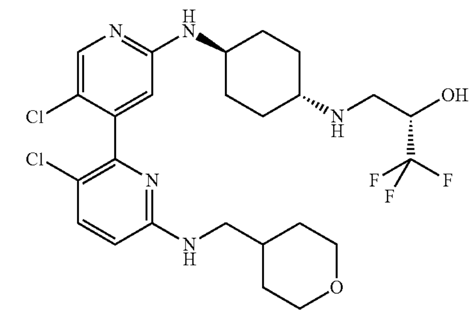 | Chiral | 562.3 | 0.7 | Example 43 |
| 291 | 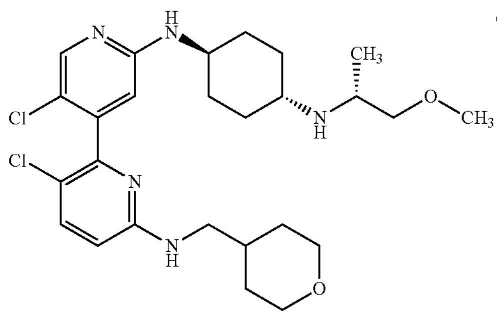 | Chiral | 522/524 | 0.62 | Example 67 |
| 292 | 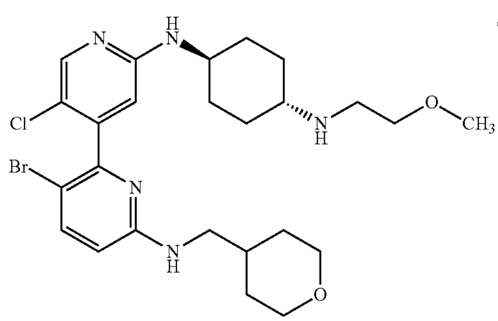 | Chiral | 554.1 | 0.61 | Example 44 |
| 293 | 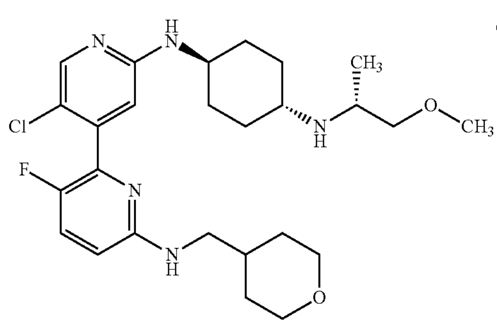 | Chiral | 506 | 0.6 | Example 39 and Example 67 |

TABLE 1-continued

| Compound # | Structure | | M + H (m/z) | retention time (min.) | method |
|---|---|---|---|---|---|
| 294 | 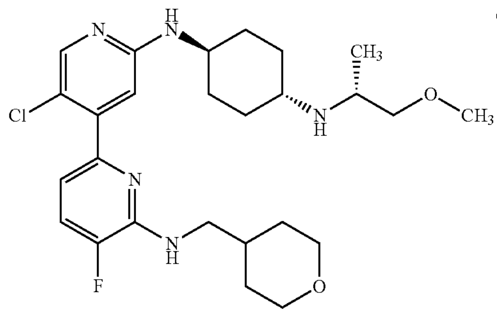 | Chiral | 506/508 | 0.62 | Example 67, Intermediate I |
| 295 | 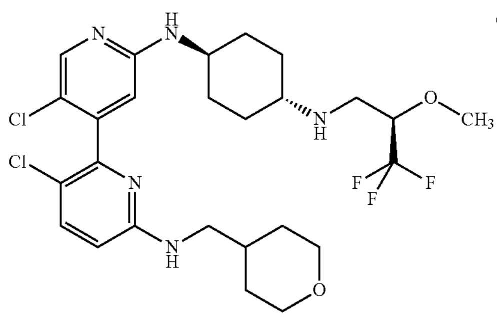 | Chiral | 576.2 | 0.78 | Example 45 |
| 296 | 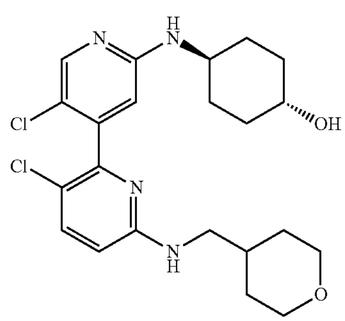 | Chiral | 451.2 | 0.65 | Example 46 |
| 297 | 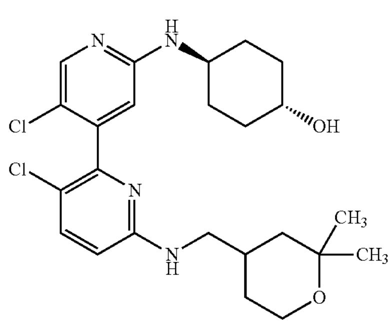 | Chiral | 479.3 | 0.72 | Example 46 |

TABLE 1-continued

| Compound # | Structure | | M + H (m/z) | retention time (min.) | method |
|---|---|---|---|---|---|
| 298 | 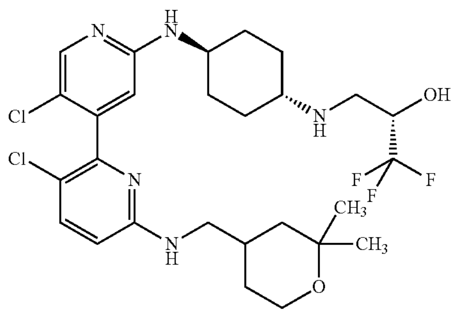 | Chiral | 590.5 | 0.71 | Example 47 |
| 299 | 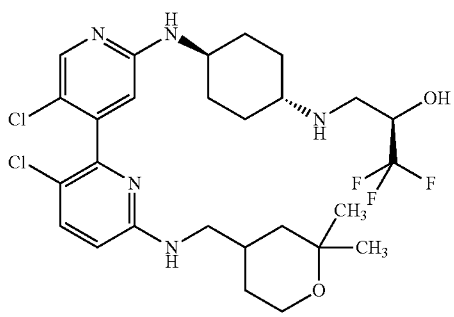 | Chiral | 590.5 | 0.71 | Example 47 |
| 300 | 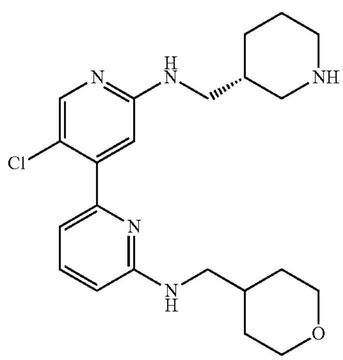 | Chiral | 416 | 0.47 | Example 1b, Intermediate D |
| 301 | 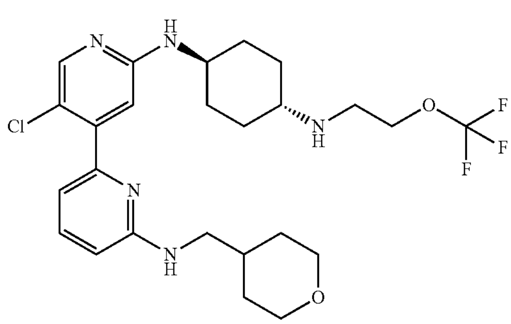 | Chiral | 528.4 | 0.53 | Example 48 |

TABLE 1-continued

| Compound # | Structure | M + H (m/z) | retention time (min.) | method |
|---|---|---|---|---|
| 302 | Chiral | 562.4 | 0.67 | Example 49 |
| 303 | Chiral | 402 | 0.48 | Example 1b, Intermediate D |
| 304 | Chiral | 402 | 0.48 | Example 1b, Intermediate D |
| 305 | Chiral | 518.4 | 0.511 | Example 2 |

TABLE 1-continued

| Compound # | Structure | | M + H (m/z) | retention time (min.) | method |
|---|---|---|---|---|---|
| 306 | 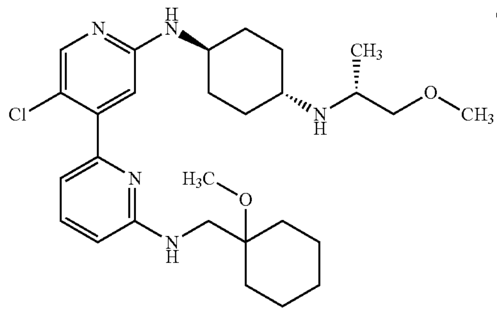 | Chiral | 516.5 | 0.653 | Example 2 |
| 307 | 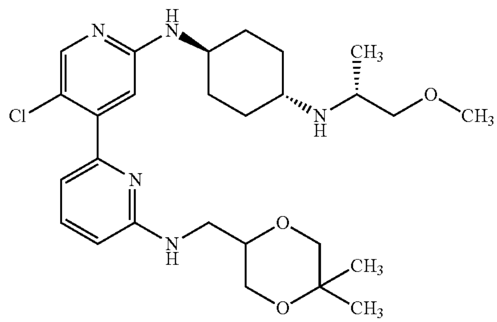 [SMILES: COC[C@@H](C)N[C@H]1CC[C@H](Nc2cc(-c3cccc(NCC4COC(C)(C)CO4)n3)c(Cl)cn2)CC1] | | 518.4 | 0.547 | Example 66 |
| 308 | 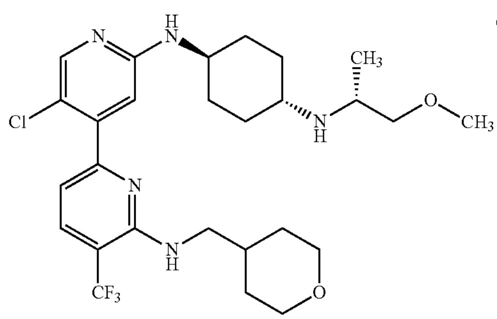 | Chiral | 556 | 0.73 | Example 2 |
| 309 | 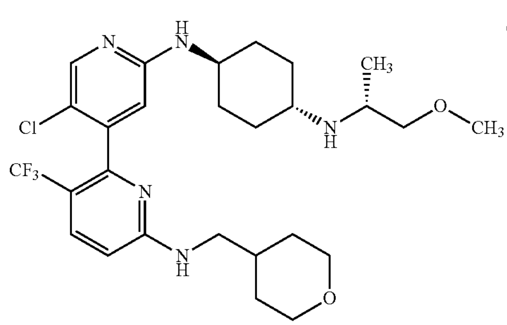 | Chiral | 556.4 | 0.675 | Example 2 |

TABLE 1-continued

| Compound # | Structure | M + H (m/z) | retention time (min.) | method |
|---|---|---|---|---|
| 310 | Chiral | 513.2 | 0.563 | Example 93 |
| 311 | 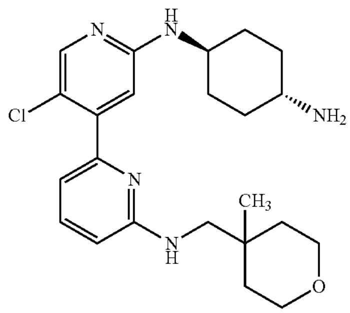 [SMILES: CC1(CNc2cccc(-c3cc(N[C@H]4CC[C@H](N)CC4)ncc3Cl)n2)CCOCC1] | 430.3 | 0.48 | Example 29 |
| 312 | 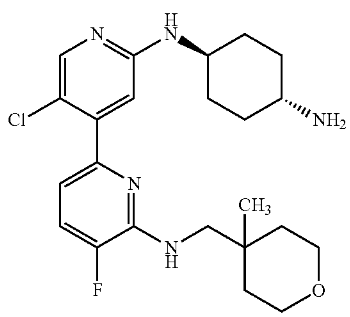 [SMILES: CC1(CNc2nc(-c3cc(N[C@H]4CC[C@H](N)CC4)ncc3Cl)ccc2F)CCOCC1] | 448.2 | 0.62 | Example 30 |
| 313 | 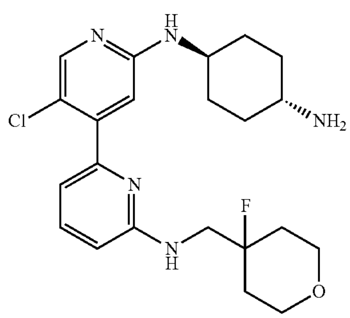 | 434.2 | 0.5 | Example 31 |
| 314 | 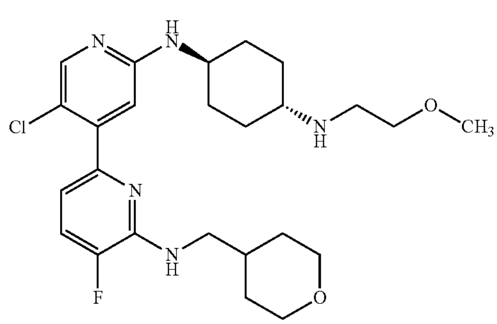 [SMILES: COCCN[C@H]1CC[C@H](Nc2cc(-c3ccc(F)c(NCC4CCOCC4)n3)c(Cl)cn2)CC1] | 492.3 | 0.6 | Example 1b, Intermeidate I |

TABLE 1-continued

| Compound # | Structure | | M + H (m/z) | retention time (min.) | method |
|---|---|---|---|---|---|
| 315 | 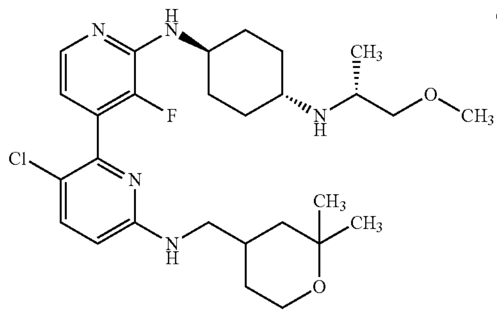 | Chiral | 534.1 | 0.64 | Example 1b, Intermeidate W |
| 316 | 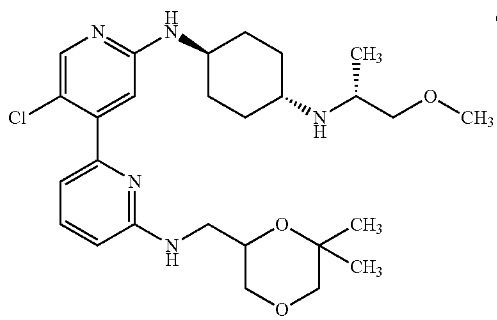 | Chiral | 301/ 303 | 0.86 | Example 65 |
| 317 | 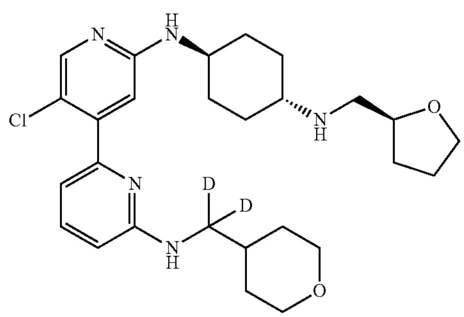 | Chiral | 502.3/ 504.3 | 0.49 | Example 58 |
| 318 | 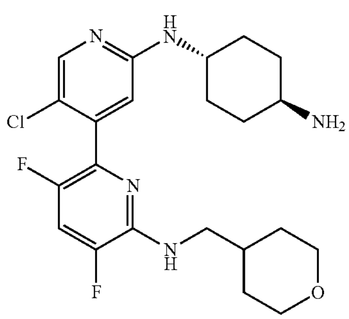 [SMILES: N[C@H]1CC[C@H](Nc2cc(-c3nc(NCC4CCOCC4)c(F)cc3F)c(Cl)cn2)CC1] | | 452 | 0.59 | Example 1b |

TABLE 1-continued

| Compound # | Structure | | M + H (m/z) | retention time (min.) | method |
|---|---|---|---|---|---|
| 319 | 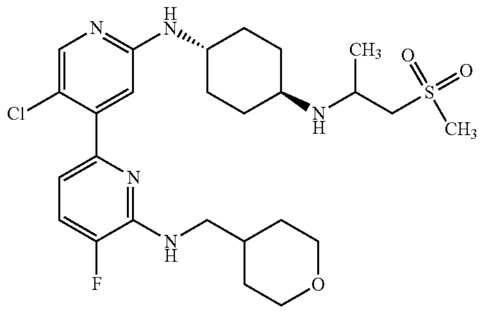 [SMILES: CC(CS(C)(=O)=O)N[C@H]1CC[C@H](Nc2cc(-c3ccc(F)c(NCC4CCOCC4)n3)c(Cl)cn2)CC1] | | 554.1 | 0.59 | Example 1b, intermediate I |
| 320 | 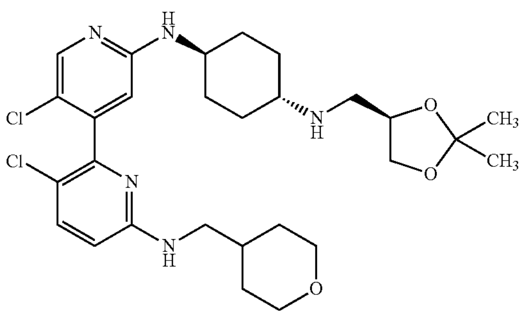 | Chiral | 564.4/ 566.3 | 0.65 | Example 72 |
| 321 | 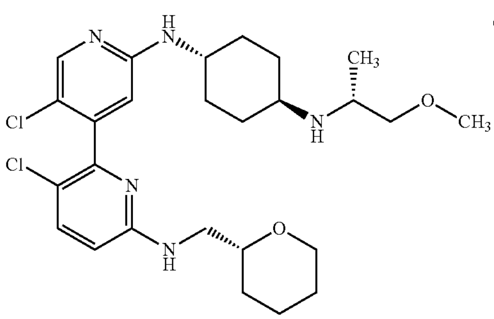 | Chiral | 522.1/ 524.0 | 0.708 | Example 74 |
| 322 | 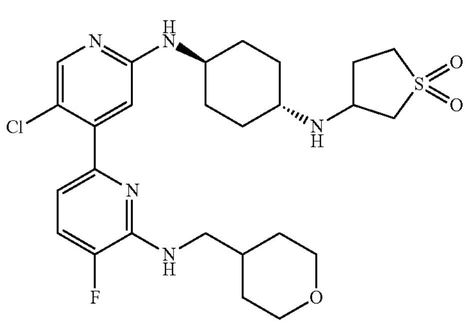 [SMILES: O=S1(=O)CCC(N[C@H]2CC[C@H](Nc3cc(-c4ccc(F)c(NCC5CCOCC5)n4)c(Cl)cn3)CC2)C1] | | 552.0/ 554.1 | 0.589 | Example 1b, Intermediate I |

TABLE 1-continued

| Compound # | Structure | | M + H (m/z) | retention time (min.) | method |
|---|---|---|---|---|---|
| 323 | 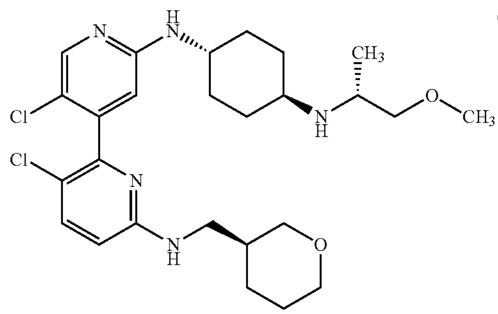 | Chiral | 522.2/ 524.1 | 0.672 | Example 73 |
| 324 | 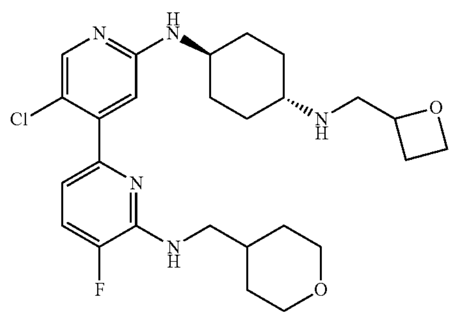 | Chiral | 504.1/ 506.1 | 0.624 | Example 1b, Intermediate I |
| 325 | 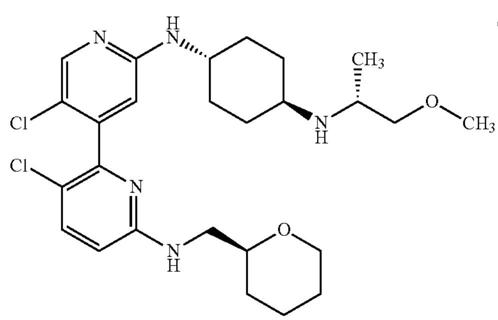 | Chiral | 522.1/ 524.1 | 0.724 | Example 74 |
| 326 | 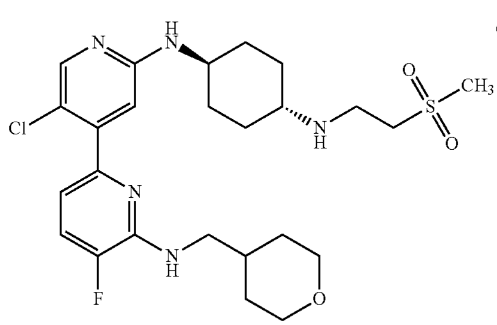 | Chiral | 540.2/ 542.2 | 0.605 | Example 1b, Intermediate I |

TABLE 1-continued

| Compound # | Structure | | M + H (m/z) | retention time (min.) | method |
|---|---|---|---|---|---|
| 327 | 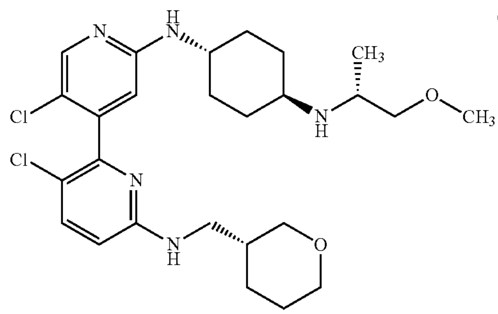 | Chiral | 522.1/ 523.9 | 0.675 | Example 73 |
| 328 | 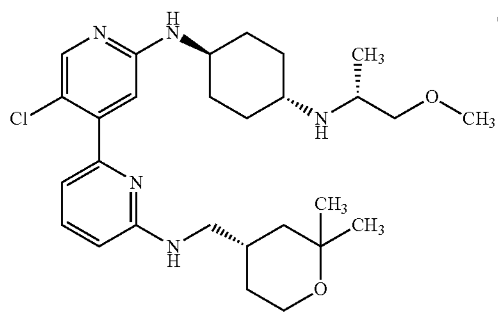 | Chiral | 516.5 | 0.55 (C18 column), 9.743 (chiral column) | Example 67, Intermediate J |
| 329 | 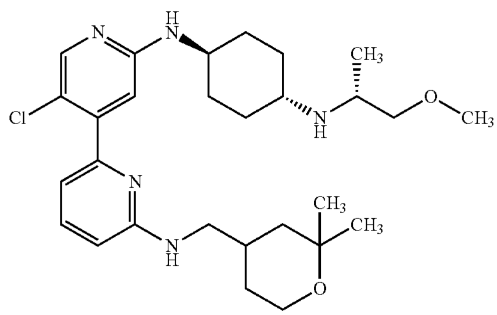 [SMILES: COC[C@@H](C)N[C@H]1CC[C@H](Nc2cc(-c3cccc(NCC4CCOC(C)(C)C4)n3)c(Cl)cn2)CC1] | Chiral | 516.5 | 0.55 | Example XL-1, Intermediate J |
| 330 | 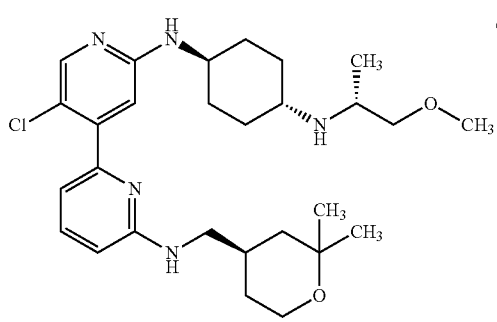 | Chiral | 516.5 | 0.55 | Example XL-1, Intermediate J |

TABLE 1-continued

| Compound # | Structure | M + H (m/z) | retention time (min.) | method |
|---|---|---|---|---|
| 331 | Chiral | 580.1 | 0.59 | Example 1b, Intermediate I |
| 332 | 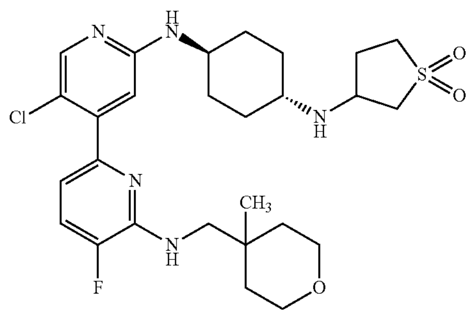 [SMILES: CC1(CNc2nc(-c3cc(N[C@H]4CC[C@H](NC5CCS(=O)(=O)C5)CC4)ncc3Cl)ccc2F)CCOCC1] | 566.2 | 0.64 | Example 89 |
| 333 | 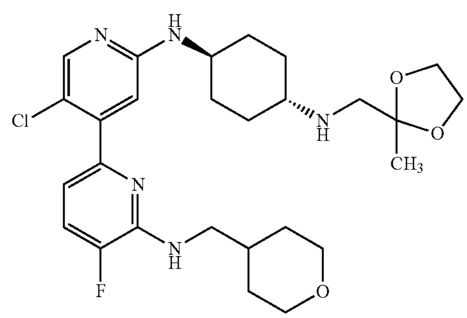 [SMILES: CC1(CN[C@H]2CC[C@H](Nc3cc(-c4ccc(F)c(NCC5CCOCC5)n4)c(Cl)cn3)CC2)OCCO1] | 534.1 | 0.62 | Example 90 |
| 334 | 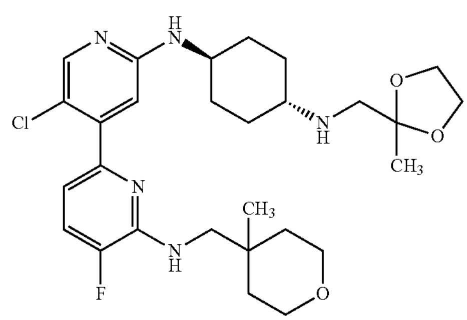 [SMILES: CC1(CNc2nc(-c3cc(N[C@H]4CC[C@H](NCC5(C)OCCO5)CC4)ncc3Cl)ccc2F)CCOCC1] | 548.2 | 0.65 | Example 90 |
| 335 | 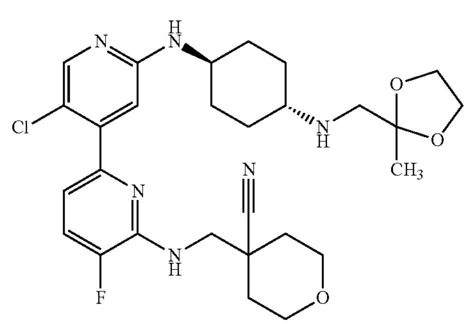 [SMILES: CC1(CN[C@H]2CC[C@H](Nc3cc(-c4ccc(F)c(NCC5(C#N)CCOCC5)n4)c(Cl)cn3)CC2)OCCO1] | 559 | 0.59 | Example 90 |

TABLE 1-continued

| Compound # | Structure | M + H (m/z) | retention time (min.) | method |
|---|---|---|---|---|
| 336 | 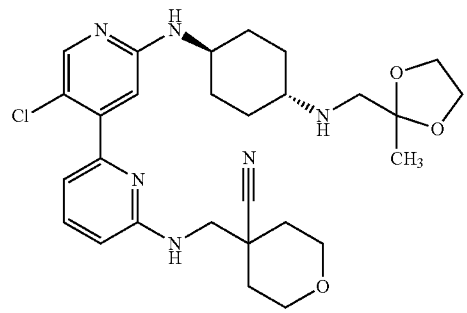 [SMILES: CC1(CN[C@H]2CC[C@H](Nc3cc(-c4cccc(NCC5(C#N)CCOCC5)n4)c(Cl)cn3)CC2)OCCO1] | 541.3 | 0.55 | Example 90 |
| 337 | 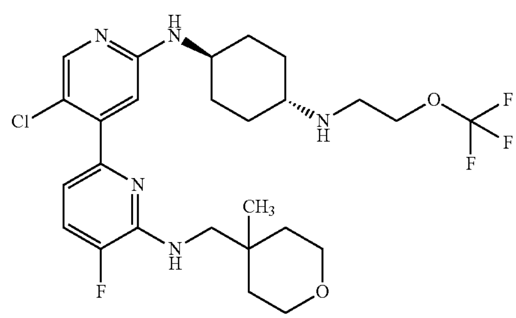 [SMILES: CC1(CNc2nc(-c3cc(N[C@H]4CC[C@H](NCCOC(F)(F)F)CC4)ncc3Cl)ccc2F)CCOCC1] | 560.1 | 0.73 | Example 48 |
| 338 | 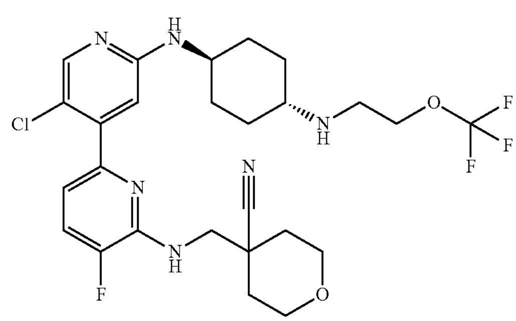 [SMILES: N#CC1(CNc2nc(-c3cc(N[C@H]4CC[C@H](NCCOC(F)(F)F)CC4)ncc3Cl)ccc2F)CCOCC1] | 571.2 | 0.65 | Example 48, 94 |
| 339 | Chiral | 517.2 | 0.576 | Example 94 |

TABLE 1-continued

| Compound # | Structure | | M + H (m/z) | retention time (min.) | method |
|---|---|---|---|---|---|
| 340 | 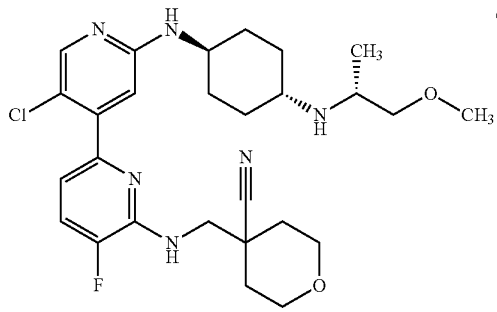 | Chiral | 531.2 | 0.595 | Example 94 |
| 341 | 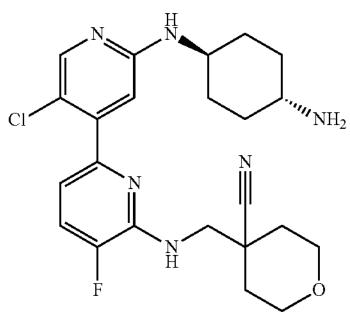 | Chiral | 459.2 | 0.547 | Example 94 |
| 342 | 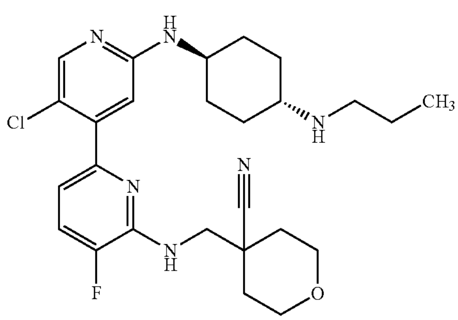 | Chiral | 501.2 | 0.627 | Example 94 |
| 343 | 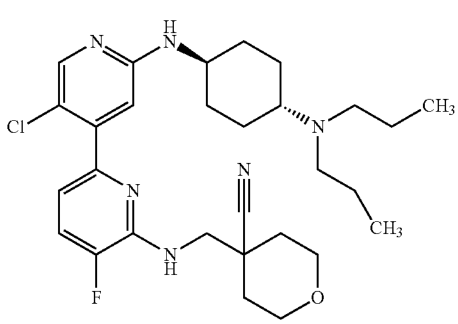 | Chiral | 543.3 | 0.692 | Example 1B |

TABLE 1-continued

| Compound # | Structure | M + H (m/z) | retention time (min.) | method |
|---|---|---|---|---|
| 344 | Chiral | 499.1 | 0.531 | Example 1B |
| 345 | Chiral | 441.1 | 0.502 | Example 1B |
| 346 | 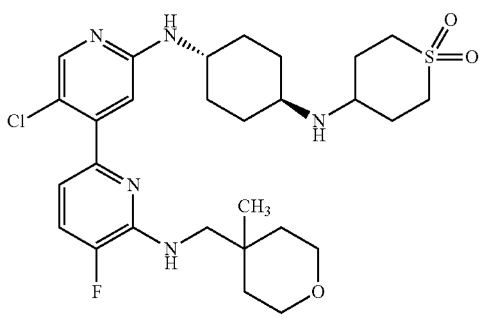 [SMILES: CC1(CNc2nc(-c3cc(N[C@H]4CC[C@H](NC5CCS(=O)(=O)CC5)CC4)ncc3Cl)ccc2F)CCOCC1] | 580.3 | 0.64 | Example 30, 92 |
| 347 | 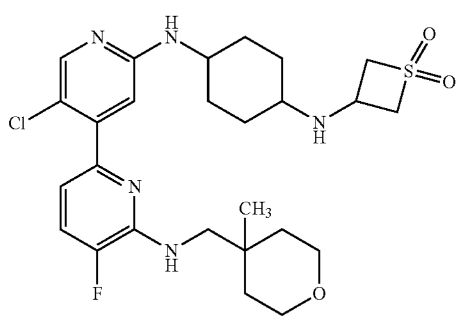 [SMILES: CC1(CNc2nc(-c3cc(NC4CCC(NC5CS(=O)(=O)C5)CC4)ncc3Cl)ccc2F)CCOCC1] | 552 | 0.63 | Example 30 |

TABLE 1-continued

| Compound # | Structure | M + H (m/z) | retention time (min.) | method |
|---|---|---|---|---|
| 348 | 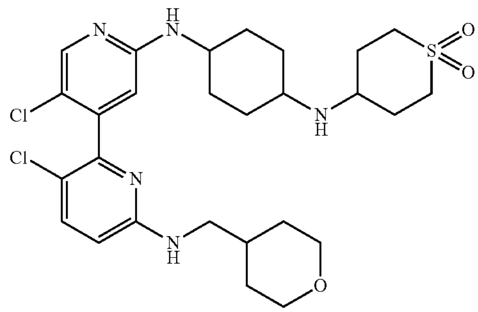 [SMILES: O=S1(=O)CCC(NC2CCC(Nc3cc(-c4nc(NCC5CCOCC5)ccc4Cl)c(Cl)cn3)CC2)CC1] | 582/584 | 0.58 | Example 92 |
| 349 | Chiral | 512.2 | 0.47 | Example 91 |
| 350 | 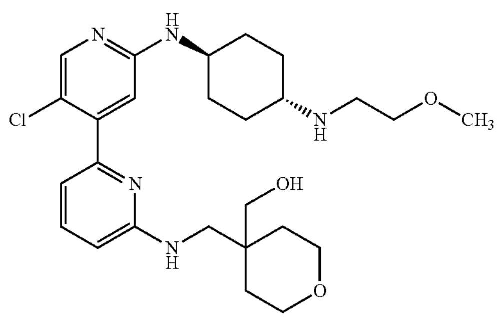 [SMILES: COCCN[C@H]1CC[C@H](Nc2cc(-c3cccc(NCC4(CO)CCOCC4)n3)c(Cl)cn2)CC1] | 504 | 0.45 | Example 91 |
| 351 | 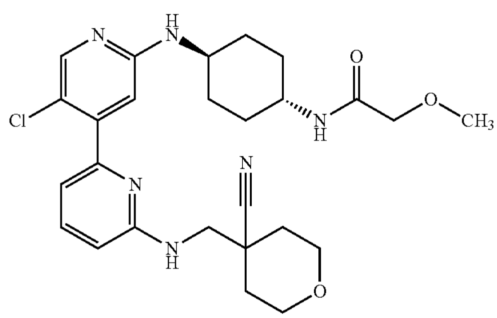 [SMILES: COCC(=O)N[C@H]1CC[C@H](Nc2cc(-c3cccc(NCC4(C#N)CCOCC4)n3)c(Cl)cn2)CC1] | 513 | 0.6 | Example 1b, 7 |
| 352 | 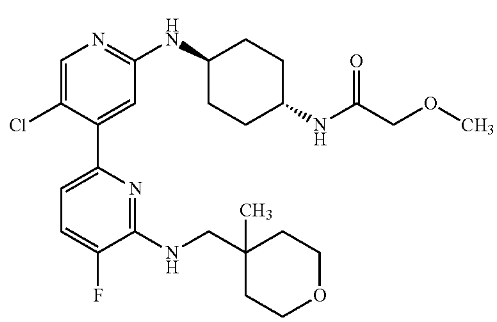 [SMILES: COCC(=O)N[C@H]1CC[C@H](Nc2cc(-c3ccc(F)c(NCC4(C)CCOCC4)n3)c(Cl)cn2)CC1] | 520.1 | 0.72 | Example 1b, 7 |

TABLE 1-continued

| Compound # | Structure | M + H (m/z) | retention time (min.) | method |
|---|---|---|---|---|
| 353 | 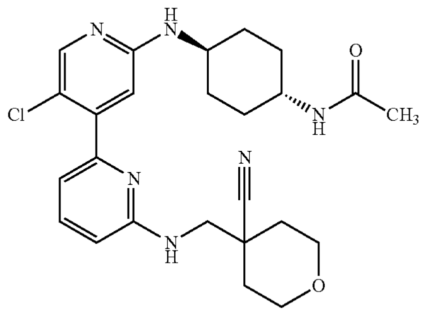 [SMILES: CC(=O)N[C@H]1CC[C@H](Nc2cc(-c3cccc(NCC4(C#N)CCOCC4)n3)c(Cl)cn2)CC1] | 483.2 | 0.56 | Example 1b, 7 |
| 354 | 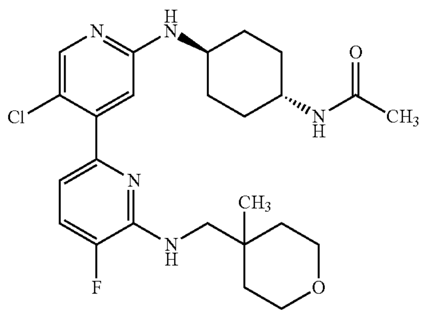 [SMILES: CC(=O)N[C@H]1CC[C@H](Nc2cc(-c3ccc(F)c(NCC4(C)CCOCC4)n3)c(Cl)cn2)CC1] | 490 | 0.69 | Example 1b, 7 |
| 355 | 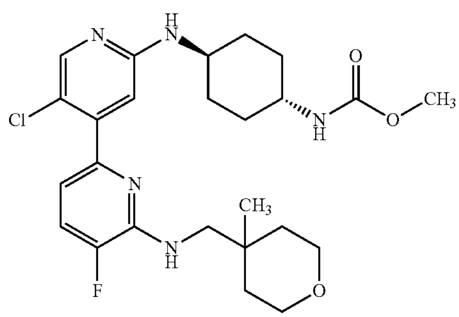 [SMILES: COC(=O)N[C@H]1CC[C@H](Nc2cc(-c3ccc(F)c(NCC4(C)CCOCC4)n3)c(Cl)cn2)CC1] | 506 | 0.78 | Example 1b, 7 |
| 356 | Chiral | | | |

The following compounds were made using procedures outlined above:

Compound/Ex. 357: 4-((5'-chloro-5-fluoro-2'-(trans-4-hydroxycyclohexylamino)-2,4'-bipyridin-6-ylamino)methyl)tetrahydro-2H-pyran-4-carbonitrile

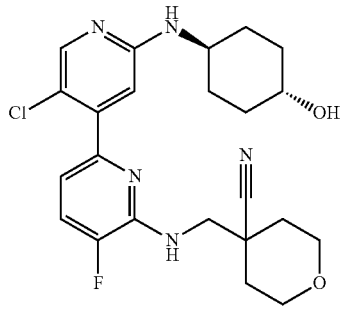

M+1 (LC/MS): 460.1; Retention Time (min. LC/MS): 0.62.
¹H NMR (400 MHz, METHANOL-d4) δ ppm 1.29-1.42 (m, 3H) 1.59-1.71 (m, 2 H) 1.75-1.80 (m, 1 H) 1.80-1.83 (m, 1 H) 1.88-1.96 (m, 2 H) 1.96-2.02 (m, 2 H) 2.02-2.13 (m, 1 H) 3.46-3.60 (m, 4 H) 3.72 (s, 2 H) 3.86 (m, J=12.13, 2.35 Hz, 2 H) 6.95 (dd, J=8.02, 2.93 Hz, 1 H) 7.10 (s, 1 H) 7.32 (dd, J=10.96, 8.22 Hz, 1 H) 7.92 (s, 1 H).

Compound/Ex. 358: 4-((5'-chloro-2'-(trans-4-((R)-1-methoxypropan-2-ylamino)cyclohexylamino)-2,4'-bipyridin-6-ylamino)methyl)tetrahydro-2H-pyran-4-carbonitrile

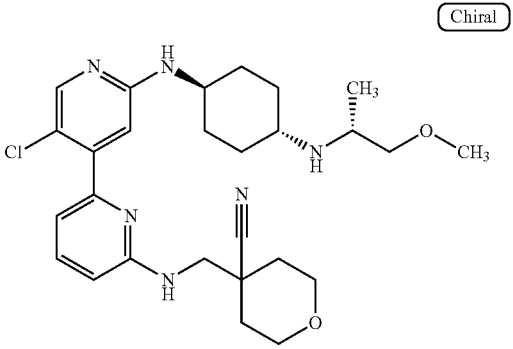 [SMILES: COC[C@@H](C)N[C@H]1CC[C@H](Nc2cc(-c3cccc(NCC4(C#N)CCOCC4)n3)c(Cl)cn2)CC1]

Compound/Ex. 359: 4-((5'-chloro-2'-(trans-4-hydroxycyclohexylamino)-2,4'-bipyridin-6-ylamino)methyl)tetrahydro-2H-pyran-4-carbonitrile

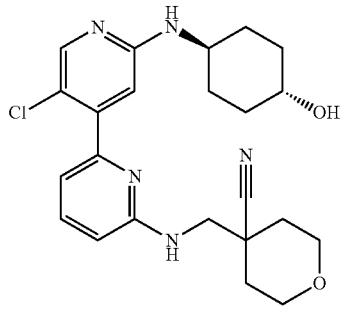 [SMILES: N#CC1(CNc2cccc(-c3cc(N[C@H]4CC[C@H](O)CC4)ncc3Cl)n2)CCOCC1]

M+1 (LC/MS): 442.1; Retention Time (min. LC/MS): 0.55.

¹H NMR (400 MHz, METHANOL-d4) δ ppm 1.29-1.42 (m, 4 H) 1.58-1.70 (m, 2 H) 1.75-1.84 (m, 2 H) 1.87-2.04 (m, 4 H) 3.45-3.60 (m, 4 H) 3.66 (s, 2 H) 3.86 (m, J=12.13, 2.74 Hz, 2 H) 6.66 (d, J=8.22 Hz, 1 H) 6.88 (d, J=7.43 Hz, 1 H) 7.07 (s, 1 H) 7.46-7.53 (m, 1 H) 7.92 (s, 1 H).

Compound/Ex. 360: 4-((5'-chloro-2'-(trans-4-(ethylamino)cyclohexylamino)-2,4'-bipyridin-6-ylamino)methyl)tetrahydro-2H-pyran-4-carbonitrile

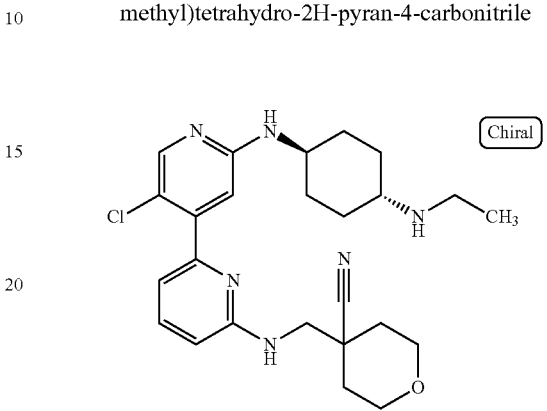

M+1 (LC/MS): 469.2; Retention Time (min. LC/MS): 0.55.
¹H NMR (400 MHz, METHANOL-d4) δ ppm 1.32 (t, J=7.24 Hz, 3 H) 1.49 (br. s., 4 H) 1.66-1.82 (m, 2 H) 1.84-1.99 (m, 2 H) 2.22 (d, J=12.52 Hz, 4 H) 3.11 (t, J=7.24 Hz, 3 H) 3.56-3.72 (m, 3 H) 3.76 (s, 2 H) 3.87-4.06 (m, 2 H) 6.81 (d, J=8.61 Hz, 1 H) 6.96 (d, J=6.65 Hz, 1 H) 7.06 (s, 1 H) 7.54-7.69 (m, 1 H) 8.06 (s, 1 H).

Compound/Ex. 361: 4-((5'-chloro-2'-(trans-4-(dimethylamino)cyclohexylamino)-2,4'-bipyridin-6-ylamino)methyl)tetrahydro-2H-pyran-4-carbonitrile

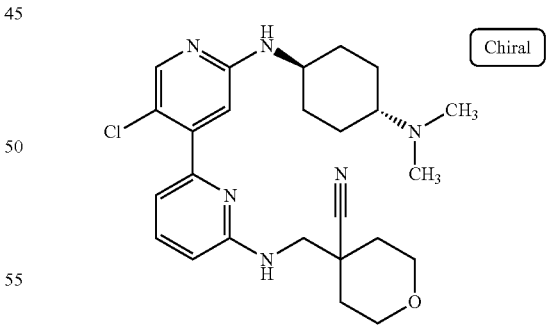

M+1 (LC/MS): 469.2; Retention Time (min. LC/MS): 0.52
¹H NMR (400 MHz, METHANOL-d4) δ ppm 1.39-1.58 (m, 2 H) 1.64-1.83 (m, 4 H) 1.90 (dd, J=13.50, 1.76 Hz, 2 H) 2.10-2.35 (m, 4 H) 2.87 (s, 6 H) 3.57-3.72 (m, 3 H) 3.76 (s, 2 H) 3.96 (ddd, J=9.98, 2.35, 2.15 Hz, 2 H) 6.82 (d, J=7.83 Hz, 1 H) 6.97 (d, J=6.65 Hz, 1 H) 7.06 (s, 1 H) 7.55-7.77 (m, 1 H) 8.07 (s, 1 H).

Compound/Ex. 362: 4-((5'-chloro-2'-(trans-4-(2-(trifluoromethoxy)ethylamino)cyclohexylamino)-2,4'-bipyridin-6-ylamino)methyl)tetrahydro-2H-pyran-4-carbonitrile

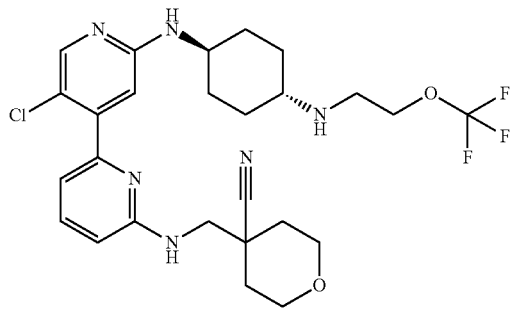

M+1 (LC/MS): 553.3; Retention Time (min. LC/MS): 0.58.

Compound/Ex. 363: 4-((5'-chloro-2'-(trans-4-(tetrahydro-2H-pyran-4-ylamino)cyclohexylamino)-2,4'-bipyridin-6-ylamino)methyl)tetrahydro-2H-pyran-4-carbonitrile

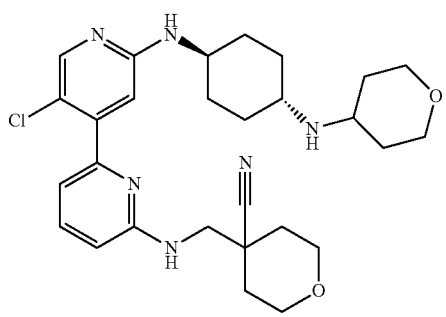 [SMILES: N#CC1(CNc2cccc(-c3cc(N[C@H]4CC[C@H](NC5CCOCC5)CC4)ncc3Cl)n2)CCOCC1]

M+1 (LC/MS): 525.1; Retention Time (min. LC/MS): 0.54.

¹H NMR (400 MHz, METHANOL-d4) ppm 1.38-1.82 (m, 8 H) 1.85-1.95 (m, 2 H) 1.96-2.06 (m, 2 H) 2.15-2.26 (m, 4 H) 3.40-3.56 (m, 3 H) 3.58-3.73 (m, 3 H) 3.75 (s, 2 H) 3.90-4.10 (m, 4 H) 6.71-6.80 (m, 1 H) 6.94 (s, 2 H) 7.54-7.65 (m, 1 H) 8.04 (s, 1 H).

Compound/Ex. 364: 5'-chloro-N6-((4-fluorotetrahydro-2H-pyran-4-yl)methyl)-N2'-(trans-4-(2-methoxyethylamino)cyclohexyl)-2,4'-bipyridine-2',6-diamine

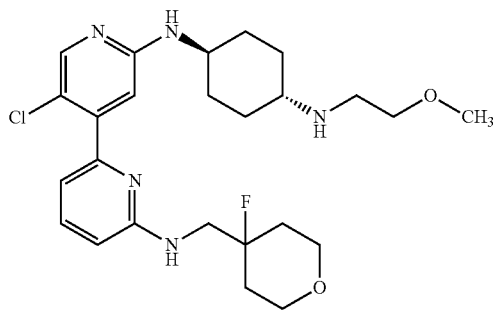 [SMILES: COCCN[C@H]1CC[C@H](Nc2cc(-c3cccc(NCC4(F)CCOCC4)n3)c(Cl)cn2)CC1]

M+1 (LC/MS): 492.2; Retention Time (min. LC/MS): 0.34.

¹H NMR (400 MHz, METHANOL-d4) δ ppm 1.32-1.48 (m, 2 H) 1.49-1.65 (m, 2 H) 1.72-1.88 (m, 4 H) 2.16-2.26 (m, 4 H) 3.20-3.27 (m, 2 H) 3.42 (s, 2 H) 3.60-3.76 (m, 6 H) 3.77-3.86 (m, 2 H) 6.78 (s, 1 H) 6.91 (d, J=7.04 Hz, 1 H) 6.96 (d, J=8.61 Hz, 1 H) 7.76 (t, J=8.02 Hz, 1 H) 8.06 (s, 1 H).

Compound/Ex. 365:

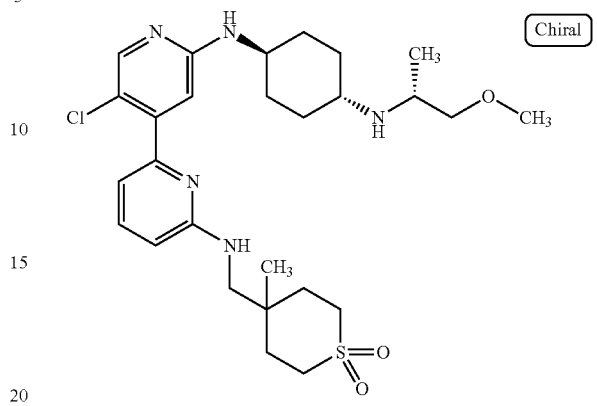

Compound/Ex. 366: 4-((5'-chloro-2'-(trans-4-(diethylamino)cyclohexylamino)-2,4'-bipyridin-6-ylamino)methyl)tetrahydro-2H-pyran-4-carbonitrile

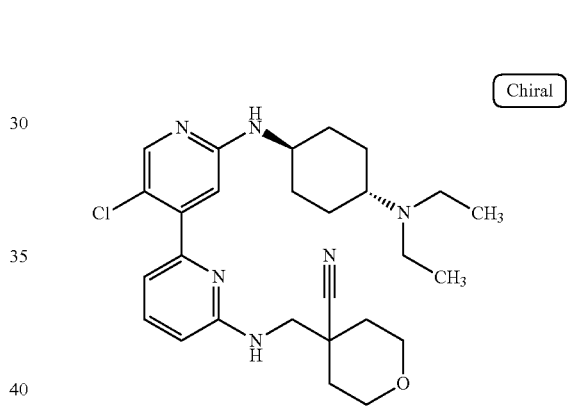

M+1 (LC/MS): 497.2; Retention Time (min. LC/MS): 0.58.

Compound/Ex. 367: 2-((5'-chloro-5-fluoro-2'-(trans-4-((R)-1-methoxypropan-2-ylamino)cyclohexylamino)-2,4'-bipyridin-6-ylamino)methyl)propane-1,3-diol

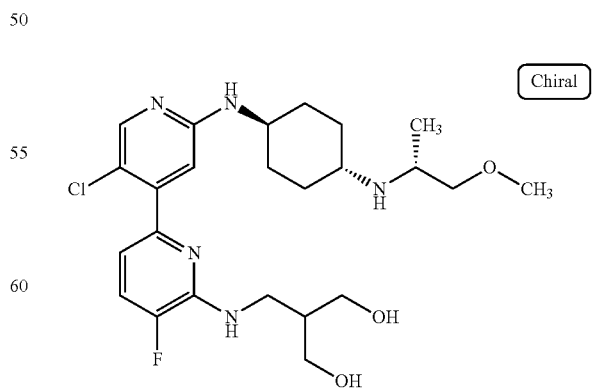

M+1 (LC/MS): 496.2; Retention Time (min. LC/MS): 0.49.

Biological Methods

Cdk9/cyclinT1 IMAP Protocol

The biological activity of the compounds of the invention can be determined using the assay described below.

Cdk9/cyclinT1 is purchased from Millipore, cat #14-685. The final total protein concentration in the assay 4 nM. The 5TAMRA-cdk7tide peptide substrate, 5TAMRA-YSPTSP-SYSPTSPSYSTPSPS-COOH, is purchased from Molecular Devices, cat#R7352. The final concentration of peptide substrate is 100 nM. The ATP substrate (Adenosine-5'-triphosphate) is purchased from Roche Diagnostics, cat#1 140965. The final concentration of ATP substrate is 6 uM. IMAP (Immobilized Metal Assay for Phosphochemicals) Progressive Binding reagent is purchased from Molecular Devices, cat#R8139. Fluorescence polarization (FP) is used for detection. The 5TAMRA-cdk7tide peptide is phosphorylated by Cdk9/cyclinT1 kinase using the ATP substrate. The Phospho-5TAMRA-cdk7tide peptide substrate is bound to the IMAP Progressive Binding Reagent. The binding of the IMAP Progressive Binding Reagent changes the fluorescence polarization of the 5TAMRA-cdk7tide peptide which is measured at an excitation of 531 nm and FP emission of 595 nm. Assays are carried out in 100 mM Tris, pH=7.2, 10 mM MgCl2, 0.05% NaN3, 0.01% Tween-20, 1 mM dithiothreitol and 2.5% dimethyl sulfoxide. IMAP Progressive Binding Reagent is diluted 1:800 in 100% 1× Solution A from Molecular Devices, cat#R7285.

General protocol is as follows: To 10 ul of cdk9/cyclinT1, 0.5 ul of test compound in dimethyl sulfoxide is added. 5TAMRA-cdk7tide and ATP are mixed. 10 ul of the 5TAMRA-cdk7tide/ATP mix is added to start the reaction. The reaction is allowed to proceed for 4.5 hrs. 60 uL of IMAP Progressive Binding Reagent is added. After >1 hr of incubation, plates are read on the Envision 2101 from Perkin-Elmer. The assay is run in a 384-well format using black Corning plates, cat#3573.

Cdk9/cyclinT1 Alpha Screen Protocol

Full length wild type Cdk9/cyclin T1 is purchased from Invitogen, cat#PV4131. The final total protein concentration in the assay 1 nM. The cdk7tide peptide substrate, biotin-GGGGYSPTSPSYSPTSPSYSPTSPS-OH, is a custom synthesis purchased from the Tufts University Core Facility. The final concentration of cdk7tide peptide substrate is 200 nM. The ATP substrate (Adenosine-5'-triphosphate) is purchased from Roche Diagnostics. The final concentration of ATP substrate is 6 uM. Phospho-Rpb1 CTD (ser2/5) substrate antibody is purchased from Cell Signaling Technology. The final concentration of antibody is 0.67 ug/ml. The Alpha Screen Protein A detection kit containing donor and acceptor beads is purchased from PerkinElmer Life Sciences. The final concentration of both donor and acceptor beads is 15 ug/ml. Alpha Screen is used for detection. The biotinylated-cdk7tide peptide is phosphorylated by cdk9/cyclinT1 using the ATP substrate. The biotinylated-cdk7tide peptide substrate is bound to the streptavidin coated donor bead. The antibody is bound to the protein A coated acceptor bead. The antibody will bind to the phosphorylated form of the biotinylated-cdk7tide peptide substrate, bringing the donor and acceptor beads into close proximity. Laser irradiation of the donor bead at 680 nm generates a flow of short-lived singlet oxygen molecules. When the donor and acceptor beads are in close proximity, the reactive oxygen generated by the irradiation of the donor beads initiates a luminescence/fluorescence cascade in the acceptor beads. This process leads to a highly amplified signal with output in the 530-620 nm range. Assays are carried out in 50 mM Hepes, pH=7.5, 10 mM MgCl2, 0.1% Bovine Serum Albumin, 0.01% Tween-20, 1 mM Dithiolthreitol, 2.5% Dimethyl Sulfoxide. Stop and detection steps are combined using 50 mM Hepes, pH=7.5, 18 mM EDTA, 0.1% Bovine Serum Albumin, 0.01% Tween-20.

General protocol is as follows: To 5 ul of cdk9/cyclinT1, 0.25 ul of test compound in dimethyl sulfoxide is added. Cdk7tide peptide and ATP are mixed. 5 ul of the cdk7tide peptide/ATP mix is added to start the reaction. The reaction is allowed to proceed for 5 hrs. 10 uL of Ab/Alpha Screen beads/Stop-detection buffer is added. Care is taken to keep Alpha Screen beads in the dark at all times. Plates are incubated at room temperature overnight, in the dark, to allow for detection development before being read. The assay is run is a 384-well format using white polypropylene Greiner plates.

The data shown in Table 2 below were generated using one of the assays described above.

TABLE 2

| Compound # in the write-up | CDK9 CYCLINT1 (IC50) |
|---|---|
| 1 | 0.007945 |
| 2 | 0.025572 |
| 3 | 0.237603 |
| 4 | 0.009055 |
| 5 | 0.039655 |
| 6 | 0.136417 |
| 7 | 0.024792 |
| 8 | 0.084843 |
| 9 | 0.007945 |
| 10 | 0.018574 |
| 11 | 0.132509 |
| 12 | 0.007945 |
| 13 | 0.007945 |
| 14 | 0.522 |
| 15 | 0.007945 |
| 16 | 0.023617 |
| 17 | 0.02323424 |
| 18 | 0.007945 |
| 19 | 0.007945 |
| 20 | 0.007945 |
| 21 | 0.007945 |
| 22 | 0.007945 |
| 23 | 0.007945 |
| 24 | 0.012416 |
| 25 | 0.008079 |
| 26 | 0.016256 |
| 27 | 0.007945 |
| 27 | 0.007945 |
| 29 | 0.007945 |
| 30 | 0.007945 |
| 31 | 0.044838 |
| 32 | 0.015002 |
| 33 | 0.026973 |
| 34 | 0.048274 |
| 35 | 0.055761 |
| 36 | 0.008906 |
| 37 | 0.007945 |
| 38 | 0.007945 |
| 39 | 0.008896 |
| 40 | 0.007945 |
| 41 | 0.01288 |
| 42 | 0.048069 |
| 43 | 0.007945 |
| 44 | 0.011238 |
| 45 | |
| 46 | 0.007945 |
| 47 | 0.007945 |
| 48 | 0.00794 |
| 49 | 0.014430 |
| 50 | 0.007945 |
| 51 | 0.017367 |
| 52 | 0.019224 |
| 53 | 0.011128 |
| 54 | 0.023156 |
| 55 | 0.007945 |
| 56 | 0.039262 |

TABLE 2-continued

| Compound # in the write-up | CDK9 CYCLINT1 (IC50) |
|---|---|
| 57 | 0.032590 |
| 58 | 0.031203 |
| 59 | 0.009128 |
| 60 | 0.007945 |
| 61 | 0.018100 |
| 62 | 0.007945 |
| 63 | 0.007945 |
| 64 | 0.054559 |
| 65 | 0.007945 |
| 66 | 0.017131 |
| 67 | 2.550202 |
| 68 | 0.274123 |
| 69 | 0.154400 |
| 70 | 0.173426 |
| 71 | 0.027388 |
| 72 | 0.114363 |
| 73 | 0.035218 |
| 74 | 0.041585 |
| 75 | 0.013530 |
| 76 | 0.011082 |
| 77 | 0.007945 |
| 78 | 0.024249 |
| 79 | 0.007945 |
| 80 | 0.031705 |
| 81 | 0.054218 |
| 82 | 0.009047 |
| 83 | 0.011615 |
| 84 | 0.014118 |
| 85 | 0.068526 |
| 86 | 0.081460 |
| 87 | 0.068978 |
| 88 | 0.011003 |
| 89 | 2.582156 |
| 90 | 2.960356 |
| 91 | 0.335581 |
| 92 | 0.295616 |
| 93 | 0.928257 |
| 94 | 0.50746 |
| 95 | 1.951420 |
| 96 | 1.276694065 |
| 97 | 0.339265455 |
| 98 | 0.415725004 |
| 99 | 0.679432727 |
| 100 | 0.308717658 |
| 101 | 0.007945668 |
| 102 | 0.120571151 |
| 103 | 0.133698728 |
| 104 | 0.140890633 |
| 105 | 0.0180851 |
| 106 | 0.059240258 |
| 107 | 0.015318231 |
| 105 | 0.084308021 |
| 106 | 0.072890252 |
| 107 | 0.007945668 |
| 108 | 0.007945668 |
| 109 | 0.015815541 |
| 110 | 0.025176571 |
| 111 | 0.030797253 |
| 112 | 0.027282158 |
| 113 | 0.050224047 |
| 114 | 0.007945668 |
| 115 | 0.007945668 |
| 116 | 0.007945668 |
| 117 | 0.123719173 |
| 118 | 0.138887135 |
| 119 | 0.154521231 |
| 120 | 0.045604039 |
| 121 | 10.49437327 |
| 122 | 0.007945668 |
| 123 | 0.042845475 |
| 124 | 0.116276412 |
| 125 | 0.278772642 |
| 126 | 0.033296354 |
| 127 | 0.139053728 |
| 128 | 0.033364795 |
| 129 | 0.390099615 |

TABLE 2-continued

| Compound # in the write-up | CDK9 CYCLINT1 (IC50) |
|---|---|
| 130 | 0.16902747 |
| 131 | 0.46977199 |
| 132 | 0.014431175 |
| 133 | 0.007945668 |
| 134 | 0.01051692 |
| 135 | 0.142053718 |
| 136 | 0.204223958 |
| 137 | 0.007945668 |
| 138 | 0.521640084 |
| 139 | 0.030140062 |
| 140 | 0.012553271 |
| 141 | 0.204786235 |
| 142 | 0.025611049 |
| 143 | 0.022738812 |
| 144 | 0.015810302 |
| 145 | 0.007945668 |
| 146 | 0.007945668 |
| 147 | 0.019350577 |
| 148 | 15.62589296 |
| 149 | 0.516196192 |
| 150 | 6.512117546 |
| 151 | 0.007945668 |
| 152 | 0.027 |
| 153 | 1.546 |
| 154 | 0.382 |
| 155 | 0.023 |
| 156 | 0.045 |
| 157 | 0.0079 |
| 158 | 0.011 |
| 159 | 1.383 |
| 160 | 0.019 |
| 161 | 0.026 |
| 162 | 0.014 |
| 163 | 0.013 |
| 164 | 0.039 |
| 165 | 0.0079 |
| 166 | 0.027 |
| 167 | 0.018 |
| 168 | 0.037 |
| 169 | 0.009 |
| 170 | 0.044 |
| 171 | 0.218 |
| 172 | 0.015 |
| 173 | 0.062 |
| 174 | 0.029 |
| 175 | 0.024 |
| 176 | 0.021 |
| 177 | 0.013 |
| 178 | 0.103 |
| 179 | 0.544 |
| 180 | 0.01213 |
| 181 | 0.00794 |
| 182 | 0.02111 |
| 183 | 0.00794 |
| 184 | 0.00911 |
| 185 | 0.11048 |
| 186 | 0.00794 |
| 187 | 2.73860 |
| 188 | 0.00794 |
| 189 | 0.00794 |
| 190 | 0.1 |
| 191 | 0.00794 |
| 192 | 0.00794 |
| 193 | 0.00794 |
| 194 | 0.04813 |
| 195 | 0.03556 |
| 196 | 0.81167 |
| 197 | 0.00794 |
| 198 | 0.00794 |
| 199 | 0.00794 |
| 200 | 0.00794 |
| 201 | 0.63424 |
| 202 | 0.01884 |
| 203 | 0.00794 |
| 204 | 0.00794 |
| 205 | 0.01747 |

TABLE 2-continued

| Compound # in the write-up | CDK9 CYCLINT1 (IC50) |
|---|---|
| 206 | 0.13378 |
| 207 | 0.114147 |
| 208 | 0.00794 |
| 209 | 0.18300 |
| 210 | 0.085970 |
| 211 | 0.02101 |
| 212 | 0.05460 |
| 213 | 0.0142 |
| 214 | 0.04169 |
| 215 | 0.06545 |
| 216 | 0.13825 |
| 217 | 0.03728 |
| 218 | 0.12766 |
| 219 | 0.007945 |
| 220 | 0.007945 |
| 221 | 0.007945 |
| 222 | 0.007945 |
| 223 | 0.007945 |
| 224 | 0.091885 |
| 225 | 0.007945 |
| 226 | 0.007945 |
| 227 | 0.025907 |
| 228 | 0.007945 |
| 229 | 0.007945 |
| 230 | 0.007945 |
| 231 | 0.014853 |
| 232 | 0.007945 |
| 233 | 0.007945 |
| 234 | 0.007945 |
| 235 | 0.007945 |
| 236 | 0.007945 |
| 237 | 0.007945 |
| 238 | 0.013635 |
| 239 | 0.018420 |
| 240 | 0.020961 |
| 241 | 0.06179 |
| 242 | 0.015408 |
| 243 | 0.007945 |
| 244 | 0.078984 |
| 245 | 0.05337 |
| 246 | 0.01154 |
| 247 | 0.02018 |
| 248 | 0.01058 |
| 249 | 0.0318 |
| 250 | 0.02839 |
| 251 | 0.04320 |
| 252 | 0.00794 |
| 253 | 0.00794 |
| 254 | 0.00833 |
| 255 | 0.04232 |
| 256 | 0.00794 |
| 257 | 0.00794 |
| 258 | 0.00794 |
| 259 | 0.00794 |
| 260 | 0.00794 |
| 261 | 0.00794 |
| 262 | 0.00794 |
| 263 | 0.00794 |
| 264 | 0.00794 |
| 265 | 0.03258 |
| 266 | 0.00794 |
| 267 | 0.27007 |
| 268 | 0.008143 |
| 269 | 0.007945 |
| 270 | 0.00794 |
| 271 | 0.00794 |
| 272 | 0.00794 |
| 273 | 0.02293 |
| 274 | 0.03777 |
| 275 | 0.14630 |
| 276 | 0.00893 |
| 277 | 0.00794 |
| 278 | 0.00794 |
| 279 | 0.01310 |
| 280 | 0.0161 |
| 281 | 0.06124 |
| 282 | 0.00794 |
| 283 | 0.001 |
| 284 | 0.001 |
| 285 | 0.002 |
| 286 | 0.001 |
| 287 | 0.003 |
| 288 | 0.003 |
| 289 | 0.004 |
| 290 | 0.002 |
| 291 | 0.001 |
| 292 | 0.002 |
| 293 | 0.001 |
| 294 | 0.001 |
| 295 | |
| 296 | 0.277 |
| 297 | 0.001 |
| 298 | 0.001 |
| 299 | 0.001 |
| 300 | 0.219 |
| 301 | 0.003 |
| 302 | 0.001 |
| 303 | 1.296 |
| 304 | 6.188 |
| 305 | 0.001 |
| 306 | 0.009 |
| 307 | 0.008 |
| 308 | 0.001 |
| 309 | 0.035 |
| 310 | 0.0003 |
| 311 | 0.001 |
| 312 | 0.0003 |
| 313 | 0.001 |
| 314 | 0.001 |
| 315 | 0.018 |
| 316 | 0.009 |
| 317 | 0.099 |
| 318 | 0.00026 |
| 319 | 0.004 |
| 320 | 0.001 |
| 321 | 0.011 |
| 322 | 0.003 |
| 323 | 0.001 |
| 324 | 0.002 |
| 325 | 0.01 |
| 326 | 0.00049 |
| 327 | 0.001 |
| 328 | 0.001 |
| 329 | 0.001 |
| 330 | 0.002 |
| 331 | 0.001 |
| 332 | 0.001 |
| 333 | 0.004 |
| 334 | 0.001 |
| 335 | 0.00027 |
| 336 | |
| 337 | |
| 338 | |
| 339 | 0.00017 |
| 340 | 0.00023 |
| 341 | 0.00015 |
| 342 | 0.00017 |
| 343 | 0.00031 |
| 344 | |
| 345 | |
| 346 | 0.001 |
| 347 | 0.001 |
| 348 | 0.002 |
| 349 | 0.001 |
| 350 | 0.001 |
| 351 | |
| 352 | |
| 353 | |
| 354 | |
| 355 | |
| 356 | |
| 357 | 0.00016 |

TABLE 2-continued

| Compound # in the write-up | CDK9 CYCLINT1 (IC50) |
|---|---|
| 358 | 0.00017 |
| 359 | 0.00024 |
| 360 | 0.00028 |
| 361 | 0.00030 |
| 362 | 0.00036 |
| 363 | 0.00043 |
| 364 | 0.00063 |
| 365 | 0.00070 |
| 366 | 0.0010 |
| 367 | 0.0031 |

The invention claimed is:

1. A compound of formula (I):

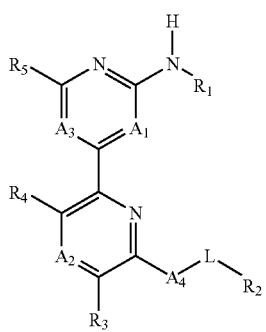

or a pharmaceutically acceptable salt thereof, wherein:
$A_1$ is $CR_6$;
$A_2$ is $CR_7$;
$A_3$ is $CR_8$;
$A_4$ is $NR_9$, or O;
L is selected from a bond, optionally substituted $C_{1-4}$alkyl, $C_{3-6}$ cycloalkyl, $C_{3-6}$ heterocycloalkyl, or $C_{2-4}$ alkenyl;
$R_1$ is X—$R_{16}$;
X is a bond, or $C_{1-4}$ alkyl and;
$R_{16}$ is selected from the group consisting of $C_{1-6}$ alkyl, $C_{3-6}$ branched alkyl, $C_{3-8}$cycloalkyl, heterocycloalkyl, $C_{3-8}$-partially unsaturated cycloalkyl, aryl, and heteroaryl;
wherein $R_{16}$ is substituted with one to three groups independently selected from halogen, hydrogen, $C_{1-6}$alkyl, $C_{1-6}$haloalkyl, $C_{3-6}$branched alkyl, $C_{3-6}$branched haloalkyl, OH, $C_{1-6}$alkoxy, $R_{22}$—$OR_{12}$, $S(O)_{0-2}R_{12}$, $R_{22}$—$S(O)_{0-2}R_{12}$, $S(O)_2NR_{13}R_{14}$, $R_{22}$—$S(O)_2NR_{13}R_{14}$, $C(O)OR_{12}$, $R_{22}$—$C(O)OR_{12}$, $C(O)R_{19}$, $R_{22}$—$C(O)R_{19}$, O—$C_{1-3}$ alkyl, $OC_{1-3}$ haloalkyl, OC(O)$R_{19}$, $R_{22}$—$OC(O)R_{19}$, $C(O)NR_{13}R_{14}$, $R_{22}$—$C(O)NR_{13}R_{14}$, $NR_{15}S(O)_2R_{12}$, $R_{22}$—$NR_{15}S(O)_2R_{12}$, $NR_{17}R_{18}$, $R_{22}$—$NR_{17}R_{18}$, $NR_{15}C(O)R_{19}$, $R_{22}$—$NR_{15}C(O)R_{19}$, $NR_{15}C(O)OCH_2Ph$, $R_{22}$—$NR_{15}C(O)OCH_2Ph$, $NR_{15}C(O)OR_{12}$, $R_{22}$—$NR_{15}C(O)OR_{12}$, $NR_{15}C(O)NR_{13}R_{14}$, and $R_{22}$—$NR_{15}C(O)NR_{13}R_{14}$;
$R_{17}$ and $R_{18}$ are each, independently, selected from the group consisting of hydrogen, hydroxyl, $C_{1-6}$alkyl, $C_{1-6}$haloalkyl, $C_{3-6}$branched alkyl, $C_{3-6}$cycloalkyl, $R_{22}$—$OR_{12}$, $R_{22}$—$S(O)_{0-2}R_{12}$, $R_{22}$—$S(O)_2NR_{13}R_{14}$, $R_{22}$—$C(O)OR_{12}$, $R_{22}$—$C(O)R_{19}$, $R_{22}$—$OC(O)R_{19}$, $R_{22}$—$C(O)NR_{13}R_{14}$, $R_{22}$—$NR_{15}S(O)_2R_{12}$, $R_{22}$—$NR_{23}R_{24}$, $R_{22}$—$NR_{15}C(O)R_{19}$, $R_{22}$—$NR_{15}C(O)$ $OCH_2Ph$, $R_{22}$—$NR_{15}C(O)OR_{12}$, $R_{22}$—$NR_{15}C(O)$ $NR_{13}R_{14}$, cycloalkyl, heterocycloalkyl and heteroaryl;

alternatively, $R_{17}$ and $R_{18}$ along with the nitrogen atom to which they are attached to can be taken together to form a four to six membered heterocyclic ring wherein the carbon atoms of said ring are optionally substituted with $R_{20}$, and the nitrogen atoms of said ring are optionally substituted with $R_{21}$;
$R_{19}$ is selected from optionally substituted alkyl, optionally substituted cycloalkyl, optionally substituted heterocycloalkyl, optionally substituted aryl, and optionally substituted heteroaryl;
$R_{20}$ is selected from the group consisting of $C_{1-6}$ alkyl or $C_{1-6}$ haloalkyl;
$R_{21}$ is selected from the group consisting of $C_{1-6}$alkyl, $C_{1-6}$haloalkyl, $C(O)R_{12}$, $C(O)OR_{12}$, $S(O)_2R_{12}$;
$R_{22}$ is selected from the group consisting of $C_{1-6}$ alkyl, $C_{1-6}$haloalkyl, $C_{3-6}$ branched alkyl, $C_{3-6}$branched haloalkyl;
$R_{23}$ and $R_{24}$ are each, independently, selected from die group consisting of hydrogen, $C_{1-6}$ alkyl, $C_{1-6}$-haloalkyl, $C_{3-6}$ branched alkyl, $C_{3-6}$ branched haloalkyl;
$R_2$ is selected from the group consisting of optionally substituted $C_{1-6}$ alkyl, optionally substituted, $C_{3-6}$ branched alkyl, optionally substituted $C_{3-8}$ cycloalkyl, optionally substituted heterocycloalkyl, optionally substituted aryl, and optionally substituted heteroaryl;
$R_4$, $R_5$, and $R_6$ are each, independently, selected from the group consisting of hydrogen, hydroxyl, cyano, halogen, $C_{1-4}$ alkyl, $C_{1-4}$haloalkyl, $C_{2-4}$ alkenyl, $C_{2-4}$ alkynyl, amino, $NR_{10}R_{11}$, and alkoxy;
$R_3$ and $R_7$ are each, independently, selected from the group consisting of hydrogen, hydroxyl, cyano, halogen, alkyl, haloalkyl, alkenyl, alkynyl, alkoxy, $NR_{10}R_{11}$, $C(O)R_{12}$, $C(O)OR_{12}$, $C(O)NR_{13}R_{14}$, $S(O)_{0-2}R_{12}$, $S(O)_{0-2}NR_{13}R_{14}$, and optionally substituted $C_{3-4}$ cycloalkyl;
$R_8$ is selected from Cl, F, and methyl;
$R_9$ is selected from the group consisting of hydrogen, $C_{1-4}$ alkyl, alkoxy, $C(O)R_{12}$, $C(O)OR_{15}$, $C(O)NR_{13}R_{14}$, $S(O)_{0-2}R_{12}$, $S(O)_{0-2}NR_{13}R_{14}$ optionally substituted $C_{3-4}$ cycloalkyl, and optionally substituted heterocycloalkyl;
$R_{10}$ and $R_{11}$ are each, independently, selected from the group consisting of hydrogen, hydroxyl, alkyl, alkoxy, $C(O)R_{12}$, $C(O)OR_{12}$, $C(O)NR_{13}R_{14}$, $S(O)_{0-2}R_{12}$, and $S(O)_{0-2}NR_{13}R_{14}$; alternatively, $R_{10}$ and $R_{11}$ along with the nitrogen atom to which they are attached to can be taken together to form an optionally substituted four to six membered heteroaromatic, or a non-aromatic heterocyclic ring;
$R_{12}$ and $R_{15}$ are each, individually, selected from the group consisting of hydrogen, alkyl, branched alkyl, haloalkyl, branched haloalkyl, $(CH_2)_{0-3}$-cycloalkyl, $(CH_2)_{0-3}$-heterocycloalkyl, $(CH_2)_{0-3}$-aryl, and heteroaryl;
$R_{13}$ and $R_{14}$ are each, independently, selected from the group consisting of hydrogen, hydroxyl, alkyl, branched alkyl, haloalkyl, branched haloalkyl, alkoxy, cycloalkyl or heterocycloalkyl; and alternatively, $R_{13}$ and $R_{14}$ along with the nitrogen atom to which they are attached to can be taken together to form an optionally substituted four to six membered heteroaromatic, or non-aromatic heterocyclic ring.

2. A compound of claim 1, wherein:
$R_8$ is Cl.

3. A compound of claim 1, wherein:
$R_1$ is X—$R_{16}$;
X is a bond, or $C_{1-2}$ alkyl;
$R_{16}$ is selected from the group consisting of $C_{1-2}$-alkyl, $C_{4-6}$cycloalkyl, heterocycloalkyl, phenyl, and heteroaryl;

wherein $R_{16}$ is substituted with one to three groups independently selected from halogen, hydrogen, $C_{1-3}$alkyl, $C_{3-6}$branched alkyl, OH, $C_{1-2}$alkoxy, $R_{22}$—$OR_{12}$, $S(O)_{1-2}R_{12}$, $C(O)OR_{12}$, $R_{22}$—$C(O)OR_{12}$, $C(O)R_{19}$, $R_{22}$—$OC(O)R_{19}$, $C(O)NR_{13}R_{14}$, $NR_{15}S(O)_2R_{12}$, $NR_{17}R_{18}$, $R_{22}$—$NR_{17}R_{18}$, $NR_{15}C(O)R_{19}$, $R_{22}$—$NR_{15}C(O)R_{19}$, and $NR_{15}C(O)OCH_2Ph$.

4. A compound of claim 1, wherein:
$R_{16}$ selected from the group consisting of $C_{1-2}$-alkyl, cyclopentyl, cyclohexyl, piperidine, piperazine, morpholine, pyridine pyrrolidine, cyclohexenyl, and tetrahydro-2H-pyran;
wherein $R_{16}$ is substituted with one to three groups selected from amino, hydroxyl, $NHCH_2$-phenyl, $CH_2$-amino, COO-t-butyl, H, methoxy, NH—$SO_2$-ethyl, $CH_2$—$NHSO_2$-ethyl, $SO_2$-ethyl, t-butyl, methyl, $CH_2$—COOH, CO—$NHCH_3$, $CON(CH_3)_2$, $NHC(CH_3)$—$CH_2$—$SO_2$—$CH_3$, NH—COO—$CH_2$-phenyl, hydroxy-methyl, $CH_2$—NH—$CH_3$, $CH_2$—NH-ethyl, NH—$CH_2$—$CH_2$-methoxy, $CH_2$—NH—CO—$CH_3$, NH—$CH_2$—$CH_2$OH, NH—CO—$CH_2$—$N(CH_3)_2$, NH—CO-methylpyrrolidine, NH—$CH_2$—$C(CH_3)$-dioxolane, NH—CO-pyridyl, NH-ethyl, pyrrolidine, $CH_2$—NH—CO-pyridyl, NH-tetrahydropyran, $COCH_2$—$N(CH_3)_2$, NH—$CH_2$—$C(CH_3)$-dimethyl-dioxolane, tetrahydropyran, CO-methylpyrrolidine, $CH_2$-methylpiperidine, NH—CO—$CH_3$, NH—$SO_2$—$CH_3$, NH—$CH(CH_2$—$OCH_3)_2$, NH—$CH_2$-tetrahydrofuran, NH—$CH_2$-oxetane, NH-tetrahydropyran, NH—$CH_2$-dioxane, $N(CH_3)$—$CH_2CH_2$—$OCH_3$, CH(OH)—$CH_2$-amino, NH—$CH_2CH_2$—$OCF_3$, $NHCH_2$—$OCH_3$, NH—$CH_2$—$CH(CF_3)$—$OCH_3$, NH—$CH(CH_3)$—$CH_2$—OH, F, NH-oxetane, $CH_2$—$CH_2OCH_3$, $CH_2$—$OCH_3$, $CH_2$-tetrahydropyran, $CH_2$-methylpiperizine, $NH_2$—$CH_2$—CH(OH)—$CF_3$, piperidine, $CH_2$-pyrrolidine, NH—$CH(CH_3)CH_2OCH_3$, NH-tetrahydrofuran, $(CH_2)_3$—$NH_2$, hydroxyethyl, propyl, $CH_2$-pyridyl, $CH_2$-piperidine, morpholine, NH-chloropyrimidine, NH—$CH_2CH_2$—$SO_2$-methyl, $(CH_3)_3$—$N(CH_3)_2$, piperizine,

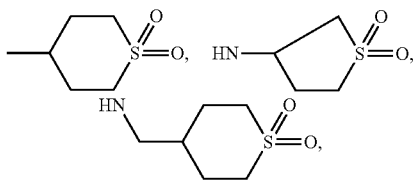

and $CH_2$-morpholine.

5. A compound of claim 1 wherein:
$R_3$ is selected from H, methyl, cyano, chloro, $CONH_2$, amino, cyclopropyl, ethyl, and fluoro;
$R_4$ is selected from halogen, methyl, hydrogen, and halomethyl;
$R_6$ is H;
$R_7$ is selected from H, COOH, Cl, F, $CONH_2$, CN, and $CF_3$;
$R_8$ is Cl;
$R_{17}$ and $R_{18}$ are each, independently, selected from the group consisting of hydrogen, $C_{1-3}$alkyl, $C_{1-4}$haloalkyl, $C_{3-6}$branched alkyl, $R_{22}$—$OR_{12}$, $R_{22}$—$S(O)_2R_{12}$, $R_{22}$—$NR_{15}S(O)_2R_{12}$, heterocycloalkyl or heteroaryl; alternatively, $R_{17}$ and $R_{18}$ along with the nitrogen atom to which they are attached to can be taken together to form a four to six membered heterocyclic ring wherein said ring carbon atoms are optionally substituted with $R_{20}$, and the ring nitrogen atoms are optionally substituted with $R_{21}$;
$R_{19}$ is selected from $C_{1-3}$-alkyl, optionally substituted heterocycloalkyl, optionally substituted aryl or optionally substituted heteroaryl;
$R_{20}$ represents the group $C_{1-3}$alkyl; and
$R_{22}$ is selection from the group consisting of $C_{1-4}$alkyl, and $C_{3-6}$ branched alkyl.

6. A compound of claim 1, wherein:
L is selected from $C_{1-4}$-alkyl, and cyclopropyl;
$R_2$ is selected from the group consisting of $C_{3-7}$ cycloalkyl, a five to seven membered heterocycloalkyl, phenyl, and pyridyl, wherein each said $R_2$ group is substituted with one, two, or three substituents independently selected from hydrogen, cyano, CO—$NH_2$, halogen, methoxy, dihalo-methoxy, trihalo-methoxy, trihalo alkyl, $C_{1-3}$-alkyl, and hydroxy; and
$R_9$ represents methyl, hydrogen, or ethyl.

7. A compound of claim 1, wherein:
L is $C_{1-2}$ alkyl, or $C_{3-4}$-cycloalkyl;
$R_1$ is X—$R_{16}$;
X is a bond, or $C_{1-2}$ alkyl;
$R_{16}$ is selected from the group consisting of $C_{1-2}$-alkyl, cyclopentyl, cyclohexyl, piperidine, piperazine, morpholine, pyridine, pyrrolidine, cyclohexenyl, and tetrahydro-2H-pyran;
wherein $R_{16}$ is substituted with one to three groups independently selected from amino, hydroxyl, $NHCH_2$-phenyl, $CH_2$-amino, COO-t-butyl, H, methoxy, NH—$SO_2$-ethyl, $CH_2$—$NHSO_2$-ethyl, $SO_2$-ethyl, t-butyl, methyl, $CH_2$—COOH, CO—$NHCH_3$, $CON(CH_3)_2$, $NHCH_2$—$CH_2$—$SO_2$—$CH_3$, NH—COO—$CH_2$-phenyl, hydroxy-methyl, $CH_2$—NH—$CH_3$, $CH_2$—NH-ethyl, NH—$CH_2$—$CH_2$-methoxy, $CH_2$—NH—CO—$CH_3$, NH—$CH_2$—$CH_2$OH, NH—CO—$CH_2$—$N(CH_3)_2$, NH—CO-methylpyrrolidine, NH—CO-pyridyl, NH-ethyl, pyrrolidine, $CH_2$—NH—CO-pyridyl, $COCH_2$—$N(CH_3)_2$, tetrahydropyran, CO-methylpyrrolidine, $CH_2$-methylpiperidine, NH—CO—$CH_3$, NH—$SO_2$—$CH_3$, NH—$CH_2$-tetrahydrofuran, NH—$CH_2$-dioxane, $N(CH_3)$—$CH_2CH_2$—$OCH_3$, CH(OH)—$CH_2$-amino, NH—$CH_2CH_2OCF_3$, $NH(CH_3)$—$CH_2$—$OCH_3$, NH—$CH_2$—$CH(CF_3)$—$OCH_3$, F, NH-oxetane, $CH_2$—$CH_2$—$OCH_3$, $CH_2$—$OCH_3$, $CH_2$-tetrahydropyran, $CH_2$-methylpiperizine, $NH_2$—$CH_2$—CH(OH)—$CF_3$, piperidine, $CH_2$-pyrrolidine, NH—$CH(CH_3)CH_2OCH_3$, NH-tetrahydrofuran, $(CH_2)_3$—$NH_2$, hydroxyethyl, propyl, $CH_2$-pyridyl, $CH_2$-piperidine, morpholine, NH-chloropyrimidine, NH—$CH_2CH_2$—$SO_2$-methyl, $(CH_3)_3$—$N(CH_3)_2$, piperizine, $CH_2$-morpholine, NH—$CH_2$—$C(CH_3)$-dioxolane, NH-tetrahydropyran, NH—$CH_2$—$C(CH_3)$-dimethyldioxolane, NH—$CH(CH_2$—$OCH_3)_2$, NH—$CH_2$-oxetane, NH-tetrahydropyran, $N(CH_3)$—$CH_2CH_2$—$OCH_3$, NH—$CH(CH_3)$—$CH_2OH$,

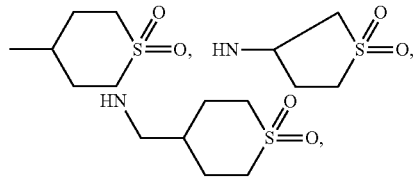

and NH—CH(CH$_3$)—CH$_2$—OH;

R$_2$ is selected from the group consisting of cyclohexyl; 1,3-dioxane, pyridinyl, phenyl, tetrahydropyranyl, cycloheptyl, 1,4-dioxane, morpholinyl, alkyl substituted dioxane, tetrahydrofuranyl, dioxepane, piperidinyl, and

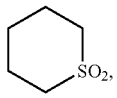

wherein each said R$_2$ group is substituted with one, two, or three substituents independently selected from Cl, Br, F, methoxy, hydroxy-methyl, hydrogen, carboxamide, cyano, dihalo-methoxy, trihalo-methoxy, trifluoro-methyl, hydroxyl, and methyl; and R$_4$, is chloro, hydrogen, trifluoro-methyl, fluoro, or bromo;

R$_5$, and R$_6$ are each independently hydrogen;

R$_3$ is selected from hydrogen, fluoro, cyano, CO—NH$_2$, chloro, amino, methyl, and cyclopropyl;

R$_7$ is selected from H, trifluoro-methyl, COOH, CO—NH$_2$, and cyano;

R$_8$ represents Cl; and

R$_9$ is selected from the group considering of H, ethyl, and methyl.

8. A compound of claim 1 selected from:

N2'-(trans-4-aminocyclohexyl)-5'-chloro-3,5-difluoro-N6-((tetrahydro-2H-pyran-4-yl)methyl)-2,4'-bipyridine-2',6-diamine;

N2'-(trans-4-aminocyclohexyl)-5'-fluoro-N6-(3-fluorobenzyl)-2,4'-bipyridine-2',6-diamine;

3,5'-dichloro-N2'-(trans-4-(((R)-2,2-dimethyl-1,3-dioxolan-4-yl)methyl)aminocyclohexyl)-N6-((tetrahydro-2H-pyran-4-yl)methyl)-2,4'-bipyridine-2',6-diamine;

5'-chloro-N6-((tetrahydro-2H-pyran-4-yl)dideuteromethyl)-N2'-(trans-4-(((S)-tetrahydrofuran-2-yl)methyl) aminocyclohexyl)-2,4'-bipyridine-2',6-diamine;

5'-chloro-5-fluoro-N2'-(trans-4-(2-(methylsulfonyl)ethylamino)cyclohexyl)-N6-((tetrahydro-2H-pyran-4-yl) methyl)-2,4'-bipyridine-2',6-diamine;

5'-chloro-5-fluoro-N2'-(trans-4-(oxetan-2-yl-methylamino)cyclohexyl)-N6-((tetrahydro-2H-pyran-4-yl) methyl)-2,4'-bipyridine-2',6-diamine;

3,5'-dichloro-N2'-(trans-4-((R)-1-methoxypropan-2-ylamino)cyclohexyl)-N6-(((S)-tetrahydro-2H-pyran-3-yl)methyl)-2,4'-bipyridine-2',6-diamine;

3,5'-dichloro-N2'-(trans-4-((R)-1-methoxypropan-2-ylamino)cyclohexyl)-N6-(((R)-tetrahydro-2H-pyran-3-yl)methyl)-2,4'-bipyridine-2',6-diamine;

4-((5'-chloro-2'-(trans-4-((R)-1-methoxypropan-2-ylamino)cyclohexylamino)-2,4'-bipyridin-6-yl-amino) methyl)tetrahydro-2H-pyran-4-carbonitrile;

N2'-(trans-4-aminocyclohexyl)-5'-chloro-5-fluoro-N6-(3-fluorobenzyl)-2,4'-bipyridine-2',6-diamine;

2'-(trans-4-aminocyclohexylamino)-5'-chloro-6-(3-fluorobenzylamino)-2,4'-bipyridine-5-carbonitrile;

N2'-(trans-4-aminocyclohexyl)-3-chloro-5'-fluoro-N6-((tetrahydro-2H-pyran-4-yl)methyl)-2,4'-bipyridine-2',6-diamine;

5'-chloro-N6-(3-fluorobenzyl)-N2'-((1R,3S)-3-((methylamino)methyl)cyclopentyl)-2,4'-bipyridine-2',6-diamine;

3,5'-dichloro-N2'-(trans-4-((R)-1-methoxypropan-2-ylamino)cyclohexyl)-N6-((tetrahydro-2H-pyran-4-yl) methyl)-2,4'-bipyridine-2',6-diamine;

5'-chloro-3-fluoro-N2'-(trans-4-((R)-1-methoxypropan-2-yl-amino)cyclohexyl)-N6-((tetrahydro-2H-pyran-4-yl) methyl)-2,4'-bipyridine-2',6-diamine;

5'-chloro-5-fluoro-N2'-(trans-4-((R)-1-methoxypropan-2-yl-amino)cyclohexyl)-N6-((tetrahydro-2H-pyran-4-yl) methyl)-2,4'-bipyridine-2',6-diamine;

5'-chloro-N6-((2,2-dimethyltetrahydro-2H-pyran-4-yl) methyl)-N2'-(trans-4-((R)-1-methoxypropan-2-yl-amino)cyclohexyl)-2,4'-bipyridine-2',6-diamine;

5'-chloro-N6-(((S)-2,2-dimethyltetrahydro-2H-pyran-4-yl)methyl)-N2'-(trans-4-((R)-1-methoxypropan-2-yl-amino)cyclohexyl)-2,4'-bipyridine-2',6-diamine;

5'-chloro-5-fluoro-N6-((tetrahydro-2H-pyran-4-yl)methyl)-N2'-(trans-4-((1,1-dioxotetrahydro-2H-thiopyran-4-yl)methyl)aminocyclohexyl)-2,4'-bipyridine-2',6-diamine;

5'-chloro-5-fluoro-N2'-(trans-4-(2-methoxyethylamino) cyclohexyl)-N6-((tetrahydro-2H-pyran-4-yl)methyl)-2,4'-bipyridine-2',6-diamine;

N2'-(trans-4-aminocyclohexyl)-5'-chloro-N6-(3-fluorobenzyl)-2,4'-bipyridine-2',6-diamine;

N2'-(trans-4-aminocyclohexyl)-5'-chloro-N6-(3,5-difluorobenzyl)-2,4'-bipyridine-2',6-diamine;

N2'-(trans-4-aminocyclohexyl)-5'-chloro-N6-((5-fluoropyridin-3-yl)methyl)-2,4'-bipyridine-2',6-diamine;

trans-4-(5'-chloro-6-(3,5-difluorobenzylamino)-2,4'-bipyridin-2'-yl-amino)cyclohexanol;

(R)-5'-chloro-N6-(3-fluorobenzyl)-N2'-(2-(piperidin-3-yl)ethyl)-2,4'-bipyridine-2',6-diamine;

N2'-(trans-4-aminocyclohexyl)-3,5'-dichloro-N6-((tetrahydro-2H-pyran-4-yl)methyl)-2,4'-bipyridine-2',6-diamine;

N2'-(trans-4-aminocyclohexyl)-3,5'-dichloro-N6-((tetrahydro-2H-pyran-4-yl)methyl)-2,4'-bipyridine-2',6-diamine;

3,5'-dichloro-N2'-(trans-4-(2-methoxyethylamino)cyclohexyl)-N6-((tetrahydro-2H-pyran-4-yl)methyl)-2,4'-bipyridine-2',6-diamine;

2-(trans-4-(3,5'-dichloro-6-((tetrahydro-2H-pyran-4-yl) methyl)amino-2,4'-bipyridin-2'-yl-amino)cyclohexylamino)ethanol;

3,5'-dichloro-N6-((tetrahydro-2H-pyran-4-yl)methyl)-N2'-(trans-4-(((R)-tetrahydrofuran-2-yl)methyl)aminocyclohexyl)-2,4'-bipyridine-2',6-diamine;

3,5'-dichloro-N6-((tetrahydro-2H-pyran-4-yl)methyl)-N2'-(trans-4-(((S)-tetrahydrofuran-2-yl)methyl)aminocyclohexyl)-2,4'-bipyridine-2',6-diamine;

3,5'-dichloro-N2'-(trans-4-((2-methoxyethyl)(methyl) amino)cyclohexyl)-N6-((tetrahydro-2H-pyran-4-yl) methyl)-2,4'-bipyridine-2',6-diamine;

5'-chloro-N6-((tetrahydro-2H-pyran-4-yl)methyl)-N2'-(trans-4-(((R)-tetrahydrofuran-2-yl)methyl)aminocyclohexyl)-2,4'-bipyridine-2',6-diamine;

5'-chloro-N6-((tetrahydro-2H-pyran-4-yl)methyl)-N2'-(trans-4-(((S)-tetrahydrofuran-2-yl)methyl)aminocyclohexyl)-2,4'-bipyridine-2',6-diamine;

N2'-(trans-4-aminocyclohexyl)-5'-chloro-3-fluoro-N6-((tetrahydro-2H-pyran-4-yl)methyl)-2,4'-bipyridine-2',6-diamine;

5'-chloro-3-fluoro-N2'-(trans-4-(2-methoxyethylamino) cyclohexyl)-N6-((tetrahydro-2H-pyran-4-yl)methyl)-2,4'-bipyridine-2',6-diamine;

N2'-(trans-4-aminocyclohexyl)-3-bromo-5'-chloro-N6-((tetrahydro-2H-pyran-4-yl)methyl)-2,4'-bipyridine-2',6-diamine;

3-bromo-5'-chloro-N2'-(trans-4-(2-methoxyethylamino)
cyclohexyl)-N6-((tetrahydro-2H-pyran-4-yl)methyl)-2,
4'-bipyridine-2',6-diamine;
trans-4-(3,5'-dichloro-6-((2,2-dimethyltetrahydro-2H-pyran-4-yl)methyl)amino-2,4'-bipyridin-2'-yl-amino)cyclohexanol;
(2S)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol;
(2R)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol;
3,5'-dichloro-N6-((tetrahydro-2H-pyran-4-yl)methyl)-N2'-(trans-4-(2-(trifluoromethoxy)ethylamino)cyclohexyl)-2,4'-bipyridine-2',6-diamine;
N2'-(trans-4-aminocyclohexyl)-5'-chloro-N6-(((R)-2,2-dimethyltetrahydro-2H-pyran-4-yl)methyl)-2,4'-bipyridine-2',6-diamine;
N2'-(trans-4-aminocyclohexyl)-5'-chloro-N6-(((S)-2,2-dimethyltetrahydro-2H-pyran-4-yl)methyl)-2,4'-bipyridine-2',6-diamine;
N2'-(trans-4-aminocyclohexyl)-3,5,5'-trichloro-N6-((tetrahydro-2H-pyran-4-yl)methyl)-2,4'-bipyridine-2',6-diamine;
N2'-(trans-4-aminocyclohexyl)-5'-chloro-5-fluoro-N6-((tetrahydro-2H-pyran-4-yl)methyl)-2,4'-bipyridine-2',6-diamine;
N2'-(trans-4-aminocyclohexyl)-5'-chloro-N6-((4-methyltetrahydro-2H-pyran-4-yl)methyl)-2,4'-bipyridine-2',6-diamine;
N2'-(trans-4-aminocyclohexyl)-5'-chloro-5-fluoro-N6-((4-methyltetrahydro-2H-pyran-4-yl)methyl)-2,4'-bipyridine-2',6-diamine;
N2'-(trans-4-aminocyclohexyl)-5'-chloro-N6-((4-fluorotetrahydro-2H-pyran-4-yl)methyl)-2,4'-bipyridine-2',6-diamine;
trans-4-(5'-chloro-6-(3-fluorobenzylamino)-2,4'-bipyridin-2'-yl-amino)cyclohexanol;
5'-chloro-N2'-(trans-4-(dimethylamino)cyclohexyl)-N6-(3-fluorobenzyl)-2,4'-bipyridine-2',6-diamine;
5'-chloro-N6-(3-fluorobenzyl)-N2'-(trans-4-(2-methoxyethylamino)cyclohexyl)-2,4'-bipyridine-2',6-diamine;
2-(trans-4-(5'-chloro-6-(3-fluorobenzylamino)-2,4'-bipyridin-2'-yl-amino)cyclohexylamino)ethanol;
5'-chloro-N6-(3,5-difluorobenzyl)-N2'-(trans-4-(2-methoxyethylamino)cyclohexyl)-2,4'-bipyridine-2',6-diamine;
5'-chloro-N6-(3-fluorobenzyl)-N2'-(trans-4-((2-methoxyethyl)(methyl)amino)cyclohexyl)-2,4'-bipyridine-2',6-diamine;
N2'-(trans-4-aminocyclohexyl)-5'-chloro-N6-(((2R,6S)-2,6-dimethyltetrahydro-2H-pyran-4-yl)methyl)-2,4'-bipyridine-2',6-diamine;
4-((5'-chloro-5-fluoro-2'-(trans-4-(2-methoxyethylamino)cyclohexylamino)-2,4'-bipyridin-6-yl-amino)methyl)tetrahydro-2H-pyran-4-carbonitrile;
4-((2'-(trans-4-aminocyclohexylamino)-5'-chloro-5-fluoro-2,4'-bipyridin-6-yl-mino)methyl)tetrahydro-2H-pyran-4-carbonitrile;
4-((5'-chloro-5-fluoro-2'-(trans-4-(propylamino)cyclohexylamino)-2,4'-bipyridin-6-yl-amino)methyl)tetrahydro-2H-pyran-4-carbonitrile;
4-((5'-chloro-2'-(trans-4-(dipropylamino)cyclohexylamino)-5-fluoro-2,4'-bipyridin-6-yl-amino)methyl)tetrahydro-2H-pyran-4-carbonitrile;
4-((5'-chloro-5-fluoro-2'-(trans-4-((R)-1-methoxypropan-2-yl-amino)cyclohexylamino)-2,4'-bipyridin-6-yl-amino)methyl)tetrahydro-2H-pyran-4-carbonitrile;
4-((5'-chloro-2'-(trans-4-((2-methyl-1,3-dioxolan-2-yl)methyl)aminocyclohexylamino)-2,4'-bipyridin-6-yl-amino)methyl)tetrahydro-2H-pyran-4-carbonitrile;
(4-((5'-chloro-2'-(trans-4-((R)-1-methoxypropan-2-yl-amino)cyclohexylamino)-2,4'-bipyridin-6-yl-amino)methyl)tetrahydro-2H-pyran-4-yl)methanol; and
5'-chloro-5-fluoro-N6-((4-methyltetrahydro-2H-pyran-4-yl)methyl)-N2'-(trans-4-(1,1-dioxotetrahydrothiophen-3-yl-amino)cyclohexyl)-2,4'-bipyridine-2',6-diamine.

9. A pharmaceutical composition comprising a compound according to claim 1, or a pharmaceutically acceptable salt thereof, and a pharmaceutically acceptable carrier, diluent or excipient.

10. A compound of claim 1, wherein:
$R_1$ is X—$R_{16}$;
X is a bond, or $C_{1-2}$ alkyl;
$R_{16}$ is selected from the group consisting of $C_{1-2}$-alkyl, cyclopentyl, cyclohexyl, piperidine, piperazine, morpholine, pyridine, pyrrolidine, cyclohexenyl, and, tetrahydro-2H-pyran;
wherein $R_{16}$ is substituted with one to three groups selected from amino, hydroxyl, NHCH$_2$-phenyl, CH$_2$-amino, COO-t-butyl, H, methoxy, NH—SO$_2$-ethyl, CH$_2$—NHSO$_2$-ethyl, SO$_2$-ethyl, t-butyl, methyl, CH$_2$—COOH, CO—NHCH$_3$, CON(CH$_3$)$_2$, NHC(CH$_3$)—CH$_2$—SO$_2$—CH$_3$, NH—COO—CH$_2$-phenyl, hydroxy-methyl, CH$_2$—NH—CH$_3$, CH$_2$—NH-ethyl, NH—CH$_2$—CH$_2$-methoxy, CH$_2$—NH—CO—CH$_3$, NH—CH$_2$—CH$_2$OH, NH—CO—CH$_2$—N(CH$_3$)$_2$, NH—CO-methylpyrrolidine, NH—CH$_2$—C(CH$_3$)-dioxolane, NH—CO-pyridyl, NH-ethyl, pyrrolidine, CH$_2$NH—CO-pyridyl, NH-tetrahydropyran, COCH$_2$—N(CH$_3$)$_2$, NH—CH$_2$—C(CH$_3$)-dimethyldioxolane, tetrahydropyran, CO-methylpyrrolidine, CH$_2$-methylpiperidine, NH—CO—CH$_3$, NH—SO$_2$—CH$_3$, NH—CH (CH$_2$—OCH$_3$)$_2$, NH—CH$_2$-tetrahydrofuran, NH—CH$_2$-oxetane, NH-tetrahydropyran, NH—CH$_2$-dioxane, N(CH$_3$)—CH$_2$CH$_2$—OCH$_3$, CH(OH)—CH$_2$-amino, NH—CH$_2$—OCF$_3$, NHCH$_2$—OCH$_3$, NH—CH$_2$—CH(CF$_3$)—OCH$_3$, NH—CH(CH$_3$)—CH$_2$—OH, F, NH-oxetane, CH$_2$—CH$_2$—OCH$_3$, CH$_2$—OCH$_3$, CH$_2$-tetrahydropyran, CH$_2$-methylpiperizine, NH$_2$—CH$_2$—CH(OH)—CF$_3$, piperidine, CH$_2$-pyrrolidine, NH—CH(CH$_3$)CH$_2$OCH$_3$, NH-tetrahydrofuran, (CH$_2$)$_3$—NH$_2$, hydroxyethyl, propyl, CH$_2$-pyridyl, CH$_2$-piperidine, morpholine, NH-chloropyrimidine, NH—CH$_2$CH$_2$—SO$_2$-methyl, (CH$_3$)$_3$—N(CH$_3$)$_2$, piperizine,

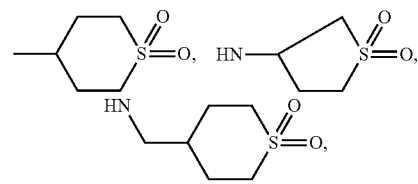

and CH$_2$-morpholine;
$R_3$ is selected from H, methyl, cyano, chloro, CONH$_2$, amino, cyclopropyl, ethyl, and fluoro;
$R_4$ is selected from halogen, methyl, hydrogen, and halomethyl;

R₆ is H;
R₇ is selected from H, COOH, Cl, F, CONH₂, CN, and CF₃;
R₈ is Cl;
R₁₇ and R₁₈ are each, independently, selected from the group consisting of hydrogen C₁₋₃alkyl, C₁₋₄haloalkyl, C₃₋₆branched alkyl, R₂₂—OR₁₂, R₂₂—S(O)₂R₁₂, R₂₂—NR₁₅S(O)₂R₁₂, heterocycloalkyl or heteroaryl; alternatively, R₁₇ and R₁₈ along with the nitrogen atom to which they are attached to can be taken together to form a four to six membered heterocyclic ring wherein said ring carbon atoms are optionally substituted with R₂₀, and the ring nitrogen atoms are optionally substituted with R₂₁;
R₁₉ is selected from C₁₋₃-alkyl, optionally substituted heterocycloalkyl, optionally substituted aryl or optionally substituted heteroaryl;
R₂₀ represents the group C₁₋₃alkyl;
R₂₂ is selection from the group consisting of C₁₋₄alkyl, and C₃₋₆ branched alkyl;
L is selected from C₁₋₄-alkyl, and cyclopropyl;
R₂ is selected from the group consisting of C₃₋₇ cycloalkyl, a five to seven membered heterocycloalkyl, phenyl, and pyridyl, wherein each said R₂ group is substituted with one, two, or three substituents independently selected from hydrogen, cyano, CO—NH₂, halogen, methoxy, dihalo-methoxy, trihalo-methoxy, trihalo alkyl, C₁₋₃-alkyl, and hydroxy; and
R₉ represents methyl, hydrogen, or ethyl.

11. A compound of claim 1, which is selected from:
3,5'-dichloro-N2'-(trans-4-(((R)-2,2-dimethyl-1,3-dioxolan-4-yl)methyl)aminocyclohexyl)-N6-((tetrahydro-2H-pyran-4-yl)methyl)-2,4'-bipyridine-2',6-diamine;
3,5'-dichloro-N2'-(trans-4-((R)-1-methoxypropan-2-yl-amino)cyclohexyl)-N6-(((S)-tetrahydro-2H-pyran-3-yl)methyl)-2,4'-bipyridine-2',6-diamine;
3,5'-dichloro-N2'-(trans-4-((R)-1-methoxypropan-2-yl-amino)cyclohexyl)-N6-(((R)-tetrahydro-2H-pyran-3-yl)methyl)-2,4'-bipyridine-2',6-diamine;
3,5'-dichloro-N2'-(trans-4-((R)-1-methoxypropan-2-yl-amino)cyclohexyl)-N6-((tetrahydro-2H-pyran-4-yl)methyl)-2,4'-bipyridine-2',6-diamine;
5'-chloro-3-fluoro-N2'-(trans-4-((R)-1-methoxypropan-2-yl-amino)cyclohexyl)-N6-((tetrahydro-2H-pyran-4-yl)methyl)-2,4'-bipyridine-2',6-diamine;
5'-chloro-5-fluoro-N2'-(trans-4-((R)-1-methoxypropan-2-yl-amino)cyclohexyl)-N6-((tetrahydro-2H-pyran-4-yl)methyl)-2,4'-bipyridine-2',6-diamine;
5'-chloro-5-fluoro-N6-((tetrahydro-2H-pyran-4-yl)methyl)-N2'-(trans-4-((1,1-dioxotetrahydro-2H-thiopyran-4-yl)methyl)aminocyclohexyl)-2,4'-bipyridine-2',6-diamine;
5'-chloro-5-fluoro-N2'-(trans-4-(2-methoxyethylamino)cyclohexyl)-N6-((tetrahydro-2H-pyran-4;
3,5'-dichloro-N2'-(trans-4-(2-methoxyethylamino)cyclohexyl)-N6-((tetrahydro-2H-pyran-4-yl)methyl)-2,4'-bipyridine-2',6-diamine;
2-(trans-4-(3,5'-dichloro-6-((tetrahydro-2H-pyran-4-yl)methyl)amino-2,4'-bipyridin-2'-yl-amino)cyclohexylamino)ethanol;
3,5'-dichloro-N6-((tetrahydro-2H-pyran-4-yl)methyl)-N2'-(trans-4-4(((R)-tetrahydrofuran-2-yl)methyl)aminocyclohexyl)-2,4'-bipyridine-2',6-diamine;
3,5'-dichloro-N6-((tetrahydro-2H-pyran-4-yl)methyl)-N2'-(trans-4-4(((S)-tetrahydrofuran-2-yl)methyl)aminocyclohexyl)-2,4'-bipyridine-2',6-diamine;
3,5'-dichloro-N2'-(trans-4(2-methoxyethyl)(methyl)amino)cyclohexyl)-N6-((tetrahydro-2H-pyran-4-yl)methyl)-2,4'-bipyridine-2',6-diamine;
5'-chloro-3-fluoro-N2'-(trans-4-(2-methoxyethylamino)cyclohexyl)-N6-((tetrahydro-2H-pyran-4-yl)methyl)-2,4'-bipyridine-2',6-diamine;
3-bromo-5'-chloro-N2'-(trans-4-(2-methoxyethylamino)cyclohexyl)-N6-((tetrahydro-2H-pyran-4-yl)methyl)-2,4'-bipyridine-2',6-diamine;
trans-4-(3,5'-dichloro-6-((2,2-dimethyltetrahydro-2H-pyran-4-yl)methyl)amino-2,4'-bipyridin-2'-yl-amino)cyclohexanol;
(2S)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol;
(2R)-3-(trans-4-(3,5'-dichloro-6-((2,2-dimethyltetrahydro-2H-pyran-4-yl)methyl)amino-2,4'-bipyridin-2'-yl-amino)cyclohexylamino)-1,1,1-trifluoropropan-2-ol;
3,5'-dichloro-N6-((tetrahydro-2H-pyran-4-yl)methyl)-N2'-(trans-4-(2-(trifluoromethoxy)ethylamino)cyclohexyl)-2,4'-bipyridine-2',6-diamine;
4-((5'-chloro-5-fluoro-2'-(trans-4-(2-methoxyethylamino)cyclohexylamino)-2,4'-bipyridin-6-yl-amino)methyl)tetrahydro-2H-pyran-4-carbonitrile;
4-((2'-(trans-4-aminocyclohexylamino)-5'-chloro-5-fluoro-2,4'-bipyridin-6-yl-amino)methyl)tetrahydro-2H-pyran-4-carbonitrile;
4-((5'-chloro-5-fluoro-2'-(trans-4-(propylamino)cyclohexylamino)-2,4'-bipyridin-6-yl-amino)methyl)tetrahydro-2H-pyran-4-carbonitrile;
4-((5'-chloro-2'-(trans-4-(dipropylamino)cyclohexylamino)-5-fluoro-2,4'-bipyridin-6-yl-amino)methyl)tetrahydro-2H-pyran-4-carbonitrile;
4-((5'-chloro-5-fluoro-2'-(trans-4-((R)-1-methoxypropan-2-yl-amino)cyclohexylamino)-2,4'-bipyridin-6-yl-amino)methyl)tetrahydro-2H-pyran-4-carbonitrile; and
5'-chloro-5-fluoro-N6-((4-methyltetrahydro-2H-pyran-4-yl)methyl)-N2'-(trans-4-(1,1-dioxotetrahydrothiophen-3-yl-amino)cyclohexyl)-2,4'-bipyridine-2',6-diamine.

12. A compound of claim 1, which is selected from:
5'-chloro-N6-((tetrahydro-2H-pyran-4-yl)dideuteromethyl)-N2'-(trans -4-(((S)-tetrahydrofuran-2-yl)methyl)aminocyclohexyl)-2,4'-bipyridine-2',6-diamine;
4-((5'-chloro-2'-(trans-4-((R)-1-methoxypropan-2-yl-amino)cyclohexylamino)-2,4'-bipyridin-6-yl-amino)methyl)tetrahydro-2H-pyran-4-carbonitrile;
5'-chloro-N6-((2,2-dimethyltetrahydro-2H-pyran-4-yl)methyl)-N2'-(trans-4-((R)-1-methoxypropan-2-yl-amino)cyclohexyl)-2,4'-bipyridine-2',6-diamine;
5'-chloro-N6-(((S)-2,2-dimethyltetrahydro-2H-pyran-4-yl)methyl)-N2'-(trans-4-((R)-1-methoxypropan-2-yl-amino)cyclohexyl)-2,4'-bipyridine-2',6-diamine;
5'-chloro-N6-((tetrahydro-2H-pyran-4-yl)methyl)-N2'-(trans-4-4(R)-tetrahydrofuran-2-yl)methyl)aminocyclohexyl)-2,4'-bipyridine-2',6-diamine;
5'-chloro-N6-((tetrahydro-2H-pyran-4-yl)methyl)-N2'-(trans-4-4(S)-tetrahydrofuran-2-yl)methyl)aminocyclohexyl)-2,4'-bipyridine-2',6-diamine;
4-((5'-chloro-2'-(trans-4-((2-methyl-1,3-dioxolan-2-yl)methyl)aminocyclohexylamino)-2,4'-bipyridin-6-yl-amino)methyl)tetrahydro-2H-pyran-4-carbonitrile; and
(4-((5'-chloro-2'-(trans-4-((R)-1-methoxypropan-2-yl-amino)cyclohexylamino)-2,4'-bipyridin-6-yl-amino)methyl)tetrahydro-2H-pyran-4-yl)methanol.

* * * * *